US007253263B1

(12) United States Patent
Hanai et al.

(10) Patent No.: US 7,253,263 B1
(45) Date of Patent: Aug. 7, 2007

(54) COMPLEMENTARITY DETERMINING REGION-GRAFTED ANTIBODY AGAINST GANGLIOSIDE GD3 AND DERIVATIVE OF ANTIBODY AGAINST GANGLIOSIDE GD3

(75) Inventors: Nobuo Hanai, Machida (JP); Kenya Shitara, Machida (JP); Kazuyasu Nakamura, Machida (JP); Rinpei Niwa, Machida (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 104 days.

(21) Appl. No.: 10/089,500

(22) PCT Filed: Sep. 29, 2000

(86) PCT No.: PCT/JP00/06774

§ 371 (c)(1),
(2), (4) Date: Mar. 29, 2002

(87) PCT Pub. No.: WO01/23432

PCT Pub. Date: Apr. 5, 2001

(30) Foreign Application Priority Data

Sep. 30, 1999 (JP) .................................. 11-278291
Apr. 6, 2000 (JP) .............................. 2000-105088

(51) Int. Cl.
*C12P 21/08* (2006.01)
*C07K 16/00* (2006.01)
*C12N 5/06* (2006.01)
*C12P 21/04* (2006.01)
*A61K 39/395* (2006.01)
*C07H 21/04* (2006.01)

(52) U.S. Cl. .............................. 530/387.3; 530/387.5; 530/388.1; 530/388.8; 530/391.7; 435/69.6; 435/328; 435/330; 424/133.1; 424/137.1; 424/141.1; 424/155.1; 424/181.1

(58) Field of Classification Search ............. 530/387.1, 530/387.3, 387.5, 388.1, 388.15, 388.8, 391.3, 530/391.7; 435/69.6, 70.21
See application file for complete search history.

(56) References Cited

U.S. PATENT DOCUMENTS

| 5,006,470 | A | | 4/1991 | Yamaguchi et al. |
| 5,091,178 | A | | 2/1992 | Hellstrom et al. |
| 5,530,101 | A | * | 6/1996 | Queen et al. |
| 5,610,280 | A | | 3/1997 | Brandt et al. |
| 5,730,981 | A | | 3/1998 | Bosslet et al. |
| 5,750,078 | A | * | 5/1998 | Shitara et al. |
| 6,437,098 | B1 | * | 8/2002 | Shitara et al. |

FOREIGN PATENT DOCUMENTS

| EP | 0 280 209 A2 | 8/1988 |
| EP | 0 493 686 A1 | 7/1992 |
| EP | 0 533 199 A2 | 3/1993 |
| EP | 533199 A2 * | 3/1993 |
| EP | 0 867 190 A1 | 9/1998 |
| JP | 5-304989 | 11/1993 |
| WO | WO 91/09967 A1 * | 7/1991 |

OTHER PUBLICATIONS

Co et al. Nature, 351:501-502, 1991.*
Fundamental Immunology, William E. Paul, M.D. ed., 3rd ed., pp. 242, 292-295, 1993.*
Chapman et al. Cancer Research, 50:1503-1509, Mar. 1, 1990.*
LeBerthon et al. Cancer Research, 51:2694-2698, 1991.*
Hanai et al. Cancer Chemotherapy and Pharmacology, 46 (Suppl):S13-S17, Jun. 2000.*
Nakamura et al. Cancer, 80(12 Suppl):2650-2655, Dec. 15, 1997.*
Rudikoff et al. Proc. Natl. Acad. Sci. USA, 79:1979-1983, 1982.*
Alberts et al. Molecular Biology of the Cell, 3rd Ed. pp. 1216-1217, 1994.*
Immunology, 3rd Edition, "Engineered Monoclonal Antibodies", Janis Kuby, 1997, W.H. Freeman and Company, New York.
Webber et al, "Preparation and characterization of a disulfide-stabilized Fv fragment of the anti-tax antibody: comparison with its single-chain analog", Molecular Immunology, vol. 32 1995, pp. 249-258.
Moutel, "Generation and characterization of a mouse single-chain antibody fragment specific for disialoganglioside (GD2)", HYBRIDOMA, vol. 16, 1997, pp. 335-346.
Morrison et al, "Chimeric human antibody molecules: Mouse antigen-binding domains with human constant region domains", Proc. Natl. Acad. Sci. U.S.A., vol. 81, 1984, pp. 6851-6855.
Jones et al, "Replacing the complementarity-determining regions in a human antibody with those from a mouse", NATURE, vol. 321, 1986, pp. 522-525.
Presentini et al, Journal of Immunoassay, 1995, vol. 16, No. 3, pp. 309-324.
Supplementary Partial European Search Report dated May 10, 2005 issued in connection with EP 00 96 2981.7.
Scott et al, Current Opinion in Immunology, 1997. vol. 9, No. 5, pp. 717-722.
Shitara et al, Cancer Immunology Immunotherapy, 1993, vol. 36, No. 6, pp. 373-380.
Ojima et al, Tohoku J. Exp. Med., 1998, vol. 185, No. 2, pp. 89-100.
Shitara et al, Cancer Immunol Immunother, 1993, vol. 36, No. 6, pp. 373-380.
Scott et al, Current Opinion in Immunology, 1997, vol. 9, No. 5, pp. 717-722.
Alpaugh et al, Medical Oncology, 1998, vol. 15, No. 3, pp. 191-198.
Nasi et al, Melanoma Research, 1997, vol. 7, No. suppl 2, pp. S155-S162.
Chapman et al, Cancer Immunol Immunother, 1994, vol. 39, No. 3, pp. 198-204.
Dippold et al, European Journal of Cancer, 1992, vol. 28A, No. 10, pp. 1605-1610.
A Process for the Production of Humanized Chimaeric Antibody, Current Opinion in Therapeutic Patents, 993, vol. 3, No. 9, pp. 1357-1358.
Supplementary European Search Report dated Aug. 18, 2005 issued in corresponding EP 00 96 2981.7.

* cited by examiner

*Primary Examiner*—Larry R. Helms
*Assistant Examiner*—David J. Blanchard
(74) *Attorney, Agent, or Firm*—Nixon & Vanderhye P.C.

(57) ABSTRACT

The present invention relates to a human CDR-grafted antibody against ganlioside GD3 (hereinafter referred to "GD3"), derivatives of an anti-GD3 antibody and cytokine, and use for treatment and diagnosis of the antibody and the derivatives.

12 Claims, 41 Drawing Sheets

FIG. 18
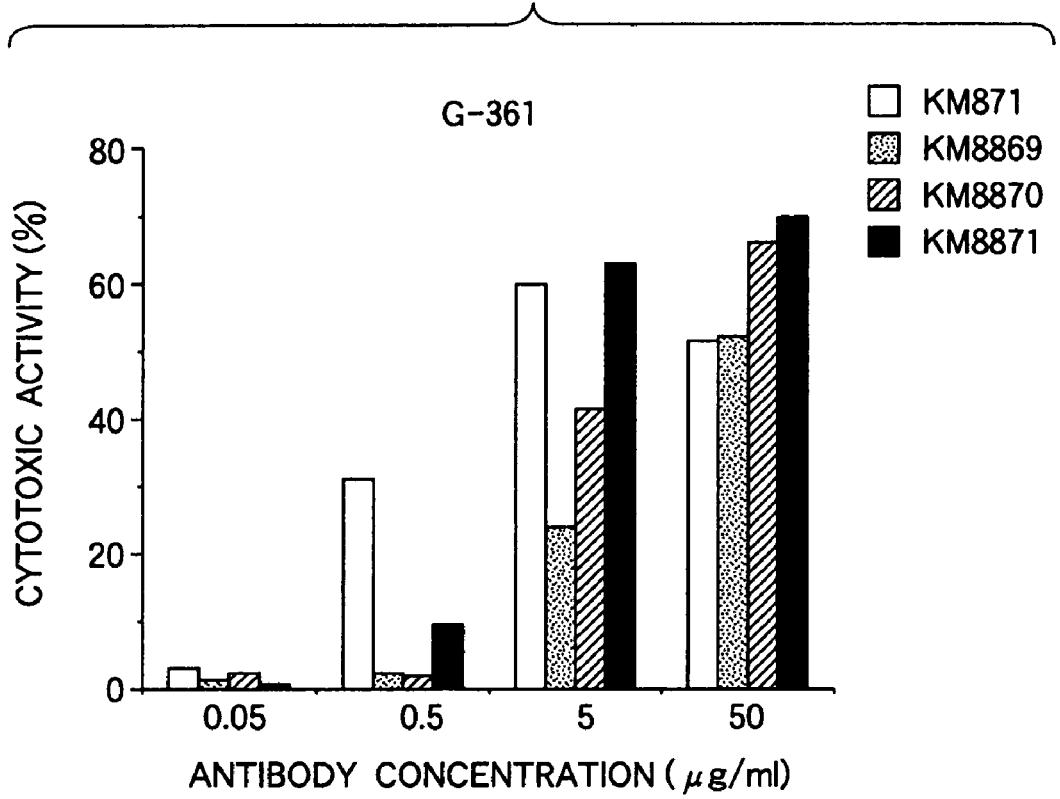
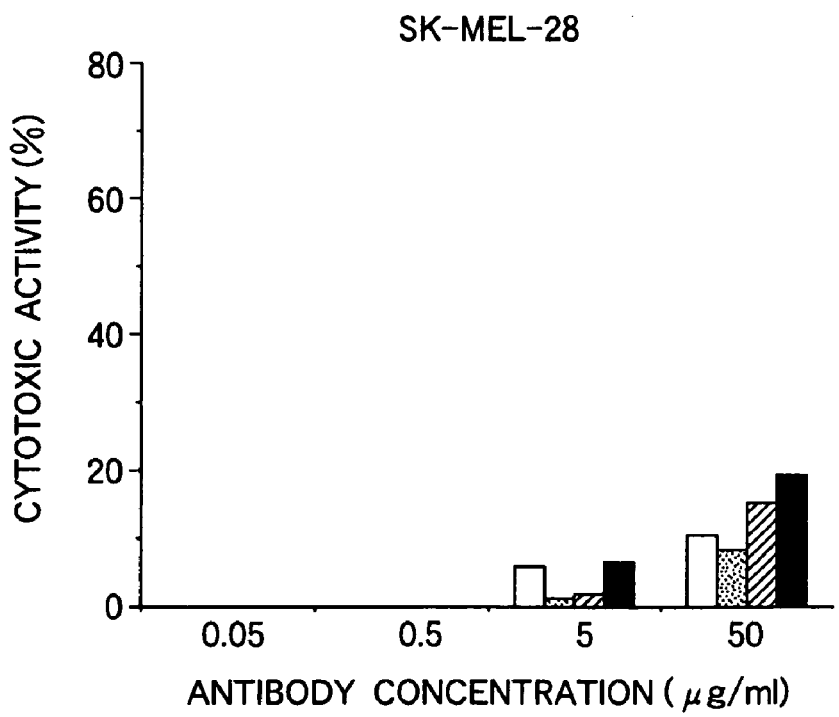

FIG.19
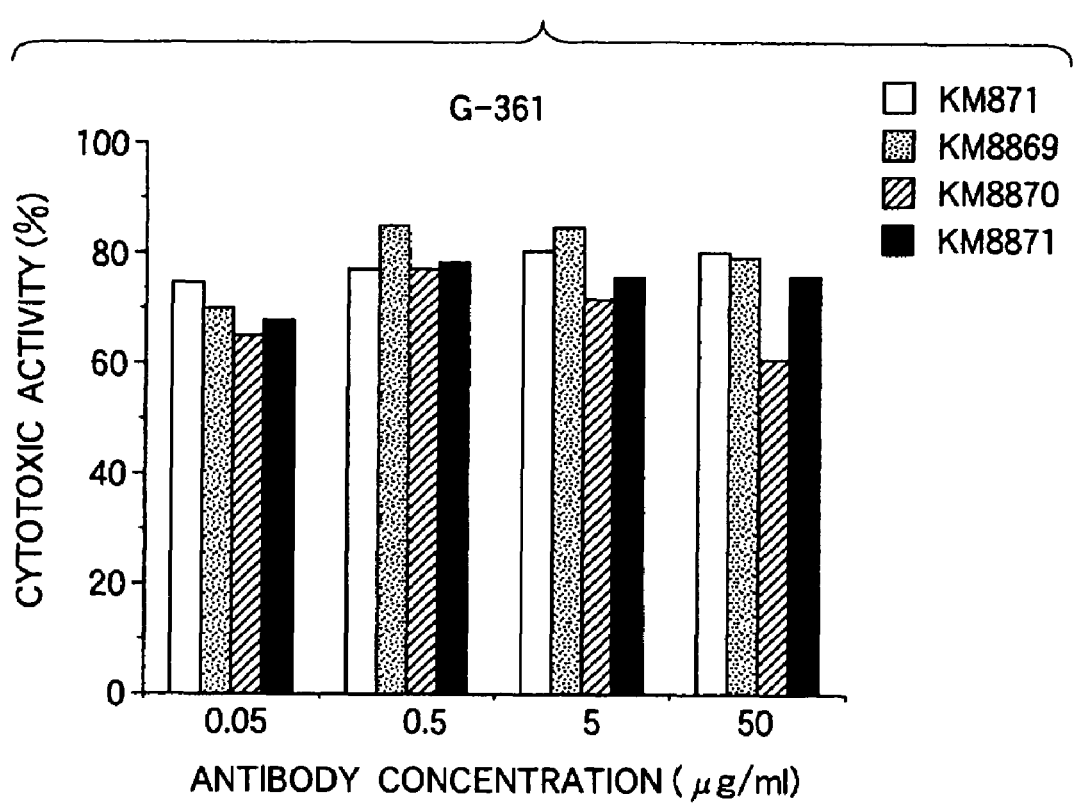
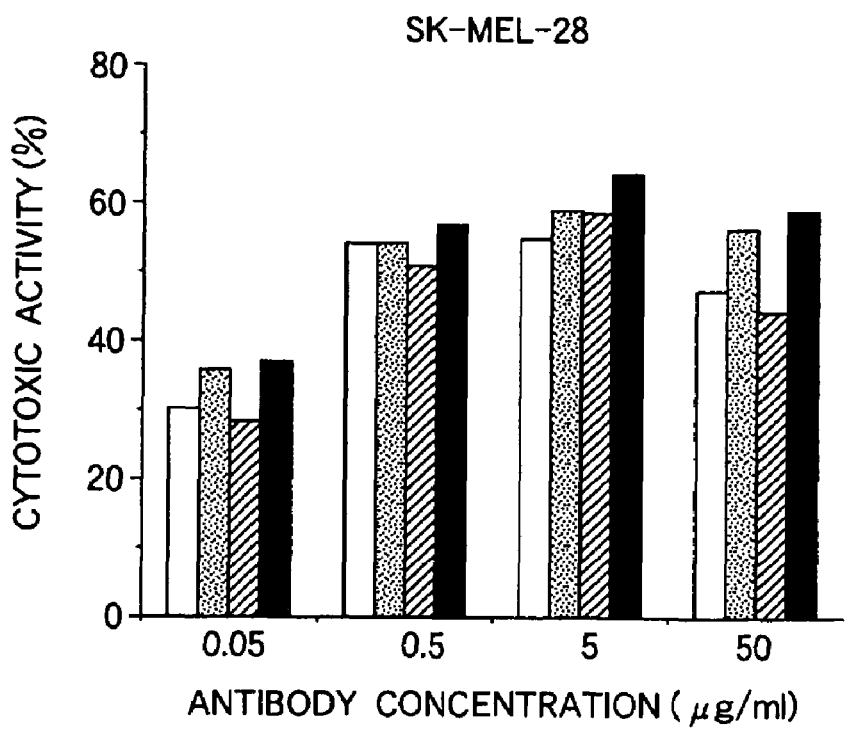

FIG. 27
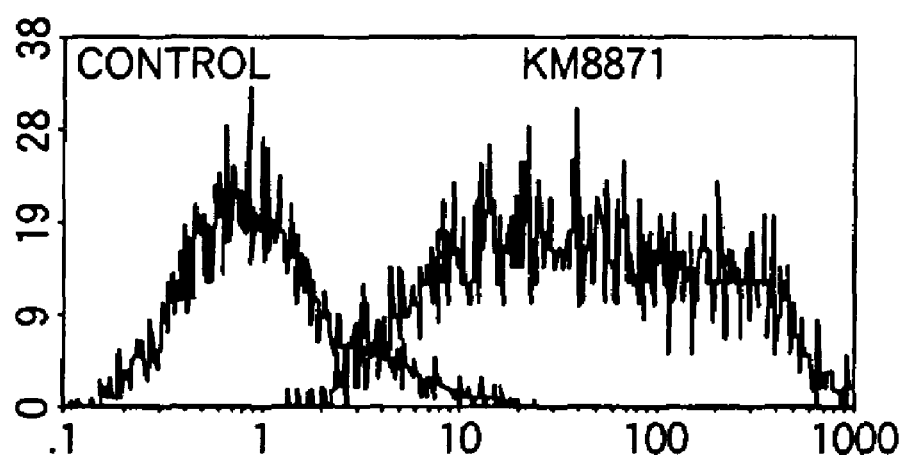
G361 CELL
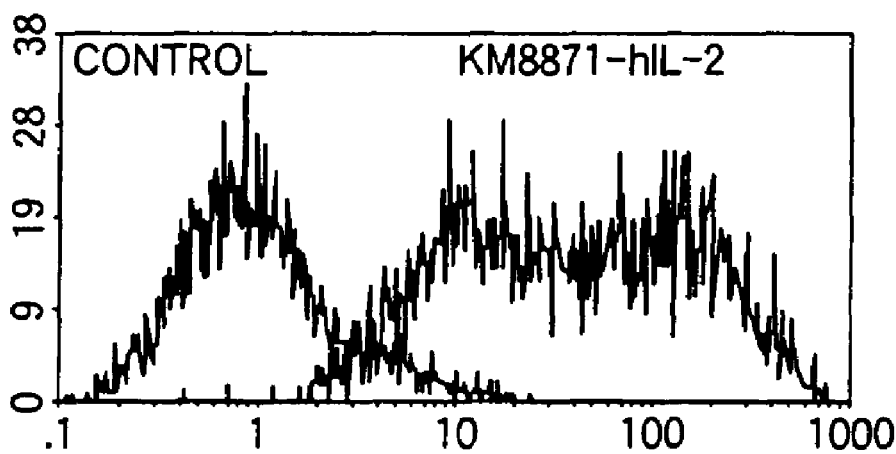

ORDINATE : NUMBER OF METASTATIC FOCI
BAR : AVERAGE OF EACH GROUP
VALUE IN THE GRAPH : METASTASIS INHIBITION RATIO
BY KM871-hIL-2 ADMINISTRATION

```
                          SEQUENCE LISTING

<160> NUMBER OF SEQ ID NOS: 57

<210> SEQ ID NO 1
<211> LENGTH: 138
<212> TYPE: PRT
<213> ORGANISM: Mus musculus

<400> SEQUENCE: 1

Met Glu Phe Gly Leu Ser Trp Leu Phe Leu Val Leu Phe Lys Gly
-19             -15                 -10                 -5

Val Gln Cys Glu Val Thr Leu Val Glu Ser Gly Gly Asp Phe Val Lys
         -1   1               5                  10

Pro Gly Gly Ser Leu Lys Val Ser Cys Ala Ala Ser Gly Phe Ala Phe
         15                  20                  25

Ser His Tyr Ala Met Ser Trp Val Arg Gln Thr Pro Ala Lys Arg Leu
 30                  35                  40                  45

Glu Trp Val Ala Tyr Ile Ser Ser Gly Ser Gly Thr Tyr Tyr Ser
                 50                  55                  60

Asp Ser Val Lys Gly Arg Phe Thr Ile Ser Arg Asp Asn Ala Lys Asn
                 65                  70                  75

Thr Leu Tyr Leu Gln Met Arg Ser Leu Arg Ser Glu Asp Ser Ala Met
             80                  85                  90

Tyr Phe Cys Thr Arg Val Lys Leu Gly Thr Tyr Tyr Phe Asp Ser Trp
         95                  100                 105

Gly Gln Gly Thr Thr Leu Thr Val Ser Ser
110                 115

<210> SEQ ID NO 2
<211> LENGTH: 128
<212> TYPE: PRT
<213> ORGANISM: Mus musculus

<400> SEQUENCE: 2

Met Met Ser Ser Ala Gln Phe Leu Gly Leu Leu Leu Leu Cys Phe Gln
-20                 -15                 -10                 -5

Gly Thr Arg Cys Asp Ile Gln Met Thr Gln Thr Ala Ser Ser Leu Pro
             -1   1               5                  10

Ala Ser Leu Gly Asp Arg Val Thr Ile Ser Cys Ser Ala Ser Gln Asp
             15                  20                  25

Ile Ser Asn Tyr Leu Asn Trp Tyr Gln Gln Lys Pro Asp Gly Thr Val
             30                  35                  40

Lys Leu Leu Ile Phe Tyr Ser Ser Asn Leu His Ser Gly Val Pro Ser
 45                  50                  55                  60

Arg Phe Ser Gly Gly Gly Ser Gly Thr Asp Tyr Ser Leu Thr Ile Ser
                 65                  70                  75

Asn Leu Glu Pro Glu Asp Ile Ala Thr Tyr Phe Cys His Gln Tyr Ser
             80                  85                  90

Lys Leu Pro Trp Thr Phe Gly Gly Gly Thr Lys Leu Glu Ile Lys Arg
```

```
<210> SEQ ID NO 3
<211> LENGTH: 5
<212> TYPE: PRT
<213> ORGANISM: Mus musculus

<400> SEQUENCE: 3

His Tyr Ala Met Ser
 1               5

<210> SEQ ID NO 4
<211> LENGTH: 17
<212> TYPE: PRT
<213> ORGANISM: Mus musculus

<400> SEQUENCE: 4

Tyr Ile Ser Ser Gly Gly Ser Gly Thr Tyr Tyr Ser Asp Ser Val Lys Gly
 1               5                  10                  15

<210> SEQ ID NO 5
<211> LENGTH: 10
<212> TYPE: PRT
<213> ORGANISM: Mus musculus

<400> SEQUENCE: 5

Val Lys Leu Gly Thr Tyr Tyr Phe Asp Ser
 1               5                  10

<210> SEQ ID NO 6
<211> LENGTH: 11
<212> TYPE: PRT
<213> ORGANISM: Mus musculus

<400> SEQUENCE: 6

Ser Ala Ser Gln Asp Ile Ser Asn Tyr Leu Asn
 1               5                  10

<210> SEQ ID NO 7
<211> LENGTH: 7
<212> TYPE: PRT
<213> ORGANISM: Mus musculus

<400> SEQUENCE: 7

Tyr Ser Ser Asn Leu His Ser
 1               5

<210> SEQ ID NO 8
<211> LENGTH: 9
<212> TYPE: PRT
<213> ORGANISM: Mus musculus

<400> SEQUENCE: 8

His Gln Tyr Ser Lys Leu Pro Trp Thr
 1               5

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence:synthetic
      protein

<400> SEQUENCE: 9
```

```
Glu Val Gln Leu Val Glu Ser Gly Gly Asp Phe Val Gln Pro Gly Gly
  1               5                  10                  15

Ser Leu Arg Val Ser Cys Ala Ala Ser Gly Phe Ala Phe Ser His Tyr
             20                  25                  30

Ala Met Ser Trp Val Arg Gln Ala Pro Gly Lys Gly Leu Glu Trp Val
         35                  40                  45

Ala Tyr Ile Ser Ser Gly Ser Gly Thr Tyr Tyr Ser Asp Ser Val
     50                  55                  60

Lys Gly Arg Phe Thr Ile Ser Arg Asp Asn Ser Lys Asn Thr Leu Tyr
 65                  70                  75                  80

Leu Gln Met Arg Ser Leu Arg Ala Glu Asp Ser Ala Val Tyr Phe Cys
                 85                  90                  95

Thr Arg Val Lys Leu Gly Thr Tyr Tyr Phe Asp Ser Trp Gly Gln Gly
            100                 105                 110

Thr Leu Leu Thr Val Ser Ser
            115
```

```
<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence:synthetic
      protein

<400> SEQUENCE: 10
```

```
Asp Ile Gln Met Thr Gln Ser Pro Ser Ser Leu Ser Ala Ser Val Gly
  1               5                  10                  15

Asp Arg Val Thr Ile Thr Cys Ser Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Phe Tyr Ser Ser Asn Leu His Ser Gly Val Pro Ser Arg Phe Ser Gly
     50                  55                  60

Gly Gly Ser Gly Thr Asp Tyr Thr Leu Thr Ile Ser Ser Leu Gln Pro
 65                  70                  75                  80

Glu Asp Phe Ala Thr Tyr Tyr Cys His Gln Tyr Ser Lys Leu Pro Trp
                 85                  90                  95

Thr Phe Gly Gln Gly Thr Lys Val Glu Ile Lys Arg
            100                 105
```

```
<210> SEQ ID NO 11
<211> LENGTH: 95
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 11
caggaaacag ctatgacgcg gccgccacca tggagtttgg gctcagctgg cttttcttg      60 tccttgtttt caaaggtgtt cagtgtgagg tgcag                                 95

<210> SEQ ID NO 12
<211> LENGTH: 97
<212> TYPE: DNA
<213> ORGANISM: Artificial Sequence
<220> FEATURE:
<223> OTHER INFORMATION: Description of Artificial Sequence:synthetic
      DNA
```

<400> SEQUENCE: 12
aaagcgaatc cagaggctgc acaggagact ctcagagacc cccccggctg tacaaagtct     60
cccccagact ccaccagctg cacctcacac tgaacac                              97

<210> SEQ ID NO 13
<211> LENGTH: 98
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 13
gcagcctctg gattcgcttt cagtcattat gccatgtctt gggtccgcca ggctccaggg     60
aaggggctgg agtgggtggc ttatattagt agtggtgg                             98

<210> SEQ ID NO 14
<211> LENGTH: 97
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 14
gatacagcgt gttcttggag ttatctctgg agatggtgaa tctgcccttt acactgtctg     60
aatagtaggt gccactacca ccactactaa tataagc                              97

<210> SEQ ID NO 15
<211> LENGTH: 98
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 15
ctccaagaac acgctgtatc tgcaaatgcg cagcctgaga gctgaggact cggctgtgta     60
tttctgtaca agagttaaac tgggaaccta ctactttg                             98

<210> SEQ ID NO 16
<211> LENGTH: 92
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 16
gttttcccag tcacgacggg cccttggtgg aggctgagga cggtgagc agggttccct       60 ggccccagga gtcaaagtag taggttccca gt                                   92

<210> SEQ ID NO 17
<211> LENGTH: 94
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 17
caggaaacag ctatgacgaa ttccaccatg atgtcctctg ctcagttcct tggtctcctg     60

```
ttgctctgtt ttcaaggtac cagatgtgac atcc                                   94

<210> SEQ ID NO 18
<211> LENGTH: 87
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 18
gcactacaag tgatggtgac tctgtctcct acagatgcag acaggagga tggagactgg        60 gtcatctgga tgtcacatct ggtacct                                           87

<210> SEQ ID NO 19
<211> LENGTH: 89
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 19
gtcaccatca cttgtagtgc aagtcaggac attagtaatt atttaaactg gtatcagcag       60
aaaccaggga aagcccctaa gctcctgat                                         89

<210> SEQ ID NO 20
<211> LENGTH: 89
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 20
taatctgtcc cagatccacc gccgctgaac cttgatggga ccccgagtg taaatttgat        60 gagtaaaaga tcaggagctt agggcttt                                          89

<210> SEQ ID NO 21
<211> LENGTH: 92
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 21
ggtggatctg ggacagatta tactctcacc atcagcagcc tgcagcctga agattttgca       60
acttattact gtcatcagta tagtaagctt cc                                     92

<210> SEQ ID NO 22
<211> LENGTH: 80
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 22
gttttcccag tcacgaccgt acgtttaatc tctaccttgg tccctggcc gaacgtccac        60 ggaagcttac tatactgatg                                                   80
```

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence:synthetic
DNA

<400> SEQUENCE: 23
agcttccatg gacgttcggt ggaggcacca agctggaaat caaac          45

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence:synthetic
DNA

<400> SEQUENCE: 24
gtacgtttga tttccagctt ggtgcctcca ccgaacgtcc atgga          45

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence:synthetic
DNA

<400> SEQUENCE: 25
gatgcaggca gggaggatgc agtctgggt          29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence:synthetic
DNA

<400> SEQUENCE: 26
acccagactg catcctccct gcctgcatc          29

<210> SEQ ID NO 27
<211> LENGTH: 384
<212> TYPE: DNA
<213> ORGANISM: Artificial Sequence
<220> FEATURE:
<223> OTHER INFORMATION: Description of Artificial Sequence:synthetic
DNA
<221> NAME/KEY: CDS
<222> LOCATION: (1)..(384)

<400> SEQUENCE: 27

```
atg atg tcc tct gct cag ttc ctt ggt ctc ctg ttg ctc tgt ttt caa      48
Met Met Ser Ser Ala Gln Phe Leu Gly Leu Leu Leu Leu Cys Phe Gln
-20             -15                 -10                 -5 ggt acc aga tgt gac atc cag atg acc cag act gca tcc tcc ctg cct      96
Gly Thr Arg Cys Asp Ile Gln Met Thr Gln Thr Ala Ser Ser Leu Pro
         -1   1               5                  10 gca tct gta gga gac aga gtc acc atc act tgt agt gca agt cag gac     144
Ala Ser Val Gly Asp Arg Val Thr Ile Thr Cys Ser Ala Ser Gln Asp
        15                  20                  25 att agt aat tat tta aac tgg tat cag cag aaa cca ggg aaa gcc cct     192
Ile Ser Asn Tyr Leu Asn Trp Tyr Gln Gln Lys Pro Gly Lys Ala Pro
    30                  35                  40
```

```
aag ctc ctg atc ttt tac tca tca aat tta cac tcg ggg gtc cca tca      240
Lys Leu Leu Ile Phe Tyr Ser Ser Asn Leu His Ser Gly Val Pro Ser
 45                  50                  55                  60 agg ttc agc ggc ggt gga tct ggg aca gat tat act ctc acc atc agc      288
Arg Phe Ser Gly Gly Gly Ser Gly Thr Asp Tyr Thr Leu Thr Ile Ser
                 65                  70                  75 agc ctg cag cct gaa gat ttt gca act tat tac tgt cat cag tat agt      336
Ser Leu Gln Pro Glu Asp Phe Ala Thr Tyr Tyr Cys His Gln Tyr Ser
         80                  85                  90 aag ctt ccg tgg acg ttc ggc cag ggg acc aag gta gag att aaa cgt      384
Lys Leu Pro Trp Thr Phe Gly Gln Gly Thr Lys Val Glu Ile Lys Arg
             95                 100                 105
```

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 28
actgatgaca gaaataagtt gcaaaa                                          26

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 29
ttttgcaact tatttctgtc atcagt                                          26

<210> SEQ ID NO 30
<211> LENGTH: 384
<212> TYPE: DNA
<213> ORGANISM: Artificial Sequence
<220> FEATURE:
<223> OTHER INFORMATION: Description of Artificial Sequence:synthetic
      DNA
<221> NAME/KEY: CDS
<222> LOCATION: (1)..(384)

<400> SEQUENCE: 30

```
atg atg tcc tct gct cag ttc ctt ggt ctc ctg ttg ctc tgt ttt caa       48
Met Met Ser Ser Ala Gln Phe Leu Gly Leu Leu Leu Leu Cys Phe Gln
-20                 -15                 -10                  -5 ggt acc aga tgt gac atc cag atg acc cag tct cca tcc tcc ctg tct       96
Gly Thr Arg Cys Asp Ile Gln Met Thr Gln Ser Pro Ser Ser Leu Ser
             -1   1               5                  10 gca tct gta gga gac aga gtc acc atc act tgt agt gca agt cag gac      144
Ala Ser Val Gly Asp Arg Val Thr Ile Thr Cys Ser Ala Ser Gln Asp
         15                  20                  25 att agt aat tat tta aac tgg tat cag cag aaa cca ggg aaa gcc cct      192
Ile Ser Asn Tyr Leu Asn Trp Tyr Gln Gln Lys Pro Gly Lys Ala Pro
     30                  35                  40 aag ctc ctg atc ttt tac tca tca aat tta cac tcg ggg gtc cca tca      240
Lys Leu Leu Ile Phe Tyr Ser Ser Asn Leu His Ser Gly Val Pro Ser
 45                  50                  55                  60 agg ttc agc ggc ggt gga tct ggg aca gat tat act ctc acc atc agc      288
Arg Phe Ser Gly Gly Gly Ser Gly Thr Asp Tyr Thr Leu Thr Ile Ser
                 65                  70                  75
```

```
agc ctg cag cct gaa gat ttt gca act tat ttc tgt cat cag tat agt      336
Ser Leu Gln Pro Glu Asp Phe Ala Thr Tyr Phe Cys His Gln Tyr Ser
            80                  85                  90 aag ctt ccg tgg acg ttc ggc cag ggg acc aag gta gag att aaa cgt      384
Lys Leu Pro Trp Thr Phe Gly Gln Gly Thr Lys Val Glu Ile Lys Arg
        95                 100                 105

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 31
ggagcttaac ggctttgtct ggtttctg                                        28

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 32
cagaaaccag acaaagccgt taagctcc                                        28

<210> SEQ ID NO 33
<211> LENGTH: 384
<212> TYPE: DNA
<213> ORGANISM: Artificial Sequence
<220> FEATURE:
<223> OTHER INFORMATION: Description of Artificial Sequence:synthetic
      DNA
<221> NAME/KEY: CDS
<222> LOCATION: (1)..(384)

<400> SEQUENCE: 33 atg atg tcc tct gct cag ttc ctt ggt ctc ctg ttg ctc tgt ttt caa       48
Met Met Ser Ser Ala Gln Phe Leu Gly Leu Leu Leu Leu Cys Phe Gln
-20             -15                 -10                 -5 ggt acc aga tgt gac atc cag atg acc cag tct cca tcc tcc ctg tct       96
Gly Thr Arg Cys Asp Ile Gln Met Thr Gln Ser Pro Ser Ser Leu Ser
            -1   1               5                  10 gca tct gta gga gac aga gtc acc atc act tgt agt gca agt cag gac      144
Ala Ser Val Gly Asp Arg Val Thr Ile Thr Cys Ser Ala Ser Gln Asp
        15                  20                  25 att agt aat tat tta aac tgg tat cag cag aaa cca gac aaa gcc gtt      192
Ile Ser Asn Tyr Leu Asn Trp Tyr Gln Gln Lys Pro Asp Lys Ala Val
    30                  35                  40 aag ctc ctg atc ttt tac tca tca aat tta cac tcg ggg gtc cca tca      240
Lys Leu Leu Ile Phe Tyr Ser Ser Asn Leu His Ser Gly Val Pro Ser
45                  50                  55                  60 agg ttc agc ggc ggt gga tct ggg aca gat tat act ctc acc atc agc      288
Arg Phe Ser Gly Gly Gly Ser Gly Thr Asp Tyr Thr Leu Thr Ile Ser
                65                  70                  75 agc ctg cag cct gaa gat ttt gca act tat tac tgt cat cag tat agt      336
Ser Leu Gln Pro Glu Asp Phe Ala Thr Tyr Tyr Cys His Gln Tyr Ser
            80                  85                  90 aag ctt ccg tgg acg ttc ggc cag ggg acc aag gta gag att aaa cgt      384
Lys Leu Pro Trp Thr Phe Gly Gln Gly Thr Lys Val Glu Ile Lys Arg
        95                 100                 105
```

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence:synthetic
     DNA

<400> SEQUENCE: 34
gttgcgatat cttcaggctg cagattgctg atggtgagac tataatct            48

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence:synthetic
     DNA

<400> SEQUENCE: 35
agattatagt ctcaccatca gcaatctgca gcctgaagat atcgcaac             48

<210> SEQ ID NO 36
<211> LENGTH: 384
<212> TYPE: DNA
<213> ORGANISM: Artificial Sequence
<220> FEATURE:
<223> OTHER INFORMATION: Description of Artificial Sequence:synthetic
     DNA
<221> NAME/KEY: CDS
<222> LOCATION: (1)..(384)

<400> SEQUENCE: 36 atg atg tcc tct gct cag ttc ctt ggt ctc ctg ttg ctc tgt ttt caa      48
Met Met Ser Ser Ala Gln Phe Leu Gly Leu Leu Leu Leu Cys Phe Gln
-20            -15                -10                -5 ggt acc aga tgt gac atc cag atg acc cag tct cca tcc tcc ctg tct      96
Gly Thr Arg Cys Asp Ile Gln Met Thr Gln Ser Pro Ser Ser Leu Ser
         -1   1                5                  10 gca tct gta gga gac aga gtc acc atc act tgt agt gca agt cag gac     144
Ala Ser Val Gly Asp Arg Val Thr Ile Thr Cys Ser Ala Ser Gln Asp
        15                  20                  25 att agt aat tat tta aac tgg tat cag cag aaa cca ggg aaa gcc cct     192
Ile Ser Asn Tyr Leu Asn Trp Tyr Gln Gln Lys Pro Gly Lys Ala Pro
     30                  35                  40 aag ctc ctg atc ttt tac tca tca aat tta cac tcg ggg gtc cca tca     240
Lys Leu Leu Ile Phe Tyr Ser Ser Asn Leu His Ser Gly Val Pro Ser
 45                  50                  55                  60 agg ttc agc ggc ggt gga tct ggg aca gat tat agt ctc acc atc agc     288
Arg Phe Ser Gly Gly Gly Ser Gly Thr Asp Tyr Ser Leu Thr Ile Ser
                 65                  70                  75 aat ctg cag cct gaa gat atc gca act tat tac tgt cat cag tat agt     336
Asn Leu Gln Pro Glu Asp Ile Ala Thr Tyr Tyr Cys His Gln Tyr Ser
             80                  85                  90 aag ctt ccg tgg acg ttc ggc cag ggg acc aag gta gag att aaa cgt     384
Lys Leu Pro Trp Thr Phe Gly Gln Gly Thr Lys Val Glu Ile Lys Arg
         95                 100                 105

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence:synthetic -continued

```
                 DNA

<400> SEQUENCE: 37
ttcaggctgc agattgctga tggtg                                           25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 38
caccatcagc aatctgcagc ctgaa                                           25

<210> SEQ ID NO 39
<211> LENGTH: 384
<212> TYPE: DNA
<213> ORGANISM: Artificial Sequence
<220> FEATURE:
<223> OTHER INFORMATION: Description of Artificial Sequence:synthetic
      DNA
<221> NAME/KEY: CDS
<222> LOCATION: (1)..(384)

<400> SEQUENCE: 39 atg atg tcc tct gct cag ttc ctt ggt ctc ctg ttg ctc tgt ttt caa       48
Met Met Ser Ser Ala Gln Phe Leu Gly Leu Leu Leu Leu Cys Phe Gln
-20             -15                 -10                  -5 ggt acc aga tgt gac atc cag atg acc cag tct cca tcc tcc ctg tct       96
Gly Thr Arg Cys Asp Ile Gln Met Thr Gln Ser Pro Ser Ser Leu Ser
            -1   1               5                  10 gca tct gta gga gac aga gtc acc atc act tgt agt gca agt cag gac      144
Ala Ser Val Gly Asp Arg Val Thr Ile Thr Cys Ser Ala Ser Gln Asp
         15                  20                  25 att agt aat tat tta aac tgg tat cag cag aaa cca ggg aaa gcc cct      192
Ile Ser Asn Tyr Leu Asn Trp Tyr Gln Gln Lys Pro Gly Lys Ala Pro
     30                  35                  40 aag ctc ctg atc ttt tac tca tca aat tta cac tcg ggg gtc cca tca      240
Lys Leu Leu Ile Phe Tyr Ser Ser Asn Leu His Ser Gly Val Pro Ser
 45                  50                  55                  60 agg ttc agc ggc ggt gga tct ggg aca gat tat act ctc acc atc agc      288
Arg Phe Ser Gly Gly Gly Ser Gly Thr Asp Tyr Thr Leu Thr Ile Ser
                 65                  70                  75 aat ctg cag cct gaa gat ttt gca act tat tac tgt cat cag tat agt      336
Asn Leu Gln Pro Glu Asp Phe Ala Thr Tyr Tyr Cys His Gln Tyr Ser
             80                  85                  90 aag ctt ccg tgg acg ttc ggc cag ggg acc aag gta gag att aaa cgt      384
Lys Leu Pro Trp Thr Phe Gly Gln Gly Thr Lys Val Glu Ile Lys Arg
         95                 100                 105

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 40
gacagaaata agttgcgata tcttcaggct                                      30

<210> SEQ ID NO 41
```

```
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 41
agcctgaaga tatcgcaact tatttctgtc                                          30

<210> SEQ ID NO 42
<211> LENGTH: 384
<212> TYPE: DNA
<213> ORGANISM: Artificial Sequence
<220> FEATURE:
<223> OTHER INFORMATION: Description of Artificial Sequence:synthetic
      DNA
<221> NAME/KEY: CDS
<222> LOCATION: (1)..(384)

<400> SEQUENCE: 42 atg atg tcc tct gct cag ttc ctt ggt ctc ctg ttg ctc tgt ttt caa        48
Met Met Ser Ser Ala Gln Phe Leu Gly Leu Leu Leu Leu Cys Phe Gln
-20             -15                 -10                 -5 ggt acc aga tgt gac atc cag atg acc cag tct cca tcc tcc ctg tct        96
Gly Thr Arg Cys Asp Ile Gln Met Thr Gln Ser Pro Ser Ser Leu Ser
            -1   1               5                  10 gca tct gta gga gac aga gtc acc atc act tgt agt gca agt cag gac       144
Ala Ser Val Gly Asp Arg Val Thr Ile Thr Cys Ser Ala Ser Gln Asp
        15                  20                  25 att agt aat tat tta aac tgg tat cag cag aaa cca ggg aaa gcc cct       192
Ile Ser Asn Tyr Leu Asn Trp Tyr Gln Gln Lys Pro Gly Lys Ala Pro
    30                  35                  40 aag ctc ctg atc ttt tac tca tca aat tta cac tcg ggg gtc cca tca       240
Lys Leu Leu Ile Phe Tyr Ser Ser Asn Leu His Ser Gly Val Pro Ser
45                  50                  55                  60 agg ttc agc ggc ggt gga tct ggg aca gat tat act ctc acc atc agc       288
Arg Phe Ser Gly Gly Gly Ser Gly Thr Asp Tyr Thr Leu Thr Ile Ser
                65                  70                  75 agc ctg cag cct gaa gat atc gca act tat ttc tgt cat cag tat agt       336
Ser Leu Gln Pro Glu Asp Ile Ala Thr Tyr Phe Cys His Gln Tyr Ser
            80                  85                  90 aag ctt ccg tgg acg ttc ggc cag ggg acc aag gta gag att aaa cgt       384
Lys Leu Pro Trp Thr Phe Gly Gln Gly Thr Lys Val Glu Ile Lys Arg
        95                  100                 105

<210> SEQ ID NO 43
<211> LENGTH: 87
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 43
gcactacaag tgatggtgac tctgtctcct acagatgcag gcaggagga tgcagactgg         60 gtcatctgga tgtcacatct ggtacct                                             87

<210> SEQ ID NO 44
<211> LENGTH: 89
<212> TYPE: DNA
<213> ORGANISM: Artificial Sequence
<220> FEATURE:
<223> OTHER INFORMATION: Description of Artificial Sequence:synthetic
      DNA
```

<400> SEQUENCE: 44

```
gtcaccatca cttgtagtgc aagtcaggac attagtaatt atttaaactg gtatcagcag    60
aaaccaggga aagccgttaa gctcctgat                                      89
```

<210> SEQ ID NO 45
<211> LENGTH: 89
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 45

```
taatctgtcc cagatccacc gccgctgaac cttgatggga cccccgagtg taaatttgat    60
gagtaaaaga tcaggagctt aacggcttt                                      89
```

<210> SEQ ID NO 46
<211> LENGTH: 92
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 46

```
ggtggatctg ggacagatta tactctcacc atcagcagcc tgcagcctga agattttgca    60
acttatttct gtcatcagta tagtaagctt cc                                  92
```

<210> SEQ ID NO 47
<211> LENGTH: 384
<212> TYPE: DNA
<213> ORGANISM: Artificial Sequence
<220> FEATURE:
<223> OTHER INFORMATION: Description of Artificial Sequence:synthetic
      DNA
<221> NAME/KEY: CDS
<222> LOCATION: (1)..(384)

<400> SEQUENCE: 47

```
atg atg tcc tct gct cag ttc ctt ggt ctc ctg ttg ctc tgt ttt caa      48
Met Met Ser Ser Ala Gln Phe Leu Gly Leu Leu Leu Leu Cys Phe Gln
-20             -15                 -10                 -5 ggt acc aga tgt gac atc cag atg acc cag tct gca tcc tcc ctg cct      96
Gly Thr Arg Cys Asp Ile Gln Met Thr Gln Ser Ala Ser Ser Leu Pro
            -1   1               5                  10 gca tct gta gga gac aga gtc acc atc act tgt agt gca agt cag gac     144
Ala Ser Val Gly Asp Arg Val Thr Ile Thr Cys Ser Ala Ser Gln Asp
         15                  20                  25 att agt aat tat tta aac tgg tat cag cag aaa cca ggg aaa gcc gtt     192
Ile Ser Asn Tyr Leu Asn Trp Tyr Gln Gln Lys Pro Gly Lys Ala Val
     30                  35                  40 aag ctc ctg atc ttt tac tca tca aat tta cac tcg ggg gtc cca tca     240
Lys Leu Leu Ile Phe Tyr Ser Ser Asn Leu His Ser Gly Val Pro Ser
 45                  50                  55                  60 agg ttc agc ggc ggt gga tct ggg aca gat tat act ctc acc atc agc     288
Arg Phe Ser Gly Gly Gly Ser Gly Thr Asp Tyr Thr Leu Thr Ile Ser
                 65                  70                  75 agc ctg cag cct gaa gat ttt gca act tat ttc tgt cat cag tat agt     336
Ser Leu Gln Pro Glu Asp Phe Ala Thr Tyr Phe Cys His Gln Tyr Ser
             80                  85                  90 aag ctt ccg tgg acg ttc ggc cag ggg acc aag gta gag att aaa cgt     384
```

```
            Lys Leu Pro Trp Thr Phe Gly Gln Gly Thr Lys Val Glu Ile Lys Arg
                 95                  100                 105

<210> SEQ ID NO 48
<211> LENGTH: 384
<212> TYPE: DNA
<213> ORGANISM: Artificial Sequence
<220> FEATURE:
<223> OTHER INFORMATION: Description of Artificial Sequence:synthetic
      DNA
<221> NAME/KEY: CDS
<222> LOCATION: (1)..(384)

<400> SEQUENCE: 48 atg atg tcc tct gct cag ttc ctt ggt ctc ctg ttg ctc tgt ttt caa        48
Met Met Ser Ser Ala Gln Phe Leu Gly Leu Leu Leu Leu Cys Phe Gln
-20                 -15                 -10                  -5 ggt acc aga tgt gac atc cag atg acc cag tct cca tcc tcc ctg tct       96
Gly Thr Arg Cys Asp Ile Gln Met Thr Gln Ser Pro Ser Ser Leu Ser
                -1   1               5                  10 gca tct gta gga gac aga gtc acc atc act tgt agt gca agt cag gac      144
Ala Ser Val Gly Asp Arg Val Thr Ile Thr Cys Ser Ala Ser Gln Asp
             15                  20                  25 att agt aat tat tta aac tgg tat cag cag aaa cca gac aaa gcc gtt      192
Ile Ser Asn Tyr Leu Asn Trp Tyr Gln Gln Lys Pro Asp Lys Ala Val
         30                  35                  40 aag ctc ctg atc ttt tac tca tca aat tta cac tcg ggg gtc cca tca      240
Lys Leu Leu Ile Phe Tyr Ser Ser Asn Leu His Ser Gly Val Pro Ser
     45                  50                  55                  60 agg ttc agc ggc ggt gga tct ggg aca gat tat act ctc acc atc agc      288
Arg Phe Ser Gly Gly Gly Ser Gly Thr Asp Tyr Thr Leu Thr Ile Ser
                 65                  70                  75 agc ctg cag cct gaa gat atc gca act tat ttc tgt cat cag tat agt      336
Ser Leu Gln Pro Glu Asp Ile Ala Thr Tyr Phe Cys His Gln Tyr Ser
             80                  85                  90 aag ctt ccg tgg acg ttc ggc cag ggg acc aag gta gag att aaa cgt      384
Lys Leu Pro Trp Thr Phe Gly Gln Gly Thr Lys Val Glu Ile Lys Arg
         95                  100                 105

<210> SEQ ID NO 49
<211> LENGTH: 76
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 49
catgcatgag gctctgcaca accactacac gcagaagagc ctctccctgt ctcccggggg     60
agaattcatt gatcag                                                    76

<210> SEQ ID NO 50
<211> LENGTH: 85
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 50
gatcctgatc aatgaattct cccccgggag acagggagag gctcttctgc gtgtagtggt     60
tgtgcagagc ctcatgcatg gggcc                                          85
```

<210> SEQ ID NO 51
<211> LENGTH: 37
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 51
gtctcccggg aaagcaccta ctagtagttc tacaaag                              37

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 52
ccctgatcaa tgaattcaag tcagtgttga gatgatgc                             38

<210> SEQ ID NO 53
<211> LENGTH: 582
<212> TYPE: PRT
<213> ORGANISM: Artificial Sequence
<220> FEATURE:
<223> OTHER INFORMATION: Description of Artificial Sequence:synthetic
      protein

<400> SEQUENCE: 53

Glu Val Gln Leu Val Glu Ser Gly Gly Asp Phe Val Gln Pro Gly Gly
 1               5                  10                  15

Ser Leu Arg Val Ser Cys Ala Ala Ser Gly Phe Ala Phe Ser His Tyr
            20                  25                  30

Ala Met Ser Trp Val Arg Gln Ala Pro Gly Lys Gly Leu Glu Trp Val
        35                  40                  45

Ala Tyr Ile Ser Ser Gly Gly Ser Gly Thr Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Arg Ser Leu Arg Ala Glu Asp Ser Ala Val Tyr Phe Cys
                85                  90                  95

Thr Arg Val Lys Leu Gly Thr Tyr Tyr Phe Asp Ser Trp Gly Gln Gly
            100                 105                 110

Thr Leu Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro

```
            225                 230                 235                 240
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280             285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Ala Pro Thr Ser Ser Thr Lys Lys Thr Gln Leu Gln Leu Glu
    450                 455                 460

His Leu Leu Leu Asp Leu Gln Met Ile Leu Asn Gly Ile Asn Asn Tyr
465                 470                 475                 480

Lys Asn Pro Lys Leu Thr Arg Met Leu Thr Phe Lys Phe Tyr Met Pro
                485                 490                 495

Lys Lys Ala Thr Glu Leu Lys His Leu Gln Cys Leu Glu Glu Glu Leu
            500                 505                 510

Lys Pro Leu Glu Glu Val Leu Asn Leu Ala Gln Ser Lys Asn Phe His
            515                 520                 525

Leu Arg Pro Arg Asp Leu Ile Ser Asn Ile Asn Val Ile Val Leu Glu
    530                 535                 540

Leu Lys Gly Ser Glu Thr Thr Phe Met Cys Glu Tyr Ala Asp Glu Thr
545                 550                 555                 560

Ala Thr Ile Val Glu Phe Leu Asn Arg Trp Ile Thr Phe Cys Gln Ser
                565                 570                 575

Ile Ile Ser Thr Leu Thr
            580

<210> SEQ ID NO 54
<211> LENGTH: 108
<212> TYPE: PRT
<213> ORGANISM: Artificial Sequence
<220> FEATURE:
<223> OTHER INFORMATION: Description of Artificial Sequence:synthetic
      protein

<400> SEQUENCE: 54
```

```
Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
             20                  25                  30

Leu Asn Trp Tyr Gln Gln Lys Pro Asp Lys Ala Val Lys Leu Leu Ile
         35                  40                  45

Phe Tyr Ser Ser Asn Leu His Ser Gly Val Pro Ser Arg Phe Ser Gly
     50                  55                  60

Gly Gly Ser Gly Thr Asp Tyr Thr Leu Thr Ile Ser Ser Leu Gln Pro
 65                  70                  75                  80

Glu Asp Ile Ala Thr Tyr Phe Cys His Gln Tyr Ser Lys Leu Pro Trp
                 85                  90                  95

Thr Phe Gly Gln Gly Thr Lys Val Glu Ile Lys Arg
            100                 105
```

<210> SEQ ID NO 55
<211> LENGTH: 119
<212> TYPE: PRT
<213> ORGANISM: Mus musculus

<400> SEQUENCE: 55

```
Glu Val Thr Leu Val Glu Ser Gly Gly Asp Phe Val Lys Pro Gly Gly
 1               5                  10                  15

Ser Leu Lys Val Ser Cys Ala Ala Ser Gly Phe Ala Phe Ser His Tyr
             20                  25                  30

Ala Met Ser Trp Val Arg Gln Thr Pro Ala Lys Arg Leu Glu Trp Val
         35                  40                  45

Ala Tyr Ile Ser Ser Gly Gly Ser Gly Thr Tyr Tyr Ser Asp Ser Val
     50                  55                  60

Lys Gly Arg Phe Thr Ile Ser Arg Asp Asn Ala Lys Asn Thr Leu Tyr
 65                  70                  75                  80

Leu Gln Met Arg Ser Leu Arg Ser Glu Asp Ser Ala Met Tyr Phe Cys
                 85                  90                  95

Thr Arg Val Lys Leu Gly Thr Tyr Tyr Phe Asp Ser Trp Gly Gln Gly
            100                 105                 110

Thr Thr Leu Thr Val Ser Ser
            115
```

<210> SEQ ID NO 56
<211> LENGTH: 108
<212> TYPE: PRT
<213> ORGANISM: Mus musculus

<400> SEQUENCE: 56

```
Asp Ile Gln Met Thr Gln Thr Ala Ser Ser Leu Pro Ala Ser Leu Gly
 1               5                  10                  15

Asp Arg Val Thr Ile Ser Cys Ser Ala Ser Gln Asp Ile Ser Asn Tyr
             20                  25                  30

Leu Asn Trp Tyr Gln Gln Lys Pro Asp Gly Thr Val Lys Leu Leu Ile
         35                  40                  45

Phe Tyr Ser Ser Asn Leu His Ser Gly Val Pro Ser Arg Phe Ser Gly
     50                  55                  60

Gly Gly Ser Gly Thr Asp Tyr Ser Leu Thr Ile Ser Asn Leu Glu Pro
 65                  70                  75                  80

Glu Asp Ile Ala Thr Tyr Phe Cys His Gln Tyr Ser Lys Leu Pro Trp
                 85                  90                  95
```

```
Thr Phe Gly Gly Gly Thr Lys Leu Glu Ile Lys Arg
            100                 105
```

<210> SEQ ID NO 57
<211> LENGTH: 582
<212> TYPE: PRT
<213> ORGANISM: Artificial Sequence
<220> FEATURE:
<223> OTHER INFORMATION: Description of Artificial Sequence:synthetic
      protein

<400> SEQUENCE: 57

```
Glu Val Thr Leu Val Glu Ser Gly Gly Asp Phe Val Lys Pro Gly Gly
 1               5                  10                  15

Ser Leu Lys Val Ser Cys Ala Ala Ser Gly Phe Ala Phe Ser His Tyr
             20                  25                  30

Ala Met Ser Trp Val Arg Gln Thr Pro Ala Lys Arg Leu Glu Trp Val
         35                  40                  45

Ala Tyr Ile Ser Ser Gly Gly Ser Gly Thr Tyr Tyr Ser Asp Ser Val
     50                  55                  60

Lys Gly Arg Phe Thr Ile Ser Arg Asp Asn Ala Lys Asn Thr Leu Tyr
 65                  70                  75                  80

Leu Gln Met Arg Ser Leu Arg Ser Glu Asp Ser Ala Met Tyr Phe Cys
                 85                  90                  95

Thr Arg Val Lys Leu Gly Thr Tyr Tyr Phe Asp Ser Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

-continued

```
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys Ala Pro Thr Ser Ser Thr Lys Lys Thr Gln Leu Gln Leu Glu
    450                 455                 460

His Leu Leu Leu Asp Leu Gln Met Ile Leu Asn Gly Ile Asn Asn Tyr
465                 470                 475                 480

Lys Asn Pro Lys Leu Thr Arg Met Leu Thr Phe Lys Phe Tyr Met Pro
                485                 490                 495

Lys Lys Ala Thr Glu Leu Lys His Leu Gln Cys Leu Glu Glu Glu Leu
            500                 505                 510

Lys Pro Leu Glu Glu Val Leu Asn Leu Ala Gln Ser Lys Asn Phe His
        515                 520                 525

Leu Arg Pro Arg Asp Leu Ile Ser Asn Ile Asn Val Ile Val Leu Glu
    530                 535                 540

Leu Lys Gly Ser Glu Thr Thr Phe Met Cys Glu Tyr Ala Asp Glu Thr
545                 550                 555                 560

Ala Thr Ile Val Glu Phe Leu Asn Arg Trp Ile Thr Phe Cys Gln Ser
                565                 570                 575

Ile Ile Ser Thr Leu Thr
                580
```

COMPLEMENTARITY DETERMINING REGION-GRAFTED ANTIBODY AGAINST GANGLIOSIDE GD3 AND DERIVATIVE OF ANTIBODY AGAINST GANGLIOSIDE GD3

This application is the US national phase of international application PCT/JP00/06774 filed Sep. 29, 2000 which designated the U.S.

TECHNICAL FIELD

The present invention relates to derivatives of a monoclonal antibody and the antibody fragment which specifically react with ganglioside GD3 (hereinafter referred to as "GD3"), and to a human CDR-grafted antibody and the antibody fragment which specifically react with GD3. Furthermore, the present invention relates to a DNA sequence which encodes the derivatives, antibody or antibody fragment. The present invention relates to a vector comprising the DNA sequence and a cell transformed with the vector. Moreover, the present invention relates to a process for producing the derivatives, antibody and antibody fragment using the transformed cell, and to a diagnostic agent and a therapeutic agent for cancers using the derivatives, antibody and antibody fragment.

BACKGROUND OF THE INVENTION

It is known that, when an antibody derived from a non-human animal, e.g., a mouse antibody, is administered to human, it is recognized as a foreign substance and thus induces a human antibody against the mouse antibody in the human body (human anti mouse antibody, hereinafter referred to as "HAMA"). It is known that the HAMA reacts with the administered mouse antibody to cause side effects (*J. Clin. Oncol.*, 2, 881 (1984); *Blood*, 65, 1349 (1985); *J. Natl. Cancer Inst.*, 80, 932 (1988); *Proc. Natl. Acad. Sci. U.S.A.*, 82, 1242 (1985)), to quicken disappearance of the administered mouse antibody from blood (*J. Nucl. Med.*, 26, 1011 (1985); *Blood*, 65, 1349 (1985); *J. Natl. Cancer Inst.*, 80, 937 (1988)) and to reduce therapeutic effects of the mouse antibody (*J. Immunol.*, 135, 1530 (1985); *Cancer Res.*, 46, 6489 (1986)).

In order to resolve these problems, attempts have been made to genetic engineeringly convert an antibody derived from a non-human animal into a humanized antibody such as a human chimeric antibody or a human complementarity determining region (hereinafter referred to as "CDR")-grafted antibody. The human chimeric antibody is an antibody in which its antibody variable region (hereinafter referred to as "V region") is derived from a non-human animal antibody and its constant region (hereinafter referred to as "C region") is derived from a human antibody (*Proc. Natl. Acad. Sci. U.S.A.*, 81, 6851 (1984)). The human CDR-grafted antibody is an antibody in which the amino acid sequence of CDR in the V region derived from a non-human animal antibody is grafted to an appropriate position of a human antibody (*Nature*, 321, 522 (1986)). These humanized antibodies have various advantages in clinically applying to human, in comparison with antibodies of non-human animals such as mouse antibodies and the like. For example, it has been reported on the immunogenicity and stability in blood that, when a human chimeric antibody is administered to human, its half-life in blood increased about six times in comparison with a mouse antibody (*Proc. Natl. Acad. Sci. U.S.A.*, 86, 4220 (1989)). It has been reported that, in a test of a human CDR-grafted antibody in monkeys, its immunogenicity is reduced and its half-life in blood is increased four to five times in comparison with a mouse antibody (*J. Immunol.*, 147, 1352 (1991)). That is, it is expected that humanized antibodies have less side effects and their therapeutic effects continue for a longer period of time than antibodies of non-human animals. In addition, when applications particularly as anti-tumor antibodies are taken into consideration, higher cytotoxic activities such as complement-dependent cytotoxicity (hereinafter referred to as "CDC"), antibody-dependent cell-mediated cytotoxic activity (hereinafter referred to as "ADCC") and the like via an antibody Fc region (region in and after the hinge region of an antibody heavy chain) are important for the therapeutic effects. It has been reported that on such cytotoxic activities, that the Fc region of human antibodies is more superior in human to the Fc region of antibodies of non-human animals, since the Fc region more effectively activates human complement components and human effector cells having Fc receptors of mononuclear cells, macrophages and NK cells on the cell surface. For example, it has been reported that when a mouse antibody against GD3 (hereinafter referred to as "anti-GD3 mouse antibody") is converted into a human chimeric antibody having a human antibody Fc region (hereinafter referred to as "anti-GD3 chimeric antibody"), its tumor cell growth-inhibitory activity by human effector cells is increased (*J. Immunol.*, 144, 1382 (1990)), and similar results have been reported on a human CDR-grafted antibody against CAMPATH-1 antigen (*Nature*, 332, 323 (1988)).

These results clearly show that humanized antibodies are preferred to non-human antibodies such as mouse antibodies and the like, as antibodies for clinical applications to human.

In addition, with the recent advance in protein engineering and genetic engineering, antibody fragments having a smaller molecular weight such as Fab, Fab', F(ab')$_2$, a single chain antibody (*Science*, 242, 423 (1988)), a disulfide stabilized V region fragment (*Molecular Immunol.*, 32, 249 (1995)) and the like, can be produced. Since these fragments have a smaller molecular weight than whole antibody molecules, they are excellent in penetrating ability into target tissues (*Cancer Res.*, 52, 3402 (1992)). It is considered that these fragments derived from humanized antibodies are more desirable than those derived from non-human animal antibodies such as mouse antibodies, when used in clinical applications to human.

Ganglioside which is one of glycolipids containing sialic acid is a molecule which constitutes animal cell membrane and is constituted by a sugar chain as a hydrophilic side chain and a sphingosine and fatty acid as hydrophobic side chains. It is known that kinds and expression levels of ganglioside vary depending on the cell types, organ species, animal species and the like. It is also known that the expression of ganglioside changes quantitatively and qualitatively in the process of malignant transformation of cells (*Cancer Res.*, 45, 2405 (1985)). Particularly, the GD3 relating to the present invention is present in an extremely small amount in normal cells but in a large amount in cancer cells such as melanoma, sarcoma, glioma, neuroblastoma and the like (*Proc. Natl. Acad. Sci. U.S.A.*, 77, 6114 (1980); *J. Exp. Med.*, 155, 1133 (1982); *Cancer Res.*, 45, 4401 (1985)), and an antibody against GD3 (hereinafter referred to as "anti-GD3 antibody") is considered to be useful for the treatment of these cancers (*Melanoma Research*, 1, S115 (1997)). Tests on its administration to melanoma patients have already been carried out using R24 as an anti-GD3 mouse antibody, and its clinical effect was observed in a part of the patients but not to an expected degree because of considerably quick disappearance of the antibody from blood due to induction of HAMA (*Melanoma Research*, 1, S115 (1997)). Under such circumstances, in order to achieve more effective clinical applications of an anti-GD3 antibody to human, the present inventors have attempted to produce an anti-GD3 chimeric antibody having similar activity to that of a mouse antibody based on an anti-GD3 mouse antibody KM641 produced by the inventors, and have succeeded in producing an anti-GD3 chimeric antibody KM871 (Japanese Published Unexamined Patent Application No. 304989/93). It is expected that, in comparison with the anti-GD3 mouse antibody, the anti-GD3 chimeric antibody KM871 reduces immunogenicity in human, prolongs half-life in blood and has a stronger anti-tumor effect. However, it was found as a result of clinical tests on other anti-GD3 chimeric antibodies in human that allergy reactions are induced due to induction of a human antibody against a V region derived from a mouse antibody in the anti-GD3 chimeric antibodies (*Cancer J. From Scientific American*, 3, S121 (1997)). Even in the anti-GD3 chimeric antibody KM871 prepared by the inventors, it is necessary to await results of clinical tests in human to know if similar reactions are induced or not, and in order to reduce a possibility of generating such a problem as low as possible, it is desirable to produce a human CDR-grafted antibody against GD3 (hereinafter referred to as "anti-GD3 CDR-grafted antibody") which is considered to have lower immunogenicity than those of anti-GD3 chimeric antibodies in human. However, to date, there are no reports on the production of an anti-GD3 CDR-grafted antibody.

With regard to antibody fragments, a single chain antibody derived from an anti-GD2 mouse antibody has been produced (*Hybridoma*, 16, 335 (1997)), but there are no reports on the production of other antibody fragments. With regard to antibody fragments derived from an anti-GD3 antibody, there are no reports on the production of antibody fragments derived from a mouse antibody and a humanized antibody. Thus, if an antibody fragment derived from a humanized antibody against GD3 (hereinafter referred to as "anti-GD3 humanized antibody") can be produced, it is expected that it has excellent target tissue penetratability and the immunogenicity is reduced.

As has been described above, it is expected that a humanized antibody and the antibody fragment have effect on diagnostic and therapeutic methods by single use, but further improvement of the effects has been examined by using them in combination with other molecules. For example, cytokine is used as one of these molecules. Cytokine is a general term for various aqueous factors which control intercellular mutual reactions in immune interactions. As cytotoxic activities of antibodies such as CDC activity, ADCC activity and the like are known and the ADCC activity is effected by effector cells having FC receptors on the cell surface such as mononuclear cells, macrophages, NK cells and the like (*J. Immunol.*, 138, 1992 (1987)). Since various kinds of cytokine activate these effector cells, their administration in combination with antibodies has been carried out to improve ADCC activity and the like of antibodies. For example, with regard to an anti-GD2 mouse antibody 14.G2a and an anti-GD2 chimeric antibody ch14.18, their administration to human in combination with a cytokine human interleukin-2 (hereinafter referred to as "hIL-2") or a human granulocyte macrophage colony-stimulating factor (hereinafter referred to as "hGM-CSF") has been carried out (*Cancer*, 80, 317 (1997); *Cancer J. From Scientific American*, 3, S121 (1997)). Regarding an anti-GD3 mouse antibody R24, combination therapy with various kinds of cytokine has also been carried out (*Cancer Res.*, 50, 7490 (1990), *Proc. Am. Soc. Clin. Oncol.*, 1186, 345 (1992), *J. Biol. Response Mod.*, 9, 319 (1990), *Proc. Am. Soc. Clin. Oncol.*, 1182, 344 (1992), *Proc. Am. Soc. Clin. Oncol.*, 1188, 346 (1992)). However, the effects as to be expected are not found in these combination therapies due to immunogenicity of mouse antibodies or side effects derived from cytokine. Thus, derivatives has been produced by conjugating an antibody or the antibody fragment thereof with a radioisotope, a protein (cytokine, toxin, enzyme or the like), a low molecular weight agent and the like, chemically or genetic engineeringly, and their clinical applications have been examined (*New Eng. J. Med.*, 329, 459 (1993), *Anticancer Res.*, 17, 1735 (1997), *Blood*, 78, 1173 (1991), *J. Clin. Oncol.*, 15, 723 (1997), *Bioconjugate Chem.*, 7, 606 (1997), *Cancer*, 61, 881 (1988), *Jpn. J. Cancer Res.*, 85, 167 (1994), *Antibody Immunoconjugates and Radiopharmaceuticals*, 3, 60 (1990), *Surgery*, 106, 533 (1989)). It is expected that these derivatives can accumulate a radioisotope, a protein (cytokine, toxin, enzyme or the like), a low molecular weight agent or the like in the periphery of a target tissue according to the binding specificity of antibodies so that more effective diagnoses and treatments having less side effects can be obtained. For example, with regard to hIL-2 which showed a certain degree of anti-tumor effect among cytokines used in the above combination therapy, its fusion protein with an anti-GD2 chimeric antibody ch14.18 was produced genetic engineeringly, and it has been reported that its antitumor effects in tests using mice were superior to those of simultaneous administration of anti-GD2 chimeric antibody ch14.18 and hIL-2 (*Proc. Natl. Acad. Sci. U.S.A.*, 89, 1428 (1992), *Proc. Natl. Acad. Sci. U.S.A.*, 91, 9626 (1994), *Cancer Immunol. Immunother.*, 42, 88 (1996), *Blood*, 91, 1706 (1998)). However, with regard to an anti-GD3 antibody, there are no reports on the production of derivatives by conjugating it with a protein (cytokine, toxin, enzyme or the like), a radioisotope, a low molecular weight agent and the like. Accordingly, also in the case of the anti-GD3 humanized antibody and the antibody fragment of the present invention, if derivatives conjugated with a radioisotope, a protein (toxin, enzyme or the like), a low molecular weight agent and the like, including fusion proteins with various kinds of cytokine, can be produced, reduction of immunogenicity, less side effects and more potent antitumor effects in the tumor region can be expected when administered to the human body.

DISCLOSURE OF THE INVENTION

In the present invention, an amino acid sequence of each CDR was identified from the amino acid sequences of H chain and L chain V regions of the anti-GD3 mouse antibody KM641 (Japanese Published Unexamined Patent Application No. 304989/93), cDNAS encoding the R chain and L chain V regions comprising the amino acid sequences of the CDRs of KM641 and amino acid sequences of the framework regions (hereinafter referred to as "FR") of human antibody H chain and L chain V regions were cloned into an expression vector for animal cell having cDNA encoding human antibody H chain and L chain C regions, and then the thus constructed anti-GD3 CDR-grafted antibody expression vector was introduced into an animal cell to produce a transformant KM8871 (FERM BP-6790) which produces an anti-GD3 CDR-grafted antibody KM8871 in a culture supernatant. Next, the anti-GD3 CDR-grafted antibody KM8871 was purified from a culture supernatant of the transformant KM8871 to find that the anti-GD3 CDR-grafted antibody KM8871 shows an antigen binding activity, an antigen binding specificity and a strong cytotoxic activity against human cancer cell lines, which are similar to those of the anti-GD3 chimeric antibody KM1871.

Furthermore, a cDNA was constructed by linking other cDNA encoding hIL-2 to the 3'-terminal of cDNA encoding the H chain of an anti-GD3 antibody, particularly anti-GD3 CDR-grafted antibody KM8871, and then the cDNA and a cDNA encoding the L chain of KM8871 were cloned into an expression vector for animal cell to construct an expression vector of a fusion protein of anti-GD3 CDR-grafted antibody KM8871 with hIL-2 (hereinafter referred to as "KM8871-hIL-2"). A transformant KM8871 hIL2 (FERM BP-6791 which produces KM8871-hIL-2 in culture supernatant was produced by introducing the KM8871-hIL-2 expression vector into an animal cell. Furthermore, KM8871-hIL-2 was purified from a culture supernatant of the transformant KM8871 hIL2 to find that KM8871-hIL-2 shows an antigen binding activity and an antigen binding specificity, which are similar to those of anti-GD3 CDR-grafted antibody KM8871, and a growth supporting activity against cell lines showing hIL-2-dependent growth, similar to that of hIL-2. Thereafter, the present invention was accomplished by finding that an activity of KM8871-hIL-2 in terms of the cytotoxic activity measured using a human peripheral blood mononuclear cell fraction is improved in comparison with that of anti-GD3 CDR-grafted antibody KM8871.

The present invention relates to the following (1) to (66).

(1) A derivative of an antibody, comprising a monoclonal antibody or the antibody fragment thereof which specifically reacts with ganglioside GD3 which is conjugated with a radioisotope, a protein or a low molecular weight agent.

(2) The derivative of an antibody according to (1), wherein the monoclonal antibody which specifically reacts with ganglioside GD3 is an antibody selected from an antibody produced by a hybridoma, a humanized antibody and a human antibody.

(3) The derivative of an antibody according to (1) or (2), wherein the monoclonal antibody comprises CDR1, CDR2 and CDR3 of H chain V region having the amino acid sequences represented by SEQ ID NOs:3, 4 and 5, respectively.

(4) The derivative of an antibody according to (1) or (2), wherein the monoclonal antibody comprises CDR1, CDR2 and CDR3 of L chain V region having the amino acid sequences represented by SEQ ID NOs:6, 7 and 8, respectively.

(5) The derivative of an antibody according to (1) or (2), wherein the monoclonal antibody comprises:

CDR1, CDR2 and CDR3 of a heavy chain (H chain) variable region (V region) having the amino acid sequences represented by SEQ ID NOs:3, 4 and 5, respectively; and CDR1, CDR2 and CDR3 of a light chain (L chain) V region having the amino acid sequences represented by SEQ ID NOs:6, 7 and 8, respectively.

(6) The derivative of an antibody according to (2), wherein the antibody produced by a hybridoma is KM641 (KM641 has been deposited on Sep. 27, 1990, under the conditions of the Budapest Treaty, as FERM BP-3116 in Fermentation Research Institute, Agency of Industrial Science and Technology Higashi 1-1-3, Tsukuba, Ibaraki, Japan (now the International Patent Organism Depositary, National Institute of Advanced Industrial Science and Technology Central 6, Higashi 1-1-1, Tsukuba, Ibaraki, Japan)).

(7) The derivative of an antibody according to (2), wherein the humanized antibody is a human chimeric antibody or a human CDR-grafted antibody.

(8) The derivative of a human chimeric antibody according to (7), wherein the human chimeric antibody comprises an H chain V region and an L chain v region of a monoclonal antibody against ganglioside GD3 produced by a hybridoma.

(9) The derivative of a human chimeric antibody according to (7), wherein the human chimeric antibody comprises:

an H chain V region and an L chain V region of a monoclonal antibody against ganglioside GD3 produced by a hybridoma; and an H chain constant region (C region) and an L chain C region of a human antibody.

(10) The derivative of a human chimeric antibody according to (8) or (9), wherein the H chain V region comprises the amino acid sequence represented by SEQ ID NO:55.

(11) The derivative of a human chimeric antibody according to (8) or (9), wherein the L chain V region comprises the amino acid sequence represented by SEQ ID NO:56.

(12) The derivative of a human chimeric antibody according to (8) or (9), wherein the H chain V region comprises the amino acid sequence represented by SEQ ID No:55; and the L chain v region comprises the amino acid sequence represented by SEQ ID NO:56.

(13) The derivative of a human chimeric antibody KM871 according to (8) or (9), wherein the H chain V region comprises the amino acid sequence represented by SEQ ID NO:55; and the L chain V region comprises the amino acid sequence represented by SEQ ID NO:56.

(14) The derivative of a human CDR-grafted antibody according to (7), wherein the human CDR-grafted antibody comprises CDR of an H chain V region and an L chain V region of a monoclonal antibody against ganglioside GD3.

(15) The derivative of a human CDR-grafted antibody according to (7), wherein the human CDR-grafted antibody comprises:

CDRs of an H chain V region and an L chain V region of a monoclonal antibody against ganglioside GD3; and framework regions (FRs) of an H chain v region and an L chain V region of a human antibody.

(16) The derivative of an antibody according to (7), wherein the human CDR-grafted antibody comprises:

CDRs of an H chain V region and an L chain v region of a monoclonal antibody against ganglioside GD3;

FRs of an H chain V region and an L chain V region of a human antibody; and an H chain C region and an L chain C region of a human antibody.

(17) The derivative of a human CDR-grafted antibody according to any one of (14) to (16), wherein the antibody comprises CDR1, CDR2 and CDR3 of the H chain v region having the amino acid sequences represented by SEQ ID NOs:3, 4 and 5, respectively.

(18) The derivative of a human CDR-grafted antibody according to any one of (14) to (16), wherein the antibody comprises CDR1, CDR2 and CDR3 of the L chain V region having the amino acid sequences represented by SEQ ID NOs:6, 7 and 8, respectively.

(19) The derivative of a human CDR-grafted antibody according to any one of (14) to (16), wherein the antibody comprises:

CDR1, CDR2 and CDR3 of the H chain V region having the amino acid sequences represented by SEQ ID NOs:3, 4 and 5, respectively; and CDR1, CDR2 and CDR3 of the L chain V region having the amino acid sequences represented by SEQ ID NOs:6, 7 and 8, respectively.

(20) The derivative of a human CDR-grafted antibody according to any one of (14) to (16), wherein the H chain V region of the antibody comprises the amino acid sequence represented by SEQ ID NO:9.

(21) The derivative of a human CDR-grafted antibody according to any one of (14) to (16), wherein the L chain V region of the antibody comprises the amino acid sequence represented by SEQ ID NO:54.

(22) The derivative of a human CDR-grafted antibody according to any one of (14) to (16), wherein the H chain V region and the L chain V region of the antibody comprises the amino acid sequences represented by SEQ ID NO:9 and SEQ ID NO:54, respectively.

(23) The derivative of a human CDR-grafted antibody KM8871 according to any one of (14) to (16), wherein the H chain V region of the antibody comprises the amino acid sequence represented by SEQ ID NO:9; and the L chain V region of the antibody comprises the amino acid sequence represented by SEQ ID NO:54.

(24) The derivative of the antibody fragment according to (1), wherein the antibody fragment is an antibody fragment selected from Fab, Fab', F(ab')$_2$, a single chain antibody (scFv), a disulfide stabilized V region fragment (dsfv) and a peptide comprising CDR.

(25) The derivative of the antibody fragment according to (1) or (24), wherein the antibody fragment comprises amino acid sequences of an R chain V region and an L chain v region of a monoclonal antibody against ganglioside GD3 produced by a hybridoma.

(26) The derivative of the antibody fragment according to (1) or (24), wherein the antibody fragment comprises an H chain V region of the antibody having the amino acid sequence represented by SEQ ID NO:55.

(27) The derivative of the antibody fragment according to (1) or (24), wherein the antibody fragment comprises an L chain V region of the antibody having the amino acid sequence represented by SEQ ID NO:56.

(28) The derivative of the antibody fragment according to (1) or (24), wherein the antibody fragment comprises:

an H chain V region of the antibody having the amino acid sequence represented by SEQ ID NO:55; and an L chain V region of the antibody having the amino acid sequence represented by SEQ ID NO:56.

(29) The derivative of the antibody fragment according to (1) or (24), wherein the antibody fragment comprises amino acid sequences of an H chain V region and an L chain V region of a human CDR-grafted antibody against ganglioside GD3.

(30) The derivative of the antibody fragment according to (1) or (24), wherein the antibody fragment comprises an H chain v region of the antibody having the amino acid sequence represented by SEQ ID NO:9.

(31) The derivative of the antibody fragment according to (1) or (24), wherein the antibody fragment comprises an L chain V region of the antibody having the amino acid sequence represented by SEQ ID NO:54.

(32) The derivative of the antibody fragment according to (1) or (24), wherein the antibody fragment comprises:

an H chain V region of the antibody having the amino acid sequence represented by SEQ ID NO:9; and an L chain V region of the antibody having the amino acid sequence represented by SEQ ID NO:54.

(33) The derivative of an antibody fragment according to (1) or (24), wherein the antibody fragment comprises CDR1, CDR2 and CDR3 of an H chain V region of the antibody having the amino acid sequences represented by SEQ ID NOS:3, 4 and 5, respectively.

(34) The derivative of the antibody fragment according to (1) or (24), wherein the antibody fragment comprises CDR1, CDR2 and CDR3 of an L chain V region of the antibody having the amino acid sequences represented by SEQ ID NOs:6, 7 and 8, respectively.

(35) The derivative of the antibody fragment according to (1) or (24), wherein the antibody fragment comprises:

CDR1, CDR2 and CDR3 of an E chain V region of the antibody having the amino acid sequences represented by SEQ ID NOs:3, 4 and 5; and CDR1, CDR2 and CDR3 of an L chain V region of the antibody having the amino acid sequences represented by SEQ ID NOs:6, 7 and 8.

(36) The derivative of a monoclonal antibody or the antibody fragment thereof according to any one of (1) to (35), wherein the protein is a cytokine.

(37) The derivative of a monoclonal antibody or the antibody fragment thereof according to (36), wherein the cytokine is human interleukin-2 (hIL-2).

(38) The derivative of an antibody according to (37), wherein the derivative of an antibody comprises a human chimeric antibody KM871 and hIL-2.

(39) The derivative of an antibody according to (38), wherein the antibody conjugated with hIL-2 comprises:

an H chain V region having the amino acid sequence represented by SEQ ID NO:57; and an L chain v region having the amino acid sequence represented by SEQ ID NO:56.

(40) The derivative of an antibody according to (37), wherein the derivative of an antibody comprises a human CDR-grafted antibody KM8871 and hIL-2.

(41) The derivative of an antibody according to (1), wherein the antibody conjugated with hIL-2 comprises:

an H chain V region having the amino acid sequence represented by SEQ ID NO:53; and an L chain V region having the amino acid sequence represented by SEQ ID NO:54.

(42) A DNA which encodes the derivative of a monoclonal antibody or the derivative of the antibody fragment thereof which specifically reacts with ganglioside GD3 according to any one of (1) to (41).

(43) A recombinant vector comprising the DNA according to (42).

(44) A transformant which is obtained by introducing the recombinant vector according to (43) into a host cell.

(45) A transformant KM871hIL2 (FERM BP-6918) which produces the antibody according to (38).

(46) A transformant KM8871hIL2 (FERM BP-6791) which produces the antibody according to (40).

(47) A process for producing an antibody, which culturing the transformant according to any one of (44) to (46) in a culture medium to produce and accumulate the derivative of a monoclonal antibody or the derivative of the antibody fragment thereof according to any one of (1) to (41) in the culture; and recovering the derivative of the antibody or the derivative of the antibody fragment thereof from the culture.

(48) A human CDR-grafted antibody or the antibody fragment thereof which specifically reacts with ganglioside GD3.

(49) The human CDR-grafted antibody or the antibody fragment thereof according to (48), wherein the human CDR-grafted antibody comprises CDRs of an H chain V region and an L chain V region of a monoclonal antibody against ganglioside GD3.

(50) The human CDR-grafted antibody or the antibody fragment thereof according to (48), wherein the human CDR-grafted anti-body comprises:

CDRs of an H chain V region and an L chain V region of a monoclonal antibody against ganglioside GD3; and FRs of an H chain V region and an L chain V region of a human antibody.

(51) The human CDR-grafted antibody or the antibody fragment thereof according to (48), wherein the human CDR-grafted antibody comprises:

CDRs of an H chain V region and an L chain V region of a monoclonal antibody against ganglioside GD3;

FRs of an H chain v region and an L chain V region of a human antibody; and an H chain C region and an L chain C region of a human antibody.

(52) The human CDR-grafted antibody or the antibody fragment thereof according to any one of (49) to (51), wherein the antibody comprises CDR1, CDR2 and CDR3 of the H chain V region having the amino acid sequences represented by SEQ ID NOs:3, 4 and 5, respectively.

(53) The human CDR-grafted antibody or the antibody fragment thereof according to any one of (49) to (51), wherein the antibody comprises CDR1, CDR2 and CDR3 of the L chain v region having the amino acid sequences represented by SEQ ID NOs:6, 7 and 8, respectively.

(54) The human CDR-grafted antibody or the antibody fragment thereof according to any one of (49) to (51), wherein the antibody comprises:

CDR1, CDR2 and CDR3 of the H chain V region having the amino acid sequences represented by SEQ ID NOs:3, 4 and 5, respectively; and CDR1, CDR2 and CDR3 of the L chain V region having the amino acid sequences represented by SEQ ID NOs:6, 7 and 8.

(55) The human CDR-grafted antibody or the antibody fragment thereof according to any one of (49) to (51), wherein the H chain V region of the antibody comprises the amino acid sequence represented by SEQ ID NO:9.

(56) The human CDR-grafted antibody or the antibody fragment thereof according to any one of (49) to (51), wherein the L chain V region of the antibody comprises the amino acid sequence represented by SEQ ID NO:54.

(57) The human CDR-grafted antibody or the antibody fragment thereof according to any one of (49) to (51), wherein the H chain V region of the antibody comprises the amino acid sequence represented by SEQ ID NO:9; and the L chain V region of the antibody comprises the amino acid sequence represented by SEQ ID NO:54.

(58) The human CDR-grafted antibody KM8871 or the antibody fragment thereof according to any one of (49) to (51), wherein the H chain V region of the antibody comprises the amino acid sequence represented by SEQ ID NO:9; and the L chain V region of the antibody comprises the amino acid sequence represented by SEQ ID NO:54.

(59) A DNA which encodes the human CDR-grafted antibody or the antibody fragment thereof which specifically reacts with ganglioside GD3 according to any one of (48) to (58).

(60) A recombinant vector comprising the DNA according to (59).

(61) A transformant which is obtained by introducing the recombinant vector according to (60) into a host cell.

(62) A transformant KM8871 (FERM BP-6790) which produces the human CDR-grafted antibody according to (58).

(63) A process for producing an antibody, which comprises:

culturing the transformant according to (61) or (62) in a culture medium to produce and accumulate the human CDR-grafted antibody or the antibody fragment thereof according to any one of (48) to (58) in the culture; and recovering the antibody or the antibody fragment thereof from the culture.

(64) A medicament comprising at least one selected from the derivative of a monoclonal antibody and the derivative of the antibody fragment thereof according to (1) to (41) and the human CDR-grafted antibody and the antibody fragment thereof according to any one of (48) to (58).

(65) A therapeutic agent for cancers, comprising, as an active ingredient, at least one selected from the derivative of a monoclonal antibody and the derivative of the antibody fragment thereof according to any one of (1) to (41) and the human CDR-grafted antibody and the antibody fragment thereof according to any one of (48) to (58).

(66) A diagnostic agent for cancers, comprising, as an active ingredient, at least one selected from the derivative of a monoclonal antibody and the derivative of the antibody fragment thereof according to any one of (1) to (41) and the human CDR-grafted antibody and the antibody fragment thereof according to any one of (48) to (58).

The present invention relates to derivatives of an antibody, comprising a monoclonal antibody which specifically reacts with ganglioside GD3 or the antibody fragment thereof which is conjugated with a radioisotope, a protein or a low molecular weight agent.

Examples of the monoclonal antibody include an antibody produced by a hybridoma, a humanized antibody, a human antibody and the like.

A hybridoma is a cell, which is obtained by subjecting a B cell prepared by immunizing a non-human mammal with an antigen to cell fusion with a myeloma cell derived from a mouse or the like which produces a desired monoclonal antibody having an antigen specificity and.

Examples of the humanized antibody include a human chimeric antibody, a human CDR-grafted antibody and the like.

A human chimeric antibody is an antibody which comprises an H chain V region (hereinafter referred to as "HV" or "VH") and an L chain V region (hereinafter referred to as "LV" or "VL") of an antibody derived from a non-human animal, an H chain C region (hereinafter referred to as "CH") of a human antibody and an L chain C region (hereinafter referred to as "CL") of a human antibody. As the non-human animal, any animal such as mouse, rat, hamster, rabbit or the like can be used, so long as a hybridoma can be prepared therefrom.

The human chimeric antibody of the present invention can be produced by obtaining cDNAs encoding VH and VL from a hybridoma which produces a monoclonal antibody which specifically reacts with GD3, constructing a human chimeric antibody expression vector by inserting them into an expression vector for animal cell having genes encoding human antibody CH and human antibody CL, and expressing the expression vector by introducing it into an animal cell.

As the CH of a human chimeric antibody, it may be any region which belongs to human immunoglobulin (hereinafter referred to as "hIg"), but those of hIgG class are suitable and any one of subclasses belonging to hIgG class, such as hIgG1, hIgG2, hIgG3 and hIgG4, can also be used. Also, as the CL of a human chimeric antibody, it may be any region which belongs to hIg, and those of κ class or λ class can be used.

Examples of the anti-GD3 chimeric antibody include KM871 described in Japanese Published Unexamined Patent Application No. 304989/93. (KM871 has been deposited on Aug. 13, 1991, under the conditions of the Budapest Treaty, as FERM BP-3512 in Fermentation Research Institute, Agency of Industrial Science and Technology Higashi 1-1-3, Tsukuba, Ibaraki, Japan (now the International Patent Organism Depositary, National Institute of Advanced Industrial Science and Technology Central 6, Higashi 1-1-1, Tsukuba, Ibaraki, Japan)).

A human CDR-grafted antibody is an antibody in which amino acid sequences of CDRs in VH and VL derived from a non-human animal antibody are grafted to appropriate positions of VH and VL of a human antibody.

The anti-GD3 CDR-grafted antibody of the present invention can be produced by constructing cDNAs encoding V regions in which CDR sequences of VH and VL of an antibody derived from a non-human animal which specifically reacts with GD3 are grafted to CDR sequences of VH and VL of an optional human antibody, constructing a human CDR-grafted antibody expression vector by inserting them into an expression vector for animal cell having genes encoding human antibody CH and human antibody CL, and expressing the human CDR-grafted antibody by introducing the expression vector into an animal cell.

As the CH of the human CDR-grafted antibody of the present invention, it may be any region which belongs to hIg, but those of hIgG class are suitable and any one of subclasses belonging to hIgG class, such as hIgG1, hIgG2, hIgG3 and hIgG4, can also be used. Also, as the CL of the human CDR-grafted antibody, it may be any region which belongs to hIg, and those of κ class or λ class can be used.

Examples of the anti-GD3 CDR-grafted antibody include antibody KM8871 in which VH of the antibody comprises the amino acid sequence represented by SEQ ID NO:9 and CH thereof comprises an amino acid sequence of a human antibody IgG1 subclass, and VL of the antibody comprises the amino acid sequence represented by SEQ ID NO:54 and CL thereof comprises an amino acid sequence of a human antibody κ class.

Originally, a human antibody is an antibody naturally present in the human body. It also includes antibodies obtained from a human antibody phage library and a human antibody-producing transgenic animal which are produced based on the recent advance in genetic engineering, cell engineering and developmental engineering techniques.

With regard to the antibody present in the human body, a lymphocyte capable of producing the antibody can be cultured by isolating a human peripheral blood lymphocyte and infecting it with EB virus or the like to thereby immortalizing it, followed by cloning, and the antibody can be purified from the culture mixture.

The human antibody phage library is a library in which antibody fragments such as Fab, scFv and the like are expressed on the phage surface by inserting an antibody gene prepared from human B cell into a phage gene. From the library, a phage expressing a desired antibody fragment having an antigen binding activity can be recovered, using its activity to bind to an antigen-immobilized substrate as the marker. The antibody fragment can be genetic engineeringly converted further into a human antibody molecule having two complete H chains and two complete L chains.

A human antibody-producing transgenic non-human animal is an animal in which a human antibody gene is introducing into cells. Specifically, a human antibody-producing transgenic animal can be produced by introducing a human antibody gene into mouse ES cell, transplanting the ES cell into an early stage embryo of other mouse and then developing it. As the preparation method of a human antibody from the human antibody-producing transgenic animal, the human antibody can be produced and accumulated in a culture mixture by obtaining a human antibody-producing hybridoma by a hybridoma production method usually carried out in non-human mammals and then culturing it.

Examples of the antibody fragment include Fab, Fab', F(ab')$_2$, scFv, dsfv, a peptide comprising CDR and the like.

An Fab is an antibody fragment having a molecular weight of about 50,000 and antigen binding activity, in which about a half of the N-terminal side of H chain and the entire L chain, among fragments obtained by treating IgG with a protease, papain (cut at the 224th position amino acid residue of the H chain), are bound together through a disulfide bond.

The Fab of the present invention can be obtained treating an antibody which specifically reacts with GD3 with a protease, papain. Also, the Fab can be produced by inserting DNA encoding Fab of the antibody into an expression vector for procaryote or an expression vector for eucaryote, and introducing the vector into a procaryote or eucaryote to express the Fab.

An F(ab')$_2$ is an antibody fragment having a molecular weight of about 100,000 and antigen binding activity, which is slightly larger than the Fab bound via a disulfide bond of the hinge region, among fragments obtained by treating IgG with a protease, pepsin (cut at the 234th position amino acid residue of the H chain).

The F(ab')$_2$ of the present invention can be obtained treating an antibody which specifically reacts with GD3 with a protease, pepsin. Also, the F(ab')$_2$ can be produced by binding Fab' described below via a thioether bond or a disulfide bond.

An Fab' is an antibody fragment having a molecular weight of about 50,000 and antigen binding activity, which is obtained by cutting a disulfide bond of the hinge region of the F(ab')$_2$.

The Fab' of the present invention can be obtained treating F(ab')$_2$ which specifically reacts with GD3 with a reducing agent, dithiothreitol. Also, the Fab' can be produced by inserting DNA encoding Fab' fragment of the antibody into an expression vector for procaryote or an expression vector for eucaryote, and introducing the vector into a procaryote or eucaryote to effect its expression.

An scFv is a VH-P-VL or VL-P-VH polypeptide in which one chain VH and one chain VL are linked using an appropriate peptide linker (hereinafter referred to as "P"). The VH and VL in the scFv used in the present invention may be any antibody of an antibody produced by a hybridoma, a humanized antibody and a human antibody.

The scFv of the present invention can be produced by obtaining cDNA encoding the VH and VL of an antibody which specifically reacts with GD3, constructing DNA encoding scFv, inserting the DNA into an expression vector for procaryote or an expression vector for eucaryote, and then introducing the expression vector into a prokaryote or eucaryote to express the scFv.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a three-dimensional structure estimation of the antibody in accordance with the method shown by Reiter et al. (*Protein Engineering*, 7: 697 (1994)). The VH and VL in the dsFv of the present invention may be any antibody of an antibody produced by a hybridoma, a humanized antibody and a human antibody.

The dsFv of the present invention can be produced by obtaining cDNA encoding the VH and VL of an antibody capable of specifically reacting with GD3, constructing DNA encoding dsFv, inserting the DNA into an expression vector for procaryote or an expression vector for eucaryote, and then introducing the expression vector into a prokaryote or eucaryote to express the dsFv.

A peptide comprising CDR is constituted by at least one region of H chain and L chain CDRs. Plural CDRs can be bound directly or via an appropriate peptide linker.

The peptide comprising CDR of the present invention can be produced by obtaining cDNA encoding the VH and VL of an antibody capable of specifically reacting with GD3, inserting the cDNA into an expression vector for prokaryote or an expression vector for eucaryote, and then introducing the expression vector into a prokaryote or eucaryote to express the peptide comprising CDR.

The peptide comprising CDR can also be produced by a chemical synthesis method such as Fmoc method (fluorenylmethoxycarbonyl method) or tBoc method (t-butyloxycarbonyl method).

The antibody derivatives of the present invention can be produced by chemically conjugating a radioisotope, a protein, a low molecular weight agent or the like to the N-terminal side or C-terminal side of the H chain or L chain of the antibody or the antibody fragment which specifically reacts with GD3, to an appropriate substituent or side chain of the antibody or the antibody fragment, or to a sugar chain of the antibody or the antibody fragment (*Antibody Engineering Handbook*, edited by Osamu Kanemitsu, published by Chijin Shokan (1994)).

Also, the antibody derivatives can be genetically produced by linking a DNA encoding an antibody or the antibody fragment which specifically reacts with GD3 to other DNA encoding a protein to be bound, inserting the DNA into an expression vector, and introducing the expression vector into a host cell.

Examples of the isotope include $^{131}$I, $^{120}$I and the like, and they can be conjugated to an antibody by, e.g., a chloramine T method.

Examples of the low molecular weight agent include anticancer agents such as alkylating agent (e.g., nitrogen mustard, cyclophosphamide, etc.), metabolic antagonist (e.g., 5-fluorouracil, methotrexate, etc.), antibiotic (e.g., daunomycin, bleomycin, mitomycin C, daunorubicin, doxorubicin, etc.), plant alkaloid (e.g., vincristine, vinblastine, vindesine, etc.), hormone drug (e.g., tamoxifen, dexamethasone, etc.) and the like (*Clinical Oncology*, edited by Japanese Society of Clinical Oncology, published by Cancer and Chemotherapy (1996)); anti-inflammatory agents such as steroid agent (e.g., hydrocortisone, prednisone, etc.), non-steroidal drug (e.g., aspirin, indometacin, etc.), immuno-modulator (e.g., aurothiomalate, penicillamine, etc.), immunosuppressing agent (e.g., cyclophosphamide, azathioprine, etc.), antihistaminic agent (e.g., chlorpheniramine maleate, clemastine, etc.) and the like (*Inflammation and Anti-inflammatory Therapy*, Ishiyaku Shuppan (1982)); and the like. Examples of the method for conjugating daunomycin to an antibody include a method in which daunomycin and an amino group of an antibody are conjugated via glutaraldehyde, a method in which an amino group of daunomycin and a carboxyl group of an antibody are conjugated via a water-soluble carbodiimide, and the like.

As the protein, cytokine which activates immunocompetent cells is preferred, and examples include hIL-2, hGM-CSF, human macrophage colony-stimulating factor (hereinafter referred to as "hM-CSF"), human interleukin 12 (hereinafter referred to as "hIL-12") and the like. Also, in order to injure cancer cells directly, toxins such as ricin, diphtheria toxin and the like can be used. For example, a fusion antibody with a protein can be produced by conjugating a cDNA encoding an antibody or the antibody fragment to other cDNA encoding the protein, constructing a DNA encoding the fusion antibody, inserting the DNA into an expression vector for prokaryote or an expression vector for eucaryote, and then introducing the expression vector into a prokaryote or eucaryote to express the fusion antibody.

Examples of the fusion protein of the anti-GD3 human antibody with cytokine include a fusion protein of anti-GD3 CDR-grafted antibody KM8871 with hIL-2 and a fusion protein of anti-GD3 chimeric antibody KM871 with hIL-2. Examples of the fusion protein of anti-GD3 CDR-grafted antibody KM8871 with hIL-2 include KM8871-hIL-2 in which the H chain V region of the antibody conjugated with hIL-2 has the amino acid sequence represented by SEQ ID NO:53, the L chain V region of the antibody has the amino acid sequence represented by SEQ ID NO:54 and the L chain C region has an amino acid sequence of a human antibody K class. Examples of the fusion protein of anti-GD3 chimeric antibody KM871 with hIL-2 include KM871-hIL-2 in which the H chain V region of the antibody conjugated with hIL-2 has the amino acid sequence represented by SEQ ID NO:57, the L chain V region of the antibody has the amino acid sequence represented by SEQ ID NO:56 and the L chain C region has an amino acid sequence of a human antibody K class.

The methods for producing a humanized antibody which specifically reacts with GD3 and derivatives of an antibody or the antibody fragment which specifically reacts with GD3.

1. Production of Humanized Antibody (1) Construction of Humanized Antibody Expression Vector The humanized antibody expression vector is an expression vector for animal cell to which genes encoding the CH and CL of a human antibody are inserted, and can be constructed by cloning the genes which encode the CH and CL of a human antibody into an expression vector for animal cell. The C regions of a human antibody can be any human antibody CH and CL, and examples include a C region belonging to IgG1 subclass of in an H chain of a human antibody (hereinafter referred to as "hCγ1") and a C region belonging to κ class in an L chain of a human antibody (hereinafter referred to as "hCκ"). A chromosomal DNA comprising an exon and an intron can be used as the gene encoding CH and CL of a human antibody, and cDNA can also be used. Any expression vector for animal cell can be used, so long as a gene encoding the human antibody C region can be inserted and expressed. Examples include pAGE107 (*Cytotechnology*, 3, 133 (1990)), pAGE103 (*J.*

*Biochem.*, 101, 1307 (1987)), pHSG274 (*Gene*, 27, 223 (1984)), pKCR (*Proc. Natl. Acad. Sci. U.S.A.*, 78, 1527 (1981)), pSG1βd2-4 (*Cytotechnology*, 4, 173 (1990)) and the like. Examples of the promoter and the enhancer used in the expression vector for animal cell include early promoter and enhancer of SV40 (*J. Biochem.*, 101, 1307 (1987)), LTR promoter and enhancer of Moloney mouse leukemia virus (*Biochem. Biophys. Res. Comun*, 149, 960 (1987)), promoter (*Cell*, 41, 479, 1985)) and enhancer (*Cell*, 33, 717 (1983)) of immunoglobulin H chain and the like.

The humanized antibody expression vector may be either of a type in which a gene encoding an antibody H chain and a gene encoding an antibody L chain exist on separate vectors or of a type in which both genes exist on the same vector (tandem type). In respect of easiness of construction of a humanized antibody expression vector, easiness of introduction into animal cells, and balance between the expression levels of antibody H and L chains in animal cells, a tandem type of the humanized antibody expression vector is more preferable (*J. Immunol. Methods*, 167, 271 (1994)). Examples of the tandem type humanized antibody expression vector include pKANTEX93 (WO 97/10354), pEE18 (*HYBRIDOMA*, 17, 559 (1998)) and the like.

The thus constructed humanized antibody expression vector can be used for the expression of the human chimeric antibody and human CDR-grafted antibody in animal cells.

(2) Preparation of cDNA Encoding V Region of Antibody Derived from Non-Human Animal cDNAs encoding VH and VL of an antibody derived from an non-human animal such as a mouse antibody are obtained as follows.

mRNA is extracted from hybridoma cells producing a mouse antibody or the like to synthesize cDNA. The synthesized cDNA is inserted into a vector such as a phage, a plasmid or the like, to prepare a cDNA library. Each of a recombinant phage or recombinant plasmid containing cDNA encoding VH and a recombinant phage or recombinant plasmid containing cDNA encoding VL is isolated from the library using a C region part or a V region part of a mouse antibody as the DNA probe. The full nucleotide sequences of the VH and VL of the mouse antibody of interest on the recombinant phage or recombinant plasmid are determined, and the full amino acid sequences of the VH and VL are deduced from the nucleotide sequences.

The non-human animal may be any animal such as mouse, rat, hamster, rabbit or the like, so long as a hybridoma cell can be produced therefrom. Examples of the method for preparing total RNA from a hybridoma cell include a guanidine thiocyanate-cesium trifluoroacetate method (*Methods in Enzymol.*, 154, 3 (1987)) and the like. Examples of the method for preparing mRNA from total RNA include an oligo (dT) immobilized cellulose column method (*Molecular Cloning: A Laboratory Manual*, Cold Spring Harbor Lab. Press, New York (1989), hereinafter referred to as "*Molecular Cloning: A Laboratory Manual*") and the like. Also, examples of a kit for preparing mRNA from a hybridoma cell include Fast Track mRNA Isolation Kit (manufactured by Invitrogen), Quick Prep mRNA Purification Kit (manufactured by Pharmacia) and the like.

Examples of the method for synthesizing cDNA and preparing a cDNA library include known methods (*Molecular Cloning: A Laboratory Manual; Current Protocols in Molecular Biology*, Supplement 1-34); a method using a commercially available kit such as SUPER SCRIPT Plasmid System for cDNA Synthesis and Plasmid Cloning (manufactured by GIBCO BRL), ZAP-cDNA Kit (manufactured by Stratagene), etc.; and the like.

The vector into which the cDNA synthesized using mRNA extracted from a hybridoma cell as the template is inserted for preparing a cDNA library may be any vector, so long as the cDNA can be inserted. Examples include ZAP Express (*Strategies*, 5: 58 (1992)), pBluescript II SK(+) (*Nucleic Acids Research*, 17: 9494 (1989)), λzapII (manufactured by Stratagene), λgt10 and λgt11 (*DNA Cloning: A Practical Approach, I*, 49 (1985)), Lambda BlueMid (manufactured by Clontech), λExCell and pT7T3 18U (manufactured by Pharmacia), pcD2 (*Mol. Cell. Biol.*, 3: 280 (1983)), puC18 (*Gene*, 33: 103 (1985)), and the like.

Any *E. coli* for introducing the cDNA library constructed by a phage or plasmid vector may be used, so long as the cDNA library can be introduced, expressed and maintained. Examples include XL1-Blue MRF' (*Strategies*, 5: 81 (1992)), C600 (*Genetics*, 39: 440 (1954)), Y1088 and Y1090 (*Science*, 222: 778 (1983)), NM522 (*J. Mol. Biol.*, 166: 1 (1983)), K802 (*J. Mol. Biol.*, 16: 118 (1966)), JM105 (*Gene*, 38: 275 (1985)), and the like.

For selecting cDNA clones encoding VH and VL of an antibody derived from a non-human animal in the cDNA library, a colony hybridization or plaque hybridization method using an isotope- or fluorescence-labeled probe may be used (*Molecular Cloning: A Laboratory Manual*, Cold Spring Harbor Lab. Press, New York (1989)). Also, the cDNAs encoding VH and VL can be prepared through polymerase chain reaction (hereinafter referred to as "PCR"; *Molecular Cloning: A Laboratory Manual; Current Protocols in Molecular Biology*) by preparing primers and using cDNA prepared from mRNA or a cDNA library as the template.

The nucleotide sequence of the cDNA can be determined by digesting the cDNA selected by the above method with appropriate restriction enzymes and the like, cloning the fragments into a plasmid such as pBluescript SK(−) (manufactured by Stratagene) or the like, carrying out the reaction by a usually used nucleotide analyzing method such as the dideoxy method of Sanger, F. et al. (*Proc. Natl. Acad. Sci. USA*, 74: 5463 (1977)) or the like, and then analyzing the sequence using an automatic nucleotide sequence analyzer such as A.L.F. DNA sequencer (manufactured by Pharmacia) or the like.

Whether the obtained cDNAs encode the full amino acid sequences of the VH and VL of the antibody containing a secretory signal sequence can be confirmed by estimating the full amino acid sequences of the VH and VL from the determined nucleotide sequence and comparing them with full amino acid sequences of the VH and VL of known antibodies (*Sequences of Proteins of Immunological Interest*, US Dept. Health and Human Services (1991), hereinafter referred to as "*Sequences of Proteins of Immunological Interest*").

(3) Analysis of Amino Acid Sequence of V Region Derived from a Non-Human Animal

Regarding the complete amino acid sequences of VH and VL of the antibody comprising a secretory signal sequence, the length of the secretory signal sequence and N-terminal amino acid sequences can be deduced and subgroups to which they belong can also be known, by comparing with full amino acid sequences of VH and VL of known antibodies (*Sequences of Proteins of Immunological Interest*). Also, regarding the amino acid sequence of each CDR of VH and VL, it can be found by comparing it with amino acid sequences of VH and VL of known antibodies (*Sequences of Proteins of Immunological Interest*).

(4) Construction of Human Chimeric Antibody Expression Vector

A human chimeric antibody expression vector can be constructed by cloning cDNAs encoding VH and VL of an antibody derived from a non-human animal in the region upstream of genes encoding CH and CL of the human antibody on the humanized antibody expression vector as described in the item 1(1). For example, each of cDNAs encoding VH and VL of an antibody derived from a non-human animal is linked with a synthesized DNA comprising nucleotide sequences at the 3' terminals of VH and VL of an antibody derived from a non-human animal and nucleotide sequences at the 5' terminals of CH and CL of a human antibody and having a recognition sequence of an appropriate restriction enzyme at both terminals, and each cDNA is cloned so that it is appropriately expressed in upstream of genes encoding the CH and CL of the humanized antibody expression vector as described in the item 1(1) to thereby construct a human chimeric antibody expression vector.

(5) Construction of cDNA Encoding V Region of Human CDR-Grafted Antibody cDNAs encoding VH and VL of a human CDR-grafted antibody can be obtained as follows. First, amino acid sequences of FRs in VH and VL of a human antibody to which amino acid sequences of CDRs in VH and VL of an antibody derived from a non-human animal antibody are grafted are selected. Any amino acid sequences of FRs in VH and VL of a human antibody can be used, so long as they are derived from human. Examples include amino acid sequences of FRs in VH and VL of human antibodies registered in database such as Protein Data Bank or the like, and amino acid sequences common to subgroups of FRs in the VH and VL of human antibodies (*Sequences of Proteins of Immunological Interest*) and the like. In order to produce a human CDR-grafted antibody having potent activity, amino acid sequences having high homology (at least 60% or more) with amino acid sequence of FRs of VH and VL of an antibody of interest derived from a non-human animal is preferably selected. Then, amino acid sequences of CDRs of VH and VL of the antibody derived from a non-human animal are grafted to the selected amino acid sequences of FRS of VH and VL of a human antibody to design amino acid sequences of the VH and VL of a human CDR-grafted antibody. The designed amino acid sequences are converted to DNA sequences by considering the frequency of codon usage found in nucleotide sequences of genes of antibodies (*Sequence of Proteins of Immunological Interest*), and the DNA sequences encoding the amino acid sequences of the VH and VL of a human CDR-grafted antibody are designed. Several synthetic DNAs having a length of about 100 nucleotides are synthesized, and PCR is carried out using them. In this case, it is preferred in each of the H chain and the L chain that 6 synthetic DNAs are designed in view of the reaction efficiency of PCR and the lengths of DNAS which can be synthesized.

Furthermore, they can be easily cloned into the humanized antibody expression vector constructed in the item 1(1) by introducing the recognition sequence of an appropriate restriction enzyme to the 5' terminal of the synthetic DNAs present on the both terminals. After the PCR, an amplified product is cloned into a plasmid such as pBluescript SK (–) (manufactured by Stratagene) or the like, and the nucleotide sequences are determined according to the method described in the item 1(2) to obtain a plasmid having DNA sequences encoding the VH and VL of a designed human CDR-grafted antibody.

(6) Modification of Amino Acid Sequence of V Region of Human CDR-Grafted Antibody It is known that when a human CDR-grafted antibody is produced by simply grafting only CDRs in VH and VL an antibody derived from a non-human animal in FRs of the VH and VL of a human antibody, its antigen binding activity is reduced in comparison with that of the original antibody derived from a non-human animal (*BIO/TECHNOLOGY*, 2, 266 (1991)). As the reason, it is considered that several amino acid residues in not only CDRs but also FRs directly or indirectly relate to the antigen binding activity in the VH and VL of the original antibody derived from a non-human animal, and that these amino acid residues are changed to different amino acid residues derived from FRs of the VH and VL of the human antibody. In order to resolve the problem, in human CDR-grafted antibodies, attempts have been made to identify, among amino acid sequences of the FR of the VH and VL of human antibodies, an amino acid residue which directly relates to binding to the antibody, an amino acid residue which is interacted with an amino acid residue of CDR or an amino acid residue which keeps three-dimensional structure of the antibody and is directly related to its binding to the antigen, and to increase the reduced antigen binding activity by changing them into amino acid residues of the original antibody derived from a non-human animal (*BIO/TECHNOLOGY*, 9, 266 (1991)). In producing a human CDR-grafted antibody, it is the most important point to efficiently identify these FR amino acid residues related to the antigen binding activity, so that construction and analysis of the three-dimensional structure of antibodies have been carried out by X-ray crystallography (*J. Mol. Biol.*, 112, 535 (1977)), computer-modeling (*Protein Engineering*, 1, 1501 (1994)) and the like. Although the information of the three-dimensional structure of antibodies has been useful in the production of a human CDR-grafted antibody, no method for producing a human CDR-grafted antibody which can be applied to any antibodies has been established yet. Therefore, various attempts must be currently be necessary, for example, several modified antibodies of each antibody are produced and the relationship between each of the modified antibodies and its antibody binding activity is examined.

Substitution of the amino acid residues of the FR in the VH and VL of a human antibody can be achieved by carrying out the PCR described in the item 1(5) using synthetic DNA for modification. With regard to an amplified product obtained by the PCR, the nucleotide sequence is determined according to the method described in the item 1(2) so that whether the objective modification has been carried out is confirmed.

(7) Construction of Human CDR-Grafted Antibody Expression Vector

A human CDR-grafted antibody expression vector can be constructed by cloning cDNAS encoding VH and VL of the human CDR-grafted antibody constructed in the items 1(5) and 1(6) into upstream of the genes encoding CH and CL of the human antibody in the humanized antibody expression vector as described in the item 1(1).

For example, when recognition sites for an appropriate restriction enzymes are introduced to the 5'-terminal of synthetic DNAs positioned at both terminals among synthetic DNAs used in the construction of VH and VL of the human CDR-grafted antibody in the items 1(5) and 1(6), cloning can be carried out so that they are expressed in an appropriate form in upstream of genes encoding CH and CL of the human antibody in the humanized antibody expression vector as described in the item 1(1).

(8) Transient Expression of Humanized Antibody

In order to efficiently evaluate the antigen binding activity of various humanized antibodies produced, the humanized antibodies can be expressed transiently using the humanized antibody expression vector as described in the items 1(4) and 1(7) or the modified expression vector thereof. Any cell can be used as a host cell, so long as the host cell can express a humanized antibody. Generally, COS-7 cell (ATCC CRL1651) is used in view of its high expression level (*Methods in Nucleic Acids Res.*, CRC Press, 283 (1991)). Examples of the method for introducing the expression vector into COS-7 cell include a DEAE-dextran method (*Methods in Nucleic Acids Res.*, CRC Press, 283 (1991)), a lipofection method (*Proc. Natl. Acad. Sci. USA*, 84, 7413 (1987)), and the like.

After introduction of the expression vector, the expression level and antigen binding activity of the humanized antibody in the culture supernatant can be measured by enzyme immunoassay (hereinafter referred to as "ELISA"; *Antibodies: A Laboratory Manual*, Cold Spring Harbor Laboratory, Chapter 14 (1988), hereinafter referred to as "*Antibodies: A Laboratory Manual*", *Monoclonal Antibodies: Principles and Practice*, Academic Press Limited (1996), hereinafter referred to as "*Monoclonal Antibodies*" (1996)) and the like.

(9) Stable Expression of Humanized Antibody

A transformant which produces a humanized antibody stably can be obtained by introducing into an appropriate host cell the humanized antibody expression vector described in the items 1(4) and 1(7).

Examples of the method for introducing the expression vector into a host cell include electroporation (Japanese Published Unexamined Patent Application No. 257891/90, *Cytotechnology*, 3, 133 (1990)) and the like.

Any cell can be used as the host cell into which the humanized antibody expression vector is to be introduced, so long as it can express a humanized antibody. Examples include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (*Proc. Natl. Acad. Sci. U.S.A.*, 77: 4216 (1980)), rat YB2/3HL.P2.G11.16Ag.20 cell (ATCC CRL1662, hereinafter referred to as "YB2/0 cell"), and the like. The YB2/0 cell is preferable, since ADCC activity of the humanized antibody is enhanced when expressed therein.

After introduction of the expression vector, transformants which express a humanized antibody stably are selected in accordance with the method disclosed in Japanese Published Unexamined Patent Application No. 257891/90, by culturing in a medium for animal cell culture containing an agent such as G418 sulfate (hereinafter referred to as "G418", manufactured by Sigma) or the like. Examples of the medium for animal cell culture include PRMI1640 medium (manufactured by Nissui Pharmaceutical), GIT medium (manufactured by Nissui Pharmaceutical), EX-CELL302 medium (manufactured by JRH), IMDM medium (manufactured by GIBCO BRL), Hybridoma-SFM medium (manufactured by GIBCO BRL), media obtained by adding various additives such as fetal bovine serum (hereinafter referred to as "FBS") to these media, and the like. The humanized antibody can be produced and accumulated in a culture medium by culturing the selected transformants in a medium. The expression level and antigen binding activity of the humanized antibody in the culture supernatant can be measured by ELISA or the like. Also, in the transformant, the expression level of the humanized antibody can be increased by using dhfr amplification system or the like according to the method disclosed in Japanese Published Unexamined Patent Application No. 257891/90.

The humanized antibody can be purified from the culture supernatant of the transformant by using a protein A column (*Antibodies, A Laboratory Manual, Monoclonal Antibodies* (1996)). Any other conventional methods for protein purification can be used. For example, the humanized antibody can be purified by a combination of gel filtration, ion-exchange chromatography, ultrafiltration and the like. The molecular weight of the H chain or the L chain of the purified humanized antibody or the antibody molecule as a whole is determined by polyacrylamide gel electrophoresis (hereinafter referred to as "SDS-PAGE") (*Nature*, 227: 680 (1970)), Western blotting (*Antibodies, A Laboratory Manual, Monoclonal Antibodies* (1996)), and the like.

(10) Evaluation of Activity of Humanized Antibody

The binding activity to an antigen and the binding activity to cultured cancer cell lines of the purified humanized antibody can be measured by ELISA, an immunofluorescent method (*Cancer Immunol. Immunother.*, 36, 373 (1993)) and the like means. The cytotoxic activity against an antigen positive culture cell line can be evaluated by measuring the CDC activity, the ADCC activity or the like (*Cancer Immunol. Immunother.*, 36, 373 (1993)).

(11) Application Method of Humanized Antibody

It is considered to be useful in the diagnosis and treatment of human cancers and the like, such as lung cancer, melanoma, glioma, neuroblastoma, etc., since the humanized antibody specifically binds to GD3 which expresses in cultured cancer cell lines derived from human and shows cytotoxic activities such as CDC activity, ADCC activity and the like. In addition, since the majority of the antibody are derived from the amino acid sequence of a human antibody in comparison with antibodies of non-human animals, it is expected that it will show strong anti-tumor effects in the human body without showing immunogenicity, and the therapeutic effects will be maintained for a prolonged period of time.

The humanized antibody of the present invention can be administered alone, but it is generally preferred to provide it in the form of a pharmaceutical formulation produced by mixing it with at least one pharmaceutically acceptable carrier in accordance with a method well known in the technical field of pharmaceutics.

It is preferred to select a route of administration which is the most effective in carrying out the intended treatment such as oral administration or parenteral administration, e.g., intraoral administration, tracheal administration, rectal administration, subcutaneous injection, intramuscular injection, intravenous injection, and the like. Intravenous injection is preferred in an antibody formulation.

The dosage form includes sprays, capsules, tablets, granules, syrups, emulsions, suppositories, injections, ointments, tapes, and the like.

Examples of formulation suitable for oral administration include emulsions, syrups, capsules, tablets, powders, granules, and the like.

Liquid preparations such as emulsions and syrups, can be produced using additives such as water, saccharides, e.g., sucrose, sorbitol, fructose, etc., glycols, e.g., polyethylene glycol, propylene glycol, etc., oils, e.g., sesame oil, olive oil, soybean oil, etc., antiseptics, e.g., p-hydroxybenzoate, etc., flavors, e.g., strawberry flavor, peppermint, etc., and the like.

Capsules, tablets, powders, granules and the like can be produced using additives such as fillers, e.g., lactose, glucose, sucrose, mannitol, etc., disintegrating agents, e.g., starch, sodium alginate, etc., lubricants, e.g., magnesium stearate, etc., binders, e.g., polyvinyl alcohol, hydroxypropylcellulose, gelatin, etc., surfactants, e.g., fatty acid ester, etc., plasticizers, e.g., glycerine, etc., and the like.

Examples of formulations suitable for parenteral administration include injections, suppositories, sprays, and the like.

Injections can be prepared using a carrier such as a salt solution, glucose solution or a mixture thereof, or the like.

Suppositories can be prepared using a carrier such as cacao butter, hydrogenated fat, a carboxylic acid, or the like.

Also, sprays can be prepared from the antibody or peptide itself or using a carrier or the like which does not stimulate oral and airway mucous membranes of patients and can facilitate absorption of the antibody or peptide by dispersing it as minute particles.

Examples of the carrier include lactose, glycerine, and the like. Depending on the properties of the antibody or peptide and the carrier to be used, aerosols, dry powders and the like can be produced. The additives exemplified in the oral preparations can also be added to the parenteral preparations.

The dose and frequency of administration vary depending on intended therapeutic effect, administration method, treating period, age, body weight and the like, but the dose is generally from 10 μg/kg to 8 mg/kg per day per adult.

2. Production of Fusion Protein of Antibody or Antibody Fragment with Cytokine (1) Construction of Gene Encoding Fusion Protein of Antibody or Antibody Fragment with Cytokine A gene encoding a fusion protein of an antibody or the antibody fragment with cytokine can be constructed by linking a gene encoding cytokine to the 5'-terminal or 3'-terminal of a gene encoding the H chain or L chain of an antibody or the antibody fragment via an appropriate synthetic DNA. Also, a gene encoding a fusion protein of an antibody or the antibody fragment with cytokine can also be constructed by introducing an appropriate restriction enzyme recognition sequence into the 5'-terminal of a primer for amplification when a gene encoding cytokine is amplified by PCR, and linking the resulting gene to the 5'-terminal or 3'-terminal of a gene encoding the H chain or L chain of an antibody or the antibody fragment. Any chromosomal DNA or cDNA can be used as the gene encoding cytokine. The nucleotide sequence of the thus constructed gene encoding a fusion protein of an antibody or antibody fragment with cytokine is determined by the method described in the item 1(2) to confirm that it is the sequence of interest.

(2) Construction of Expression Vector of Fusion Protein of Antibody or Antibody Fragment with Cytokine An expression vector of a fusion protein of an antibody or the antibody fragment with cytokine can be constructed by substituting a part or whole of a gene encoding the H chain or L chain of an antibody or the antibody fragment on the humanized antibody expression vector described in the items 1(4) and 1(7) by the gene encoding a fusion protein of an antibody or the antibody fragment with cytokine described in the item 2(1). For example, when a fusion protein in which cytokine is conjugated with the C-terminal of the H chain of an antibody is prepared, the expression vector can be constructed by linking a gene encoding cytokine to the 3'-terminal of a gene encoding the CH of an antibody or the antibody fragment to thereby construct a gene encoding a fusion protein of the CH of an antibody or the antibody fragment with cytokine according to the item 2(1), and substituting, with the gene, a gene encoding the CH of an antibody or the antibody fragment on the humanized antibody expression vector described in the items 1(4) and 1(7).

(3) Stable Expression of Fusion Protein of Antibody or Antibody Fragment with Cytokine Stable expression of a fusion protein of an antibody or the antibody fragment with cytokine in accordance with the method described in the item 1(9) using the expression vector of a fusion protein of an antibody or the antibody fragment with cytokine described in the item 2(2) is carried out so that a transformant capable of stably expressing the fusion protein of an antibody or the antibody fragment with cytokine can be obtained, the fusion protein of an antibody or antibody fragment with cytokine is purified from its culture supernatant, and its molecular weight and the like can be analyzed.

(4) Evaluation of In Vitro Activity of Fusion Protein of Antibody or Antibody Fragment with Cytokine Among activities of the thus purified fusion protein of an antibody or the antibody fragment with cytokine, activities of the antibody moiety, namely binding activity with an antigen and its binding activity to cultured cancer cell lines can be measured by ELISA, an immunofluorescent method and the like. Also, its cytotoxic activities against antigen-positive cultured cancer cell lines can be evaluated by measuring its CDC activity, ADCC activity and the like. On the other hand, activity of the cytokine moiety can be evaluated, e.g., using growth-supporting activity of a cultured cell line which shows concentration-dependent growth against cytokine, as an index (*Proc. Natl. Acad. Sci. U.S.A.,* 21, 9626 (1994)).

(5) Evaluation of In Vivo Activity of Fusion Protein of an Antibody or Antibody Fragment with Cytokine Antitumor effect of the fusion protein of an antibody or the antibody fragment with cytokine can be evaluated by administering to a syngenic graft mouse model in which an antigen-expressing cultured mouse cancer cell line is transplanted into a wild type mouse having normal immune system. Also, its antitumor effect in the living body can be evaluated by comparing respective cases of the administration of the antibody alone, cytokine alone and simultaneous administration of the antibody and cytokine to the syngenic graft mouse model (*Proc. Natl. Acad. Sci. U.S.A.,* 93, 7826 (1996)). To date, there are no reports on GD2- or GD3-positive mouse culture cell lines, which are specifically expressed in human melanoma and neuroblastoma. However, a GD2- or GD3-positive transformant can be produced by introducing a ganglioside synthase gene of interest to be specifically expressed into a mouse culture cell line which expresses GM2 or GM3 as a biosynthesis precursor of GD2 or GD3 (*Proc. Natl. Acad. Sci. U.S.A.,* 91, 10455 (1994)). A syngenic graft model can be produced by transplanting this transformant into a wild type mouse having a normal immune system.

The thus prepared mouse model can be used in the in vivo evaluation of a fusion protein of an antibody or the antibody fragment with cytokine against a ganglioside of interest.

(6) Application Method of Fusion Proteins of Humanized Antibody or Antibody Fragment with Cytokine Since the fusion protein of an antibody or the antibody fragment with cytokine of the present invention specifically binds to GD3 expressing in cultured cancer cell lines of human origin and shows cytotoxic activities such as CDC activity, ADCC activity and the like, it is considered to be useful in the diagnosis and treatment of human cancers and the like such as lung cancer, melanoma, glioma, neuroblastoma, etc. Since the majority of the humanized antibody or antibody fragment of the present invention are derived from the amino acid sequence of a human antibody in comparison with antibodies of non-human animals, it is expected that it will show strong anti-tumor effects in the human body without showing immunogenicity, and the therapeutic effects will be maintained for a prolonged period of time, and since it can activate immunocompetent cells in the periphery of a cancer by the activity of the conjugated cytokine moiety, stronger antitumor effects are expected than the administration of the antibody alone, cytokine alone or simultaneous administration of the antibody and cytokine, and reduction of side effects is expected in comparison with the systemic administration of cytokine.

The fusion protein of a humanized antibody or the antibody fragment with cytokine of the present invention can be administered alone, but it is generally preferred to provide it in the form of a pharmaceutical formulation produced by mixing it with at least one pharmaceutically acceptable carrier in accordance with a method well known in the technical field of pharmaceutics.

It is preferred to select a route of administration which is the most effective in carrying out the intended treatment such as oral administration or parenteral administration, e.g., intraoral administration, tracheal administration, rectal administration, subcutaneous injection, intramuscular injection, intravenous injection, and the like. Intravenous injection is preferred in a protein formulation.

The dosage form includes sprays, capsules, tablets, granules, syrups, emulsions, suppositories, injections, ointments, tapes, and the like.

Examples of formulation suitable for oral administration include emulsions, syrups, capsules, tablets, powders, granules, and the like.

Liquid preparations such as emulsions and syrups, can be produced using additives such as water, saccharides, e.g., sucrose, sorbitol, fructose, etc., glycols, e.g., polyethylene glycol, propylene glycol, etc., oils, e.g., sesame oil, olive oil, soybean oil, etc., antiseptics, e.g., p-hydroxybenzoate, etc., flavors, e.g., strawberry flavor, peppermint, etc., and the like.

Capsules, tablets, powders, granules and the like can be produced using additives such as fillers, e.g., lactose, glucose, sucrose, mannitol, etc., disintegrating agents, e.g., starch, sodium alginate, etc., lubricants, e.g., magnesium stearate, etc., binders, e.g., polyvinyl alcohol, hydroxypropylcellulose, gelatin, etc., surfactants, e.g., fatty acid ester, etc., plasticizers, e.g., glycerine, etc., and the like.

Examples of formulations suitable for parenteral administration include injections, suppositories, sprays, and the like.

Injections can be prepared using a carrier such as a salt solution, glucose solution or a mixture thereof, or the like.

Suppositories can be prepared using a carrier such as cacao butter, hydrogenated fat, a carboxylic acid, or the like.

Also, sprays can be prepared from the antibody or peptide itself or using a carrier or the like which does not stimulate oral and airway mucous membranes of patients and can facilitate absorption of the antibody or peptide by dispersing it as minute particles.

Examples of the carrier include lactose, glycerine, and the like. Depending on the properties of the antibody or peptide and the carrier to be used, aerosols, dry powders and the like can be produced. The additives exemplified in the oral preparations can also be added to the parenteral preparations.

The dose and frequency of administration vary depending on intended therapeutic effect, administration method, treating period, age, body weight and the like, but the dose is generally from 10 µg/kg to 8 mg/kg per day per adult.

BRIEF DESCRIPTION OF THE DRAWINGS

FIG. 18 is a drawing showing CDC activity of purified anti-GD3 chimeric antibody KM871 and purified anti-GD3 CDR-grafted antibodies KM8869, KM8870 and KM8871 against human melanoma cell lines G-361 and SK-MEL-28. The ordinate and the abscissa are the cytotoxic activity and the antibody concentration, respectively. "□", "□", "□" and "■" show the reactivities of KM871, KM8869, KM8870 and KM8871, respectively.

FIG. 19 is a drawing showing ADCC activity of purified anti-GD3 chimeric antibody KM871 and purified anti-GD3 CDR-grafted antibodies KM8869, KM8870 and KM8871 against human melanoma cell lines G-361 and SK-MEL-28. The ordinate and the abscissa are the cytotoxic activity and the antibody concentration, respectively. "□", "□", "□" and "■" show the reactivities of KM871, KM8869, KM8870 and KM8871, respectively.

FIG. 3 is a drawing showing construction steps of plasmid pKANTEX8871-hIL-2.

FIG. 27 is a drawing showing reactivity of purified anti-GD3 CDR-grafted antibody KM8871 and purified fusion protein KM8871-hIL-2 with human melanoma cell line G-361. The ordinate and the abscissa are the number of cells and the fluorescence intensity, respectively. The drawings show the reactivities of KM8871 and KM8871-hIL-2, respectively, from the upper column.

BEST MODE FOR CARRYING OUT THE INVENTION

Figure 1:
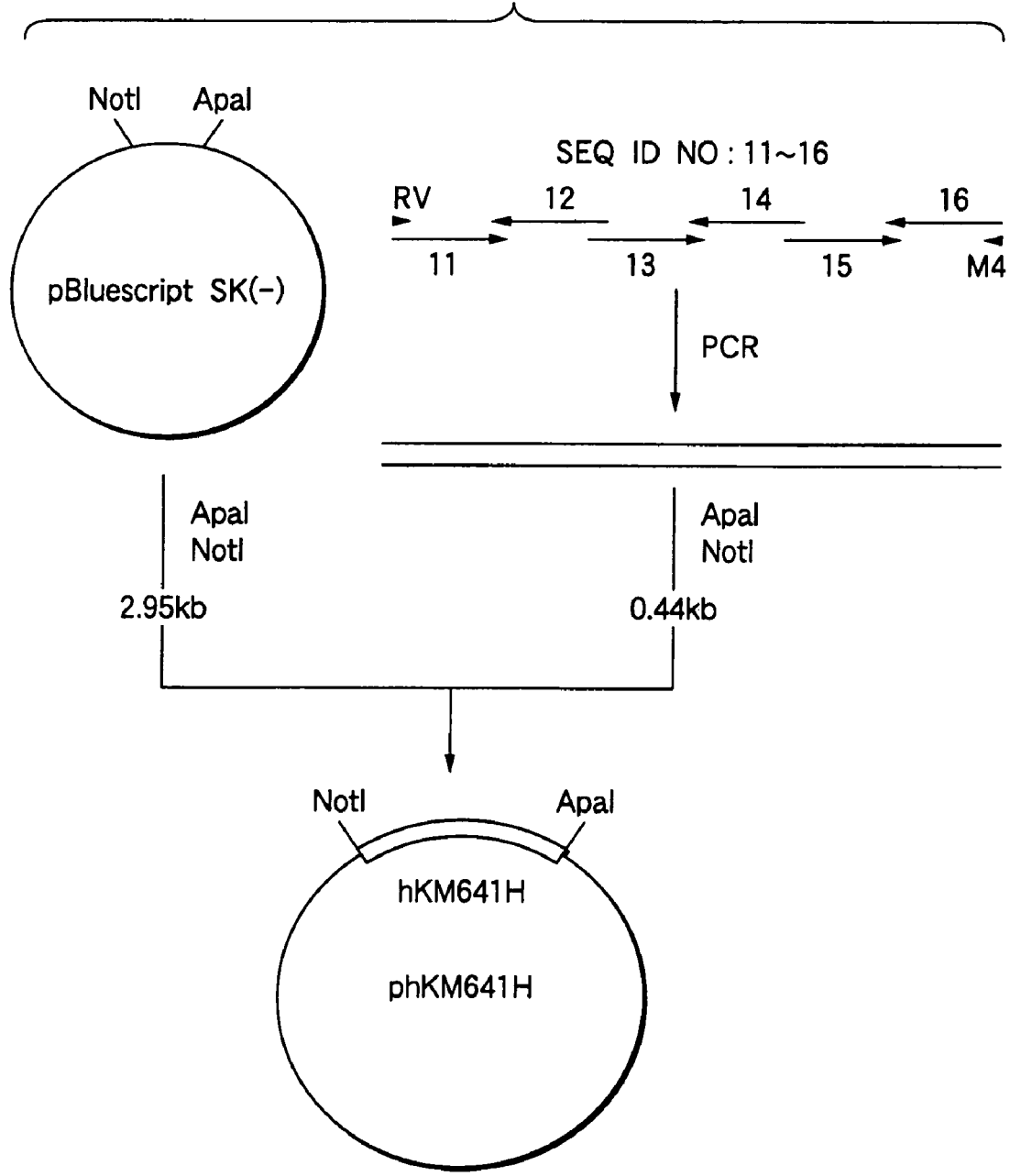
FIG. 1 is a drawing showing construction steps of plasmid phKM641H.

Examples of the present invention are shown below, though the scope of the present invention is not restricted thereby.

Example 1

Production of Anti-GD3 CDR-Grafted Antibody:

1. Analysis of Amino Acid Sequence of V Region of Anti-GD3 Mouse Antibody KM641

A full amino acid sequence of VH of anti-GD3 mouse antibody KM641 disclosed in Japanese Published Unexamined Patent Application No. 304989/93 is represented by SEQ ID NO:1, and a full amino acid sequence of VL thereof is represented by SEQ ID NO:2. Based on the comparison of both sequences with analytical results of amino acid sequences of known antibodies (*Sequences of Proteins of Immunological Interest*) and N-terminal amino acid sequences of H chain and L chain of purified anti-GD3 mouse antibody KM641, it was confirmed that positions (−19) to (−1) in the amino acid sequence of H chain and positions (−20) to (−1) in the amino acid sequence of L chain are secretory signal sequences. Full amino acid sequences of the secretory VH and VL are represented by SEQ ID NO:55 and SEQ ID NO:56, respectively. Also, it was found that CDRs 1, 2 and 3 of VH have the amino acid sequences represented by SEQ ID NOs:3, 4 and 5, and CDRs 1, 2 and 3 of VL have those represented by SEQ ID NOs:6, 7 and 8.

2. Measurement of Binding Activity of Antibody to Various Ganglioside (ELISA)

The binding activity of antibodies to various gangliosides was measured as follows.

Each ganglioside (2 nmol) was dissolved in 2 ml of ethanol solution containing 10 μg of dipalmitoylphosphatidylcholine (manufactured by SIGMA) and 5 μg of cholesterol (manufactured by SIGMA). In each well of a 96 well plate for ELISA use (manufactured by Greiner), 20 μl of the solution (becomes 20 pmol/well) or 20 μl of the solution diluted with ethanol was respectively dispensed, followed by air-drying, and then PBS containing 1% BSA thereinafter referred to as "1% BSA-PBS") was added in 100 μl/well and allowed to react at room temperature for 1 hour to thereby block remaining active groups. After discarding 1% BSA-PBS, culture supernatants of transformants or diluted solutions of humanized antibodies were added in 50 μl/well and allowed to react at room temperature for 1 hour. After the reaction, each well was washed with PBS containing 0.05% Tween 20 (hereinafter referred to as "Tween-PBS") and then a peroxidase-labeled goat anti-human IgG(γ) antibody solution (manufactured by Kirkegaard & Perry Laboratories) diluted 1,000 folds with 1% BSA-PBS was added as a secondary antibody solution in 50 μl/well and allowed to react at room temperature for 1 hour. After the reaction and subsequent washing with Tween-PBS, an ABTS substrate solution (a solution prepared by dissolving 0.55 g of 2,2'-azinobis (3-ethylbenzothiazoline-6-sulfonic acid) in 1 L of 0.1 M citrate buffer (pH 4.2) and adding 1 μl/ml hydrogen peroxide just before the use) was added in 50 μl/well for color development and the absorbance at 415 nm (hereinafter referred to as "OD415") was measured.

3. Construction of cDNAs Encoding VH and VL of Anti-GD3 CDR-Grafted Antibody (1) Design of Amino Acid Sequences of VH and VL of Anti-GD3 CDR-Grafted Antibody First, an amino acid sequence of VH of an anti-GD3 CDR-grafted antibody was designed as follows. In order to graft the CDR amino acid sequences of VH of the anti-GD3 mouse antibody KM641 identified in the item 1 of Example 1, an FR amino acid sequence of VH of a human antibody was selected. Kabat et al. have classified the VH of various known human antibodies into three subgroups (HSG I to III) based on the homology of the amino acid sequences and then reported consensus sequences among respective subgroups (*Sequences of Proteins of Immunological Interest*). Since these consensus sequences have a possibility that the immunogenicity is reduced in human, it was decided to design a VH amino acid sequence of an anti-GD3 CDR-grafted antibody based on these consensus sequences. In order to produce an anti-GD3 CDR-grafted antibody having higher activity in designing it, it was decided to select an FR amino acid sequence having the highest homology with the FR amino acid sequence of VH of KM641, among FR amino acid sequences of consensus sequences of the three subgroups of VH of human antibodies. Results of the homology search are shown in Table 1. As shown in Table 1, the FR amino acid sequence of VH of KM641 showed the most high homology with the subgroup III.

TABLE 1

Homology between FR amino acid sequence of consensus sequence of each subgroup of human antibody H chain V region and FR amino acid sequence of H chain V region of KM641

| HSG I | HSG II | HSG III |
|---|---|---|
| 62.1% | 56.3% | 78.2% |

Based on the above results, an amino acid sequence HV.0 of VH of the anti-GD3 CDR-grafted antibody was designed by grafting the CDR amino acid sequence of VH of the anti-GD3 mouse antibody KM641 to an appropriate position of the amino acid sequence of FR of the consensus sequence of subgroup III of VH of the human antibody.

Next, an amino acid sequence of VL of an anti-GD3 CDR-grafted antibody was designed as follows. In order to graft the CDR amino acid sequence of VL of the anti-GD3 mouse antibody KM641 identified in the item 1 of Example 1, an FR amino acid sequence of VL of a human antibody was selected. Kabat et al. have classified the VL of various known human antibodies into four subgroups (HSG I to IV) based on the homology of the amino acid sequences and then reported consensus sequences among respective subgroups (*Sequences of Proteins of Immunological Interest*). Accordingly, similar to the H chain, an FR amino acid sequence having most high homology with the FR amino acid sequence of VL of KM641 was selected from FR amino acid sequences of consensus sequences of the four subgroups of VL of human antibodies. Results of the homology search are shown in Table 2. As shown in Table 2, the FR amino acid sequence of VL of KM641 showed the most high homology with the subgroup I.

TABLE 2

Homology between FR amino acid sequence of
consensus sequence of each subgroup of
human antibody L chain V region and
FR amino acid sequence of L chain V region of KM641

| HSG I | HSG II | HSG III | HSG IV |
|---|---|---|---|
| 76.2% | 60.0% | 62.5% | 67.5% |

Based on the above results, an amino acid sequence LV.0 of VL of the anti-GD3 CDR-grafted antibody was designed by grafting the CDR amino acid sequence of VL of the anti-GD3 mouse antibody KM641 to an appropriate position of the amino acid sequence of FR of the consensus sequence of subgroup I of VL of the human antibody.

The thus designed amino acid sequence HV.0 of VH and amino acid sequence LV.0 of VL of the anti-GD3 CDR-grafted antibody are sequences in which only the CDR amino acid sequence of the anti-GD3 mouse antibody is grafted to the FR amino acid sequence of the selected human antibody. In general, in the human CDR-grafted antibodies, the antigen binding activity is reduced in many cases by grafting of a mouse antibody CDR amino acid sequence alone. Thus, in order to avoid the reduction of the antigen binding activity of antibodies, among FR amino acid residues different between a human antibody and a mouse antibody, amino acid residues considered to be exerting influences on the antigen binding activity are grafted together with a CDR amino acid sequence. Accordingly, identification of FR amino acid residues considered to have influences on the activity was carried out.

First, a three-dimensional structure of an antibody V region comprised of the amino acid sequence HV.0 of VH and amino acid sequence LV.0 of VL of anti-GD3 CDR-grafted antibody designed in the above (hereinafter referred to as "HV0LV0") was constructed using computer-modeling. The production of three-dimensional structure coordinates was carried out using a software AbM (manufactured by Oxford Molecular) and the display of three-dimensional structure was carried out using a software Pro-Explore (manufactured by Oxford Molecular) in accordance with the respective manufacture's instructions. Also, a computer model of the three-dimensional structure of the V region of anti-GD3 mouse antibody KM641 was constructed in the same manner. In addition, a three-dimensional structure model of a modified HV0LV0 having an amino acid sequence in which at least one amino acid residue different from anti-GD3 mouse antibody KM641 in the FR amino acid sequences of VH and VL of HV0LV0 was substituted by the amino acid residues of positions corresponding to the anti-GD3 mouse antibody KM641 in order was also constructed. Three-dimensional structures of V regions of the anti-GD3 mouse antibody KM641, HV0LV0 and modified product were compared. As a result, amino acid residues considered to have influences on the antigen binding activity by changing three-dimensional structure of the antigen-binding region were selected from the FR amino acid residues of HV0LV0. As a result of substituting the thus selected FR amino acid residues of HV0LV0 by the amino acid residues found in the mouse antibody KM641, an amino acid sequence hKM641H of VH of the anti-GD3 CDR-grafted antibody represented by SEQ ID NO:9 and an amino acid sequence hKM641L of VL of the anti-GD3 CDR-grafted antibody represented by SEQ ID NO:10 were designed. In the hKM641H, the 10th position Gly, the 11th position Leu, the 20th position Leu, the 28th position Thr, the 84th position Asn, the 91st position Thr, the 95th position Tyr, the 97th position Ala and the 115th position Val in the FR amino acid sequence of HV.0 were replaced by Asp, Phe, Val, Ala, Arg, Ser, Phe, Thr and Leu, respectively, as amino acid residues of positions corresponding to the VH of anti-GD3 mouse antibody KM641. In the hKM641L, the 49th position Tyr, the 65th position Ser and the 71st position Phe in the FR amino acid sequence of LV.0 were replaced by Phe, Gly and Tyr, respectively, as amino acid residues of positions corresponding to the VL of anti-GD3 mouse antibody KM641.

(2) Construction of cDNA Encoding VH of Anti-GD3 CDR-Grafted Antibody

A cDNA encoding the anti-GD3 CDR-grafted antibody VH amino acid sequence hKM641H designed in the item 3(1) of Example 1 was constructed as follows.

First, the designed amino acid sequence was ligated with the secretory signal sequence of H chain of anti-GD3 mouse antibody KM641 represented by SEQ ID NO:1 to produce a full antibody amino acid sequence. Next, the amino acid sequence is converted into genetic codons. When two or more genetic codons were present for one amino acid residue, corresponding genetic codon was determined by taking the frequency of codon usage found in nucleotide sequences of antibody genes into consideration (*Sequences of Proteins of Immunological Interest*). A nucleotide sequence of cDNA encoding the complete antibody V region amino acid sequence was designed by ligating the thus determined genetic codons, and nucleotide sequences of primer binding site for use in the PCR amplification (including restriction enzyme recognition sequences for cloning into a humanized antibody expression vector) were added to the 5'-terminal and 3'-terminal. The thus designed nucleotide sequence was divided into a total of 6 nucleotide sequences from the 5'-terminal side, each having about 100 bases (adjoining nucleotide sequences are designed such that the termini have an overlapping sequence of about 20 bases), and they were synthesized in alternating order of the sense chain and the antisense chain using an automatic DNA synthesizer (380A, manufactured by Applied Biosystems).

Specifically, 6 synthetic DNA fragments of SEQ ID NO:11 to SEQ ID NO:16 were synthesized. Each DNA was added to 50 μl of a buffer comprising 10 mM Tris-HCl (pH 8.3), 50 mM potassium chloride, 1.5 mM magnesium chloride, 0.001% gelatin, 200 μM dNTPs, 0.5 μM M13 primer RV (manufactured by Takara Shuzo), 0.5 μM M13 primer M4 (manufactured by Takara Shuzo) and 2 units of TaKaRa Taq DNA polymerase (manufactured by Takara Shuzo) to give a final concentration of 0.1 μM, and the solution was covered with 50 μl of mineral oil and set to a DNA thermal cycler (PJ480, manufactured by PERKIN ELMER) to carry out 30 cycles of the reaction, each cycle including 2 minutes at 94° C., 2 minutes at 55° C. and 2 minutes at 72° C. The reaction solution was purified using QIAquick PCR Purification Kit (manufactured by QIAGEN) in accordance with the manufacture's instructions and made into 30 μl of a buffer comprising 10 mM Tris-HCl (pH 7.5), 10 mM magnesium chloride and 1 mM DTT, and 10 units of a restriction enzyme ApaI (manufactured by Takara Shuzo) were further added thereto to carry out the reaction at 37° C. for 1 hour. The reaction solution was precipitated with ethanol, added to 10 μl of a buffer comprising 50 mM Tris-HCl (pH 7.5), 100 mM sodium chloride, 10 mM magnesium chloride, 1 mM DTT, 100 μg/ml BSA and 0.01% Triton X-100, and 10 units of a restriction enzyme NotI (manufactured by Takara Shuzo) were further added to carry out the reaction at 37° C. for 1 hour. The reaction solution was fractionated by agarose gel electrophoresis to recover about 0.2 μg of an ApaI-NotI fragment of about 0.44 kb using QIAquick Gel Extraction Kit (manufactured by QIAGEN) in accordance with the manufacture's instructions.

Next, 3 μg of a plasmid pBluescript SK(−) was added to 10 μl a buffer comprising 10 mM Tris-HCl (pH 7.5), 10 mM magnesium chloride and 1 mM DTT, and 10 units of a restriction enzyme ApaI (manufactured by Takara Shuzo) were further added thereto to carry out the reaction at 37° C. for 1 hour. The reaction solution was precipitated with ethanol and added to 10 μl of a buffer comprising 50 mM Tris-HCl (pH 7.5), 100 mM sodium chloride, 10 mM magnesium chloride, 1 mM DTT, 100 μg/ml BSA and 0.01% Triton X-100, and 10 units of a restriction enzyme NotI (manufactured by Takara Shuzo) were further added thereto to carry out the reaction at 37° C. for 1 hour. The reaction solution was fractionated by agarose gel electrophoresis to recover about 2 μg of an ApaI-NotI fragment of about 2.95 kb using QIAquick Gel Extraction Kit (manufactured by QIAGEN) in accordance with the manufacture's instructions.

Next, 0.1 μg of the ApaI-NotI fragment of the PCR product of VH of anti-GD3 CDR-grafted antibody and 0.1 μg of the ApaI-NotI fragment of the plasmid pBluescript SK(−), both obtained in the above, were added to 20 μl in total volume of sterile water and ligated using Ready-To-Go T4 DNA Ligase (manufactured by Pharmacia). Using the thus obtained recombinant plasmid DNA solution, an *Escherichia coli* line HB101 was transformed. Each plasmid DNA was produced from 10 clones of the transformants, allowed to react in accordance with the manufacture's instructions attached to AutoRead Sequencing Kit (manufactured by Pharmacia) and then subjected to electrophoresis using A.L.F. DNA Sequencer (manufactured by Pharmacia) to determine the nucleotide sequence, and as a result, the plasmid phKM641H shown in FIG. 1 having the nucleotide sequence of interest was obtained.

(3) Construction of cDNA Encoding VL of Anti-GD3 CDR-Grafted Antibody

A cDNA encoding the anti-GD3 CDR-grafted antibody VL amino acid sequence hKM641L designed in the item 3(1) of Example 1 was constructed as follows using the PCR similar to the VH. In this case, the amino acid sequence of L chain of anti-GD3 mouse antibody KM641 represented by SEQ ID NO:2 was used as the secretory signal sequence.

First, 6 synthetic DNA fragments of SEQ ID NO:17 to SEQ ID NO:22 were synthesized using an automatic DNA synthesizer (380A, manufactured by Applied Biosystems). Each of the thus synthesized DNA fragments was added to 50 μl of a buffer comprising 10 mM Tris-HCl (pH 8.3), 50 mM potassium chloride, 1.5 mM magnesium chloride, 0.001% gelatin, 200 μM dNTPs, 0.5 μM M13 primer RV (manufactured by Takara Shuzo), 0.5 μM M13 primer M4 (manufactured by Takara Shuzo) and 2 units of TaKaRa Taq DNA polymerase (manufactured by Takara Shuzo) to give a final concentration of 0.1 μM, and the solution was covered with 50 μl of mineral oil and set to a DNA thermal cycler (PJ480, manufactured by PERKIN ELMER) to carry out 30 cycles of the reaction, each cycle including 2 minutes at 94° C., 2 minutes at 55° C. and 2 minutes at 72° C. The reaction solution was purified using QIAquick PCR Purification Kit (manufactured by QIAGEN) in accordance with the manufacture's instructions and made into 30 μl of a buffer comprising 50 mM Tris-HCl (pH 7.5), 100 mM sodium chloride, 10 mM magnesium chloride, 1 mM DTT and 100 μg/ml BSA, and 10 units of a restriction enzyme EcoRI (manufactured by Takara Shuzo) and a restriction enzyme SplI (manufactured by Takara Shuzo) were further added thereto to carry out the reaction at 37° C. for 1 hour. The reaction solution was fractionated by agarose gel electrophoresis to recover about 0.2 μg of an EcoRI-SplI fragment of about 0.39 kb using QIAquick Gel Extraction Kit (manufactured by QIAGEN) in accordance with the manufacturers instructions.

Next, 3 μg of a plasmid pBSL3 described in Japanese Published Unexamined Patent Application No. 257893/98 was added to 10 μl of a buffer comprising 50 mM Tris-HCl (pH 7.5), 100 mM sodium chloride, 10 mM magnesium chloride, 1 mM DTT and 100 μg/ml BSA, and 10 units of a restriction enzyme EcoRI (manufactured by Takara Shuzo) and a restriction enzyme SplI (manufactured by Takara Shuzo) were further added thereto to carry out the reaction at 37° C. for 1 hour. The reaction solution was fractionated by agarose gel electrophoresis to recover about 2 μg of an EcoRI-SplI fragment of about 2.95 kb using QIAquick Gel Extraction Kit (manufactured by QIAGEN) in accordance with the manufacture's instructions.

Figure 2:
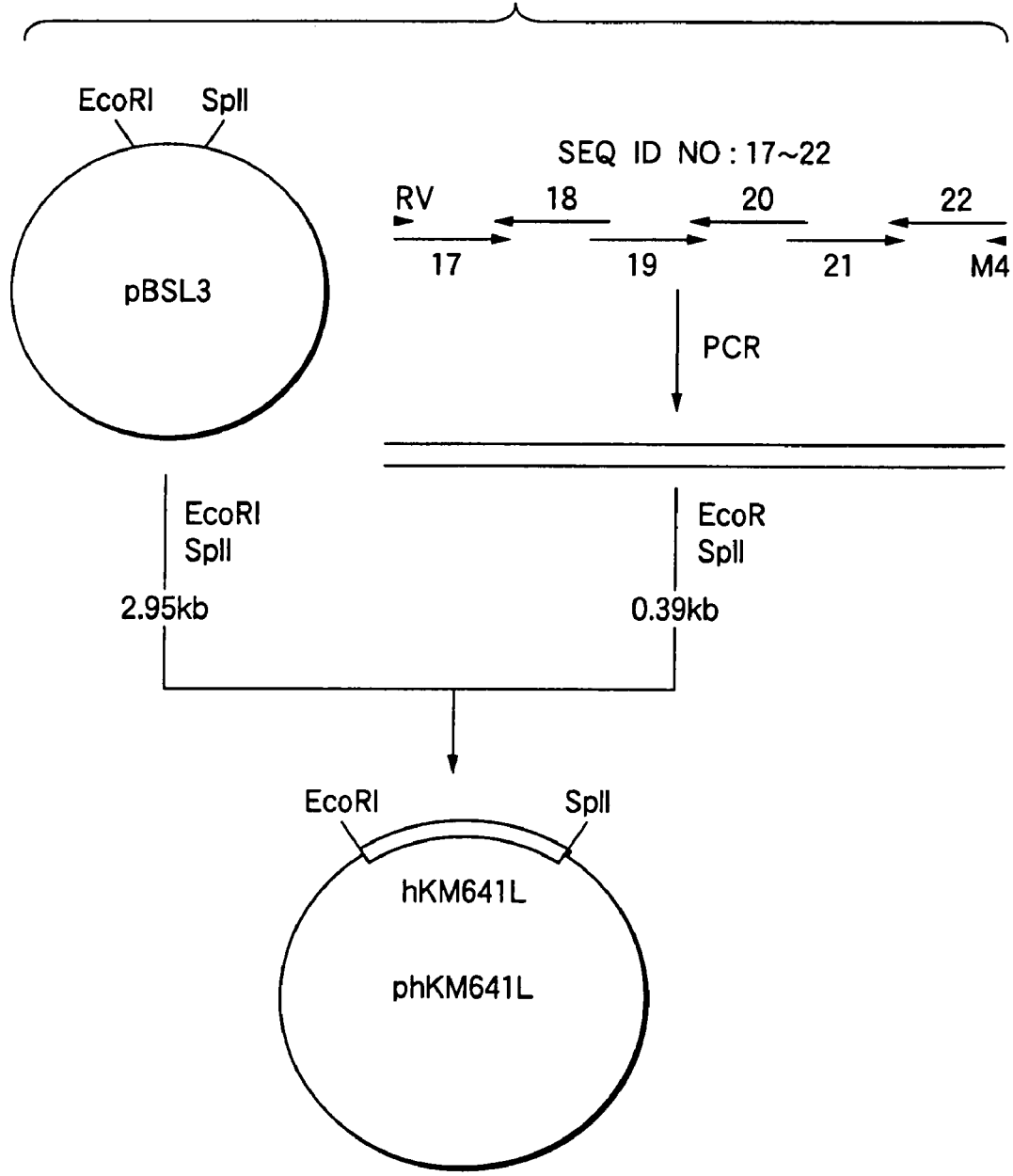
FIG. 2 is a drawing showing construction steps of plasmid phKM641L.

Next, 0.1 μg of the EcoRI-SplI fragment of the PCR product of VL of anti-GD3 CDR-grafted antibody and 0.1 μg of the EcoRI-SplI fragment of the plasmid pBSL3, both obtained in the above, were added to 20 μl in total volume of sterile water and ligated using Ready-To-Go T4 DNA Ligase (manufactured by Pharmacia). Using the thus obtained recombinant plasmid DNA solution, an *E. coli* line HB101 was transformed. Each plasmid DNA was prepared from 10 clones of the transformants, allowed to react in accordance with the manufacture's instructions attached to AutoRead Sequencing Kit (manufactured by Pharmacia) and then subjected to electrophoresis using A.L.F. DNA Sequencer (manufactured by Pharmacia) to determine the nucleotide sequence, and as a result, the plasmid phKM641L shown in FIG. 2 having the nucleotide sequence of interest was obtained.

4. Activity Evaluation of Anti-GD3 CDR-Grafted Antibody by Transient Expression Using Animal Cell In order to carry out activity evaluation of anti-GD3 CDR-grafted antibody more quickly, transient expression of anti-GD3 CDR-grafted antibody was carried out as follows using COS-7 cell (ATCC CRL 1651).

(1) Construction of Anti-GD3 Chimeric Antibody KM871 Transient Expression Vector pT641

In order to use as a positive control in the activity evaluation of anti-GD3 CDR-crafted antibody by Transient expression, a transient expression vector pT641 for anti-GD3 chimeric antibody KM871 was constructed as follows.

Since the efficiency of transient expression using animal cells generally depends on the copy number of introduced expression vector, it was considered that smaller expression vector has higher expression efficiency. Accordingly, the transient expression vector pT641 for anti-GD3 chimeric antibody KM871 was constructed as follows using the transient expression vector pT796 for anti-ganglioside GM2 chimeric antibody KM966 described in Japanese Published Unexamined Patent Application No. 257893/98 and the plasmid pKM641HF1 having VH of anti-GD3 mouse antibody KM641 and plasmid pKM641LA2 having VL of anti-GD3 mouse antibody KM641 described in Japanese Published Unexamined Patent Application No. 304989/93.

First, 3 µg of the plasmid pKM641LA2 having VL of anti-GD3 mouse antibody KM641 described in Japanese Published Unexamined Patent Application No. 304989/93 was added to 10 µl of a buffer comprising 10 mM Tris-HCl (pH 7.5), 50 mM sodium chloride, 10 mM magnesium chloride and 1 mM DTT and the solution was further mixed with 10 units of a restriction enzyme HindIII (manufactured by Takara Shuzo) to carry out the reaction at 37° C. for 1 hour. The reaction solution was precipitated with ethanol and added to 10 µl of a buffer comprising 50 mM Tris-HCl (pH 7.5), 100 mM sodium chloride, 10 mM magnesium chloride and 1 mM DTT, and 10 units of a restriction enzyme EcoRI (manufactured by Takara Shuzo) were further added to carry out the reaction at 37° C. for 1 hour. The reaction solution was fractionated by agarose gel electrophoresis to recover about 0.2 µg of an HindIII-EcoRI fragment of about 0.35 kb using QIAquick Gel Extraction Kit (manufactured by QIAGEN) in accordance with the manufacture's instructions.

Next, 3 µg of the transient expression vector pT796 for anti-ganglioside GM2 chimeric antibody KM966 described in Japanese Published Unexamined Patent Application No. 257893/98 was added to 10 µl of a buffer comprising 50 mM Tris-HCl (pH 7.5), 100 mM sodium chloride, 10 mM magnesium chloride, 1 mM DTT and 100 µg/ml BSA, and the solution was further mixed with 10 units of a restriction enzyme EcoRI (manufactured by Takara Shuzo) and a restriction enzyme SplI (manufactured by Takara Shuzo) to carry out the reaction at 37° C. for 1 hour. The reaction solution was fractionated by agarose gel electrophoresis to recover about 2 µg of an EcoRI-SplI fragment of about 9.20 kb using QIAquick Gel Extraction Kit (manufactured by QIAGEN) in accordance with the manufacture's instructions.

Next, synthetic DNA fragments respectively having the nucleotide sequences represented by SEQ ID NO:23 and SEQ ID NO:24 were synthesized using an automatic DNA synthesizer (380A, manufactured by Applied Biosystems). A 0.3 µg of each of the thus obtained synthetic DNA fragments was added to 15 µl of sterile water and heated at 65° C. for 5 minutes. After allowing the reaction solution to stand at room temperature for 30 minutes, this was mixed with 2 µl of a 10× buffer solution (500 mM Tris-HCl (pH 7.6), 100 mM magnesium chloride, 50 mM DTT) and 2 µl of 10 µM ATP and further mixed with 10 units of T4 Polynucleotide Kinase (manufactured by Takara Shuzo) to carry out the reaction at 37° C. for 30 minutes to thereby phosphorylate the 5'-terminal.

Figure 3:
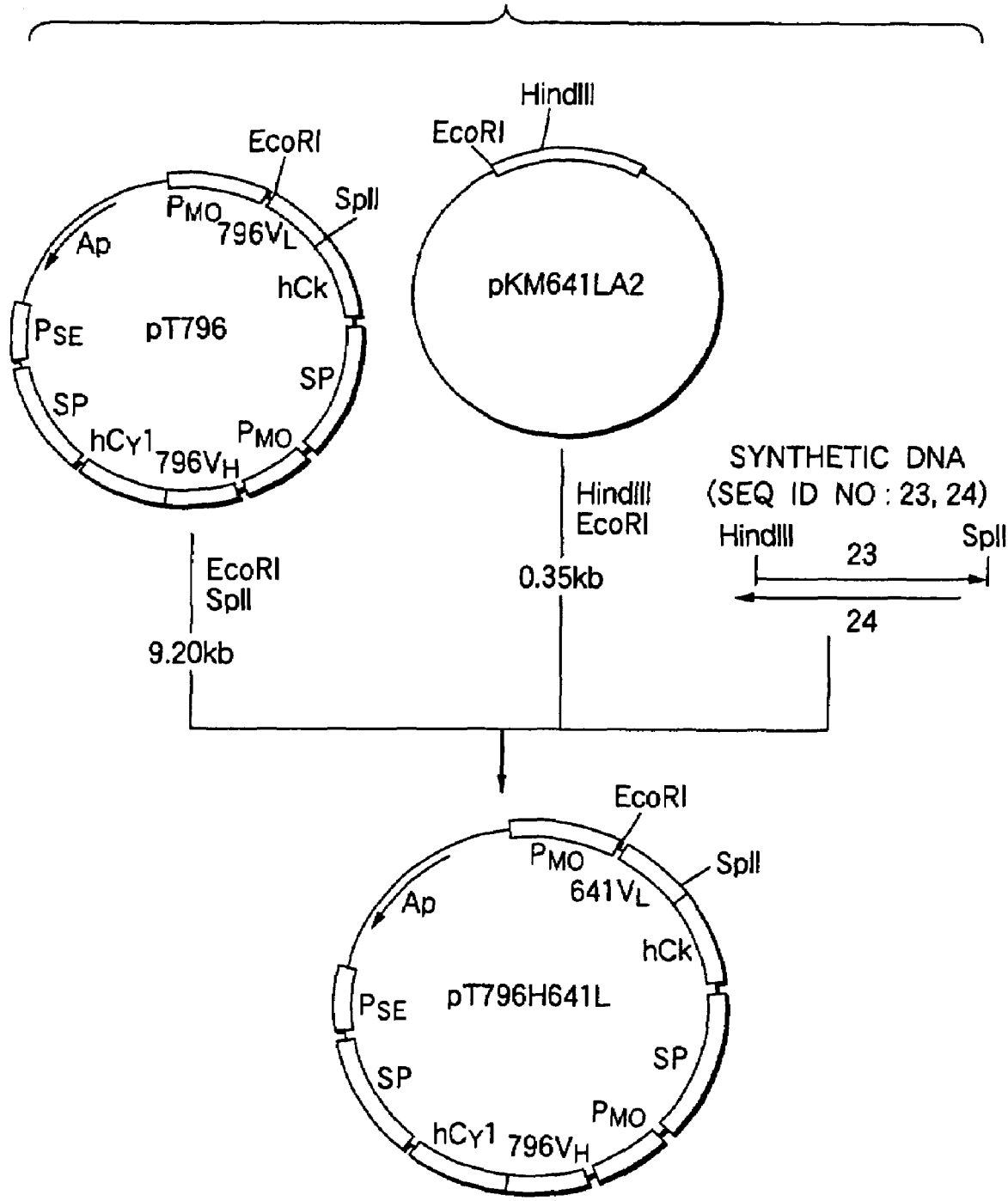
FIG. 3 is a drawing showing construction steps of plasmid pT796H641L.

Next, 0.1 µg of the HindIII-EcoRI fragment derived from the plasmid pKM641LA2, 0.1 µg of the EcoRI-SplI fragment derived from the plasmid pT796 and 0.05 µg of the phosphorylated synthetic DNA, obtained in the above, were added to 20 µl in total volume of sterile water and ligated using Ready-To-Go T4 DNA Ligase (manufactured by Pharmacia). Using the thus obtained recombinant plasmid DNA solution, an E. coli HB101 was transformed to obtain the plasmid pT796H641L shown in FIG. 3. The thus obtained plasmid (10 µg) was allowed to react in accordance with the manufacture's instructions attached to AutoRead Sequencing Kit (manufactured by Pharmacia) and then subjected to an electrophoresis using A.L.F. DNA Sequencer (manufactured by Pharmacia) to determine the nucleotide sequence, and as a result, it was confirmed that a plasmid into which the DNA of interest was cloned was obtained.

Next, 3 µg of a plasmid pBluescript SK(–) (manufactured by Stratagene) was added to 10 µl of a buffer comprising 10 mM Tris-HCl (pH 7.5), 50 mM sodium chloride, 10 mM magnesium chloride, 1 mM DTT and 100 µg/ml BSA and the solution was further mixed with 10 units of a restriction enzyme XbaI (manufactured by Takara Shuzo) to carry out the reaction at 37° C. for 1 hour. The reaction solution was precipitated with ethanol, added to 30 µl of a buffer comprising 30 mM sodium acetate (pH 5.0), 100 mM sodium chloride, 1 mM zinc acetate and 5% glycerol, and further mixed with 30 units of a modification enzyme Mung Bean Nuclease (manufactured by Takara Shuzo) to carry out the reaction at 25° C. for 15 minutes. The reaction solution was precipitated with ethanol, added to 10 µl of a buffer comprising 10 mM Tris-HCl (pH 7.5), 10 mM magnesium chloride and 1 mM DTT, and further mixed with 10 units of a restriction enzyme ApaI (manufactured by Takara Shuzo) to carry out the reaction at 37° C. for 1 hour. The reaction solution was fractionated by an agarose gel electrophoresis to recover about 2 µg of a Blunt end-ApaI fragment of about 2.95 kb using QIAquick Gel Extraction Kit (manufactured by QIAGEN) in accordance with the manufacture's instructions.

Next, 3 µg of the plasmid pKM641HF1 was added to 10 µl of a buffer comprising 50 mM Tris-HCl (pH 7.5), 100 mM sodium chloride, 10 mM magnesium chloride and 1 mM DTT, and the solution was further mixed with 10 units of a restriction enzyme EcoRI (manufactured by Takara Shuzo) to carry out the reaction at 37° C. for 1 hour. The reaction solution was precipitated with ethanol, and the 5' protruding end formed by the restriction enzyme digestion was changed to blunt end using DNA Blunting Kit (manufactured by Takara Shuzo). The reaction solution was precipitated with ethanol, added to 10 µl of a buffer comprising 10 mM Tris-HCl (pH 7.5), 10 mM magnesium chloride and 1 mM DTT, and further mixed with 10 units of a restriction enzyme ApaI (manufactured by Takara Shuzo) to carry out the reaction at 37° C. for 1 hour. The reaction solution was fractionated by an agarose gel electrophoresis to recover about 0.2 µg of a Blunt end-ApaI fragment of about 0.44 kb using QIAquick Gel Extraction Kit (manufactured by QIAGEN) in accordance with the manufacture's instructions.

Figure 4:
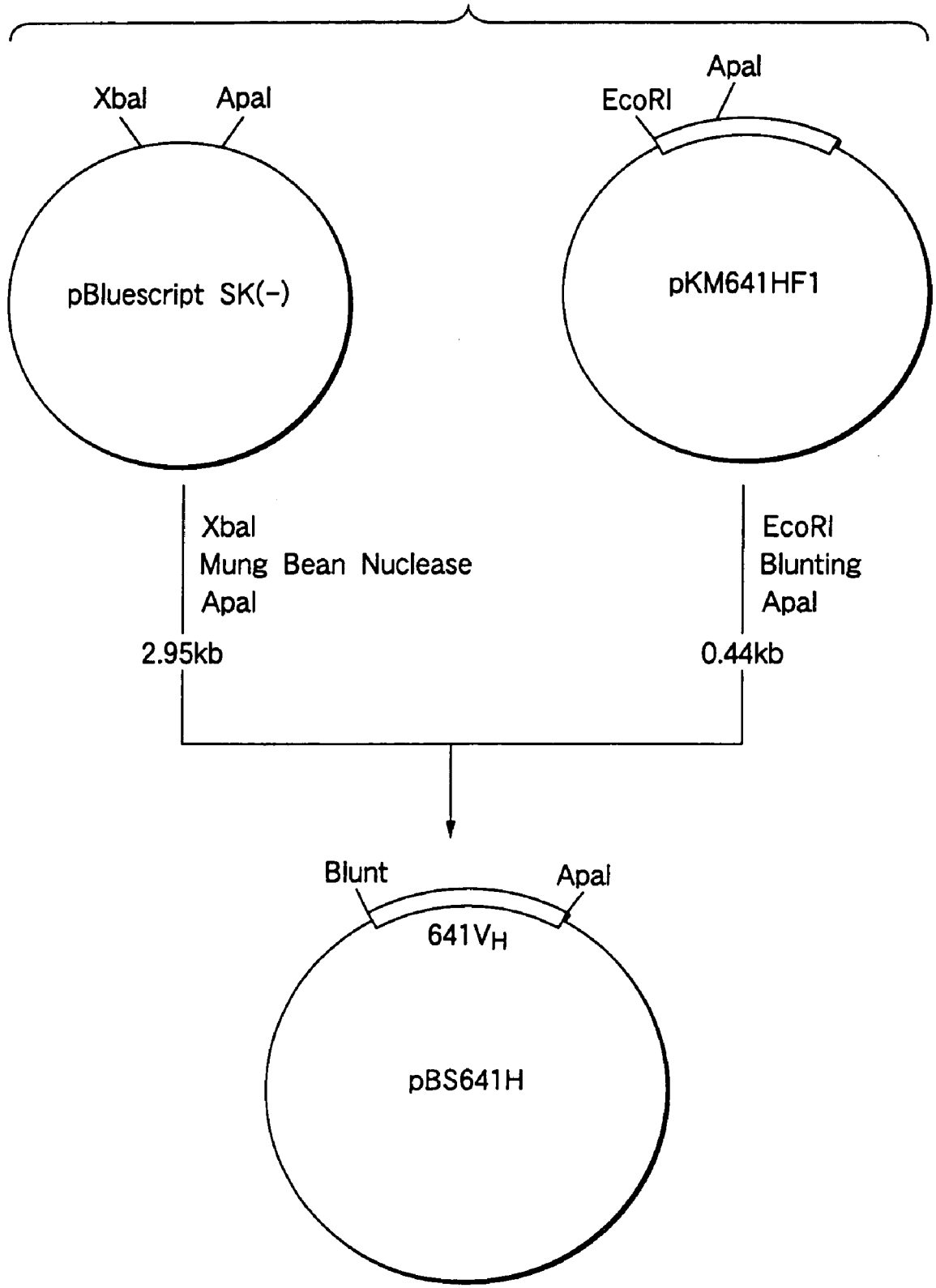
FIG. 4 is a drawing showing construction steps of plasmid pBS641H.

Next, 0.1 µg of Blunt end-ApaI fragment derived from the plasmid pBluescript SK(–) and 0.1 µg of the Blunt end-ApaI fragment derived from the plasmid pKM641HF1, obtained in the above, were added to 20 µl in total volume of sterile water and ligated using Ready-To-Go T4 DNA Ligase (manufactured by Pharmacia). Using the thus obtained recombinant plasmid DNA solution, an *E. coli* HB101 was transformed to obtain the plasmid pBS641H shown in FIG. 4.

Next, 3 μg of the plasmid pT796H641L obtained in the above was added to 10 μl of a buffer comprising 10 mM Tris-HCl (PE 7.5), 10 mM magnesium chloride and 1 mM DTT and the solution was further mixed with 10 units of a restriction enzyme ApaI (manufactured by Takara Shuzo) to carry out the reaction at 37° C. for 1 hour. The reaction solution was precipitated with ethanol, added to 10 μl of a buffer comprising 50 mM Tris-HCl (pH 7.5), 100 mM sodium chloride, 10 mM magnesium chloride, 1 mM DTT, 100 μg/ml BSA and 0.01% Triton X-100, and further mixed with 10 units of a restriction enzyme NotI (manufactured by Takara Shuzo) to carry out the reaction at 37° C. for 1 hour. The reaction solution was fractionated by an agarose gel electrophoresis to recover about 0.2 μg of an ApaI-NotI fragment of about 9.16 kb using QIAquick Gel Extraction Kit (manufactured by QIAGEN) in accordance with the manufacture's instructions.

Next, 3 μg of the plasmid pBS641H obtained in the above was added to 10 μl of a buffer comprising 10 mM Tris-HCl (pH 7.5), 10 mM magnesium chloride and 1 mM DTT and the solution was further mixed with 10 units of a restriction enzyme ApaI (manufactured by Takara Shuzo) to carry out the reaction at 37° C. for 1 hour. The reaction solution was precipitated with ethanol, added to 10 μl of a buffer comprising 50 mM Tris-HCl (pH 7.5), 100 mM sodium chloride, 10 mM magnesium chloride, 1 mM DTT, 100 μg/ml BSA and 0.01% Triton X-100, and further mixed with 10 units of a restriction enzyme NotI (manufactured by Takara Shuzo) to carry out the reaction at 37° C. for 1 hour. The reaction solution was fractionated by an agarose gel electrophoresis to recover about 2 μg of an ApaI-NotI fragment of about 0.44 kb using QIAquick Gel Extraction Kit (manufactured by QIAGEN) in accordance with the manufacture's instructions.

Figure 5:
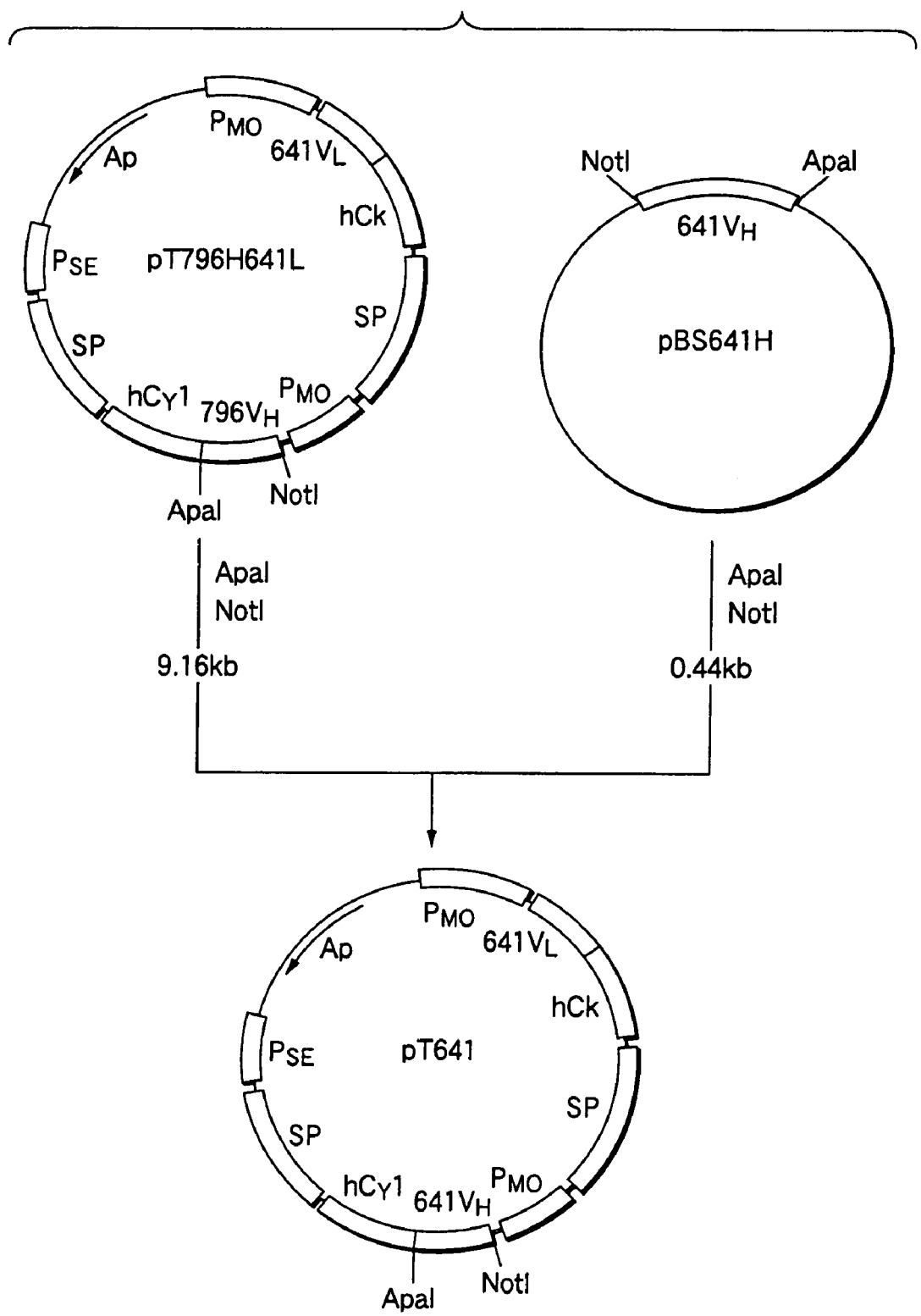
FIG. 5 is a drawing showing construction steps of plasmid pT641.

Next, 0.1 μg of the ApaI-NotI fragment derived from the plasmid pT796H641L and 0.1 μg of the ApaI-NotI fragment derived from the plasmid pBS641H, obtained in the above, were added to 20 μl in total volume of sterile water and ligated using Ready-To-Go T4 DNA Ligase (manufactured by Pharmacia). Using the thus obtained recombinant plasmid DNA solution, an *E. coli* HB101 was transformed to obtain the plasmid pT641 shown in FIG. 5.

(2) Construction of an Anti-GD3 CDR-Grafted Antibody KM871 Transient Expression Vector A transient expression vector for anti-GD3 CDR-grafted antibody was constructed as follows using the transient expression vector pT641 for anti-GD3 chimeric antibody described in the item 4(1) of Example 1 and the plasmids phKM641H and phKM641L described in the items 3(2) and (3) of Example 1.

First, 3 μg of the plasmid phKM641H obtained in the item 3(2) of Example 1 was added to 10 μl of a buffer comprising 10 mM Tris-HCl (pH 7.5), 10 mM magnesium chloride and 1 mM DTT and the solution was further mixed with 10 units of a restriction enzyme ApaI (manufactured by Takara Shuzo) to carry out the reaction at 37° C. for 1 hour. The reaction solution was precipitated with ethanol, added to 10 μl of a buffer comprising 50 mM Tris-HCl (pH 7.5), 100 mM sodium chloride, 10 mM magnesium chloride, 1 mM DTT, 100 μg/ml BSA and 0.01% Triton X-100, and further mixed with 10 units of a restriction enzyme NotI (manufactured by Takara Shuzo) to carry out the reaction at 37° C. for 1 hour. The reaction solution was fractionated by an agarose gel electrophoresis to recover about 0.2 μg of an ApaI-NotI fragment of about 0.44 kb using QIAquick Gel Extraction Kit (manufactured by QIAGEN) in accordance with the manufactures instructions.

Next, 3 μg of the plasmid pT641 obtained in the item 4(1) of Example 1 was added to 10 μl of a buffer comprising 10 mM Tris-HCl (pH 7.5), 10 mM magnesium chloride and 1 mM DTT, and the solution was further mixed with 10 units of a restriction enzyme ApaI (manufactured by Takara Shuzo) to carry out the reaction at 37° C. for 1 hour. The reaction solution was precipitated with ethanol, added to 10 μl of a buffer comprising 50 mM Tris-HCl (pH 7.5), 100 mM sodium chloride, 10 mM magnesium chloride, 1 mM DTT, 100 μg/ml BSA and 0.01% Triton X-100, and further mixed with 10 units of a restriction enzyme NotI (manufactured by Takara Shuzo) to carry out the reaction at 37° C. for 1 hour. The reaction solution was fractionated by an agarose gel electrophoresis to recover about 2 μg of an ApaI-NotI fragment of about 9.16 kb using QIAquick Gel Extraction Kit (manufactured by QIAGEN) in accordance with the manufacturers instructions.

Figure 6:
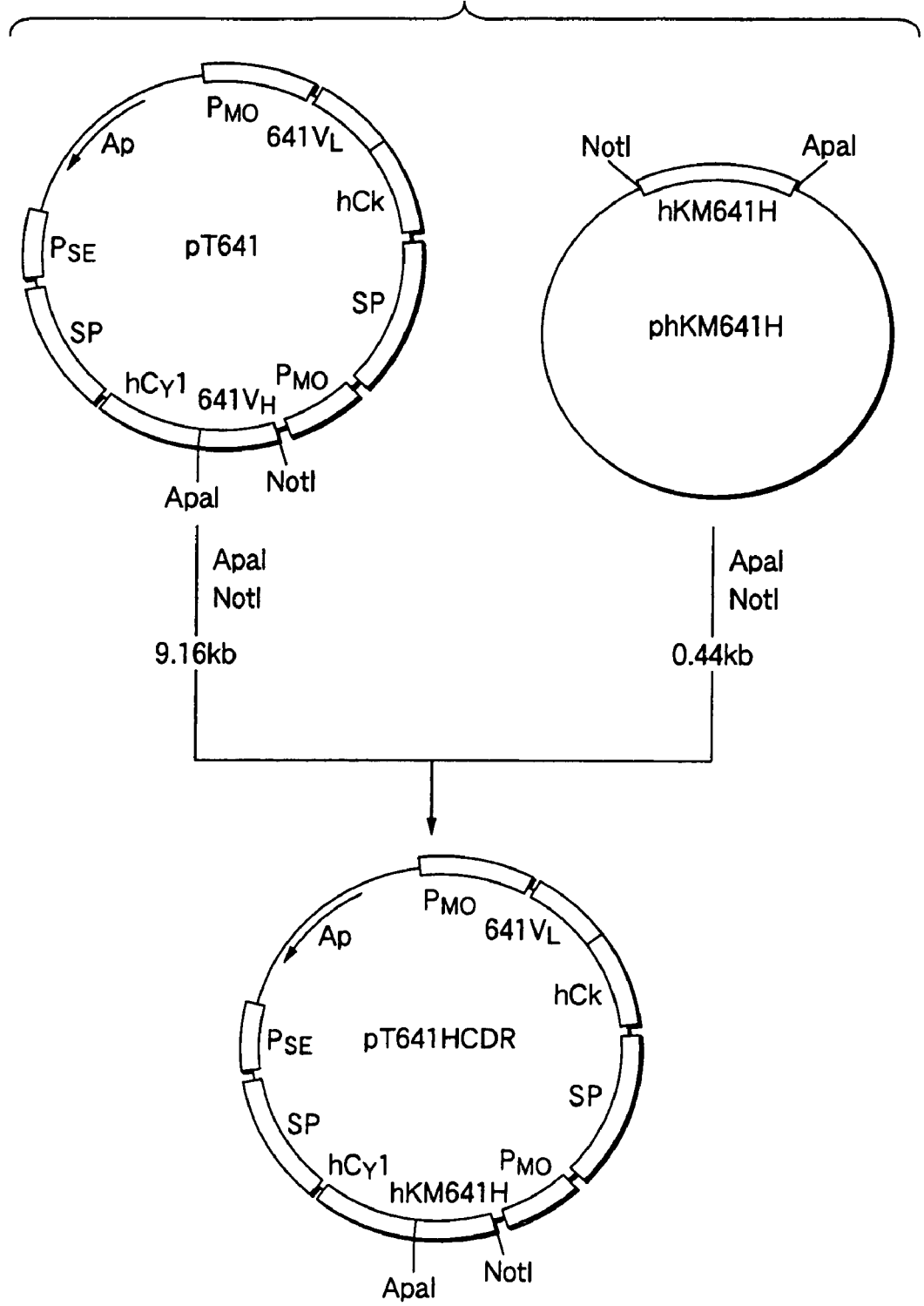
FIG. 6 is a drawing showing construction steps of plasmid pT641HCDR.

Next, 0.1 μg of the ApaI-NotI fragment derived from the plasmid phKM641H and 0.1 μg of the ApaI-NotI Fragment derived from the plasmid pT641 were added to 20 μl in total volume of sterile water and ligated using Ready-To-Go T4 DNA Ligase (manufactured by Pharmacia). Using the thus obtained recombinant plasmid DNA solution, an *E. coli* HB101 was transformed to obtain the plasmid pT641HCDR shown in FIG. 6.

Next, 3 μg of the plasmid phKM641L obtained in the item 3(3) of Example 1 was added to 10 μl of a buffer comprising 50 mM Tris-HCl (pH 7.5), 100 mM sodium chloride, 10 mM magnesium chloride, 1 mM DTT and 100 μg/ml BSA, and the solution was further mixed with 10 units of a restriction enzyme EcoRI (manufactured by Takara Shuzo) and a restriction enzyme SplI (manufactured by Takara Shuzo) to carry out the reaction at 37° C. for 1 hour. The reaction solution was fractionated by an agarose gel electrophoresis to recover about 0.2 μg of an EcoRI-SplI fragment of about 0.39 kb using QIAquick Gel Extraction Kit (manufactured by QIAGEN) in accordance with the manufacture's instructions.

Next, 3 μg of each of the plasmid pT641 obtained in the item 4(1) of Example 1 and the plasmid pT641HCDR obtained in the above was added to 10 μl of a buffer comprising 50 mM Tris-HCl (pH 7.5), 100 mM sodium chloride, 10 mM magnesium chloride, 1 mM DTT and 100 μg/ml BSA, and the solution was further mixed with 10 units of a restriction enzyme EcoRI (manufactured by Takara Shuzo) and a restriction enzyme SplI (manufactured by Takara Shuzo) to carry out the reaction at 37° C. for 1 hour. The reaction solution was fractionated by an agarose gel electrophoresis to recover about 2 μg of an EcoRI-SplI fragment of about 9.20 kb derived from each plasmid using QIAquick Gel Extraction Kit (manufactured by QIAGEN) in accordance with the manufacture's instructions.

Figure 7:
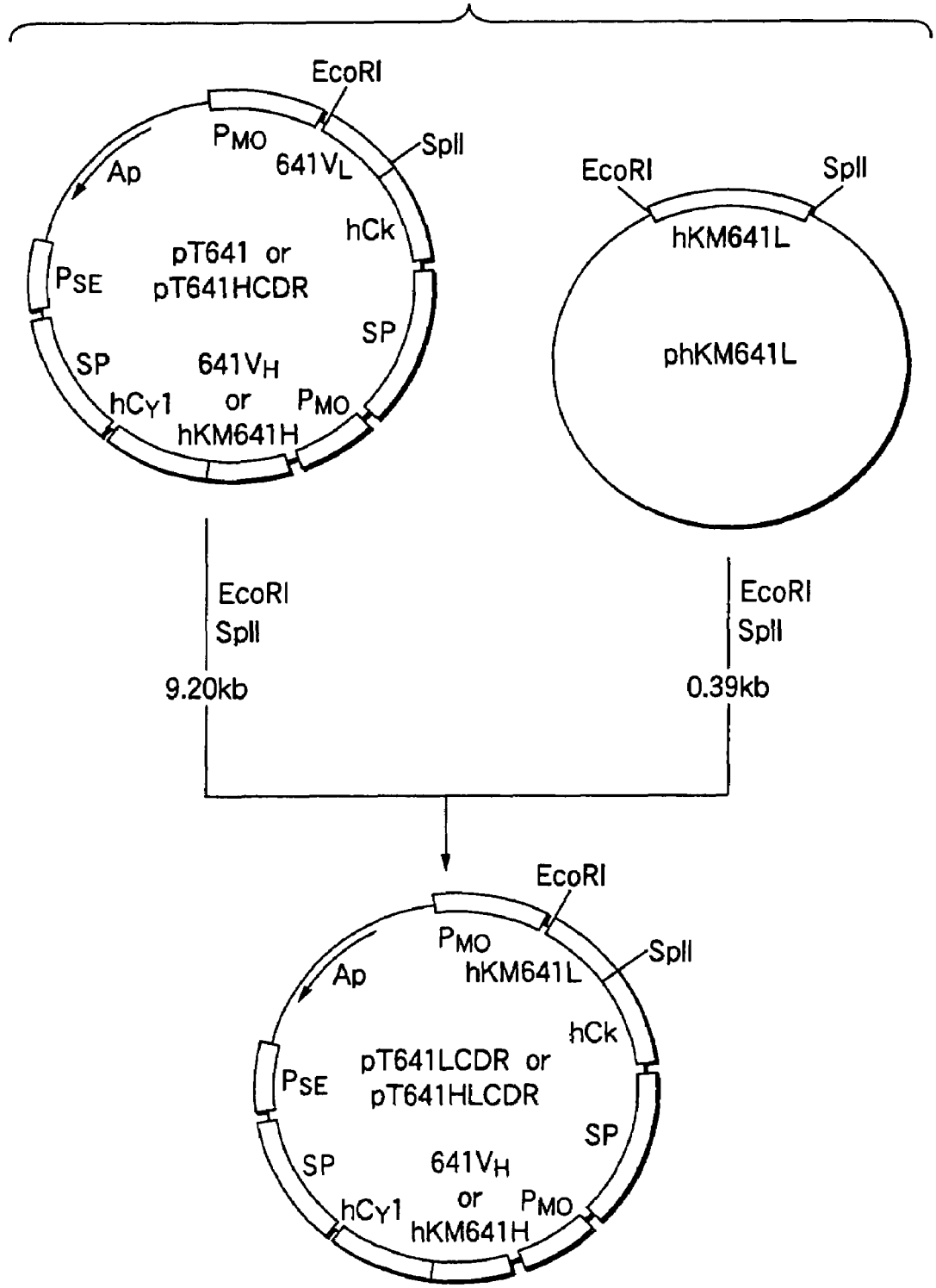
FIG. 7 is a drawing showing construction steps of plasmids pT641LCDR and pT641HLCDR.

Next, 0.1 μg of the EcoRI-SplI fragment derived from the plasmid phKM641L and 0.1 μg of the EcoRI-SplI fragment derived from the plasmid pT641, obtained in the above, were added to 20 μl in total volume of sterile water and ligated using Ready-To-Go T4 DNA Ligase (manufactured by Pharmacia). Also, 0.1 μg of the EcoRI-SplI fragment derived from the plasmid phKM641L and 0.1 μg of the EcoRI-SplI fragment derived from the plasmid pT641HCDR, obtained in the above, were added to 20 μl in total volume of sterile water and ligated using Ready-To-Go T4 DNA Ligase (manufactured by Pharmacia). Using each of the thus obtained recombinant plasmid DNA solutions, an *E. coli* HB101 was transformed to obtain the plasmids pT641LCDR and pT641HLCDR shown in FIG. 7.

(3) Activity Evaluation of Anti-GD3 Chimeric Antibody and Anti-GD3 CDR-Grafted Antibody by Transient Expression Using Animal Cells Transient expression of antibodies was carried out using the transient expression vector pT641 for anti-GD3 chimeric antibody, the transient expression vector pT641HLCDR for anti-GD3 CDR-grafted antibody and the transient expression vectors pT641HCDR and pT641LCDR for anti-GD3 hybrid antibodies having V regions of mouse antibody and human CDR-grafted antibody, obtained in the items 4(1) and (2) of Example 1.

Figure 8:
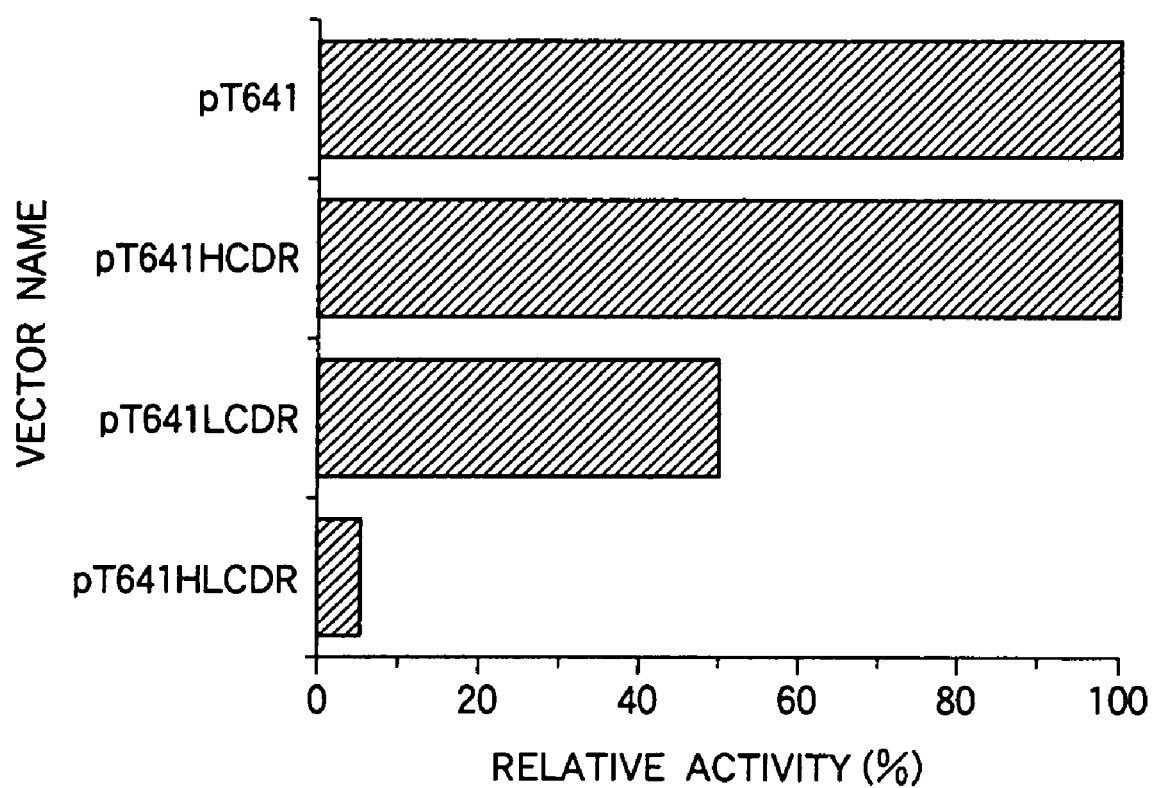
FIG. 8 is a drawing showing activity evaluation of an anti-GD3 chimeric anti-body and an anti-GD3 CDR-grafted antibody by their transient expression using plasmids pT641, pT641HCDR, pT641LCDR and pT641HLCDR. The ordinate and the abscissa represent the expression vector name and the relative activity (%) when the activity of anti-GD3 chimeric antibody is defined as 100, respectively.

COS-7 cells (ATCC CRL 1651) were dispensed in 2 ml at a density of 1×10$^5$ cells/ml into a 6 well plate (manufactured by Falcon) and cultured overnight at 37° C. By adding 2 μg of each expression vector to 100 μl of OPTI-MEM medium (manufactured by GIBCO BRL) and further adding a solution in which 10 μl of LIPOFECTAMINE Reagent (manufactured by GIBCO BRL) was added to 100 μl of the OPTI-MEM medium, the reaction was carried out at room temperature for 40 minutes to effect formation of a DNA-liposome complex. The overnight-cultured COS-7 cells were washed twice with 2 ml of the OPTI-MEM medium (manufactured by GIBCO BRL), mixed with a solution prepared by adding 0.8 ml of OPTI-MEM medium to the complex-containing solution and cultured at 37° C. for 7 hours, the solution was discarded and then the cells were mixed with 2 ml of 10% FBS-containing DME medium (manufactured by GIBCO BRL) and cultured at 37° C. After the introduction of each expression vector, the culture supernatant was recovered 72 hours thereafter and its concentration operation was carried out as occasion demands, and then binding activity of the anti-GD3 humanized antibody for GD3 (manufactured by DIA-IATRON) in the culture supernatant was measured by the ELISA method described in the item 2 of Example 1, by measuring concentration of the anti-GD3 humanized antibody in the culture supernatant by the ELISA method described in the item 4 which will be described later and calculating the activity from the measured values as relative activity (%) when the activity of the positive control anti-GD3 chimeric antibody is defined as 100. Results are shown in FIG. 8. As shown in FIG. 8, the anti-GD3 hybrid antibody derived from the transient expression vector pT641HCDR (VH is derived from a human CDR-grafted antibody and VL is derived from a chimeric antibody) showed almost the same binding activity of that of the anti-GD3 hybrid antibody derived from the transient expression vector pT641, but the anti-GD3 hybrid antibody derived from the transient expression vector pT641LCDR (VH is derived from a chimeric antibody and VL is derived from a human CDR-grafted antibody) showed a binding activity of about 50% of the anti-GD3 chimeric antibody. In addition, the anti-GD3 CDR-grafted antibody derived from the transient expression vector pT641HLCDR showed a binding activity of only about 5% of the anti-GD3 chimeric antibody, showing considerable decrease in the activity.

Based on these results, binding activity of the anti-GD3 CDR-grafted antibody having VH and VL designed in the item 3(1) of Example 1 is considerably reduced and the main cause of the activity reduction is considered to be due to VL, but since about 50% of the activity is found by its combination with the VH of anti-GD3 chimeric antibody, it was suggested that there is a problem particularly at the interaction region with VH. Accordingly, an attempt was made to increase the antibody activity by further modifying amino acid residues of the VL designed in the item 3(1) of Example 1.

(4) Measurement of the Concentration of Humanized Antibody in Transient Expression Culture Supernatant by ELISA Method A solution (50 μl) prepared by diluting a goat anti-human IgG (γ-chain) antibody (manufactured by Medical & Biological Laboratories) 400 folds with PBS was dispensed in each well of a 96 well plate for ELISA use (manufactured by Greiner) and allowed to react at 4° C. overnight. After discarding the antibody solution, 1% BSA-PBS was added in 100 μl/well and allowed to react at room temperature for 1 hour to thereby block the remaining active groups. After discarding 1% BSA-PBS, the transient expression culture supernatants obtained in the item 4(3) of Example 1 or diluted solutions of the purified anti-GD3 chimeric antibody KM871 were added in 50 μl/well and allowed to react at room temperature for 1 hour. After the reaction, each well was washed with Tween-PBS and then a solution prepared by diluting a peroxidase-labeled mouse anti-human κ L chain antibody (manufactured by Zymed) 500 folds with PBS was added in 50 μl/well and allowed to react at room temperature for 1 hour. After the reaction and subsequent washing with Tween-PBS, an ABTS substrate solution (a solution prepared by dissolving 0.55 g of 2,2'-azinobis(3-ethylbenzothiazoline-6-sulfonic acid) in 1 L of 0.1 M citrate buffer (pH 4.2) and adding 1 μl/ml of hydrogen peroxide just before the use) was added in 50 μl/well for color development and OD415 was measured.

5. Increase of the Binding Activity by Modifying Amino Acid Residues of VL of Anti-GD3 CDR-Grafted Antibody Increase of the binding activity by modifying amino acid residues of VL of the anti-GD3 CDR-grafted antibody designed in the item 3(1) of Example 1 was carried out as follows.

(1) Modification of Amino Acid Residues of VL of Anti-GD3 CDR-Grafted Antibody and Construction of cDNA Encoding the Modified VL First, amino acid residues which are amino acid residues positioned in the interaction region of VH and VL and amino acid residues considered to be exerting influence on the three-dimensional structure of each CDR of VL and are also different from the amino acid residues of mouse antibody in the VL of human CDR-grafted antibody were identified from computer models of the three-dimensional structures of various antibodies constructed in the item 3(1) of Example 1. As a result, the 7th position Ser, the 8th position Pro, the 12th position. Ser, the 41st position Gly, the 44th position Pro, the 72nd position Thr, the 77th position Ser, the 83rd position Phe and the 87th Tyr of hKM641L as the amino acid sequence of VL of anti-GD3 CDR-grafted antibody represented by SEQ ID NO:10 were identified. By replacing these amino acid residues by amino acid residues found in the mouse antibody, 8 VLs of modified anti-GD3 CDR-grafted antibody were designed. That is, the 8th position Pro, the 12th position Ser, the 44th position Pro and the 87th position Tyr among the hKM641L amino sequence were respectively replaced by Ala, Pro, Val and Phe in the case of hKM641NL, and the 7th position Ser, the 8th position Pro and the 12th position Ser among the hKM641L amino sequence respectively by Thr, Ala and Pro in the case of hKM641Lm-1, the 87th position Tyr among the hKM641L amino sequence by Phe in the case of hKM641Lm-4, the 41st position Gly and the 44th position Pro among the hKM641L amino sequence respectively by Asp and Val in the case of hKM641Lm-6, the 72nd position Thr, the 77th position Ser and the 83rd position Phe among the hKM641L amino sequence respectively by Ser, Asn and Ile in the case of hKM641Lm-7, the 77th position Ser among the hKM641L amino sequence by Asn in the case of hKM641Lm-8, the 83rd position Phe and the 87th position Tyr among the hKM641L amino sequence respectively by Ile and Phe in the case of hKM641Lm-9, and the 41st position Gly, the 44th position Pro and the 83rd position Phe among the hKM641L amino sequence respectively by Asp, Val and Ile in the case of hKM641Lm-69. Among these modified VLs, cDNA encoding each of 6 modified VLs excluding hKM641NL and hKM641Lm-69 was constructed as follows by PCR-aided mutagenesis. That is, antisense chain and sense chain DNA primers were synthesized using an automatic DNA synthesizer (380A, manufactured by Applied Biosystems) for introducing mutation, and a first PCR was carried out in accordance with the method described in the item 3(2) of Example 1 using 1 ng of the plasmid phKM641L as the template and 0.5 μM in final concentration of M13 primer RV (manufactured by Takara Shuzo) and the antisense chain DNA primer and M13 primer M4 (manufactured by Takara Shuzo) and the sense chain DNA primer. Each of the reaction solutions was purified using QIAquick PCR Purification Kit (manufactured by QIAGEN) in accordance with the manufacture's instructions by eluting with 20 μl of 10 mM Tris-HCl (pH 8.0), and then a second PCR was carried out using 5 μl of each eluate in accordance with the method described in the item 3(2) of Example 1. The reaction solution was purified using QIAquick PCR Purification Kit (manufactured by QIAGEN) in accordance with the manufacture's instructions and made into 30 μl of a buffer comprising 50 mM Tris-HCl (pH 7.5), 100 mM sodium chloride, 10 mM magnesium chloride, 1 mM DTT and 100 μg/ml BSA, and 10 units of a restriction enzyme EcoRI (manufactured by Takara Shuzo) and a restriction enzyme SplI (manufactured by Takara Shuzo) were further added thereto to carry out the reaction at 37° C. for 1 hour. The reaction solution was fractionated by agarose gel electrophoresis to recover about 0.2 μg of an EcoRI-SplI fragment of about 0.39 kb using QIAquick Gel Extraction Kit (manufactured by QIAGEN) in accordance with the manufacturers instructions.

Next, 0.1 μg of the EcORI-SplI fragment of the PCR product of VL of the modified anti-GD3 CDR-grafted antibody obtained in the above and 0.1 μg of the EcoRI-SplI fragment of the plasmid pBSL3 obtained in the item 3(3) of Example 1 were added to 20 μl in total volume of sterile water and ligated using Ready-To-Go T4 DNA Ligase (manufactured by Pharmacia). Using the thus obtained recombinant plasmid DNA solution, an E. coli HB101 was transformed. Each plasmid DNA was produced from 10 clones of the transformants, allowed to react in accordance with the manufacture's instructions attached to AutoRead Sequencing Kit (manufactured by Pharmacia) and then subjected to electrophoresis using A.L.F. DNA Sequencer (manufactured by Pharmacia) to determine the nucleotide sequence to thereby obtain a plasmid having cDNA to which the intended modification was applied.

Specifically, a plasmid phKM641Lm-1 having the nucleotide sequence represented by SEQ ID NO:27 was obtained by carrying out a series of the above operations using the synthetic DNA of SEQ ID NO:25 as the antisense chain DNA primer and the synthetic DNA of SEQ ID NO:26 as the sense chain DNA primer. The hKM641Lm-1 as an amino acid sequence encoded by the nucleotide sequence is also represented by SEQ ID NO:27.

A plasmid phKM641Lm-4 having the nucleotide sequence represented by SEQ ID NO:30 was obtained by carrying out a series of the above operations using the synthetic DNA of SEQ ID NO:28 as the antisense chain DNA primer and the synthetic DNA of SEQ ID NO:29 as the sense chain DNA primer. The hKM641Lm-4 as an amino acid sequence encoded by the nucleotide sequence is also represented by SEQ ID NO:30.

A plasmid phKM641Lm-6 having the nucleotide sequence represented by SEQ ID NO:33 was obtained by carrying out a series of the above operations using the synthetic DNA of SEQ ID NO:31 as the antisense chain DNA primer and the synthetic DNA of SEQ ID NO:32 as the sense chain DNA primer. The hKM641Lm-6 as an amino acid sequence encoded by the nucleotide sequence is also represented by SEQ ID NO:33.

A plasmid phKM641Lm-7 having the nucleotide sequence represented by SEQ ID NO:36 was obtained by carrying out a series of the above operations using the synthetic DNA of SEQ ID NO:34 as the antisense chain DNA primer and the synthetic DNA of SEQ ID NO:35 as the sense chain DNA primer. The hKM641Lm-7 as an amino acid sequence encoded by the nucleotide sequence is also represented by SEQ ID NO:36.

A plasmid phKM641Lm-8 having the nucleotide sequence represented by SEQ ID NO:39 was obtained by carrying out a series of the above operations using the synthetic DNA of SEQ ID NO:37 as the antisense chain DNA primer and the synthetic DNA of SEQ ID NO:38 as the sense chain DNA primer. The hKM641Lm-8 as an amino acid sequence encoded by the nucleotide sequence is also represented by SEQ ID NO:39.

A plasmid phKM641Lm-9 having the nucleotide sequence represented by SEQ ID NO:42 was obtained by carrying out a series of the above operations using the synthetic DNA of SEQ ID NO:40 as the antisense chain DNA primer and the synthetic DNA of SEQ ID NO:41 as the sense chain DNA primer. The hKM641Lm-9 as an amino acid sequence encoded by the nucleotide sequence is also represented by SEQ ID NO:42.

Among the modified VLs, cDNA encoding the hKM641NL was constructed by synthesizing 6 synthetic DNA fragments of SEQ ID NOs:17, 22 and 43 to 46 using an automatic DNA synthesizer (380A, manufactured by Applied Biosystems) and carrying out the procedure described in the item 3(3) of Example 1 using these fragments. As a result, a plasmid phKM641NL having the nucleotide sequence represented by SEQ ID NO:47 in which the modification of interest was effected was obtained. The hKM641NL as an amino acid sequence encoded by the nucleotide sequence is also represented by SEQ ID NO:47.

Among the modified VLs, cDNA encoding the hKM641Lm-69 was constructed as follows using the plasmids phKM641Lm-6 and phKM641Lm-9 having cDNA of modified VL obtained in the above.

First, 3 μg of the plasmid phKM641Lm-6 was added to 10 μl of a buffer comprising 50 mM Tris-HCl (pH 7.5), 100 mM of sodium chloride, 10 mM magnesium chloride and 1 mM DTT and 10 units of restriction enzymes EcoRI (manufactured by Takara Shuzo) and PstI (manufactured by Takara Shuzo) were further added thereto to carry out the reaction at 37° C. for 1 hour. The reaction solution was fractionated by agarose gel electrophoresis to recover about 0.3 μg of an EcoRI-PstI fragment of about 0.30 kb using QIAquick Gel Extraction Kit (manufactured by QIAGEN) in accordance with the manufacture's instructions.

Next, 3 μg of the plasmid phKM641Lm-9 was added to 10 μl of a buffer comprising 50 mM Tris-HCl (pH 7.5), 100 mM of sodium chloride, 10 mM magnesium chloride and 1 mM DTT and 10 units of restriction enzymes EcoRI (manufactured by Takara Shuzo) and PstI (manufactured by Takara Shuzo) were further added thereto to carry out the reaction at 37° C. for 1 hour. The reaction solution was fractionated by agarose gel electrophoresis to recover about 2 μg of an EcoRI-PstI fragment of about 3.05 kb using QIAquick Gel Extraction Kit (manufactured by QIAGEN) in accordance with the manufacture's instructions.

Figure 9:
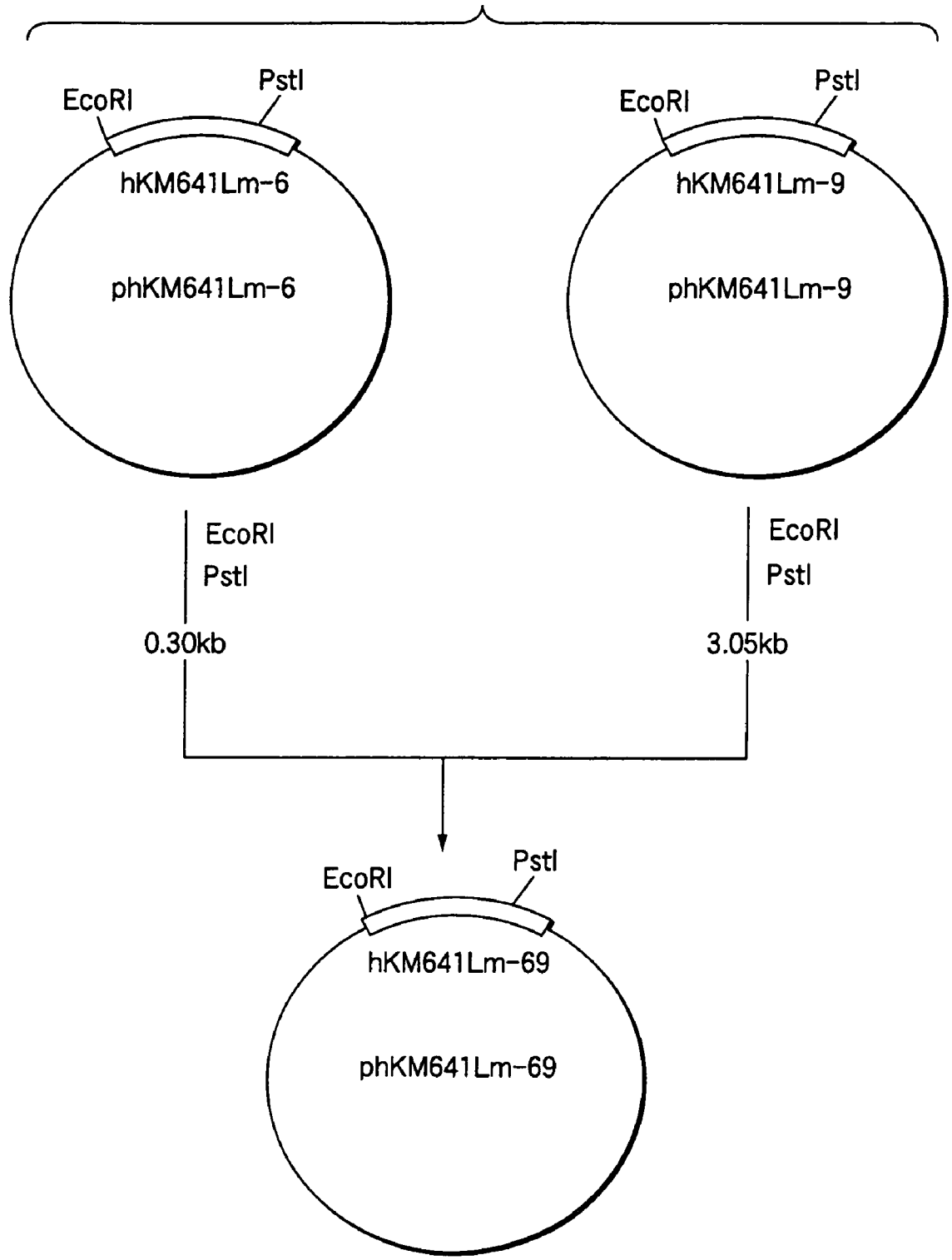
FIG. 9 is a drawing showing construction steps of plasmid phKM641Lm-69.

Next, 0.1 μg of the EcoRI-PstI fragment derived from the plasmid phKM641LM-6 and 0.1 μg of the EcoRI-PstI fragment derived from the plasmid phKM641Lm-9, both obtained in the above, were added to 20 μl in total volume of sterile water and ligated using Ready-To-Go T4 DNA Ligase (manufactured by Pharmacia). Using the thus obtained recombinant plasmid DNA solution, an E. coli HB101 was transformed to obtain the plasmid phKM641Lm-69 shown in FIG. 9. The reaction was carried out using 10 μg of the thus obtained plasmid in accordance with the manufacture's instructions attached to AutoRead Sequencing Kit (manufactured by Pharmacia) and then the resulting mixture was subjected to electrophoresis using A.L.F. DNA Sequencer (manufactured by Pharmacia) to determine the nucleotide sequence, and as a result, it was confirmed that it has the nucleotide sequence represented by SEQ ID NO:48 in which the modification of interest was carried out. The hKM641LM-69 as an amino acid sequence encoded by the nucleotide sequence is also represented by SEQ ID NO:48.

(2) Construction of Transient Expression Vector for Anti-GD3 CDR-Grafted Antibodies Having Modified VL Transient expression vectors for anti-GD3 CDR-grafted antibodies having various modified VLs were constructed as follows using the plasmids having cDNA molecules encoding various modified VLs, obtained in the item 5(1) of Example 1, and the transient expression vector pT641HCDR for anti-GD3 hybrid antibodies obtained in the item 4(2) of Example 1.

First, 3 μg of each of the plasmids phKM641NL, phKM641Lm-1, phKM641Lm-4, phKM641Lm-6, phKM641Lm-7, phKM641Lm-8, phKM641Lm-9 and phKM641Lm-69 obtained in the item 5(1) of Example 1 was added to 10 μl of a buffer comprising 50 mM Tris-HCl (pH 7.5), 100 mM of sodium chloride, 10 mM magnesium chloride, 1 mM DTT and 100 μg/ml of BSA, and 10 units of a restriction enzyme EcoRI (manufactured by Takara Shuzo) and a restriction enzyme SpII (manufactured by Takara Shuzo) were further added thereto to carry out the reaction at 37° C. for 1 hour. The reaction solution was fractionated by agarose gel electrophoresis to recover about 0.2 μg of an EcoRI-SpII fragment of about 0.39 kb using QIAquick Gel Extraction Kit (manufactured by QIAGEN) in accordance with the manufacture's instructions.

Figure 10:
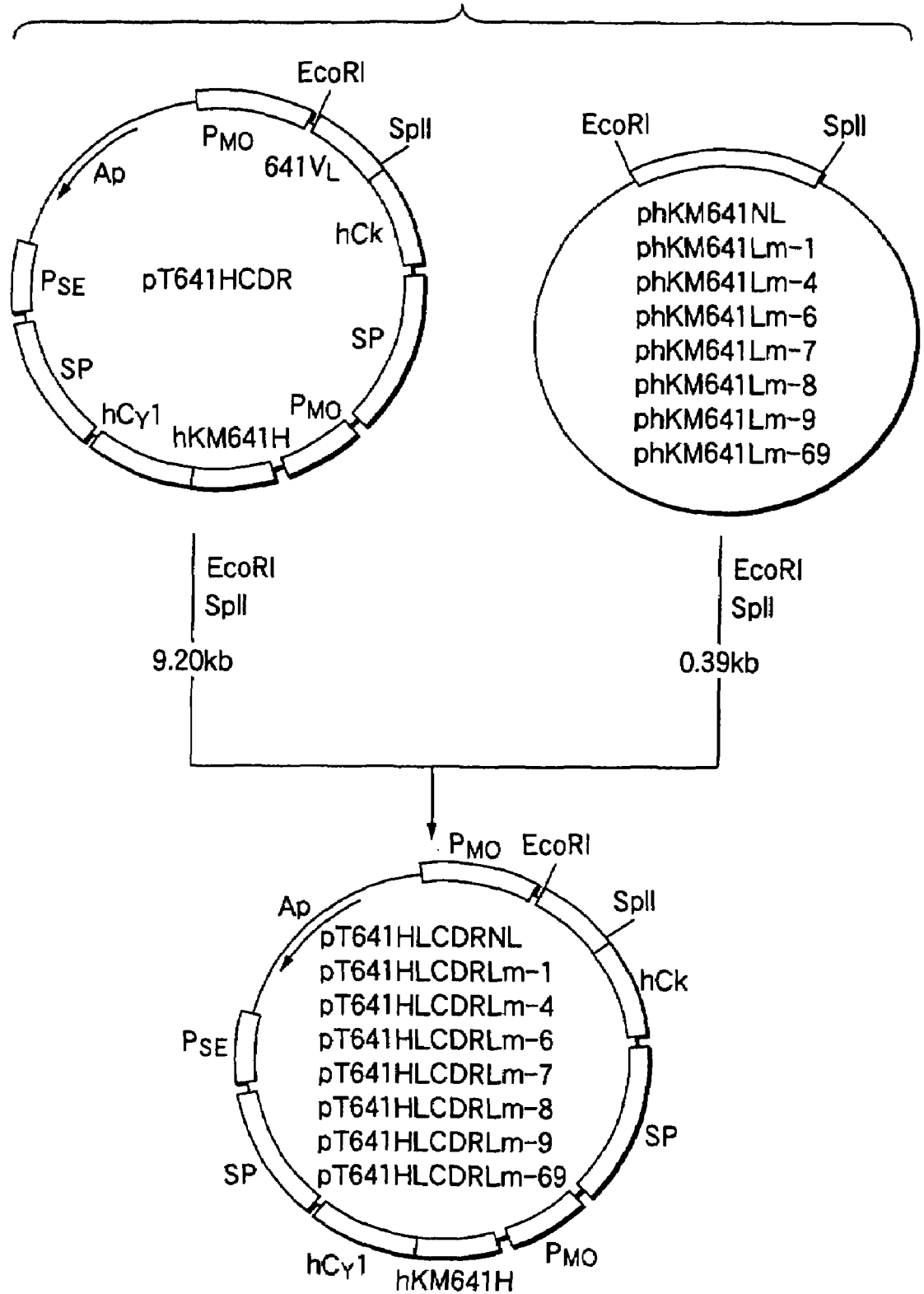
FIG. 10 is a drawing showing construction steps of plasmids pT641HLCDRNL, pT641HLCDRLm-1, pT641HLCDRLm-4, pT641HLCDRLm-6, pT641HLCDRLm-7, pT641HLCDRLm-8, pT641HLCDRLm-9 and pT641HLCDRLm-69.

Next, 0.1 μg of each of the thus obtained EcoRI-SpII fragments of various modified VLs and 0.1 μg of the EcoRI-SpII fragment of the transient expression vector pT641HCDR for anti-GD3 hybrid antibody obtained in the item 4(2) of Example 1, were added to 20 μl in total volume of sterile water and ligated using Ready-To-Go T4 DNA Ligase (manufactured by Pharmacia). Using the thus obtained respective recombinant plasmid DNA solutions, an E. coli HB101 was transformed to obtain the transient expression vectors for anti-GD3 CDR-grafted antibodies having various modified VLs, pT641HLCDRNL, pT641HLCDRLm-1, pT641HLCDRLm-4, pT641HLCDRLm-6, pT641HLCDRLm-7, pT641HLCDRLm-8, pT641HLCDRLm-9 and pT641HLCDRLm-69, shown in FIG. 10.

Figure 11:
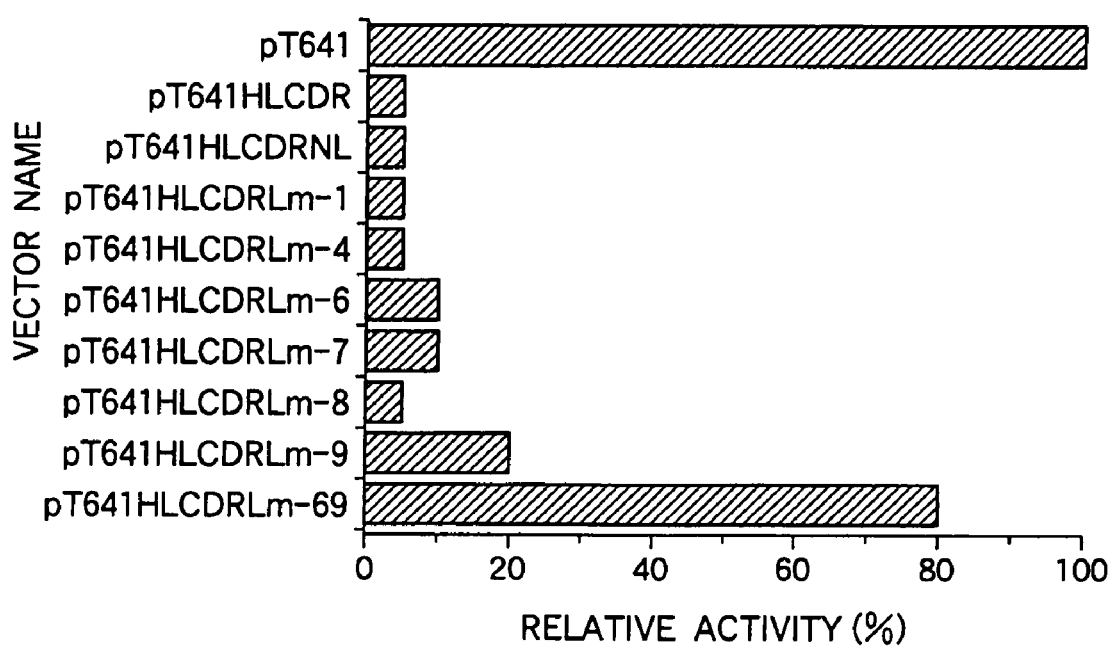
FIG. 11 is a drawing showing activity evaluation of anti-GD3 chimeric antibody and anti-GD3 CDR-grafted antibody by their transient expression using plasmids pT641, pT641HLCDR, pT641HLCDRNL, pT641HLCDRLm-1, pT641HLCDRLm-4, pT641HLCDRLm-6, pT641HLCDRLm-7, pT641HLCDRLm-8, pT641HLCDRLm-9 and pT641HLCDRLm-69. The ordinate and the abscissa represent the expression vector name and the relative activity (%) when the activity of anti-GD3 chimeric antibody is defined as 100, respectively.

(3) Evaluation of Activity of Anti-GD3 CDR-Grafted Antibody Having Modified VLs by Transient Expression Using Animal Cell Transient expression and evaluation of activity of each antibody were carried out in accordance with the method described in the item 4(3) of Example, 1 using the transient expression vector pT641 for ant-GD3 chimeric antibody and the transient expression vector pT641HLCDR for anti-GD3 CDR-grafted antibody, both obtained in the item 4(2) of Example 1, and the transient expression vectors, pT641HLCDRNL, pT641HLCDRLm-1, pT641HLCDRLm-4, pT641HLCDRLm-6, pT641HLCDRLm-7, pT641HLCDRLm-8, pT641HLCDRLm-9 and pT641HLCDRLm-69, for anti-GD3 CDR-grafted antibodies having various modified VLs, obtained in the item 5(2) of Example 1. Results are shown in FIG. 11. As shown in FIG. 11, the modified anti-GD3 CDR-grafted antibodies derived from the transient expression vectors, pT641HLCDRLm-6, pT641HLCDRLm-7, pT6411HLCDRLm-9 and pT641HLCDRLm-69, showed increased binding activity in comparison with the anti-GD3 CDR-grafted antibodies before modification, particularly, the modified anti-GD3 CDR-grafted antibody derived from the transient expression vector pT641HLCDRLm-69 showed its binding activity of about 80% of the anti-GD3 chimeric antibody. On the other hand, the modified anti-GD3 CDR-grafted antibodies derived from other transient expression vectors showed no increase in the binding activity in comparison with the anti-GD3 CDR-grafted antibodies before modification. Based on these results, it was found that, among the modified amino acid residues of VL identified in the item 5(1) of Example 1, the 41st position, 44th position, 83rd position and 87th position amino acid residues greatly contribute to the increase of binding activity. It was also found that simultaneous substitution of two amino acid residues of the 41st position and 44th position or the 83rd position and 87th position contributes to synergistic increase in the activity, and simultaneous modification of four amino acid residues of the 41st position, 44th position, 83rd position and 87th position also contributes to synergistic increase in the activity. Based on the computer models of three-dimensional structures of V regions of various antibodies constructed in the item 3(1) of Example 1, it was suggested that the 41st position and 44th position amino acid residues exert influence on the interaction with VH, and the 83rd position and 87th position amino acid residues on the three-dimensional structure of CDR3 of VL, and it was considered that three-dimensional structure of an antibody as a whole is suitably maintained by modifying these amino acid residues into amino acid residues found in a mouse antibody and, as a result, its binding activity increases. This information shows that it is necessary to take the interaction regions of VH and VL also into consideration in preparing human CDR-grafted antibodies and that it is necessary to carry out various examinations on the identification of these interaction regions based on the information from three-dimensional structures of antibody V regions. With regard to these interaction regions, it can be easily analogize that they are different in individual antibodies and it is difficult to find a general law at present, so that it is necessary to carry out trial and error in response to each antibody of interest.

6. Stable Expression of Anti-GD3 CDR-Grafted Antibody Using Animal Cell

Based on the results described in the item 5(3) of Example 1, it was suggested that the anti-GD3 CDR-grafted antibodies derived from transient expression vectors pT641HLCDRLm-9 and pT641HLCDRLm-69 have about 20% and about 80% of binding activity for GD3, respectively, in comparison with anti-GD3 chimeric antibodies. Accordingly, in order to evaluate the activity of these anti-GD3 CDR-grafted antibodies more in detail, transformed cell lines capable of stably expressing anti-GD3 CDR-grafted antibodies were obtained by the following method, and purification of anti-GD3 CDR-grafted antibodies from culture supernatants of the transformed cell lines was carried out. Also, for comparison, stable expression and purification of the anti-GD3 CDR-grafted antibody derived from the transient expression vector pT641HLCDR were carried out in the same manner.

(1) Construction of Stable Expression Vector for Anti-GD3 CDR-Grafted Antibody

Stable expression vectors were constructed by introducing a resistance gene against an agent G418 and the dhfr gene into various transient expression vectors constructed in the item 5(2) of Example 1.

First, 3 μg of the humanized antibody expression vector pKANTEX93 described in WO 97/10354 was added to 10 μl of a buffer comprising 20 mM Tris-HCl (pH 8.5), 10 mM magnesium chloride, 1 mM DTT and 100 mM potassium chloride, and 10 units of a restriction enzyme BamHI (manufactured by Takara Shuzo) and a restriction enzyme XhoI (manufactured by Takara Shuzo) were further added thereto to carry out the reaction at 37° C. for 1 hour. The reaction solution was fractionated by agarose gel electrophoresis to recover about 1 μg of a BamHI-XhoI fragment of about 8.68 kb using QIAquick Gel Extraction Kit (manufactured by QIAGEN) in accordance with the manufacture's instructions.

Next, 3 μg of each of the transient expression vectors, pT641HLCDRLm-9, pT641HLCDRLm-69 and pT641HLCDR, was added to 10 μl of a buffer comprising 20 mM Tris-HCl (pH 8.5), 10 mM magnesium chloride, 1 mM DTT and 100 mM potassium chloride, and 10 units of a restriction enzyme BamHI (manufactured by Takara Shuzo), a restriction enzyme XhoI (manufactured by Takara Shuzo) and a restriction enzyme StuI (manufactured by Takara Shuzo) were further added thereto to carry out the reaction at 37° C. for 1 hour. The reaction solution was fractionated by agarose gel electrophoresis to recover about 1 μg of a BamHI-XhoI fragment of about 4.90 kb using QIAquick Gel Extraction Kit (manufactured by QIAGEN) in accordance with the manufacture's instructions.

Figure 12:
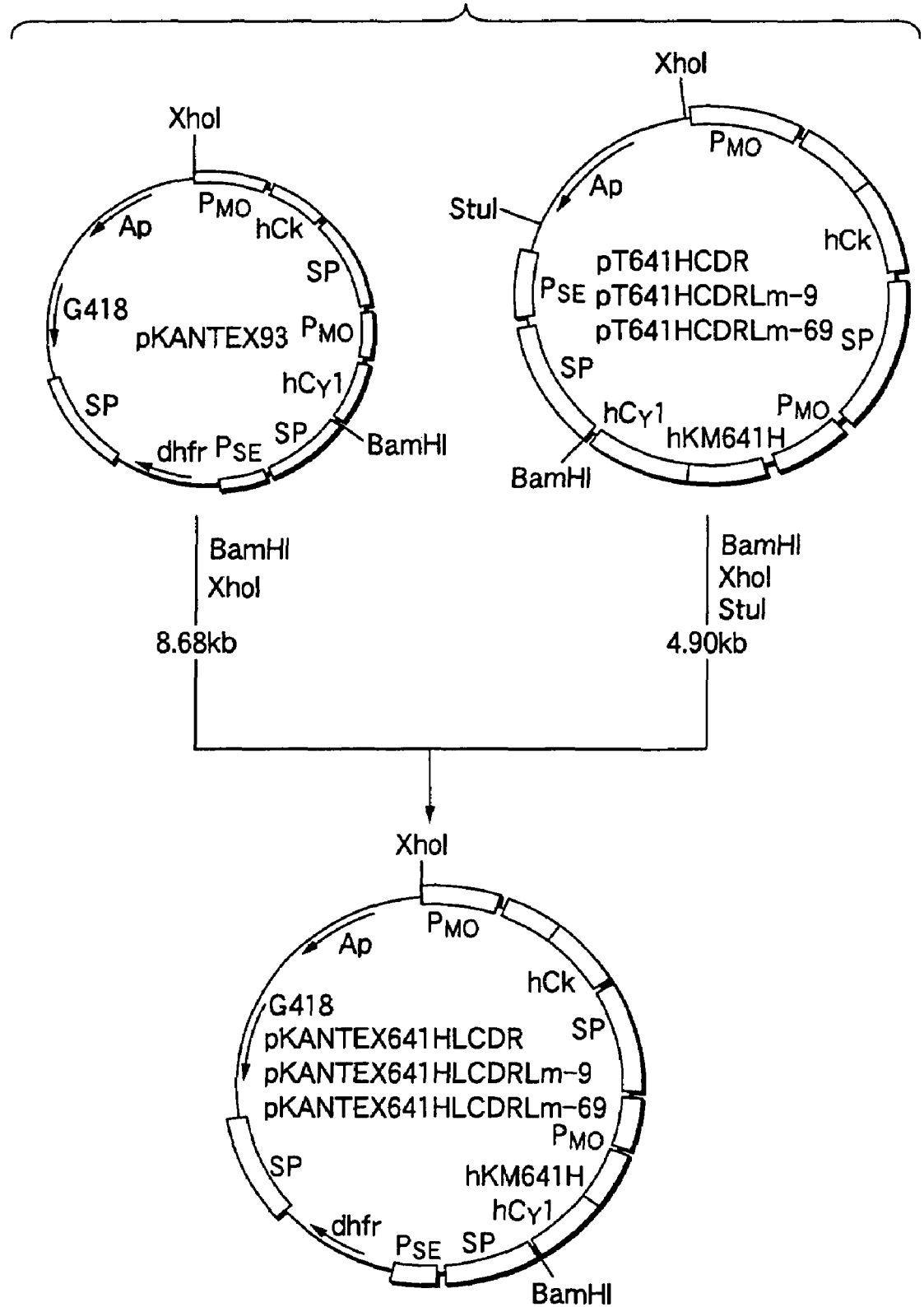
FIG. 12 is a drawing showing construction steps of plasmids pKANTEX641HLCDR, pKANTEX641HLCDRLm-9 and pKANTEX641HLCDRLm-69.

Next, 0.1 μg of the BamHI-XhoI fragment derived from the plasmid pKANTEX93 and 0.1 μg of the BamHI-XhoI fragment derived from each of the transient expression vectors, obtained in the above, were added to 20 μl in total volume of sterile water and ligated using Ready-To-Go T4 DNA Ligase (manufactured by Pharmacia). Using each of the thus obtained recombinant plasmid DNA solutions, an *E. coli* HB100 was transformed to obtain the anti-GD3 CDR-grafted antibody stable expression vectors, pKANTEX641HLCDRLm-9, pKANTEX641HLCDRLm-69 and pKANTEX641HLCDR, shown in FIG. 12.

(2) Stable Expression of Anti-GD3 CDR-Grafted Antibody Using Animal Cell

Using the various stable expression vectors for anti-GD3 CDR-grafted antibody obtained in the item 6(1) of Example 1, expression of anti-GD3 CDR-grafted antibody in animal cells was carried out as follows.

Each of the anti-GD3 CDR-grafted antibody expression vectors (4 μg) was introduced into $4 \times 10^6$ cells of a rat myeloma cell line YB2/0 cell (ATCC CRL 1662) by the electroporation method (*Cytotechnology*, 3, 133 (1990)), and the cells were suspended in 40 ml of RPMI640-FBS(19) (RPMI1640 medium containing 10% of fetal bovine serum (FBS)) and dispensed in 200 μl/well into a 96 well microtiter plate (manufactured by Sumitomo Bakelite). After culturing at 37° C. for 24 hours in a 5% $CO_2$ incubator, G418 was added to give a concentration of 0.5 mg/ml, followed by culturing for 1 to 2 weeks. Culture supernatants were recovered from wells in which colonies of transformants showing G418-resistance were formed and became confluent, and the antigen binding activity of various anti-GD3 CDR-grafted antibodies in the supernatants was measured by the ELISA shown in the item 2 of Example 1 (a peroxidase-labeled goat anti-human IgG(γ) antibody was used as the secondary antibody).

With regard to the transformants of wells in which expression of anti-GD3 CDR-grafted antibodies was found in the culture supernatants, in order to increase antibody expression quantity making use of a dhfr gene amplification system, they were suspended in the RPMI1640-FBS(10) medium containing 0.5 mg/ml of G418 and 50 nM methotrexate (hereinafter referred to as "MTX": manufactured by SIGMA) as an inhibitor of the dhfr gene product dihydrofolate reductase (hereinafter referred to as "DHFR") to give a density of 1 to $2 \times 10^5$ cells/ml, and dispensed in 2 ml into a 24 well plate (manufactured by Greiner). By culturing at 37° C. for 1 to 2 weeks in a 5% $CO_2$ incubator, transformants showing 50 nM MTX resistance were induced. When the transformants became confluent, the antigen binding activity of various anti-GD3 CDR-grafted antibodies in the supernatants was measured by the ELISA shown in the item 2 of Example 1. With regard to the transformants of wells in which expression of anti-GD3 CDR-grafted antibodies was found in the culture supernatants, the MTX concentration was increased to 100 nM and then to 200 nM by the method similar to the above, and transformants capable of growing in the RPMI1640-FBS(10) medium containing 0.5 mg/ml of G418 and 200 nM of MTX and of highly expressing anti-GD3 CDR-grafted antibodies were finally obtained. With regard to the thus obtained transformants, single cell isolation (cloning) was carried out twice by limiting dilution analysis. The transformed cell clones obtained by introducing the stable expression vectors, pKANTEX641HLCDRLm-9, pKANTEX641HLCDRLm-69 and pKANTEX641HLCDR, were named KM8870, KM8871 and KM8869, respectively, and expression levels of anti-GD3 CDR-grafted antibody by transformed cell clones were about 5 μg/$10^6$ cells/24 hr, about 10 μg/$10^6$ cells/24 hr and about 30 μg/$10^6$ cells/24 hr, respectively.

(3) Purification of Anti-GD3 CDR-Grafted Antibody from Culture Filtrate

Figure 13:
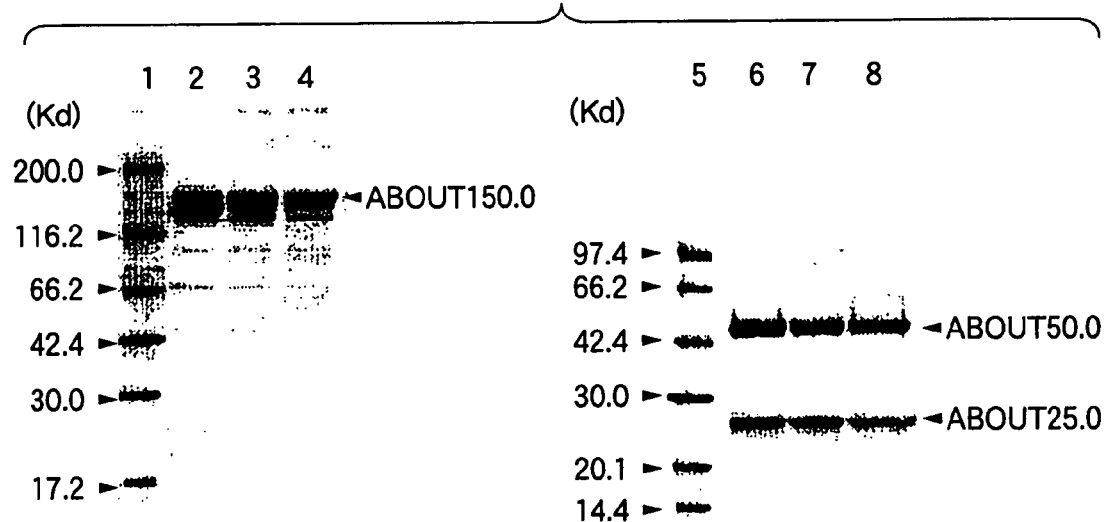
FIG. 13 is a drawing showing SDS-PAGE (using a 4 to 15% gradient gel) electrophoresis patterns of purified anti-GD3 CDR-grafted antibodies KM8869, KM8870 and KM8871. The left side shows results of electrophoresis carried out under non-reducing conditions, and the right side shows those under reducing conditions. Lanes 1, 2, 3, 4, 5, 6, 7 and 8 show electrophoresis patterns of high molecular weight markers, KM8869, KM8870, KM8871, low molecular weight markers, KM8869, KM8870 and KM8871, respectively.

Each of the transformed cell clones, KM8870, KM8871 and KM8869, obtained in the item 6(2) of Example 1 which express various anti-GD3 CDR-grafted antibodies was suspended in GIT medium (manufactured by Nippon Pharmaceutical) containing 200 nM MTX to give a density of 1 to $2 \times 10^5$ cells/ml, and dispensed in 200 ml into 175 cm² flasks (manufactured by Greiner). The cells were cultured at 37° C. for 5 to 7 days until they became confluent and then the culture supernatant was recovered. Each anti-GD3 CDR-grafted antibody was purified from the culture supernatant using Prosep-A (manufactured by Bioprocessing) column in accordance with the manufacture's instructions. About 3 mg of anti-GD3 CDR-grafted antibody KM8870 was obtained from 500 ml of the culture supernatant of KM8870, and about 25 mg of anti-GD3 CDR-grafted antibody KM8871 from 1,600 ml of the culture supernatant of KM8871 and about 65 mg of anti-GD3 CDR-grafted antibody KM8869 from 1,000 ml of the culture supernatant of KM8869. About 4 μg of each of the thus obtained anti-GD3 CDR-grafted antibodies was subjected to an electrophoresis in accordance with the known method (*Nature*, 227, 680 (1970)) to examine its molecular weight and purification degree. Results are shown in FIG. 13. As shown in FIG. 13, molecular weight of each purified anti-GD3 CDR-grafted antibody was about 150 kilodaltons (hereinafter referred to as "Kd") under non-reducing conditions, and two bands of about 50 Kd and about 25 Kd were found under reducing conditions. The molecular weights almost coincided with the molecular weights deduced from the cDNA nucleotide sequences of H chain and L chain of the antibody (H chain: about 49 Kd, L chain: about 24 Kd, whole molecule: about 146 Kd), and also coincided with the reports that the IgG type antibody has a molecular weight of about 150 Kd under non-reducing conditions and is degraded into E chains having a molecular weight of about 50 Kd and L chains a molecular weight of about 25 Kd under reducing conditions due to cutting of the disulfide bond (hereinafter referred to as "S—S bond") in the molecule (*Antibodies: A Laboratory Manual, Monoclonal Antibodies: Principles and Practice*), so that it was confirmed that each anti-GD3 CDR-grafted antibody was expressed as an antibody molecule of a correct structure. Also, when N-terminal amino acid sequences of the H chain and L chain of each of the purified anti-GD3 CDR-grafted antibodies were analyzed by Edman degradation using a protein sequencer (470A, manufactured by Applied Biosystems), it was confirmed that they coincide with the H chain and L chain N-terminal amino acid sequences deduced from respective cDNA nucleotide sequences.

7. Evaluation of Activity of Anti-GD3 CDR-Grafted Antibody (1) Reactivity of Anti-GD3 CDR-Grafted Antibody with GD3 (ELISA)

Figure 14:
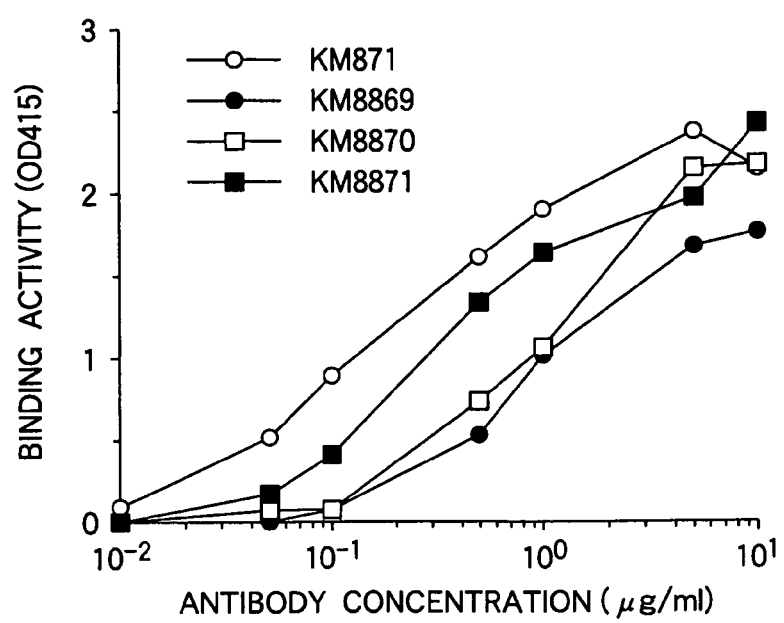
FIG. 14 is a drawing showing binding activity of purified anti-GD3 chimeric antibody KM871 and purified anti-GD3 CDR-grafted antibodies KM8869, KM8870 and KM8871 to GD3 measured by changing the antibody concentration. The ordinate and the abscissa are the binding activity to GD3 and the antibody concentration, respectively. "○", "●", "□" and "■" show the activities of KM871, KM8869, KM8870 and KM8871, respectively.
Figure 15:
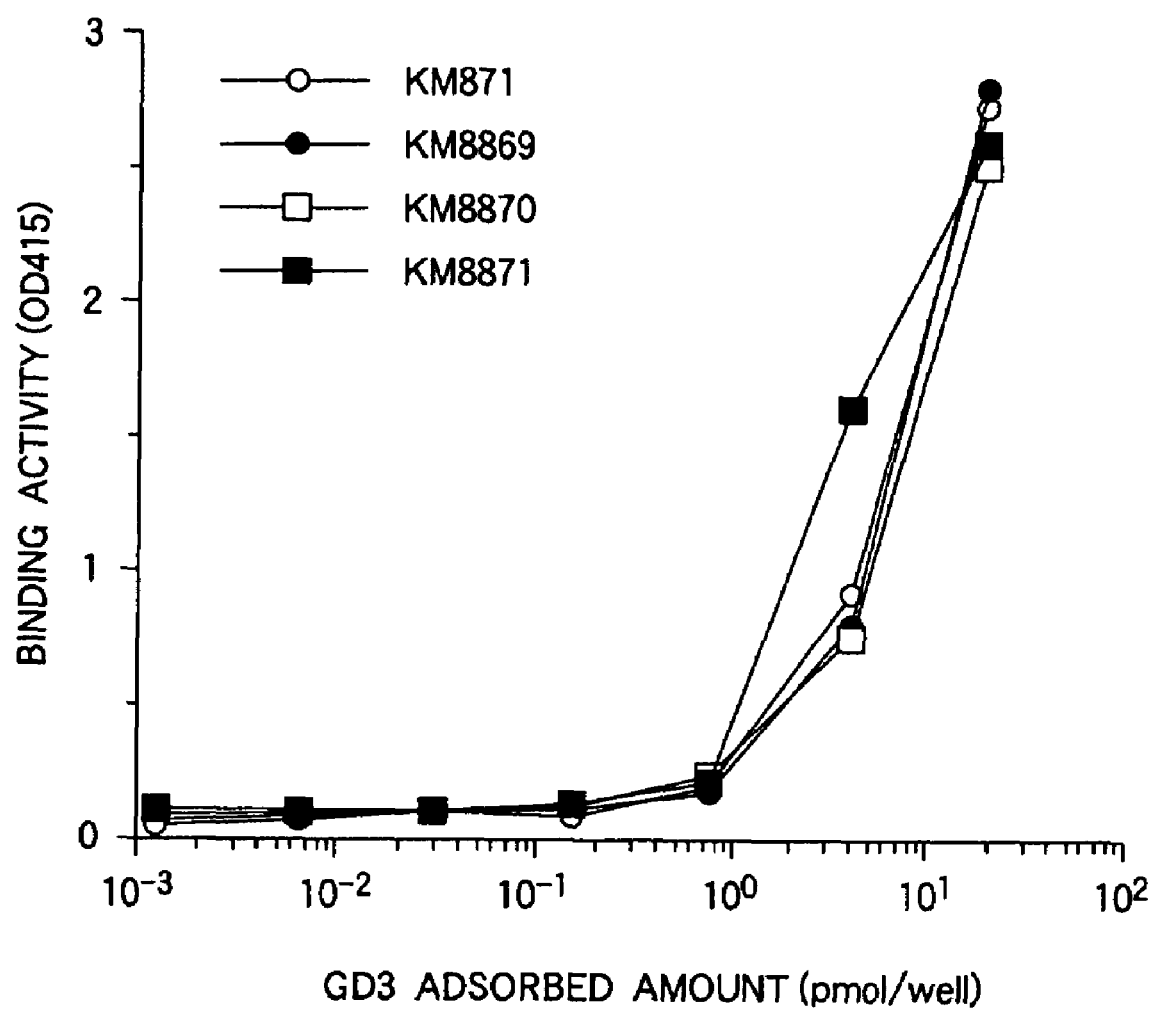
FIG. 15 is a drawing showing binding activity of purified anti-GD3 chimeric antibody KM871 and purified anti-GD3 CDR-grafted antibodies KM8869, KM8870 and KM8871 to GD3 measured by changing an amount of GD3 to be adsorbed to a plate. The ordinate and the abscissa are the binding activity to GD3 and the amount of GD3 adsorbed to the plate, respectively. "○", "●", "□" and "■" show the activities of KM871, KM8869, KM8870 and KM8871, respectively.
Figure 16:
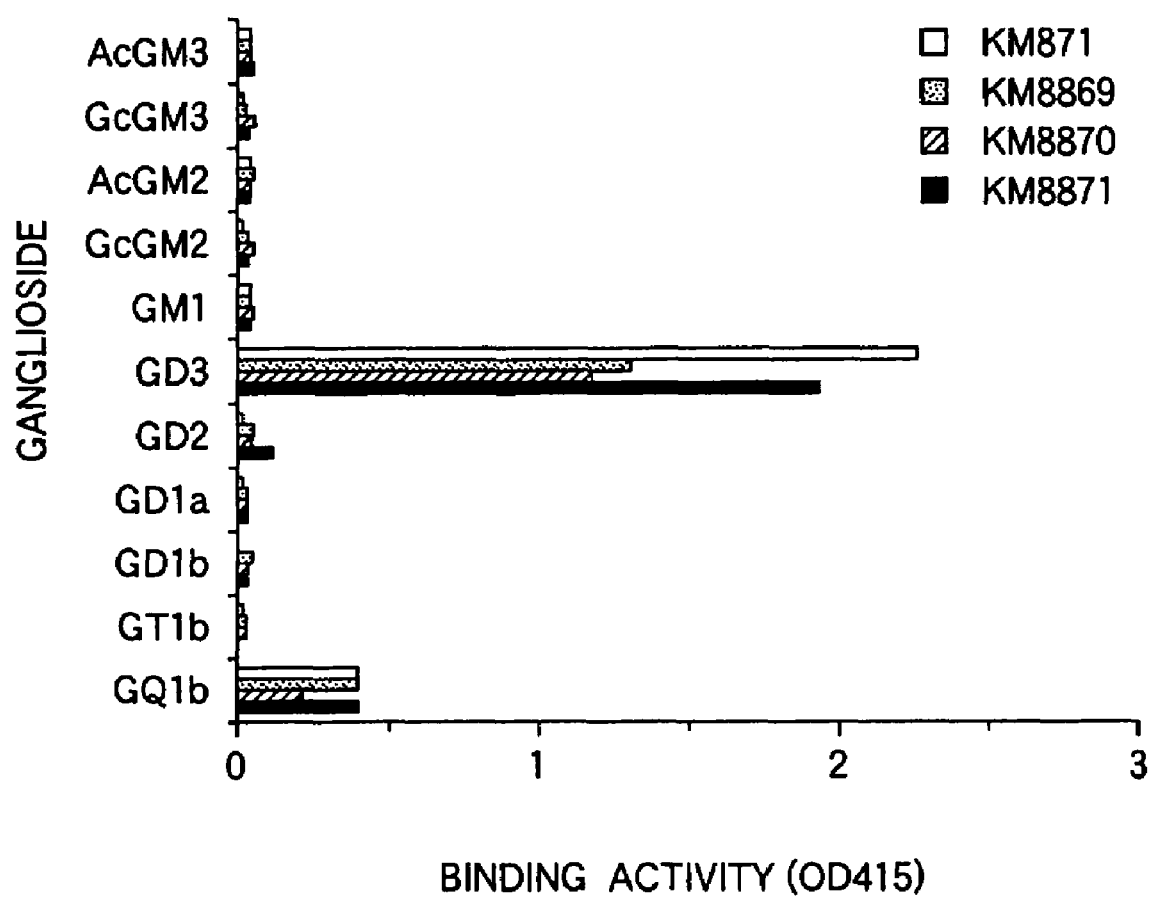
FIG. 16 is a drawing showing reactivity of purified anti-GD3 chimeric antibody KM871 and purified anti-GD3 CDR-grafted antibodies KM8869, KM8870 and KM8871 with various gangliosides. The ordinate and the abscissa are the kind of ganglioside and the binding activity, respectively. AcGM2, GcGM2, AcGM3, and GcGM3 indicate N-acetylGM2, N-glycolylGM2, N-acetylGM3 and N-glycolylGM3. "□", "□", "□" and "■" show the reactivities of KM871, KM8869, KM8870 and KM8871, respectively.

Reactivity of purified anti-GD3 CDR-grafted antibodies KM8869, KM8870 and KM8871 with GD3 (manufactured by DIA-IATRON) was measured by the ELISA shown in the item 2 of Example 1. FIG. 14 shows a result of the examination of the reactivity carried out by fixing the amount of GD3 to be adsorbed to each well of a plate for ELISA to 20 pmol/well and changing the concentration of anti-GD3 chimeric antibody KM871 and anti-GD3 CDR-grafted antibodies KM8869, KM8870 and KM8871 to be added. As shown in FIG. 14, among the anti-GD3 CDR-grafted antibodies, KM8871 showed the most highest binding activity which was about ½ of the anti-GD3 chimeric antibody KM8871. FIG. 15 shows a result of the examination of the reactivity of a constant concentration (10 μg/ml) of anti-GD3 chimeric antibody KM871 and anti-GD3 CDR-grafted antibodies. KM8869, KM8870 and KM8871, carried out by changing the amount of GD3 to be adsorbed to each well of a plate for ELISA use. As shown in FIG. 15, among the anti-GD3 CDR-grafted antibodies, KM8871 showed the most highest binding activity which was equivalent to the anti-GD3 chimeric antibody KM871. FIG. 16 shows a result of the examination of the reactivity of a constant concentration (10 μg/ml) of anti-GD3 chimeric antibody K4871 and anti-GD3 CDR-grafted antibodies KM8869, KM8870 and KM8871, carried out by changing the kind of ganglioside to be adsorbed to each well of a plate for ELISA use (adsorption amount: 20 pmol/well). A total of 11 kinds of ganglioside, GM1, N-acetylGM2 (manufactured by Boehringer Mannheim, hereinafter referred to as "AcGM2"), N-glycolylGM2 (hereinafter referred to as "GcGM2"), N-acetylGM3 (hereinafter referred to as "AcGM3"), N-glycolylGM3 (hereinafter referred to as "GcGM3"), GD1a and GD1b (manufactured by DIA-IATRON), GD2 and GD3 (manufactured by DIA-IATRON), GQ1b (manufactured by DIA-IATRON) and GT1b (manufactured by Funakoshi), were used. In this case, GM1 and GD1a were purified from bovine brain, and N-glycolylGM2 and N-glycolylGM3 from mouse liver, N-acetylGM3 from canine erythrocyte and GD2 from a human neuroblastoma culture cell line IMR32 (ATCC CCL 127), respectively in accordance with the known method (*J. Biol. Chem.*, 2, 10915 (1988)). As shown in FIG. 16, each of the anti-GD3 CDR-grafted antibodies KM8869, KM8870 and KM8871 bound strongly to GD3 and weakly to GQ1b similar to the case of the anti-GD3 chimeric antibody KM871 but did not bind to other gangliosides. Thus, it was shown that they maintain the binding specificity of chimeric antibody KM871.

(2) Reactivity of Anti-GD3 CDR-Grafted Antibody with Human Cancer Cell (Immunofluorescent Method)

Figure 17:
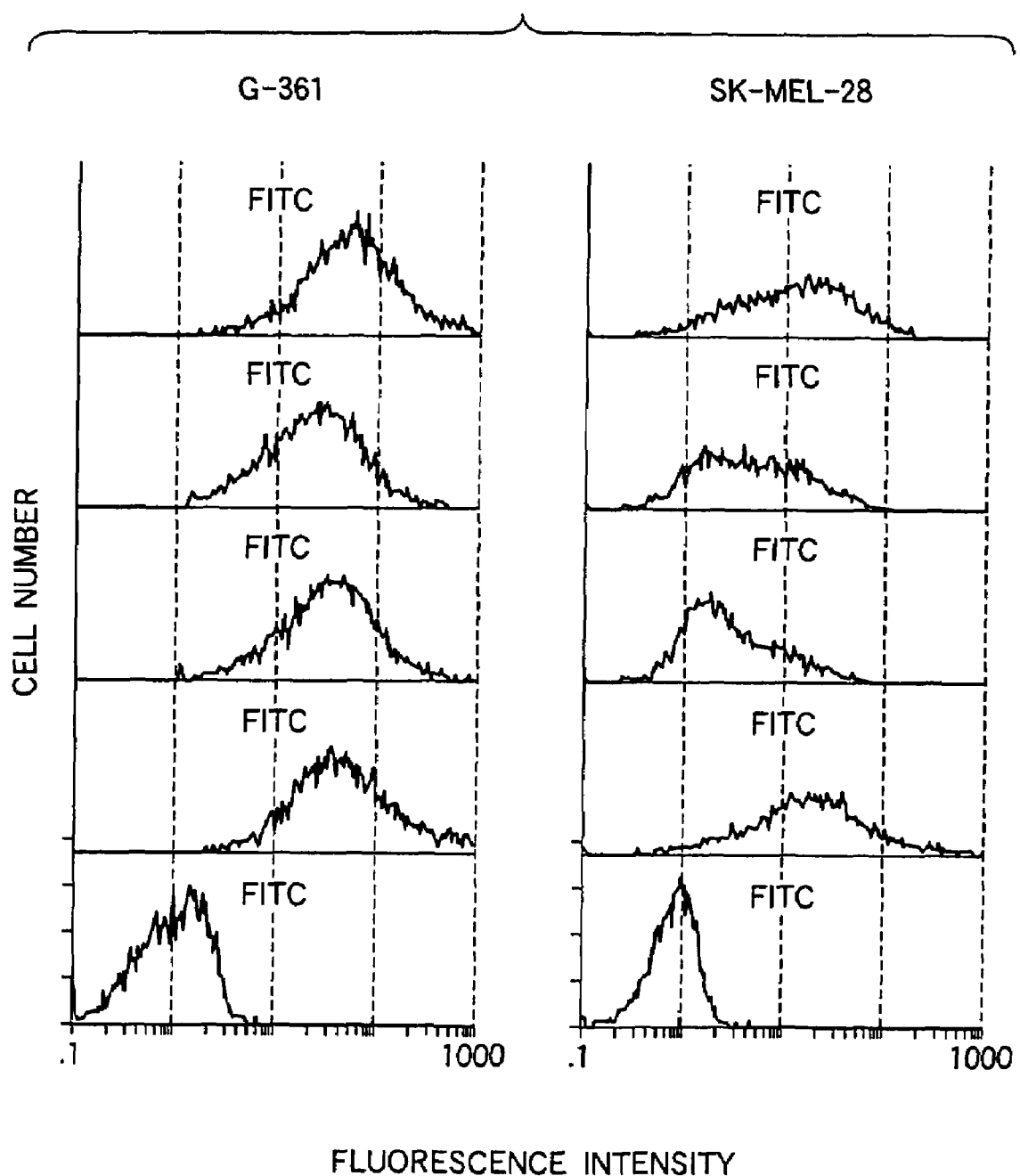
FIG. 17 is a drawing showing reactivity of purified anti-GD3 chimeric antibody KM871 and purified anti-GD3 CDR-grafted antibodies KM8869, KM8870 and KM8871 with human melanoma cell lines G-361 and SK-MEL-28. The ordinate and the abscissa are the number of cells and the fluorescence intensity, respectively. The graphs show reactivities of control, KM871, KM8869, KM8870 and KM48871, respectively, from the bottom.

Reactivity of purified anti-GD3 CDR-grafted antibodies KM8869, KM8870 and KM8871 with human cancer cells was measured as follows. That is, $1 \times 10^6$ cells of each of human melanoma culture cell lines G-361 (ATCC CRL 1424) and SK-MEL-28 (ATCC HTB72) were suspended in PBS, put into microtubes and centrifuged (2,000 rpm for 2 minutes), and the thus washed cells were stirred after adding 50 μl of the anti-GD3 chimeric antibody KM871 or the anti-GD3 CDR-grafted antibody, KM8869, KM8870 or KM8871 (a solution adjusted to 5 μg/ml with 1% BSA-PBS) and then allowed to react at 4° C. for 1 hour. After the reaction, followed by centrifugation three times with PBS for washing, 20 μl of rabbit anti-human IgG (H+L) F(ab')$_2$ solution (manufactured by Wako Pure chemical Industries, used by diluting 30 times with 1% 3SA-PBS) fluorescence-labeled with fluorescein isothiocyanate (hereinafter referred to as "FITC") was added thereto, followed by stirring, and then the reaction was carried out at 4° C. for 1 hour. After the reaction, followed by centrifugation three times with PBS for washing, the cells were again suspended in PBS to carry out the analysis using a flow cytometer EPICS Elite (manufactured by COULTER). As a control, the analysis was carried out by the same procedure without adding antibodies. Results are shown in FIG. 17. As shown in FIG. 17, all of the anti-GD3 chimeric antibody KM871 and the anti-GD3 CDR-grafted antibodies KM8869, KM8870 and KM8871 showed the reactivity with both cell lines. Among the anti-GD3 CDR-grafted antibodies, KM8871 showed the most strongest reactivity. The above results show that the anti-GD3 CDR-grafted antibodies are useful in the diagnosis, treatment and the like of GD3-positive human tumors including melanoma.

(3) In Vitro Cytotoxic Activity of Anti-GD3 CDR-Grafted Antibodies (CDC Activity)

In order to evaluate in vitro cytotoxic activity of the purified anti-GD3 CDR-grafted antibodies KM8869, KM8870 and KM8871, the CDC activity was measured by the following method.

a. Preparation of Target Cell Suspension

Each of human melanoma culture cell lines, G-361 (ATCC CRL 1424) and SK-MEL-28 (ATCC HTB72), was cultured in RPMI1640-FBS(10) medium and adjusted to $5 \times 10^6$ cells, and the cells were isotope-labeled by adding 3.7 MBq equivalent of a radioactive substance $Na_2^{51}CrO_4$ and carrying out the reaction at 37° C. for 1 hour. After the reaction, the cells were washed three times by their suspension in RPMI1640-FBS(10) medium and centrifugation, re-suspended in the medium and then incubated in ice at 4° C. for 30 minutes to thereby spontaneously release the radioactive substance. After centrifugation, the precipitate was adjusted to $1 \times 10^6$ cells/ml by adding 5 ml of RPMI1640-FBS(10) medium and used as the target cell suspension.

b. Preparation of Complement Solution

Sera of three healthy persons were mixed and used as the human complement source. At the time of its use, it was diluted to 15% vol/vol with RPMI1640-FBS(10) medium and used as the complement solution.

c. Measurement of CDC Activity

To each well of a 96 well U bottom plate (manufactured by Falcon), 50 μl of the target cell suspension prepared in "a" was added ($5 \times 10^4$ cells/well), and then the anti-GD3 chimeric antibody KM871 or the anti-GD3 CDR-grafted antibody, KM8869, KM8870 or KM8871, was added to give a final concentration of 0.05 to 50 μg/ml and allowed to react at room temperature for 30 minutes. After the reaction, the plate was centrifuged to remove the supernatant, and 150 μl of the human complement solution prepared in "b" was added thereto and allowed to react at 37° C. for 1 hour. After centrifugation, the amount of $^{51}Cr$ released in the supernatant was measured by a γ-counter. The amount of the spontaneously dissociated $^{51}Cr$ was calculated by carrying out the same procedure using the medium alone instead of the antibody solution and complement solution and measuring the amount of $^{51}Cr$ in the supernatant. Amount of the total dissociated $^{51}Cr$ was calculated by carrying out the same procedure by adding the medium alone instead of the antibody solution, and 5 N sodium hydroxide instead of the complement solution, and measuring the amount of $^{51}Cr$ in the supernatant. The CDC activity was calculated by the following equation.

$$CDC\ activity\ (\%) = \frac{(amount\ of\ ^{51}Cr\ in\ sample\ supernatant) - (amount\ of\ spontaneously\ released\ ^{51}Cr)}{(amount\ of\ total\ ^{51}Cr) - (amount\ of\ spontaneously\ released\ ^{51}Cr)} \times 100$$

Results are shown in FIG. 18. As shown in FIG. 18, it was found that all of the anti-GD3 chimeric antibody KM871 and the anti-GD3 CDR-grafted antibodies KM8869, KM8870 and KM8871 show the CDC activity for both cell lines, particularly show remarkably strong cytotoxic activity for the human melanoma culture cell line G-361. Among the anti-GD3 CDR-grafted antibodies, KM8871 showed the most stronger cytotoxic activity which was about ⅓ of the anti-GD3 chimeric antibody KM871.

(4) In Vitro Cytotoxic Activity or Anti-GD3 CDR-Grafted Antibody (ADCC Activity)

In order to evaluate in vitro cytotoxic activity of the purified anti-GD3 CDR-grafted antibodies KM8869, KM8870 and KM8871, the ADCC activity was measured by the following method.

a. Preparation of Target Cell Suspension

Each of human melanoma culture cell lines, G-361 (ATCC CRL 1424) and SK-MEL-28 (ATCC HTB72), was cultured in RPMI1640-FBS(10) medium and adjusted to $1 \times 10^6$ cells, and the cells were isotope-labeled by adding 1.85 MBq equivalent of a radioactive substance $Na_2^{51}CrO_4$ and carrying out the reaction at 37° C. for 1 hour. After the reaction, the cells were washed three times by their suspension in RPMI1640-FBS(10) medium and centrifugation, re-suspended in the medium and then incubated in ice at 4° C. for 30 minutes to thereby spontaneously release the radioactive substance. After centrifugation, the precipitate was adjusted to $2 \times 10^5$ cells/ml by adding 5 ml of RPMI1640-FBS(10) medium and used as the target cell suspension.

b. Preparation of Effector Cell Suspension

Healthy human vein blood (50 ml) was collected, and 0.5 ml of heparin sodium (manufactured by Takeda Pharmaceutical) was gently added thereto. The resulting mixture was centrifuged (1,500 to 1,800×g for 30 minutes) using Polymorphprep (manufactured by Nycomed Pharma AS) in accordance with the manufacture's instructions to separate a mononuclear cell layer. The separated cells were three times centrifuged (1,500 to 1,800×g for 5 minutes) with RPMI1640-FBS(10) medium for washing and then re-suspended in the medium to give a density of $5 \times 10^6$ cells/ml to be used as the effector cell suspension.

c. Measurement of ADCC Activity

Into each well of a 96 well U bottom plate (manufactured by Falcon), 50 μl of the target cell suspension prepared in "a" was dispensed ($1 \times 10^4$ cells/well). Next, 100 μl of the effector cell suspension prepared in "b" was added ($5 \times 10^5$ cells/well, ratio of the effector cells to the target cells becomes 50:1). Thereafter, each of the anti-GD3 chimeric antibody KM871 and the anti-GD3 CDR-grafted antibodies KM8869, KM8870 and KM8871 was added to give a final concentration of 0.05 to 50 μg/ml and allowed to react at 37° C. for 4 hours. After the reaction, the plate was centrifuged and the amount of $^{51}Cr$ in the supernatant was measured by a γ-counter. The amount of the spontaneously dissociated $^{51}Cr$ was calculated by carrying out the same procedure using the medium alone instead or the effector cell suspension and antibody solution and measuring the amount of $^{51}Cr$ in the supernatant. The amount of the total dissociated $^{51}Cr$ was calculated by carrying out the same procedure by adding the medium alone instead of the antibody solution, and 5 N sodium hydroxide instead of the effector cell suspension, and measuring the amount of $^{51}Cr$ in the supernatant. The ADCC activity was calculated by the following equation.

$$ADCC\ activity\ (\%) = \frac{(amount\ of\ ^{51}Cr\ in\ sample\ supernatant) - (amount\ of\ spontaneously\ released\ ^{51}Cr)}{(amount\ of\ total\ ^{51}Cr) - (amount\ of\ spontaneously\ released\ ^{51}Cr)} \times 100$$

Results are shown in FIG. 19. As shown in FIG. 19, it was found that all of the anti-GD3 chimeric antibody KM871 and the anti-GD3 CDR-grafted antibodies, KM8869, KM8870 and KM8871, show strong ADCC activity for both cell lines. Among the anti-GD3 chimeric antibody KM871 and the anti-GD3 CDR-grafted antibodies KM8869, KM8870 and KM8871, difference in the cytotoxic activity was not found.

The above results show that the anti-GD3 CDR-grafted antibodies are useful in the diagnosis, treatment and the like of GD3-positive human tumors similar to the case of the anti-GD3 chimeric antibody KM871. In addition, it is expected that immunogenicity of the anti-GD3 CDR-grafted antibodies is reduced in human and the effect is further prolonged.

The transformed cell clone KM8871 capable of producing KM8871 which showed the most high activity among the anti-GD3 CDR-grafted antibodies has been deposited on Jul. 22, 1999, under the conditions of the Budapest Treaty, as FERM BP-6790 in National Institute of Bioscience and Human Technology, Agency of Industrial Science and Technology (Higashi 1-1-3, Tsukuba, Ibaraki, Japan (now the International Patent Organism Depositary, National Institute of Advanced Industrial Science and Technology Central 6. Higashi 1-1-1, Tsukuba. Ibaraki, Japan)).

Example 2

Preparation of Fusion Protein of Anti-GD3 CDR-Grafted Antibody with Human Cytokine:

As an example of a fusion protein of anti-GD3 CDR-grafted antibody with human cytokine, a fusion protein of the anti-GD3 CDR-grafted antibody KM8871 with human IL-2, KM8871-hIL-2, was prepared as follows and evaluation of the activity was carried out.

1. Construction of cDNA Encoding a Fusion Protein of hCγ1 with hIL-2

(1) Construction of a Plasmid pBSΔhCγ1-IL-2 Having a cDNA Comprised of About 65 Bases of 3'-Terminal of hCγ1 cDNA and Full Length cDNA of Matured Type hIL-2

A plasmid pBluescript SK(−) (3 µg, manufactured by Stratagene) was added to 10 µl of a buffer comprising 10 mM Tris-HCl (pH 7.5), 10 mM magnesium chloride and 1 mM DTT, and the solution was further mixed with 10 units of a restriction enzyme ApaI (manufactured by Takara Shuzo) to carry out the reaction at 37° C. for 1 hour. The reaction solution was precipitated with ethanol, added to 10 µl of a buffer comprising 20 mM Tris-HCl (pH 8.5), 10 mM magnesium chloride, 1 mM DTT and 100 mM potassium chloride, and further mixed with 10 units of a restriction enzyme BamHI (manufactured by Takara Shuzo) to carry out the reaction at 30° C. for 1 hour. The reaction solution was fractionated by an agarose gel electrophoresis to recover about 2 µg of an ApaI-BamHI fragment of about 2.95 kb using QIAquick Gel Extraction Kit (manufactured by QIAGEN) in accordance with the manufacturers instructions.

Next, synthetic DNA fragments respectively having the nucleotide sequences represented by SEQ ID NO:49 and SEQ ID NO:50 were synthesized using an automatic DNA synthesizer (380A, manufactured by Applied Biosystems). A 0.3 µg of each of the thus obtained synthetic DNA fragments was added to 15 µl of sterile water and heated at 65° C. for 5 minutes. After allowing the reaction solution to stand at room temperature for 30 minutes, this was mixed with 2 µl of a 10× buffer solution (500 mM Tris-HCl (pH 7.6), 100 mM magnesium chloride, 50 mM DTT) and 2 µl of 10 mM ATP and further mixed with 10 units of T4 Polynucleotide Kinase (manufactured by Takara Shuzo) to carry out the reaction at 37° C. for 30 minutes to thereby phosphorylate the 5'-terminal.

Figure 20:
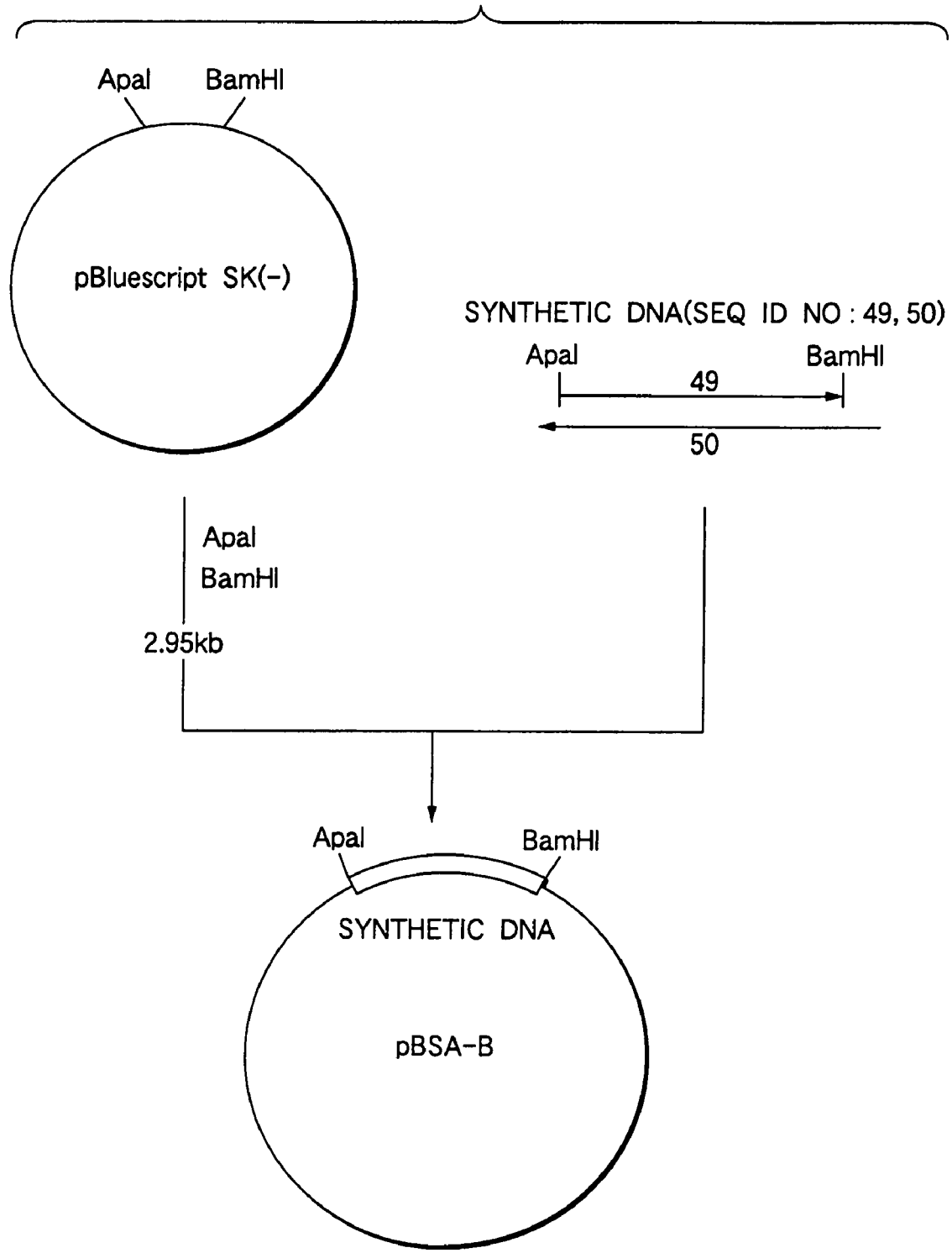
FIG. 20 is a drawing showing construction steps of plasmid pBSA-B.

Next, 0.1 µg of the ApaI-BamHI fragment derived from the plasmid pBluescript SK(−) and 0.05 µg of the phosphorylated synthetic DNA, both obtained in the above, were added to 10 µl in total volume of sterile water and ligated using DNA Ligation Kit Ver. 2 (manufactured by Takara Shuzo) in accordance with the manufacture's instructions. Using the thus obtained recombinant plasmid DNA solution, an E. coli line DH5α (manufactured by Stratagene) was transformed to obtain the plasmid pBSA-B shown in FIG. 20. The thus obtained plasmid (10 µg) was allowed to react in accordance with the manufacture's instructions attached to AutoRead Sequencing Kit (manufactured by Pharmacia) and then subjected to an electrophoresis using A.L.F. DNA Sequencer (manufactured by Pharmacia) to determine the nucleotide sequence, and as a result, it was confirmed that a plasmid into which the DNA of interest was cloned was obtained.

Next, 3 µg of the thus obtained plasmid pBSA-B was added to 10 µl of a buffer comprising 50 mM Tris-HCl (pH 7.5), 100 mM sodium chloride, 10 mM magnesium chloride and 1 mM DTT, and the solution was further mixed with 10 units of a restriction enzyme EcoRI (manufactured by Takara Shuzo) to carry out the reaction at 37° C. for 1 hour. The reaction solution was precipitated with ethanol, added to 10 µl of a buffer comprising 33 mM Tris-acetate (pH 7.9), 66 mM potassium acetate, 10 mM magnesium acetate, 0.5 mM DTT and 100 µg/ml BSA, and further mixed with 10 units of a restriction enzyme SmaI (manufactured by Takara Shuzo) to carry out the reaction at 30° C. for 1 hour. The reaction solution was fractionated by an agarose gel electrophoresis to recover about 2 µg of an EcoRI-SmaI fragment of about 3.00 kb using QIAquick Gel Extraction Kit (manufactured by QIAGEN) in accordance with the manufacture's instructions.

Next, the following PCR was carried out using a plasmid pILL4 containing full length cDNA of matured type hIL-2 (Agric. Biol. Chem., 51, 1135 (1987)) as the template. The plasmid pILL4 (1 ng) was added to 100 µl of a reaction solution (1× concentration Ex Taq buffer (manufactured by Takara Shuzo), 200 µM dNTPs, 1.0 µM rev1 primer (SEQ ID NO:51), 1.0 µM fw2 primer (SEQ ID NO:52) and 2.5 units of TaKaRa Ex Taq DNA polymerase (manufactured by Takara Shuzo)), and the solution was covered with 100 µl of mineral oil and set to a DNA thermal cycler (PJ480, manufactured by PERKIN ELMER) to carry out the reaction at 94° C. for 3 minutes, subsequent 30 cycles of each cycle at 96° C. for 30 seconds, 55° C. for 1 minute and 72° C. for 1 minute, and finally at 72° C. or 7 minutes. The reaction solution was precipitated with ethanol, added to 30 µl of a buffer comprising 50 mM Tris-HCl (pH 7.5), 100 mM sodium chloride, 10 mM magnesium chloride and 1 mM DTT, and further mixed with 10 units of a restriction enzyme EcoRI (manufactured by Takara Shuzo) to carry out the reaction at 37° C. for 1 hour. The reaction solution was precipitated with ethanol, added to 10 µl of a buffer comprising 33 mM Tris-acetate (pH 7.9), 66 mM potassium acetate, 10 mM magnesium acetate, 0.5 mM DTT and 100 µg/ml BSA, and further mixed with 10 units of a restriction enzyme SmaI (manufactured by Takara Shuzo) to carry out the reaction at 30° C. for 1 hour. The reaction solution was fractionated by an agarose gel electrophoresis to recover about 1 µg of an EcoRI-SmaI fragment of about 0.41 kb using QIAquick Gel Extraction Kit (manufactured by QIAGEN) in accordance with the manufacturers instructions.

Figure 21:
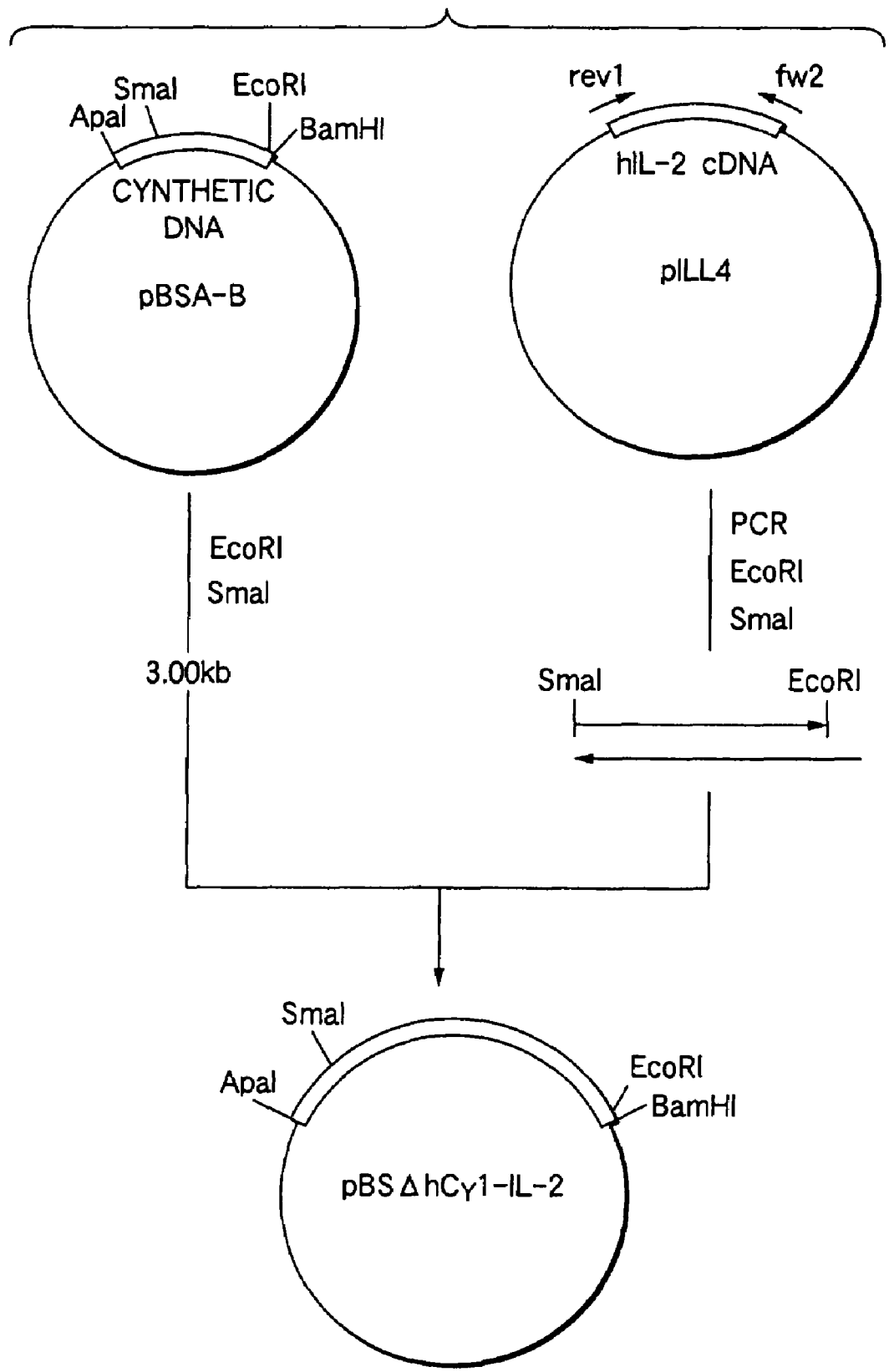
FIG. 21 is a drawing showing construction steps of plasmid pBSΔhCγ1-IL-2.

Next, 0.1 µg of the thus obtained EcoRI-SmaI fragment of the plasmid pBSA-B and 0.1 µg of the EcoRI-SmaI fragment of the PCR product of full length cDNA of matured type hIL-2 were added to 10 µl in total volume of sterile water and ligated using DNA Ligation Kit Ver. 2 (manufactured by Takara Shuzo) in accordance with the manufacture's instructions. Using the thus obtained recombinant plasmid DNA solution, an *E. coli* DH5a was transformed. Each plasmid DNA was prepared from 10 clones of the transformants, allowed to react in accordance with the manufacture's instructions attached to AutoRead Sequencing Kit (manufactured by Pharmacia) and then subjected to an electrophoresis using A.L.F. DNA Sequencer (manufactured by Pharmacia) to determine nucleotide sequence of the inserted cDNA, and as a result, the plasmid pBSΔhCγ1-IL-2 shown in FIG. 21 having the nucleotide sequence of interest was obtained.

(2) Construction of a Plasmid pBShCγ1-IL-2 having a cDNA comprised of hCγ1 full length cDNA and full length cDNA of matured type hIL-2

First, 3 µg of the plasmid pBShCγ1 described in Japanese Published Unexamined Patent Application No. 257893/98 was added to 10 µl of a buffer comprising 10 mM Tris-HCl (pH 7.5), 10 mM magnesium chloride and 1 mM DTT, and the solution was further mixed with 10 units of a restriction enzyme ApaI (manufactured by Takara Shuzo) to carry, out the reaction at 37° C. for 1 hour. The reaction solution was precipitated with ethanol, added to 10 µl of a buffer comprising 50 µM Tris-HCl (pH 7.5), 10 mM magnesium chloride, 1 mM DTT and 100 mM potassium chloride, and further mixed with 10 units of a restriction enzyme EcoT22I (manufactured by Takara Shuzo) to carry out the reaction at 30° C. for 1 hour. The reaction solution was fractionated by an agarose gel electrophoresis to recover about 1 µg of an ApaI-EcoT22I fragment of about 0.92 kb using QIAquick Gel Extraction Kit (manufactured by QIAGEN) in accordance with the manufacture's instructions.

Next, 3 µg of the plasmid pBSΔhCγ1-IL-2 obtained in the item 1(1) of Example 2 was added to 10 µl of a buffer comprising 10 mM Tris-HCl (pH 7.5), 10 mM magnesium chloride and 1 mM DTT, and the solution was further mixed with 10 units of a restriction enzyme ApaI (manufactured by Takara Shuzo) to carry out the reaction at 37° C. for 1 hour. The reaction solution was precipitated with ethanol, added to 10 µl of a buffer comprising 50 mM Tris-HCl (pH 7.5), 10 mM magnesium chloride, 1 mM DTT and 100 mM sodium chloride, and further mixed with 10 units of a restriction enzyme EcoT22I (manufactured by Takara Shuzo) to carry out the reaction at 30° C. for 1 hour. The reaction solution was fractionated by an agarose gel electrophoresis to recover about 2 µg of an ApaI-EcoT22I fragment of about 3.40 kb using QIAquick Gel Extraction Kit (manufactured by QIAGEN) in accordance with the manufacture's instructions.

Figure 22:
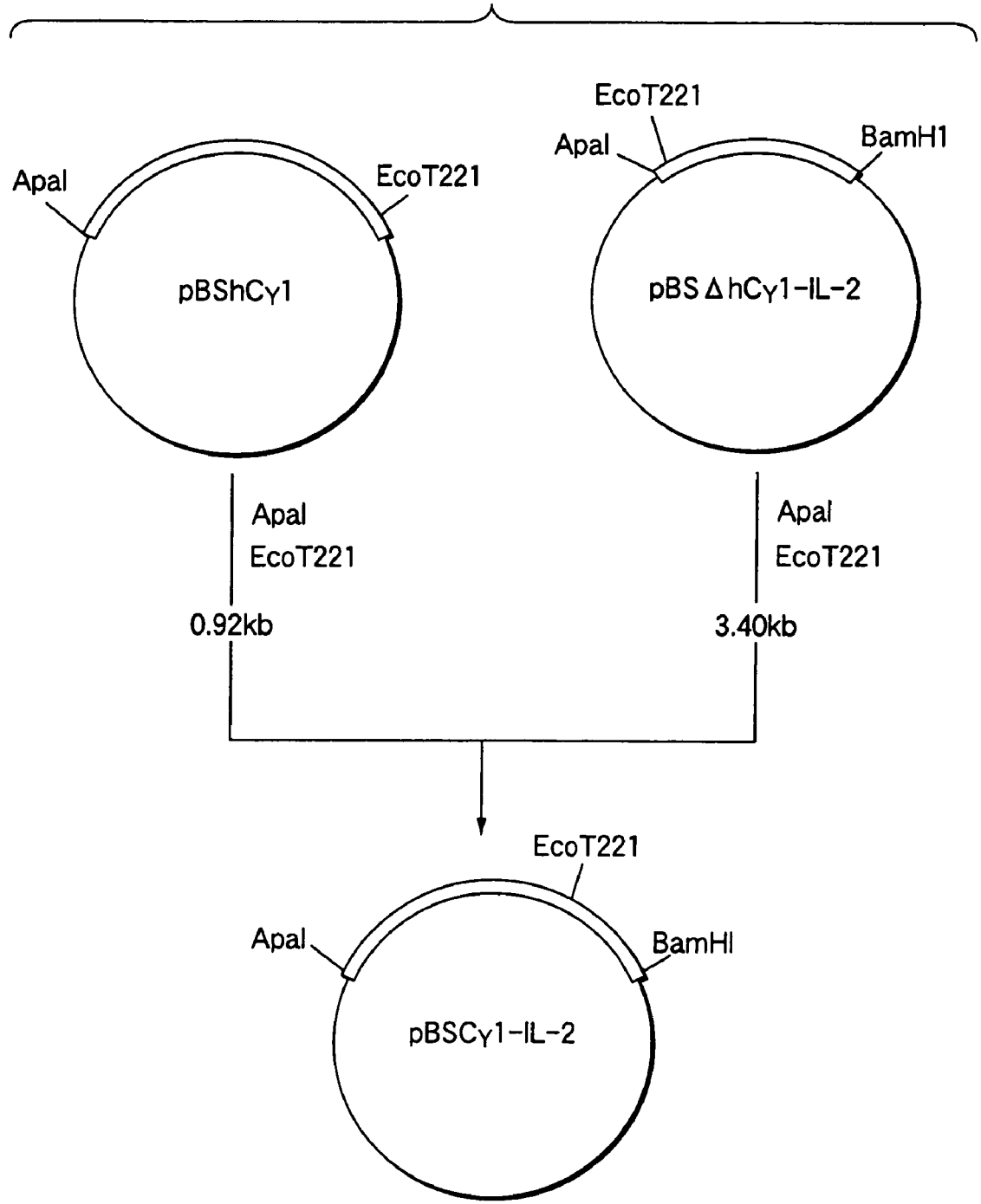
FIG. 22 is a drawing showing construction steps of plasmid pBShCγ1-IL-2.

Next, 0.1 µg of the thus obtained ApaI-EcoT22I fragment of pBShCγ1 and 0.1 µg of the ApaI-EcoT22I of pBSΔhCγ1-IL-2 were added to 10 µl in total volume of sterile water and ligated using DNA Ligation Kit Ver. 2 (manufactured by Takara Shuzo) in accordance with the manufacture's instructions. Using the thus obtained recombinant plasmid DNA solution, the *E. coli* DH5α was transformed to obtain the plasmid pBShCγ1-IL-2 shown in FIG. 22. The thus obtained plasmid (10 µg) was allowed to react in accordance with the manufacture's instructions attached to AutoRead Sequencing Kit (manufactured by Pharmacia) and then subjected to an electrophoresis using A.L.F. DNA Sequencer (manufactured by Pharmacia) to determine nucleotide sequence of the inserted cDNA, and as a result, it was confirmed that a plasmid having the nucleotide sequence of interest was obtained.

2. Stable Expression of KM8871-hIL-2 Using Animal Cells (1) Construction of Stable Expression Vector for KM8871-hIL-2

A stable expression vector for KM8871-hIL-2 was constructed as follows using the vector pKANTEX641HLCDRLm-69 obtained in the item 6(1) of Example 1 for stable expression of anti-GD3 CDR-grafted antibody KM8871 and the plasmid pBShCγ1-IL-2 obtained in the item 1(2) of Example 2 having cDNA encoding the fusion protein of hCγ1 with hIL-2.

The plasmid pKANTEX641HLCDRLm-69 (3 µg) obtained in the item 6(1) of Example 1 was added to 10 µl of a buffer comprising 10 mM Tris-HCl (pH 7.5), 10 mM magnesium chloride and 1 mM DTT, and the solution was further mixed with 10 units of a restriction enzyme ApaI (manufactured by Takara Shuzo) to carry out the reaction at 37° C. for 1 hour. The reaction solution was precipitated with ethanol and added to 10 µl of a buffer comprising 20 mM Tris-HCl (pH 8.5), 10 mM magnesium chloride, 1 mM DTT and 100 mM potassium chloride, and the solution was further mixed with 10 units of a restriction enzyme BamHI (manufactured by Takara Shuzo) to carry out the reaction at 37° C. for 1 hour. The reaction solution was fractionated by an agarose gel electrophoresis to recover about 2 µg of an ApaI-BamHI fragment of about 12.57 kb using QIAquick Gel Extraction Kit (manufactured by QIAGEN) in accordance with the manufacture's instructions.

Next, 3 µg of each of the plasmid pBShCγ1-IL-2 obtained in the item 1(2) of Example 2 was added to 10 µl of a buffer comprising 10 mM Tris-HCl (pH 7.5), 10 mM magnesium chloride and 1 mM DTT, and the solution was further mixed with 10 units of a restriction enzyme ApaI (manufactured by Takara Shuzo) to carry out the reaction at 37° C. for 1 hour. The reaction solution was precipitated with ethanol and added to 10 µl of a buffer comprising 20 mM Tris-HCl (pH 8.5), 10 mM magnesium chloride, 1 mM DTT and 100 mM potassium chloride, and the solution was further mixed with 10 units of a restriction enzyme BamHI (manufactured by Takara Shuzo) to carry out the reaction at 37° C. for 1 hour. The reaction solution was fractionated by an agarose gel electrophoresis to recover about 2 µg of an ApaI-BamHI fragment of about 1.45 kb using QIAquick Gel Extraction Kit (manufactured by QIAGEN) in accordance with the manufacture's instructions.

Figure 23:
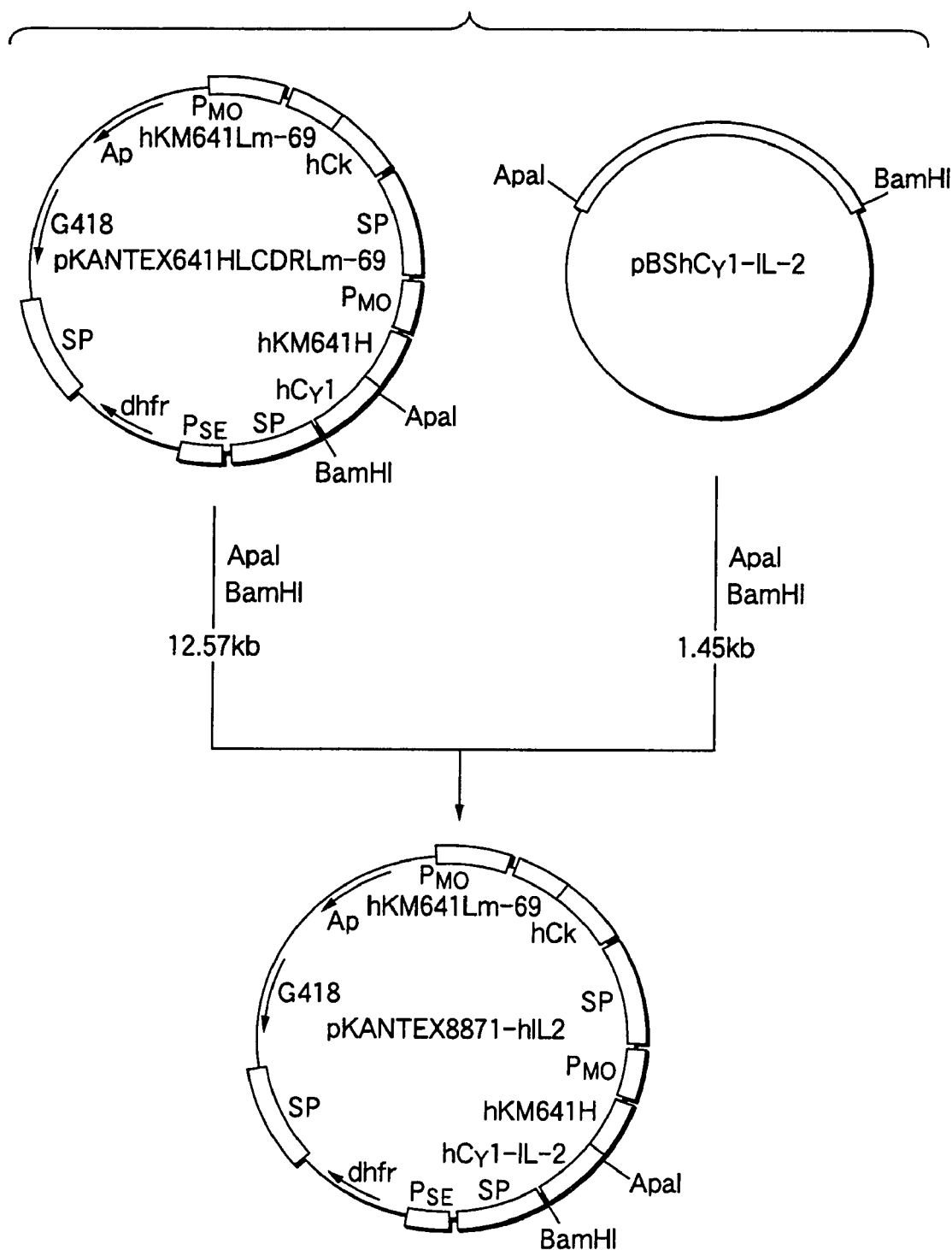

Next, 0.1 µg of the thus obtained ApaI-BamHI fragment of the plasmid pKANTEX641HLCDRLm-69 and 0.1 µg of the ApaI-BamHI fragment of the plasmid pBShCγ1-IL-2 were added to 10 µl in total volume of sterile water and ligated using DNA Ligation Kit Ver. 2 (manufactured by Pharmacia) in accordance with the manufacture's instructions. Using the thus obtained recombinant plasmid DNA solution, an *E. coli* DH5α was transformed to obtain the KM8871-hIL-2 stable expression vector pKANTEX8871-hIL2 shown in FIG. 23. The thus obtained plasmid (10 µg) was allowed to react in accordance with the manufacture's instructions attached to AutoRead Sequencing Kit (manufactured by Pharmacia) and then subjected to an electrophoresis using A.L.F. DNA Sequencer (manufactured by Pharmacia) to determine the nucleotide sequence, and as a result, it was confirmed that a plasmid into which the DNA of interest was cloned was obtained.

(2) Expression of KM8871-hIL-2 in Animal Cells

Using 4 µg of the KM8871-hIL-2 stable expression vector pKANTEX8871-hIL-2 obtained in the item 2(1) of Example 2, YB2/0 cell (ATCC CRL 1581) was transformed in accordance with the method described in the item 6(2) of Example 1, and selection was carried out finally with G418 (0.5 mg/ml) and MTX (200 nM) to obtain a transformed cell clone KM8871hIL2 showing an expression level of about 4 μg/$10^6$ cells/24 hours. Also, the KM8871hIL2 has been deposited on Jul. 22, 1999, as FERM BP-6791 in National Institute of Bioscience and Human Technology, Agency of Industrial Science and Technology (Higashi 1-1-3, Tsukuba, Ibaraki, Japan).

(3) Purification of KM8871-hIL-2 from Culture Supernatant

Figure 24:
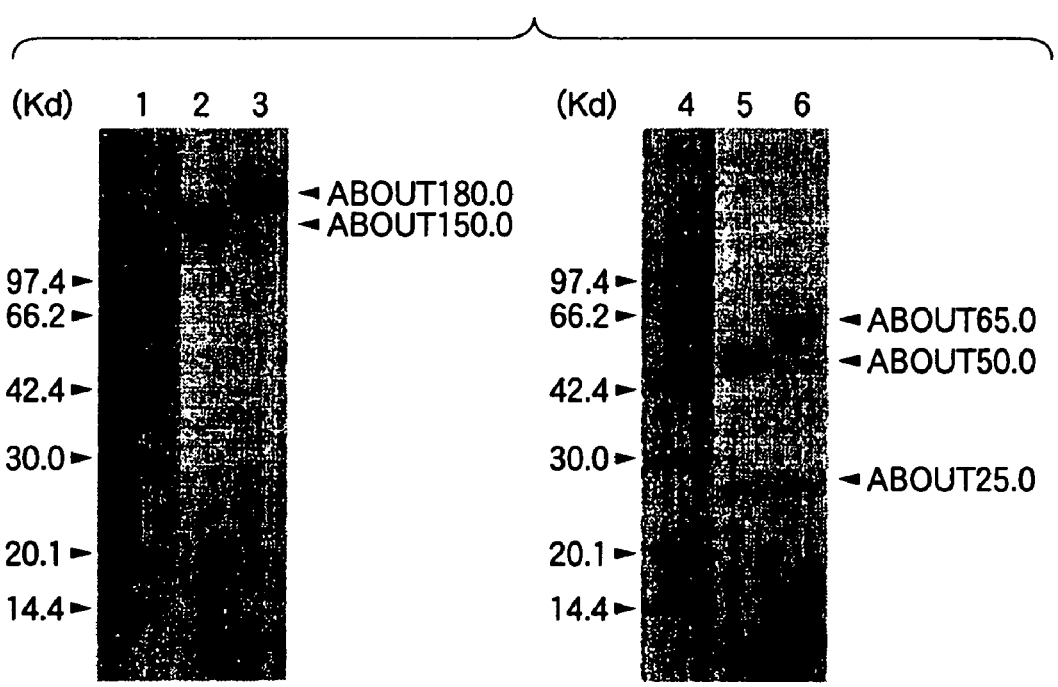
FIG. 24 is a drawing showing SDS-PAGE (using a 4 to 15% gradient gel) electrophoresis patterns of purified anti-GD3 CDR-grafted antibody KM8871 and purified fusion protein KM8871-hIL-2. The left side and the right side are results of electrophoresis carried out under non-reducing conditions, and those under reducing conditions, respectively. Lanes 1, 2, 3, 4, 5 and 6 show electrophoresis patterns of low molecular weight markers, KM8871, KM8871-hIL-2, low molecular weight markers, KM8871 and KM8871-hIL-2, respectively.

In accordance with the method described in the item 6(3) of Example 1, the transformed cell clone KM8871hIL2 obtained in the item 2(2) of Example 2 capable of expressing KM8871-hIL-2 was cultured to obtain about 10.0 mg of purified KM8871-hIL-2 from about 3 L of the culture supernatant. A result of SDS-PAGE of the purified KM8871-hIL-2 is shown in FIG. 24. As shown in FIG. 24, molecular weight of the purified KM8871-hIL-2 was about 180 Kd under non-reducing conditions, and two bands of about 65 Kd and about 25 Kd were found under reducing conditions. These molecular weights almost coincided with the molecular weights deduced from the cDNA nucleotide sequences of H chain of KM8871-hIL-2 and hIL-2 and L chain (H chain and hIL-2: about 64 Kd, L chain: about 24 Kd, whole molecule: about 176 Kd), and it was confirmed that the structure as antibody molecule was maintained after fusion of hIL-2.

3. Evaluation of Activity of KM8871-hIL-2

(1) Reactivity of KM8871-hIL-2 with GD3 (ELISA Method)

Figure 25:
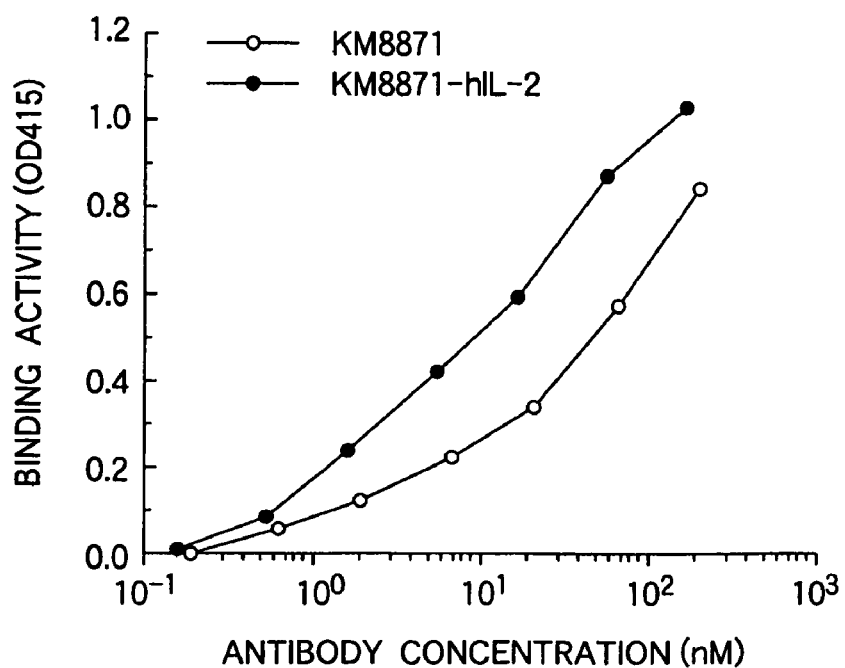
FIG. 25 is a drawing showing binding activity of purified anti-GD3 CDR-grafted antibody KM8871 and purified fusion protein KM8871-hIL-2 to GD3 measured by changing the antibody concentration. The ordinate and the abscissa are the binding activity to GD3 and the antibody concentration. "○" and "●" show the activities of KM8871 and of KM8871-hIL-2, respectively.
Figure 26:
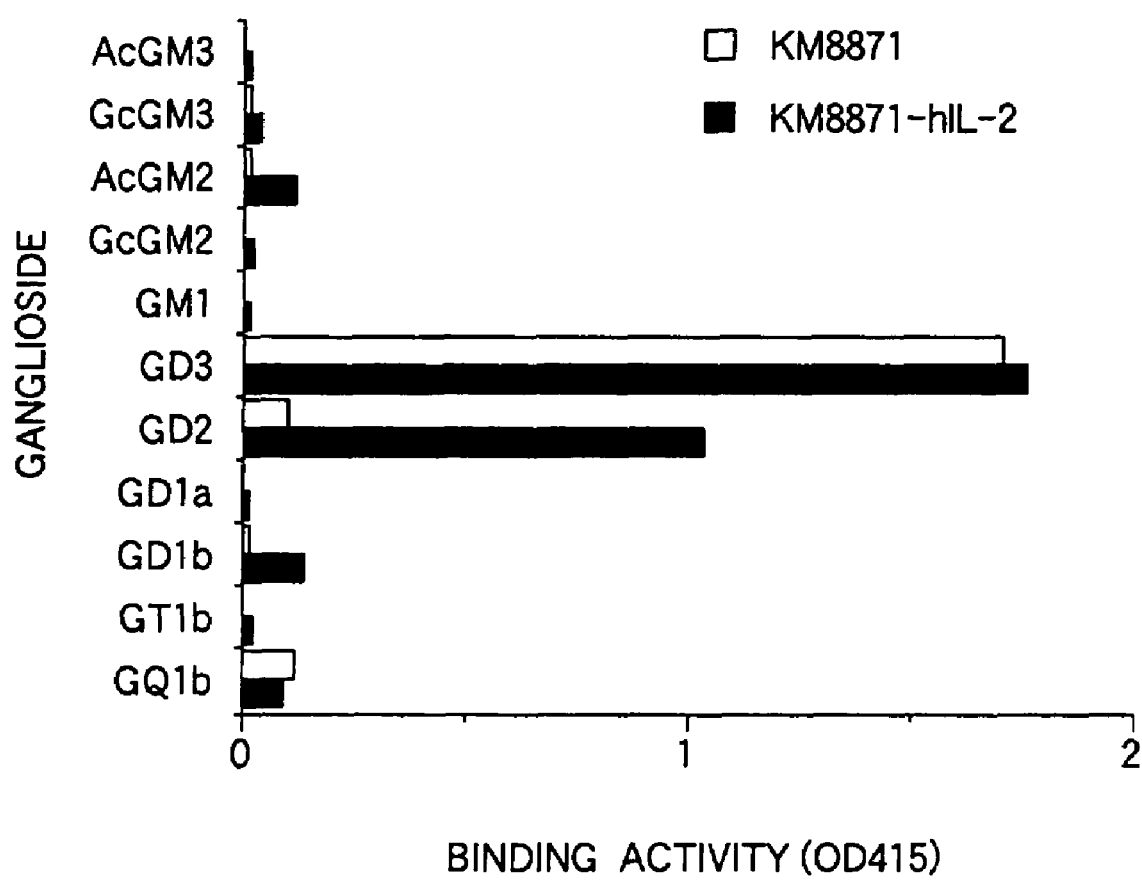
FIG. 26 is a drawing showing reactivity of purified anti-GD3 CDR-grafted antibody KM8871 and purified fusion protein KM8871-hIL-2 with various gangliosides. The ordinate and the abscissa are the kind of ganglioside and the binding activity. AcGM2, GcGM2, AcGM3 and GcGM3 indicate N-acetylGM2, N-glycolylGM2, N-acetylGM3 and N-glycolylGM3, respectively. "□" and "■" show the reactivities of KM8871 and KM8871-hIL-2, respectively.

Reactivity of the purified KM8871-hIL-2 with GD3 (manufactured by DIA-IATRON) was measured in accordance with the method described in the item 2 of Example 1. In this case, a peroxidase-labeled goat anti-human IgG (H & L) antibody (manufactured by American Qualex, used by diluting 3,000 times with 1% BSA-PBS) was used as the secondary antibody solution. FIG. 25 shows a result of the examination of the reactivity carried out by fixing the amount of GD3 to be adsorbed to each well of a plate for ELISA use to 20 pmol/well and changing the concentration of the anti-GD3 CDR-grafted antibody KM8871 and KM8871-hIL-2 to be added. As shown in FIG. 25, it was found that KM8871-hIL-2 has a GD3 binding activity similar to or higher than that of the anti-GD3 CDR-grafted antibody KM8871. FIG. 26 shows a result of the examination of the reactivity of a constant concentration (10 μg/ml) of anti-GD3 CDR-grafted antibody KM8871 and KM8871-hIL-2, carried out by changing the kinds of ganglioside to be adsorbed to each well of a plate for ELISA use (adsorption amount: 20 pmol/well). As shown in FIG. 26, it was found that the KM8871-hIL-2 strongly binds to GD3 similar to the case of the anti-GD3 CDR-grafted antibody KM8871, and it was observed that KM8871-hIL-2 also strongly binds to GD2. As the cause of the cross-reactivity of KM8871-hIL-2 with GD2, a possibility of the binding of hIL-2 with GD2, as well as a possibility of the change in binding specificity caused by a change in the three-dimensional structure of antibody V region due to fusion of hIL2, a possibility of the change in the reactivity of secondary antibody caused by a change in she three-dimensional structure of antibody C region due to fusion of hIL2, and the like can be considered.

(2) Reactivity of KM8871-hIL-2 with Cell Surface GD3 (an Immunofluorescent Method)

Reactivity of the purified KM8871-hIL-2 with human cancer cells was measured in accordance with the method described in the item 7(2) of Example 1. Results are shown in FIG. 27. As shown in FIG. 27, KM8871-hIL-2 showed a strong reactivity with the human melanoma culture cell line G361, which was almost identical to that of the anti-GD3 CDR-grafted antibody KM8871. This result shows that the KM8871-hIL-2 is useful in the treatment and the like of GD3-positive human tumors including melanoma.

(3) Evaluation of hIL-2 Activity of KM8871-hIL-2

Figure 28:
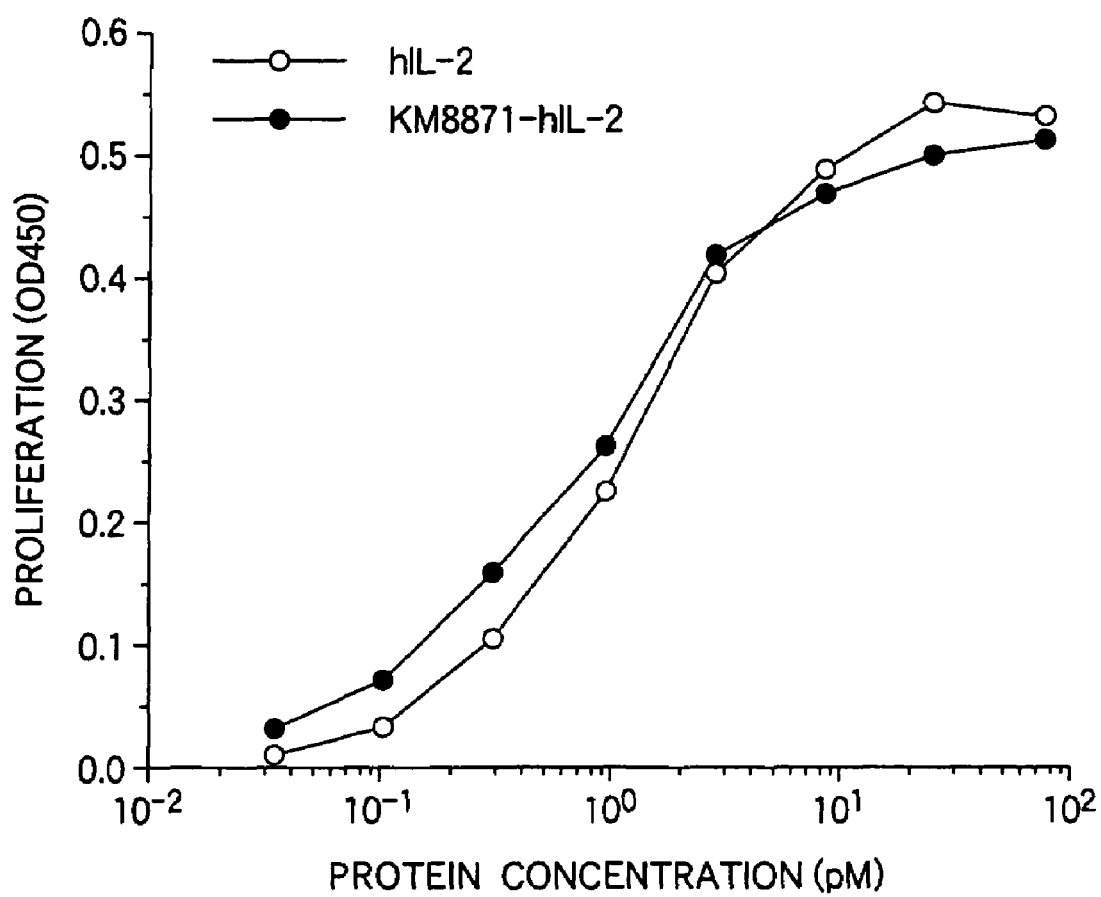
FIG. 28 is a drawing showing growth-supporting activity of hIL-2 and purified fusion protein KM8871-hIL-2 against hIL-1-dependent cell CTLL-2 measured by changing concentration of each protein. The ordinate and the abscissa are the growth-supporting activity and the protein concentration, respectively. "○" and "●" indicate the activities of hIL-2 and KM8871-hIL-2, respectively.

Activity of the purified KM8871-hIL-2 as hIL-2 was measured in accordance with the following method. A mouse T cell line CTLL-2 (ATCC TIB214) of which growth shows dependency on hIL-2 concentration was suspended in RPMI1640-FBS(10) medium at a density of $2\times10^5$ cells/ml and dispensed in 50 μl/well into a 96 well microtiter plate (manufactured by Sumitomo Bakelite). A solution (50 μl) prepared by diluting hIL-2 (manufactured by R & D SYSTEMS) or purified KM8871-hIL-2 to various concentrations with RPMI1640-FBS(10) medium was added to each well and cultured at 37° C. for 30 hours in a 5% $CO_2$ incubator. After the culturing the number of intact cells was counted using Cell Counting Kit (manufactured by Dojindo Laboratories) in accordance with the manufacture's instructions. Results are shown in FIG. 28. As shown in FIG. 28, KM8871-hIL-2 showed a biological activity to support CTLL-2 growth similar to that of hIL-2. These results show that the activity of KM8871-hIL-2 as hIL-2 is maintained after its fusion with the anti-GD3 CDR-grafted antibody KM8871.

(4) Activation of Human Effector Cell and Enhancement of Cytotoxic Activity by KM8871-hIL-2

In order to evaluate activation of human effector cells and accompanying enhancement of cytotoxic activity by the hIL-2 moiety of KM8871-hIL-2 in vitro, the cytotoxic activity was measured by the following method.

a. Preparation of Target Cell Suspension

In accordance with the method described in "a" of the item 7(4) of Example 1, a human melanoma culture cell line G-361 was adjusted to a density of $2\times10^5$ cells/ml and used as the target cell suspension.

b. Preparation of Human Effector Cell Suspension

In accordance with the method described in "b" of the item 7(4) of Example 1, mononuclear cells were separated from venous blood of healthy person and re-suspended to a density of $5\times10^6$ cells/ml to be used as the effector cell suspension.

c. Activation of Human Effector Cells

The effector cell suspension (100 μl) prepared in "b" was dispensed into each well of a 96 well U bottom plate (manufactured by Falcon) ($5\times10^4$ cells/well). Furthermore, 50 μl of the anti-GD3 CDR-grafted antibody KM8871 or KM8871-hIL-2 was added thereto to give a final concentration of 11.1 nM and allowed to react at 37° C. for 24 hours in a 5% $CO_2$ incubator.

d. Measurement of Cytotoxic Activity

The target cell suspension (50 μl) prepared in "a" was added to each well of the plate prepared in "c" ($1\times10^4$ cells/well). In this case, the ratio of the effector cells to the target cells becomes 5:1. After the reaction at 37° C. for 4 hours, the plate was centrifuged and the amount of $^{51}Cr$ in the supernatant was measured by a γ-counter. The amount of the spontaneously dissociated $^{51}Cr$ was calculated by carrying out the same procedure using the medium alone instead of the effector cell suspension and antibody solution and measuring the amount of $^{51}Cr$ in the supernatant. The amount of the total dissociated $^{51}Cr$ was calculated by carrying out the same procedure by adding the medium alone instead of the antibody solution, and 1 N hydrochloric acid instead of the effector cell suspension, and measuring the amount of $^{51}Cr$ in the supernatant. The cytotoxic activity was calculated by the following equation.

$$\text{ADCC activity (\%)} = \frac{(\text{amount of } ^{51}Cr \text{ in sample supernatant}) - (\text{amount of spontaneously released } ^{51}Cr)}{(\text{amount of total } ^{51}Cr) - (\text{amount of spontaneously released } ^{51}Cr)} \times 100$$

Figure 29:
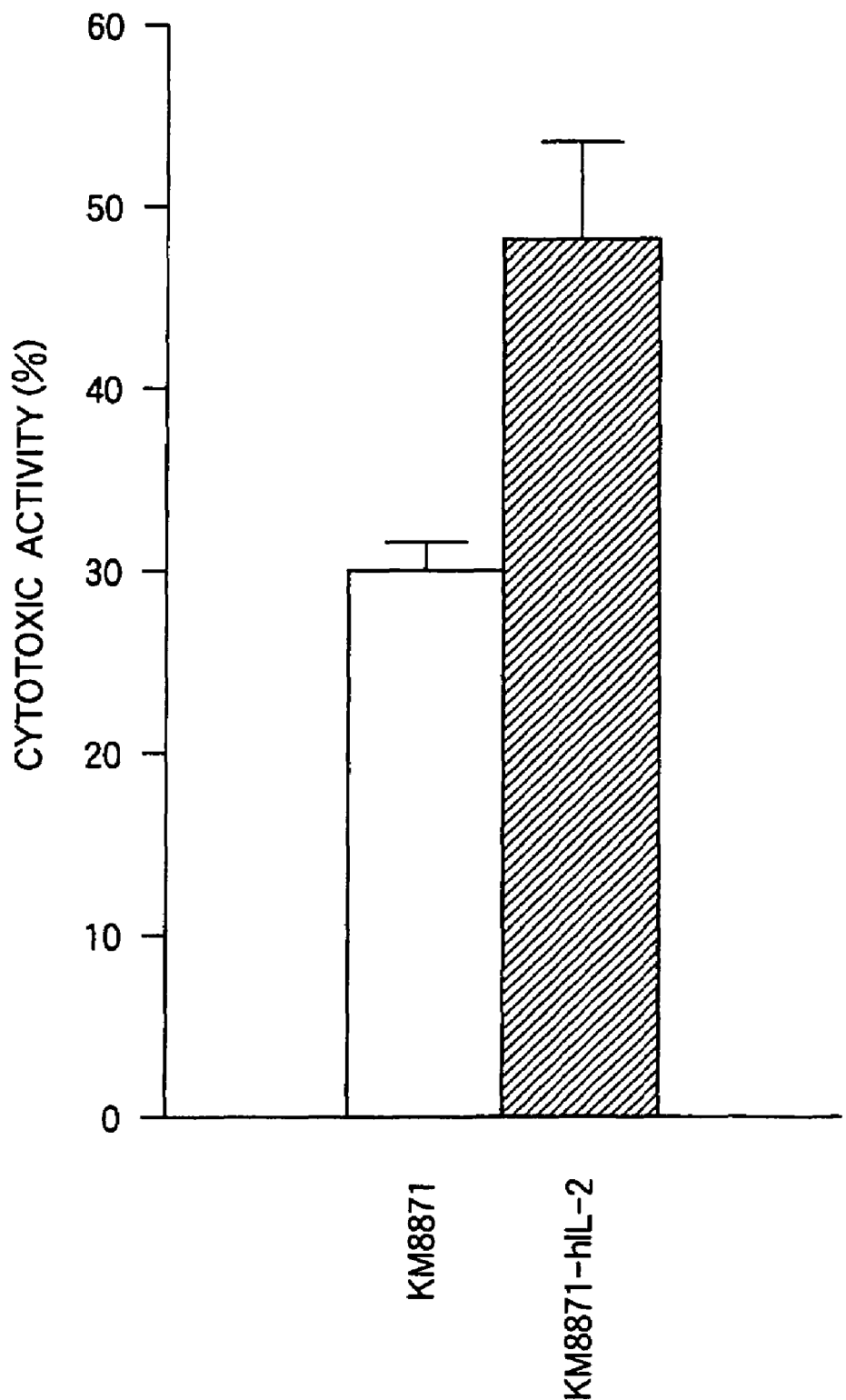
FIG. 29 is a drawing showing results of the measurement of the activation and accompanying cytotoxic activity of human effector cells by purified anti-GD3 CDR-grafted antibody KM8871 and purified fusion protein KM8871-hIL-2. The ordinate and the abscissa are the cytotoxic activity and the used protein, respectively. "□" and "■" indicate the activities of KM8871 and KM8871-hIL-2, respectively.

Results are shown in FIG. 29. As shown in FIG. 29, it was found that the cytotoxic activity induced by KM8871-hIL-2 was stronger than that induced by the anti-GD3 CDR-grafted antibody KM8871. This result shows that human effector cells can be activated and the cytotoxic activity can be enhanced by using KM8871-hIL-2. Thus, it was indicated that similar effects can be expected in its clinical application to human.

Example 3

Production of Fusion Protein of Anti-GD3 Chimeric Antibody with Human Cytokine:

As an example of fusion protein of anti-GD3 chimeric antibody with human cytokine, a fusion protein of the anti-GD3 chimeric antibody KM871 with human IL-2, KM871-hIL-2, was prepared as follows to carry out evaluation of the activity.

1. Stable Expression of KM871-hIL-2 Using Animal Cells (1) Construction of Stable Expression Vector for KM871-hIL-2

A stable expression vector for KM871-hIL-2 was constructed as follows using the vector pKANTEX641 for stable expression of anti-GD3 chimeric antibody KM871 (Japanese Published Unexamined Patent Application No. 304989/93) and the plasmid pBShCγ1-IL-2 obtained in the item 1(2) of Example 2 having cDNA encoding the fusion protein of hCγ1 with hIL-2.

The plasmid pKANTEX641 (3 μg) obtained in the item 6(1) of Example 1 was added to 10 μl of a buffer comprising 10 mM Tris-HCl (pH 7.5), 10 mM magnesium chloride and 1 mM DTT, and 10 units of a restriction enzyme ApaI (manufactured by Takara Shuzo) were further added thereto to carry out the reaction at 37° C. for 1 hour. The reaction solution was precipitated with ethanol and added to 10 μl of a buffer comprising 20 mM Tris-HCl (pH 8.5), 10 mM magnesium chloride, 1 mM DTT and 100 mM potassium chloride, and 10 units of a restriction enzyme BamHI (manufactured by Takara Shuzo) were further added thereto to carry out the reaction at 30° C. for 1 hour. The reaction solution was fractionated by agarose gel electrophoresis to recover about 2 μg of an ApaI-BamHI fragment of about 12.57 kb using QIAquick Gel Extraction Kit (manufactured by QIAGEN) in accordance with the manufacture's instructions.

Next, 3 μg of each of the plasmid pBShCγ1-IL-2 obtained in the item 1(2) of Example 2 was added to 10 μl of a buffer comprising 10 mM Tris-HCl (pH 7.5), 10 mM magnesium chloride and 1 mM DTT, and 10 units of a restriction enzyme ApaI (manufactured by Takara Shuzo) were further added thereto to carry out the reaction at 37° C. for 1 hour. The reaction solution was precipitated with ethanol and added to 10 μl of a buffer comprising 20 mM Tris-HCl (pH 8.5), 10 mM magnesium chloride, 1 mM DTT and 100 mM potassium chloride, and 10 units of a restriction enzyme BamHI (manufactured by Takara Shuzo) were further added thereto to carry out the reaction at 37° C. for 1 hour. The reaction solution was fractionated by agarose gel electrophoresis to recover about 2 μg of an ApaI-BamHI fragment of about 1.45 kb using QIAquick Gel Extraction Kit (manufactured by QIAGEN) in accordance with the manufacture's instructions.

Figure 30:
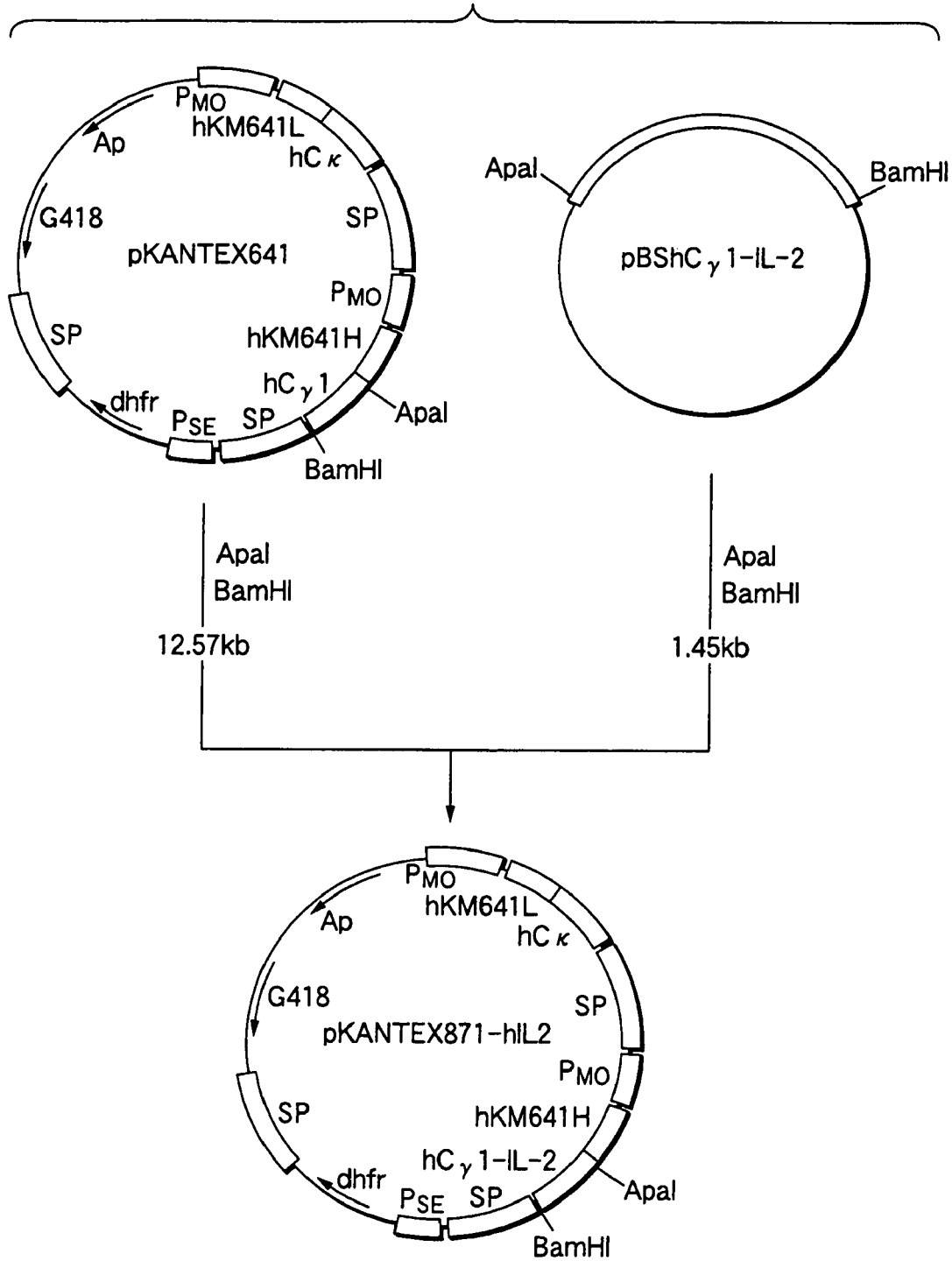
FIG. 30 is a drawing showing construction steps of plasmid pKANTEX871-hIL-2.

Next, 0.1 μg of the thus obtained ApaI-BamHI fragment of the plasmid pKANTEX641 and 0.1 μg of the ApaI-BamHI fragment of the plasmid pBShCγ1-IL-2 were added to 10 μl in total volume of sterile water and ligated using DNA Ligation Kit Ver. 2 (manufactured by Pharmacia) in accordance with the manufacture's instructions. Using the thus obtained recombinant plasmid DNA solution, an E. coli DE5α was transformed to obtain the KM871-hIL-2 stable expression vector pKANTEX871-hIL2 shown in FIG. 30. The thus obtained plasmid (10 μg) was allowed to react in accordance with the manufacturers instructions attached to AutoRead Sequencing Kit (manufactured by Pharmacia) and then subjected to electrophoresis using A.L.F. DNA Sequencer (manufactured by Pharmacia) to determine the nucleotide sequence, and as a result, it was confirmed that a plasmid into which the DNA of interest was cloned was obtained.

(2) Expression of KM871-hIL-2 in Animal Cells

Using 4 μg of the KM871-hIL-2 stable expression vector pKANTEX871-hIL-2 obtained in the item 1(1) of Example 3, YB2/0 cell (ATCC CRL 1581) was transformed in accordance with the method described in the item 6(2) of Example 1, and selection was carried out finally with G418 (0.5 mg/ml) and MTX (200 nM) to obtain a transformed cell clone KM871hIL2 showing an expression level of about 4 μg/$10^6$ cells/24 hours. Also, the KM871hIL2 has been deposited on Oct. 19, 1999, as FERM BP-6918 in National Institute of Bioscience and Human Technology, Agency of Industrial Science and Technology (Higashi 1-1-3, Tsukuba, Ibaraki, Japan).

(3) Purification of KM871-hIL-2 from Culture Supernatant

Figure 31:
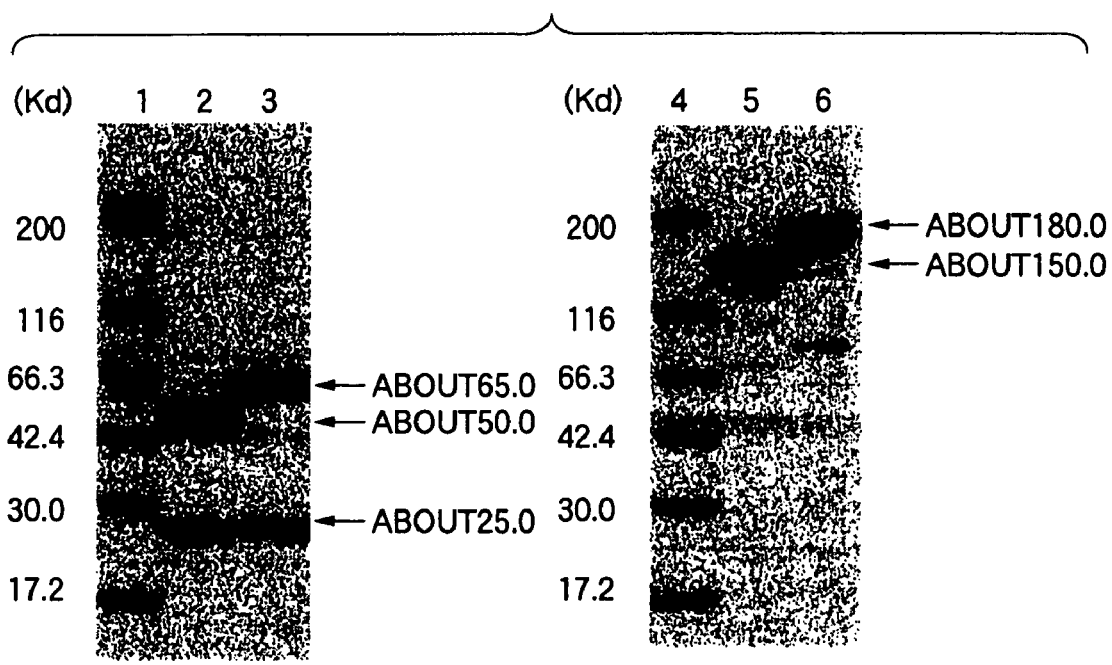
FIG. 31 is a drawing showing SDS-PAGE (using a 4 to 15% gradient gel) electrophoresis patterns of anti-GD3 chimeric antibody KM871 and purified fusion protein KM871-hIL-2. The left side and the right side are results of electrophoresis carried out under reducing conditions and under non-reducing conditions, respectively. Lanes 1, 2, 3, 4, 5 and 6 show electrophoresis patterns of low molecular weight markers, KM871, KM871-hIL-2, low molecular weight markers, KM871 and KM871-hIL-2, respectively.

In accordance with the method described in the item 6(3) of Example 1, the transformed cell clone KM871hIL2 obtained in the item 1(2) of Example 3 which expresses KM871-hIL-2 was cultured to obtain about 10.0 mg of purified KM871-hIL-2 from about 3 L of the culture supernatant. A result of SDS-PAGE of the purified KM871-hIL-2 is shown in FIG. 31. As shown in FIG. 31, molecular weight of the purified KM871-hIL-2 was about 180 Kd under non-reducing conditions, and two bands of about 65 Kd and about 25 Kd were found under reducing conditions. These molecular weights almost coincided with the molecular weights deduced from the cDNA nucleotide sequences of H chain of KM871-hIL-2 and hIL-2 and L chain (H chain and hIL-2: about 64 Kd, L chain: about 24 Kd, whole molecule: about 176 Kd), and it was confirmed that the structure as antibody molecule was maintained after fusion of hIL-2.

2. In Vitro Evaluation of KM871-hIL-2

(1) Reactivity of KM871-hIL-2 with GD3 (ELISA Method)

Figure 32:
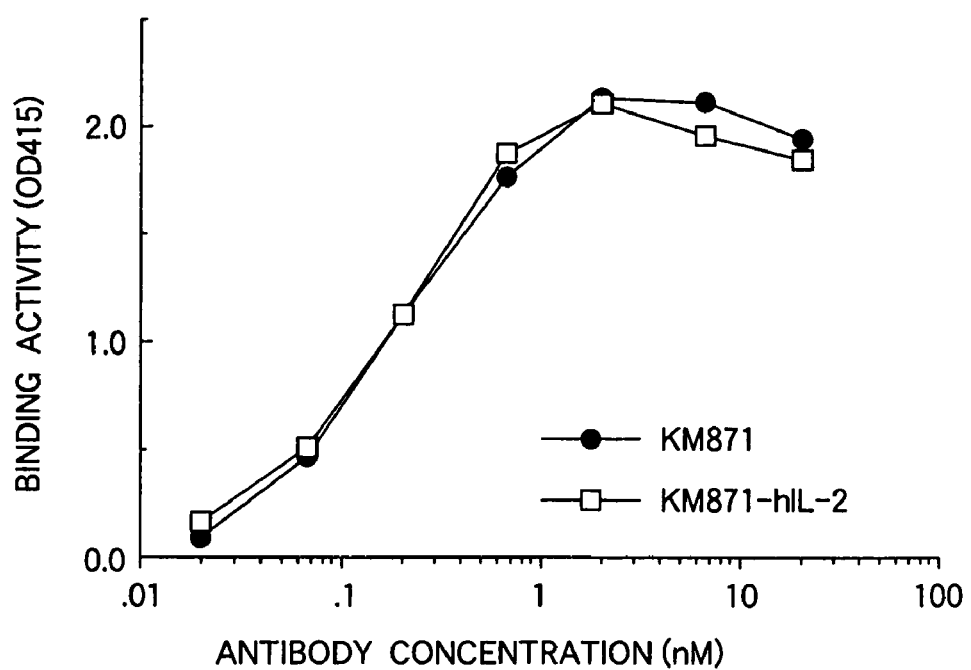
FIG. 32 is a drawing showing binding activity of anti-GD3 chimeric antibody KM8871 and purified fusion protein KM871-hIL-2 to GD3 measured by changing the antibody concentration. The ordinate and the abscissa are the binding activity to GD3 and the antibody concentration, respectively. "●" and "□" show the activities of KM871 and KM871-hIL-2, respectively.
Figure 33:
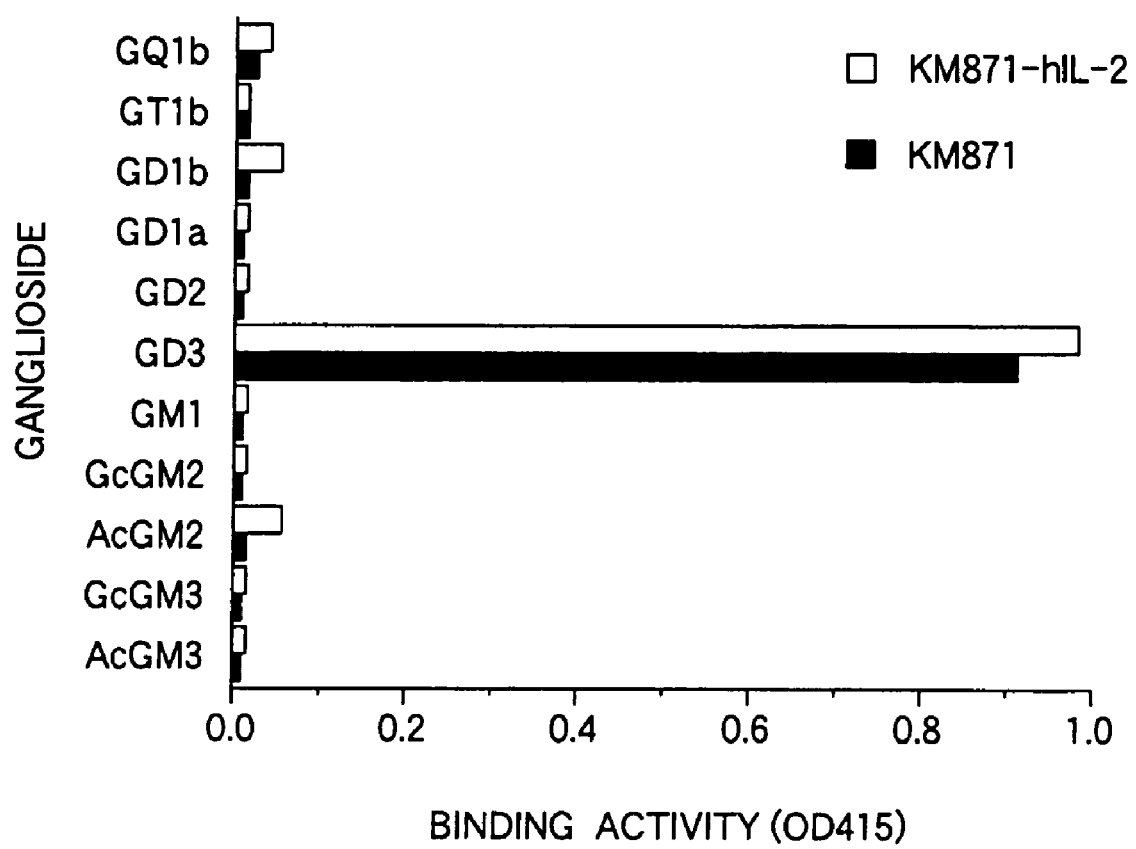
FIG. 33 is a drawing showing reactivity of anti-GD3 chimeric antibody KM871 and purified fusion protein KM871-hIL-2 with various gangliosides. The ordinate and the abscissa are the kind of ganglioside and the binding activity, respectively. AcGM2, GcGM2, AcGM3 and GcGM3 indicate N-acetylGM2, N-glycolylGM2, N-acetylGM3 and N-glycolylGM3, respectively. "■" and "□" show the reactivities of KM871 and KM871-hIL-2, respectively.

Reactivity of the purified KM871-hIL-2 with GD3 (manufactured by DIA-IATRON) was measured in accordance with the method described in the item 2 of Example 1. In this case, a peroxidase-labeled goat anti-human IgG (H & L) antibody (manufactured by American Qualex, used by diluting 3,000 times with 1% BSA-PBS) was used as the secondary antibody solution. FIG. 32 shows results of the examination of the reactivity carried out by fixing the amount of GD3 to be adsorbed to each well of a plate for ELISA to 20 pmol/well and changing the concentration of the anti-GD3 chimeric antibody KM871 and KM871-hIL-2 to be added. As shown in FIG. 32, it was found that KM871-hIL-2 has a GD3 binding activity similar to or higher than that of the anti-GD3 chimeric antibody KM871. FIG. 33 shows results of the examination of the reactivity of a constant concentration (6.7 nM) of anti-GD3 chimeric antibody KM871 and KM871-hIL-2, carried out by changing the kinds of ganglioside to be adsorbed to each well of a plate for ELISA use (adsorption amount: 20 pmol/well). As shown in FIG. 33, it was found that the KM871-hIL-2 strongly binds to GD3 similar to the anti-GD3 chimeric antibody KM871, and it was confirmed that the addition of hIL-2 does not have large influence on the antigen specificity of KM871.

(2) Reactivity of KM871-hIL-2 with Cell Surface GD3 (Immunofluorescent Method)

Figure 34:
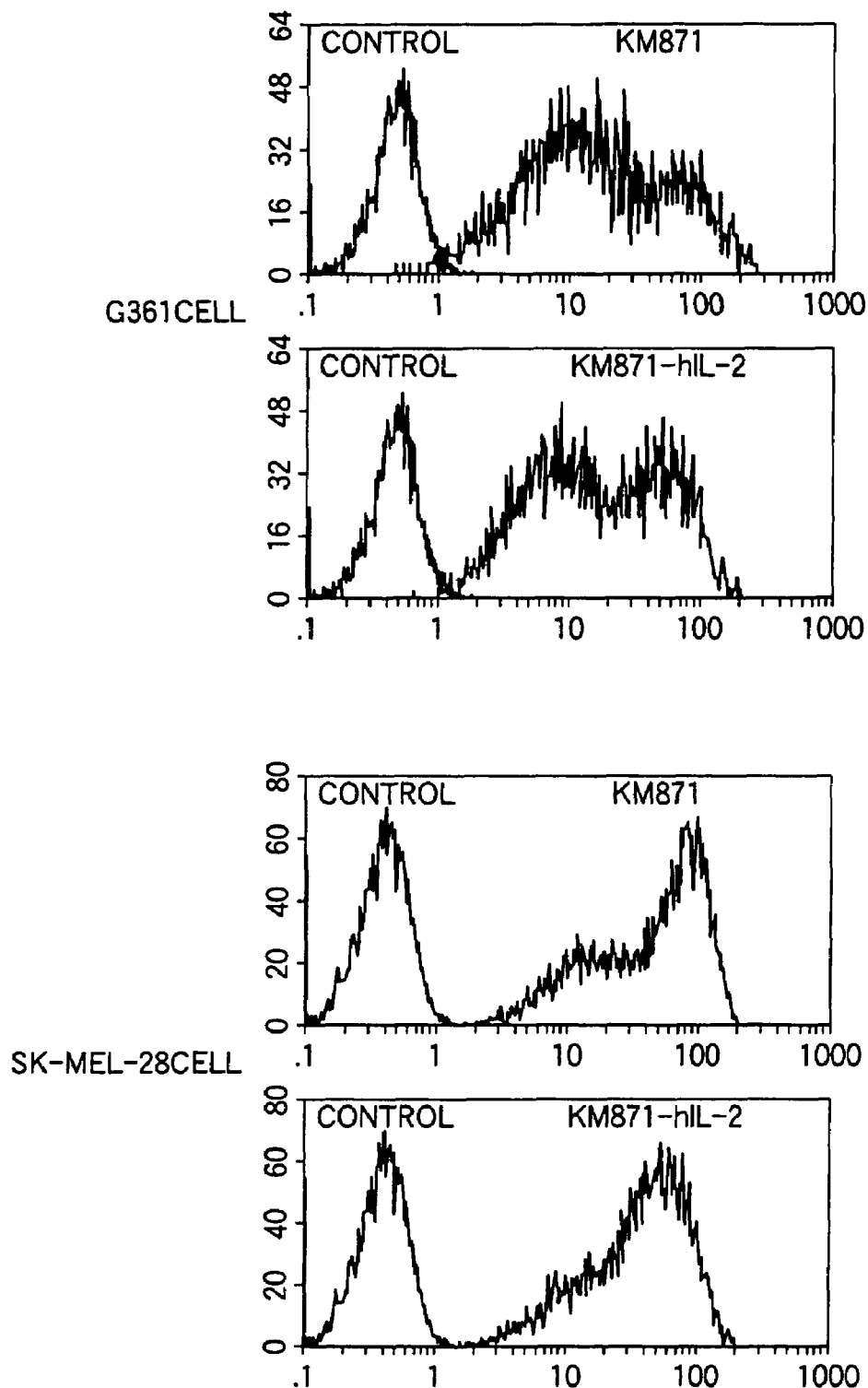
FIG. 34 is a drawing showing reactivity of anti-GD3 chimeric antibody KM871 and purified fusion protein KM871-hIL-2 with human melanoma cell lines G-361 and SK-MEL-28. The ordinate and the abscissa are the number of cells and the fluorescence intensity, respectively. The graphs show the reactivities of KM871 to G361 cell, KM871-hIL-2 to G361 cell, KM871 to SK-MEL-28 and KM871-hIL-2 to SK-MEL-28, respectively, from the upper column.

Reactivity of the purified KM871-hIL-2 with human cancer cells was measured in accordance with the method described in the item 7(2) of Example 1. Results are shown in FIG. 34. As shown in FIG. 34, KM871-hIL-2 showed a strong reactivity with the human melanoma culture cell line G361 and SK-MEL-28, which was almost identical to that of the anti-GD3 chimeric antibody KM871. The results show that the KM871-hIL-2 is useful in the treatment and the like of GD3-positive human tumors including melanoma.

(3) Evaluation of hIL-2 Activity of KM871-hIL-2

Figure 35:
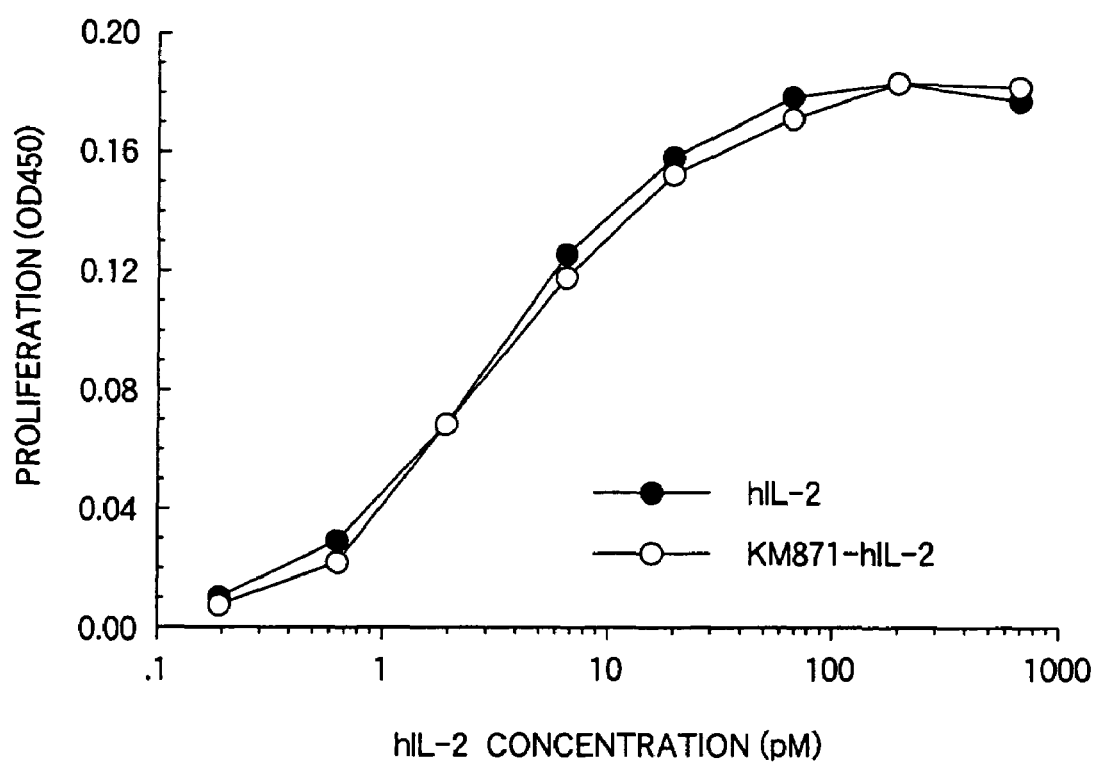
FIG. 35 is a drawing showing growth-supporting activity of hIL-2 and purified fusion protein KM871-hIL-2 against hIL-2-dependent cell CTLL-2 measured by changing concentration of each protein. The ordinate and the abscissa are the growth-supporting activity and the protein concentration, respectively. "●" and "○" indicate the activities of hIL-2 and KM871-hIL-2, respectively.

Activity of the purified KM871-hIL-2 as hIL-2 was measured in accordance with the item 3(2) of Example 2, and results are shown in FIG. 35. As shown in FIG. 35, KM871-hIL-2 showed a biological activity to support CTLL-2 growth similar to that of hIL-2. The results show that the activity of KM871-hIL-2 as hIL-2 is maintained after its fusion with the anti-GD3 chimeric antibody KM871.

(4) Activation of Human Lymphocyte by KM871-hIL-2

In order to evaluate activation of human lymphocyte and accompanying enhancement of cytotoxic activity by the hIL-2 moiety of KM871-hIL-2 in vitro, the cytotoxic activity was measured by the following method in which the method described in the item 7(4) of Example 1 was partially changed.

a. Preparation of Target Cell Suspension

In accordance with the method described in "a" of the item 7(4) of Example 1, a human melanoma culture cell line G-361 was adjusted to give a density of $2 \times 10^5$ cells/ml and used as the target cell suspension.

b. Preparation of Effector Cell Suspension

In accordance with the method described in "b" of the item 7(4) of Example 1, mononuclear cells were separated from venous blood of healthy person and re-suspended to give a density of $1 \times 10^7$ cells/ml to be used as the effector cell suspension.

c. Activation of Lymphocyte

The effector cell suspension (50 µl) prepared in "b" was dispensed into each well of a 96 well U bottom plate (manufactured by Falcon) ($5 \times 10^4$ cells/well). Furthermore, 50 µl of RPMI1640-FBS(10) medium to which the anti-GD3 chimeric antibody KM871 or KM871-hIL-2 had been added was added thereto to give a final concentration of 1 nM (molecular weight of KM871 was calculated as 150 Kd, and molecular weight of KM871-hIL-2 as 180 Kd) and incubated at 37° C. for 72 hours in a 5% $CO_2$ incubator.

d. Measurement of Cytotoxic Activity

Figure 36:
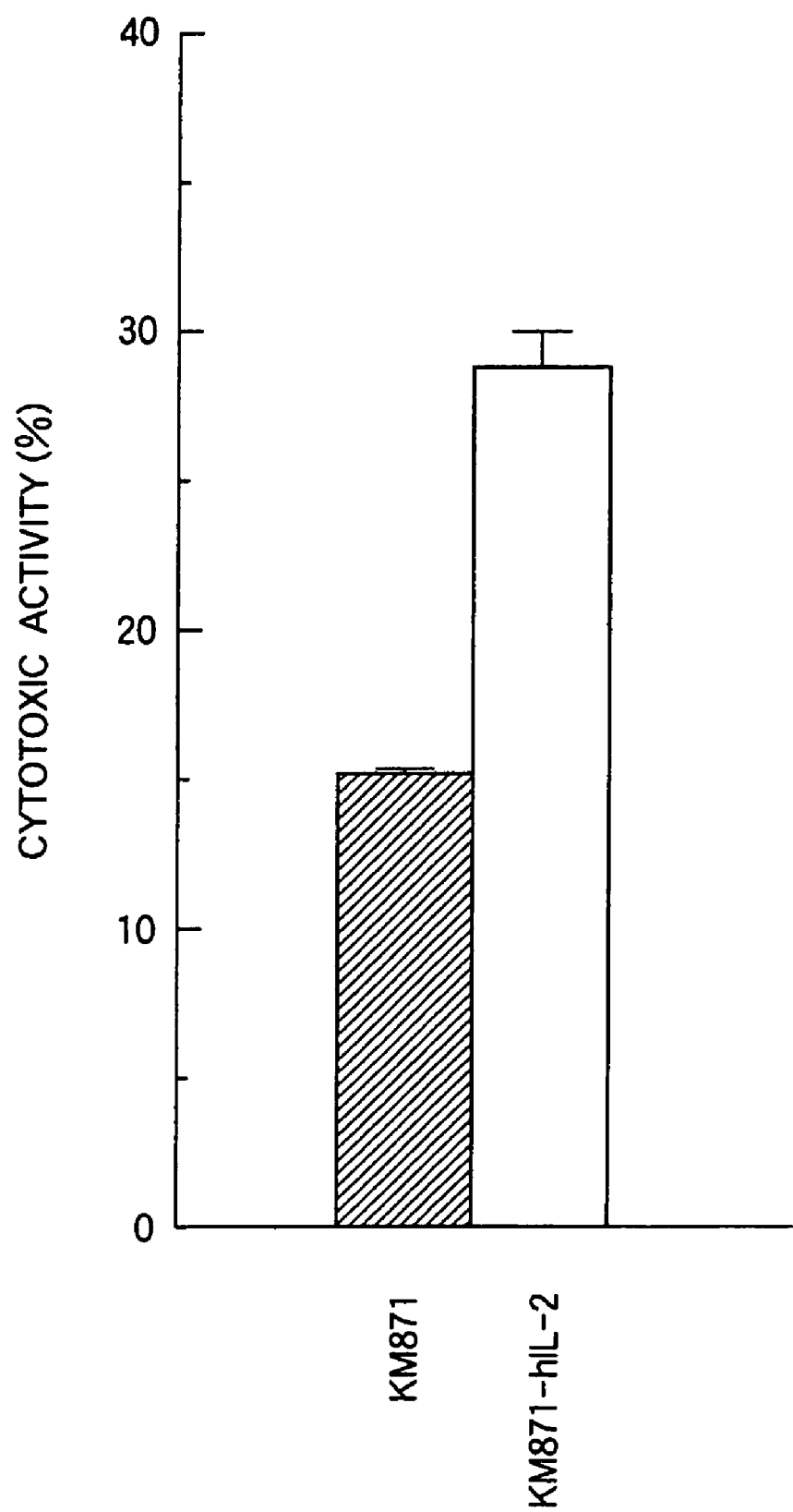
FIG. 36 is a drawing showing results of the measurement of the activation and accompanying cytotoxic activity of human effector cells by anti-GD3 chimeric antibody KM871 and purified fusion protein KM871-hIL-2. The ordinate and the abscissa are the cytotoxic activity and the used protein, respectively. "■" and "□" indicate activities of KM871 and KM871-hIL-2, respectively.

The target cell suspension (50 µl) prepared in "a" was added to each well of the plate prepared in "c", ($1 \times 10^4$ cells/well). In this case, the ratio of the effector cells to the target cells becomes 5:1. Furthermore, 50 µl of RPMI1640-FBS(10) medium to which the anti-GD3 chimeric antibody KM871 or KM871-hIL-2 had been added was added thereto to give a final concentration of 1 nM to carry out the reaction at 37° C. for 4 hours, and then the plate was centrifuged and the amount of $^{51}Cr$ in the supernatant was measured by a γ-counter. The amount of the spontaneously dissociated $^{51}Cr$ was calculated by carrying out the same procedure using the medium alone instead of the effector cell suspension and antibody solution and measuring the amount of $^{51}Cr$ in the supernatant. The amount of the total dissociated $^{51}Cr$ was calculated by carrying out the same procedure by adding the medium alone instead of the antibody solution, and 1 N hydrochloric acid instead of the effector cell suspension, and measuring the amount of $^{51}Cr$ in the supernatant. The cytotoxic activity was calculated by the method described in "b" of the item 7(4) of Example 1, and results are shown in FIG. 36. As shown in FIG. 36, it was found that a cytotoxic activity induced by KM871-hIL-2 was stronger than that induced by KM871. Based on the results, it is expected that the KM871-hIL-2 will also enhance therapeutic effects of KM871 in the clinical application of GD3-positive human tumors by the activation of human lymphocyte via the hIL-2 moiety.

3. In Vivo Evaluation of KM871-hIL-2

(1) Production of B16 Cell Transfectants Introduced with GD3 Synthase Gene for Mouse Syngenic Model a. Construction of GD3 Synthase Gene Stable Expression Vector A vector pAMo-GD3 (3 µg; WO 94/23020) for expressing GD3 synthase gene in animal cell was added to 10 µl of a buffer comprising 10 mM Tris-HCl (pH 7.5), 50 mM sodium chloride, 10 mM magnesium chloride and 1 mM DTT, and 10 units of a restriction enzyme HindIII (Manufactured by Takara Shuzo) were further added thereto to carry out the reaction at 37° C. for 1 hour. The reaction solution was precipitated with ethanol and added to 10 µl of a buffer comprising 50 mM Tris-HCl (pH 7.5), 100 mM sodium chloride, 10 mM magnesium chloride, 1 mM DTT, 100 µg/ml BSA and 0.01% Triton X-100, and 10 units of a restriction enzyme NotI (manufactured by Takara Shuzo) were further added thereto to carry out the reaction at 37° C. for 1 hour. The reaction solution was precipitated with ethanol, and the 5' protruding end formed by the restriction enzyme digestion was changed to blunt end using DNA Blunting Kit (manufactured by Takara Shuzo). The reaction solution was fractionated by agarose gel electrophoresis to recover about 2 µg of a blunt-ended HindIII-NotI fragment of about 2.1 kb using QIAquick Gel Extraction Kit (manufactured by QIAGEN) in accordance with the manufacture's instructions.

Next, 3 µg of the anti-GD3 chimeric antibody expression vector pKANTEX641 was added to 10 µl of a buffer comprising 50 mM Tris-HCl (pH 7.5), 100 mM sodium chloride, 10 mM magnesium chloride and 1 mM DTT, and 10 units of a restriction enzyme EcoRI (manufactured by Takara Shuzo) were further added thereto to carry out the reaction at 37° C. for 1 hour. The reaction solution was precipitated with ethanol, and the 5' protruding end formed by the restriction enzyme digestion was changed to blunt end using DNA Blunting Kit (manufactured by Takara Shuzo). The reaction solution was precipitated with ethanol, added to 10 μl of a buffer comprising 50 mM Tris-HCl (pH 7.5) and 10 mM magnesium chloride, and the solution was further mixed with 10 units of a 5'-terminal dephosphorylation enzyme, calf intestine-derived alkaline phosphatase (manufactured by Takara Shuzo), and allowed to react at 37° C. for 1 hour for dephosphorylation of the 5' end. The reaction solution was subjected to phenol treatment and then fractionated by agarose gel electrophoresis to recover about 2 μg of a blunt end-dephosphorylated EcoRI-NruI fragment of about 9.4 kb using QIAquick Gel Extraction Kit (manufactured by QIAGEN) in accordance with the manufacture's instructions.

Figure 37:
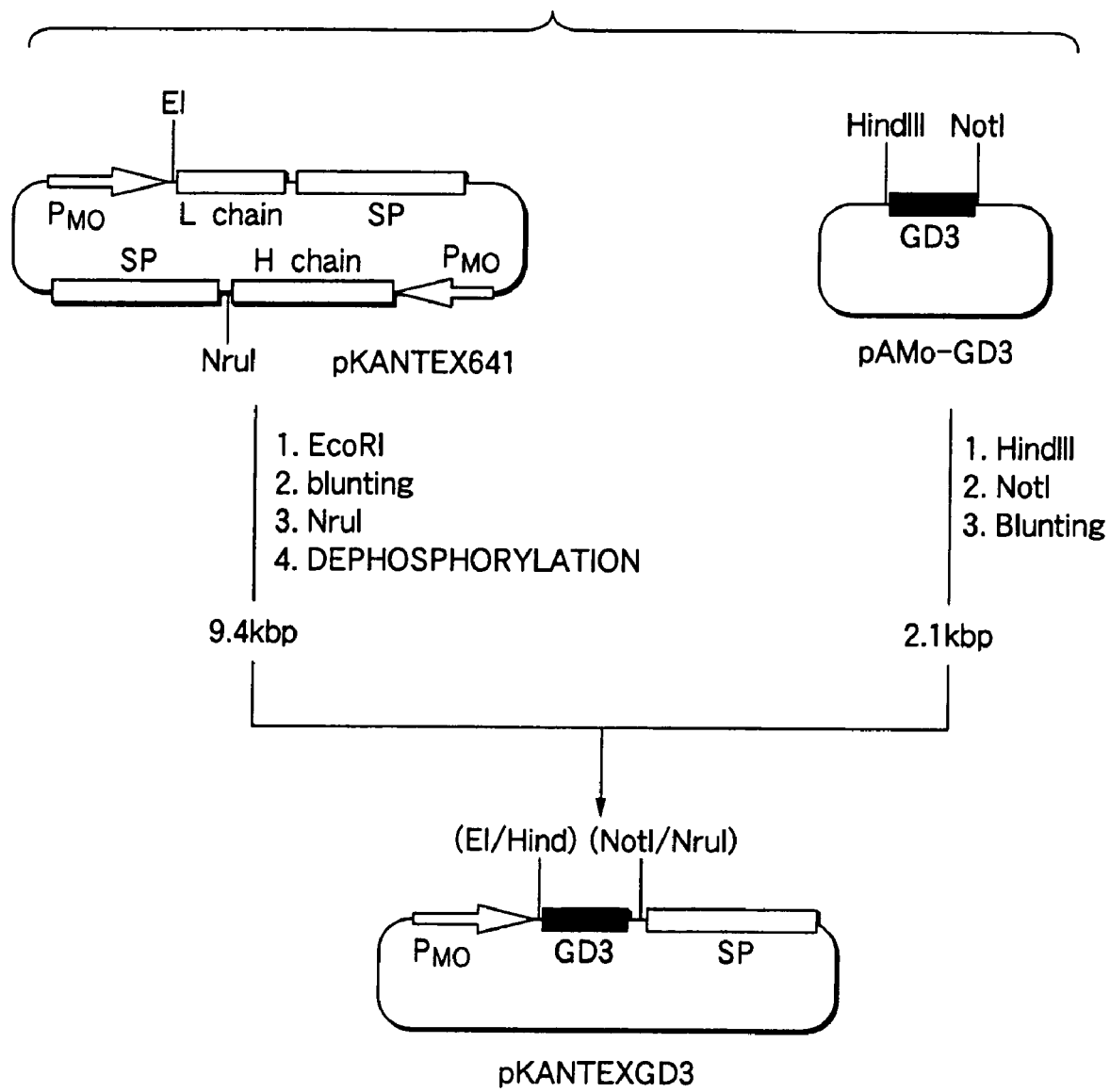
FIG. 37 is a drawing showing construction steps of plasmid pKANTEXGD3.

Next, 0.1 μg of the EcoRI-NruI fragment derived from the plasmid pKANTEX641 and 0.1 μg of the HindIII-NotI fragment derived from the plasmid pAMoGD3, both obtained in the above, were added to 10 μl in total volume of sterile water and ligated using DNA Ligation Kit Ver. 2 (manufactured by Takara Shuzo) in accordance with the manufacture's instructions. Using the thus obtained recombinant plasmid DNA solution, an *E. coli* DH5α was transformed to obtain the GD3 synthase-stable expression vector pKANTEXGD3 shown in FIG. 37.

b. Introduction of GD3 Synthase-Expression Vector into B16 Cells

Figure 38:
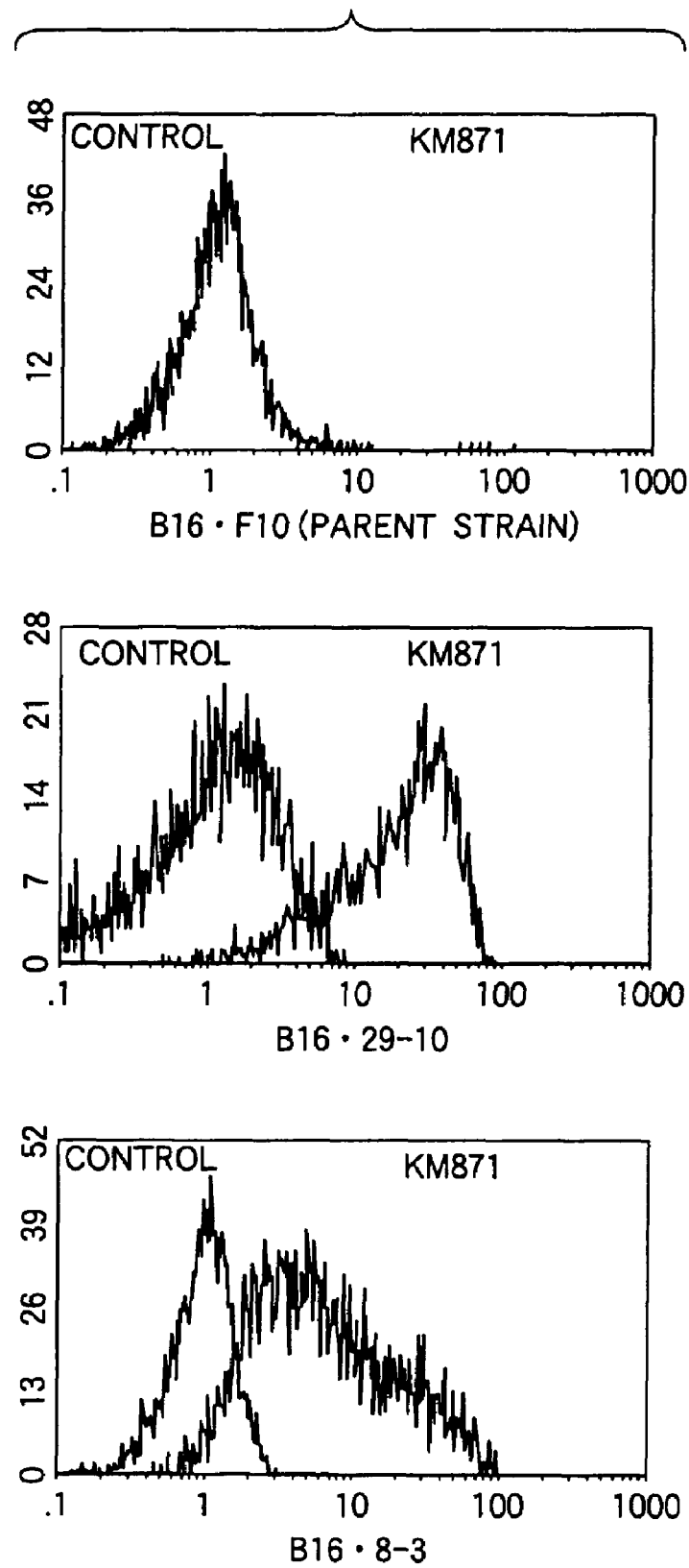
FIG. 38 is a drawing showing reactivity of anti-GD3 chimeric antibody KM871 with GD3 synthase gene-introduced B16 cell lines B16·29-10 and B16·8-3 and the parent line B16·F10 cell. The ordinate and the abscissa are the number of cells and the fluorescence intensity, respectively. The drawings show the reactivities of B16·F10 cell, B16·29-10 and B16·8-3, respectively, from the upper column.

Using 4 μg of the GD3 synthase gene-stable expression vector pKANTEXGD3 obtained in "a" of the item 3(1) of Example 3, B16·F10 cell (ATCC CRL 1581) was transformed in accordance with the method described in the item 6(2) of Example 1, and selection was carried out finally by G418 (0.5 mg/ml) to obtain transfectant clones B16·8-3 and B16·29-10.

c. Analysis of GD3 Expression Level of GD3-Expressing Line by Immunofluorescent Method Each of 1×10$^6$ cells of she GD3 synthase gene transfectants B16·8-3 and B16·29-10 obtained in "b" of the item 3(1) of Example 3 and the parent line B16·F10 cell were suspended in PBS, put into microtubes and centrifuged (2,000 rpm for 2 minutes), and the thus washed cells were stirred after adding 50 μl of the anti-GD3 chimeric antibody KM871 (a solution prepared by adjusting to 5 μg/ml with 1% BSA-PBS, negative control was 1% BSA-PBS alone) and then allowed to react at 4° C. for 1 hour. After the reaction, followed by centrifugation three times with PBS for washing, the cells were mixed with 100 μl of biotin-labeled goat anti-human IgG (H+L) solution (manufactured by VECTOR, used by diluting 400 times with 1% BSA-BS), stirred and then allowed to react at 4° C. for 1 hour. After centrifugation three times with PBS for washing, 100 μl of a streptoavidin-labeled Cy5 pigment solution (Streptavidin-RED670 manufactured by GIBCO, used by diluting 100 times with 1% BSA-PBS) was added and stirred and then allowed to react at 4° C. for 1 hour. After the reaction, followed by centrifugation three times with PBS for washing, the cells were again suspended in PBS to carry out the analysis using a flow cytometer EPICS Elite (manufactured by COULTER). Results are shown in FIG. 38. AS shown in FIG. 38, the anti-GD3 chimeric antibody KM871 reacted only with B16·8-3 and B16·29-10 but did not show reactivity with the parent line B16·F10 cells. The above results show that both of the transfectants B16·8-3 and B16·29-10 express GD3 on the surface and can be used as a model for measuring in vivo antitumor effects of KM871-hIL-2 by transplanting them into C57 BL/6 mouse as the origin of B16 cells.

(2) Measurement of In Vivo Antitumor Effects of KM871-hIL-2 a. Evaluation with Mice Transplanted with GD3-Expressing Transformant B16·29-10

The GD3-expressing B16 cell B16·29-10 obtained in "b" of the item 3(1) of Example 3 was suspended in PBS to give a density of 2.5×10$^6$ cells ml, and 100 μl of the suspension was injected into a C57 BL/6 Cr slc mouse (female, 8 week-old, available from Japan SLC) through its tail vein. Also, starting on the day of tumor transplantation, 50 or 200 μg/day of KM871 or 20 or 50 μg/day of KM871-hIL-2 was administered intravenously once a day continuously for 5 days. The lungs were excised on the 15th day after the tumor transplantation, and visible black metastatic foci on the surface were counted, and results are shown in Table 3 and FIG. 39.

TABLE 3

| Group | | The number of metastatic foci on the lung surface | Average value |
|---|---|---|---|
| Non-administered group | | 147/136/106/72/70 | 106.2 |
| KM871-hIL-2 | 20 μg | 20/15/11/2/2/1 | 8.5 |
| KM871-hIL-2 | 50 μg | 15/12/5/2/0/0 | 5.7 |
| KM871 | 50 μg | 185/114/86/77 | 115.5 |
| KM871 | 200 μg | 113/87/86/86/77/55 | 84 |

Figure 39:
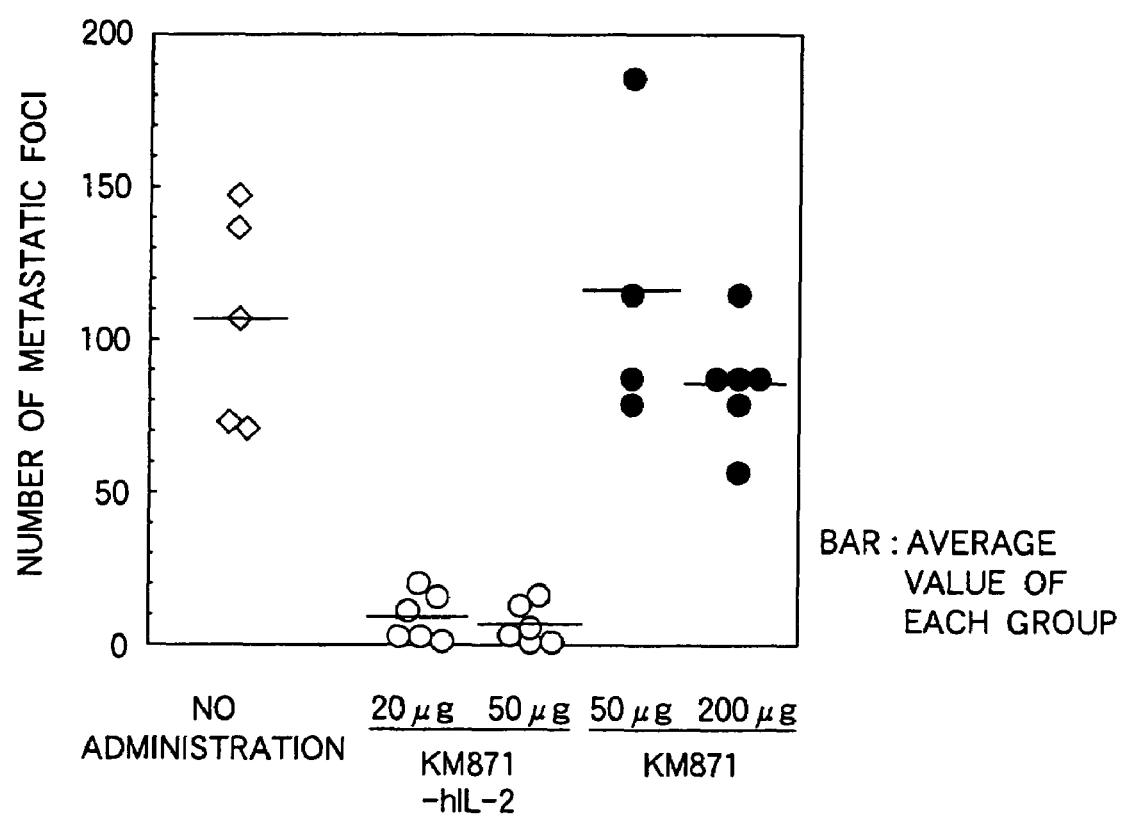
FIG. 39 is a drawing showing results of the measurement of anti-metastatic effects of anti-GD3 chimeric antibody KM871 and KM871-hIL-2 on BL/6 mice into which a GD3-positive B16 cell line B16·29-10 is transplanted. The ordinate and the bar of the graph show the number of metastatic foci on the lung surface and the average value of each group, respectively. No administration means a control group in which the antibody is not administered. "◇", "○" and "●" indicate the numbers of lung-metastasized foci in mice of the control group, the KM871-hIL-2-administered group and the KM871-administered group, respectively.

As shown in Table 3 and FIG. 39, KM871-hIL-2 showed clearly more potent anti-metastatic effect than that of KM871 in the model mouse of the clone B16·29-10.

b. Evaluation with Mice Transplanted with GD3-Expressing Transformant B16·8-3

Using the GD3-expressing B16 cell B16·8-3 obtained in "b" of the item 3(1) of Example 3, anti-metastatic effect of KM871-hIL-2 was measured in accordance with the method described in "a" of the item 3(2) of Example 3. The dose was 40 or 100 μg/day for both KM871 and KM871-hIL-2. Results are shown in Table 4 and FIG. 40.

TABLE 4

| Group | | The number of metastatic foci on the lung surface | Average value |
|---|---|---|---|
| Non-administered group | | 170/128/113/66/42/16/0 | 76.4 |
| KM871-hIL-2 | 40 μg | 1/0/0 | 0.3 |
| KM871-hIL-2 | 100 μg | 3/0/0 | 1 |
| KM871 | 40 μg | 128/70/30 | 76 |
| KM871 | 100 μg | 26/20/17 | 21 |

Figure 40:
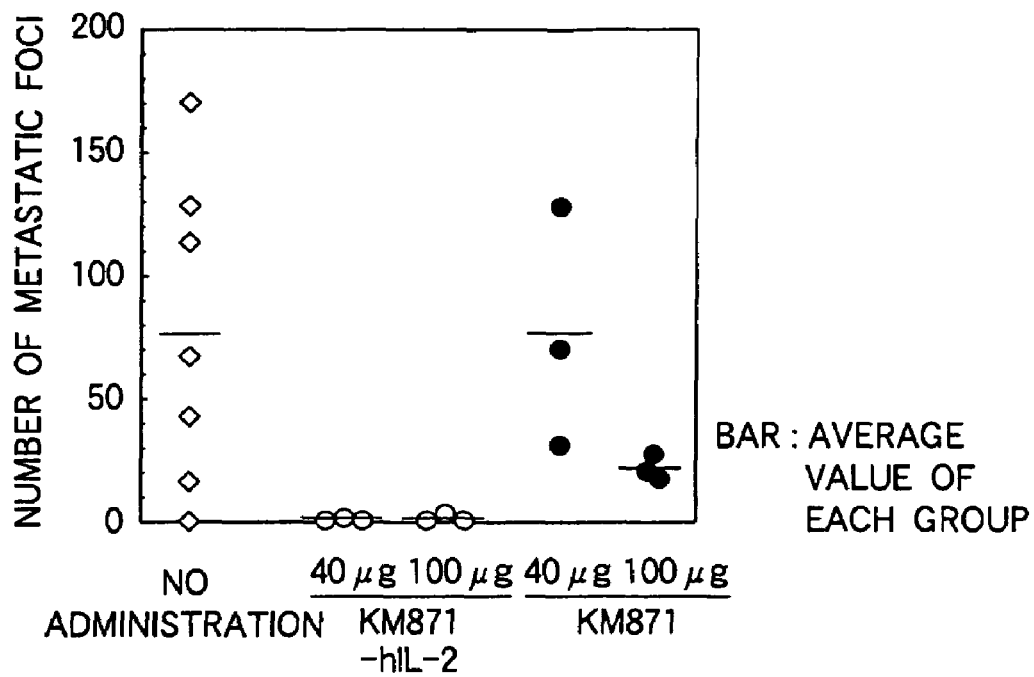
FIG. 40 is a drawing showing a result of the measurement of anti-metastatic effects of anti-GD3 chimeric antibody KM871 and KM871-hIL-2 on BL/6 mice into which a GD3-positive B16 cell line B16·8-3 is transplanted. The ordinate and the bar of the graph show the number of metastatic foci on the lung surface and the average value of each group, respectively. No administration means a control group in which the antibody is not administered. "◇", "○" and "●" indicate the numbers of lung-metastasized foci in mice of the control group, the KM871-hIL-2-administered group and the KM871-administered group, respectively.

As shown in Table 4 and FIG. 40, KM871-hIL-2 showed more potent anti-metastatic effect than that of KM871 in the model mouse of the clone B16·8-3.

c. Comparison with Combined Administration of KM871 and hIL-2

The GD3-expressing B16 cells B16·29-10 obtained in "b" of the item 3(1) of Example 3 were suspended in PBS to give a density of 2.5×10$^6$ cells/ml, and 100 μl of the suspension was injected into a C57 BL/6 Cr slc mouse (female, 8 week-old, available from Japan SLC) through its tail vein. Also, starting on the day of tumor transplantation, 6 μg/day (0.0333 nmol) or 18 μg/day (0.1 nmol) of KM871-hIL-2 was administered intravenously once a day continuously for 5 days. Using other groups, a mixed solution of KM871 and hIL-2 (manufactured by Peprotech) corresponding to the amount of the administered KM871-hIL-2 (5 μg (0.0333 nmol) of KM871 and 1 μg (0.0667 nmol) of hIL-2, or 15 μg (0.1 nmol) of KM871 and 3 μg (0.2 nmol) of hIL-2) was administered through the tail vein once a day continuously for 5 days, starting on the day of tumor transplantation. The lungs were excised on the 15th day after the tumor transplantation, and visible black metastatic foci on the surface were counted, and results are shown in Table 5 and FIG. 41.

TABLE 5

| Group | | The number of metastatic foci on the lung surface | Average value |
|---|---|---|---|
| Non-administered group | | 163/132/97/95/88/57 | 105.3 |
| KM871-hIL-2 | 6 μg | 26/26/17/12/8 | 17.8 |
| KM871-hIL-2 | 18 μg | 43/34/28/13/2 | 24 |
| KM871 + hIL-2 | 5 μg + 1 μg | 215/117/97/85/56 | 114 |
| KM871 + hIL-2 | 15 μg + 3 μg | 92/61/48/46/42 | 57.8 |

Figure 41:
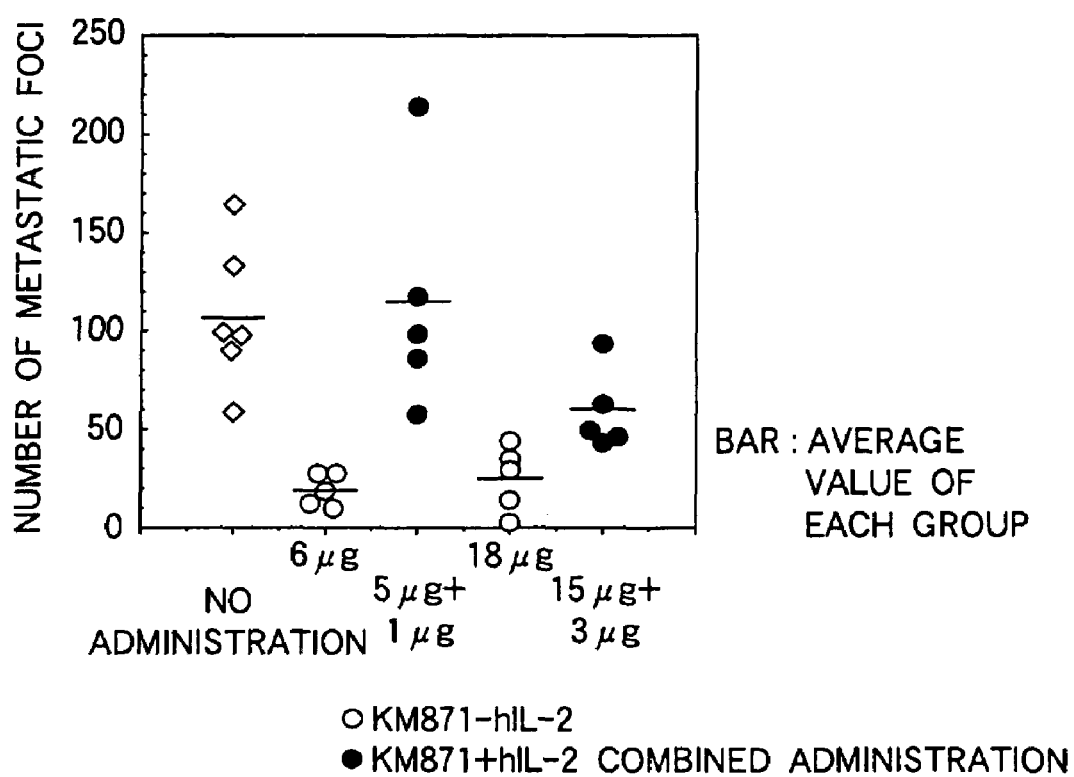
FIG. 41 is a drawing showing results of the measurement of anti-metastatic effects by combined administration of anti-GD3 chimeric antibody KM871 and hIL-2 and administration of KM871-hIL-2 on BL/6 mice into which a GD3-positive B16 cell line B16·29-10 is transplanted. The ordinate and the bar of the graph show the number of metastatic foci on the lung surface and the average value of each group. No administration means a control group in which the antibody is not administered. "◇", "○" and "●" indicate the number of lung-metastasized foci in mice of the control group, the KM871-hIL-2-administered group and the KM871/hIL-2 combined administered group, respectively.

As shown in Table 5 and FIG. 41, KM871-hIL-2 showed more potent anti-metastatic effect than that of the combined administration of the equivalent amount of KM871 and hIL-2 in the model mouse of the clone B16·29-10. The results show that the in vivo antitumor effect shown by KM871-hIL-2 is not a simple additive effect of KM871 and hIL-2 but a result of the efficient induction of antitumor immunity due to activation of peripheral lymphocytes by the hIL-2 moiety of KM871-hIL-2 accumulated in the tumor, thus showing a possibility that KM871-hIL-2 will become a therapeutic agent having higher therapeutic effect than that of the conventional administration of hIL-2 alone or its combination use with an antibody and also having reduced side effects derived from hIL-2.

d. Evaluation by Solid Tumor Early Model of B16·29-10 Cell

The GD3-expressing B16 cell B16·29-10 obtained in "b" of the item 3(1) of Example 3 was suspended in PBS to give a density of $1\times10^7$ cells/ml, and 50 μl of the suspension was transplanted subcutaneously in C57 BL/6 mice (male, 7 week-old, available from Charles River Japan). By setting the following administration groups, each agent was administered intravenously once a day continuously for 5 days, starting on the day of tumor transplantation.

| Non-administered group | |
|---|---|
| hIL-2: | 10 μg/day (0.667 nmol) |
| KM871: | 50 μg/day (0.333 nmol) |
| KM871-hIL-2: | 60 μg/day (0.333 nmol) |

The test was carried out using 5 animals for each group. Each agent was prepared to give a concentration of 200 μl/animal by diluting with a citrate buffer. Five day after the transplantation, the tumor diameter was measured periodically using slide calipers, and the antitumor effect was judged based on the ratio of the average value of tumor volumes in each administered group to the average value of tumor volumes in non-administered group and on the number of survived days after commencement of the administration. The tumor volume was calculated by the following equation Tumor volume=(width)$^2$×length×0.5.

Figure 42:
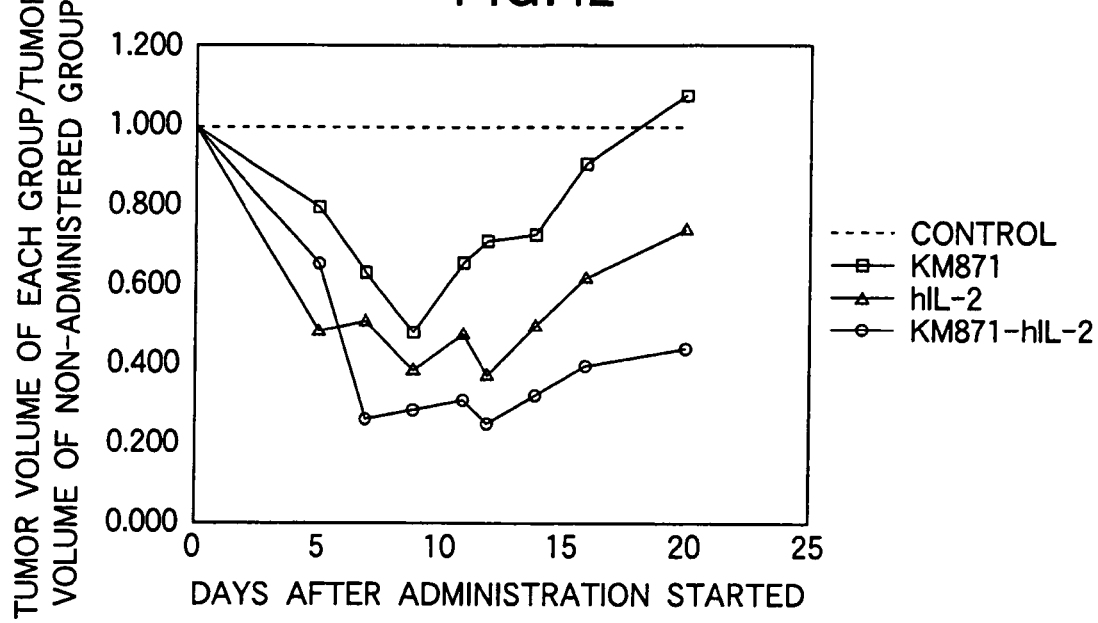
FIG. 42 is a drawing showing results of the measurement of growth inhibition effects of KM871-hIL-2 on a solid tumor early stage model of BL/6 mice into which a GD3-positive B16 cell line B16·29-10 is subcutaneously transplanted. The ordinate and the abscissa of the graph show the ratio of the average value of tumor volumes in each group to the average value of tumor volumes in the control group and days after commencement of the agent administration, respectively. Dotted line, "□", "Δ" and "○" indicate control, the KM871-administered group, the hIL-2-administered group and the KM871-hIL-2-administered group, respectively.

The average value of tumor volumes in each group is shown in Table 6, results of the ratio of the average value of tumor volumes in each group to the average value of tumor volumes in non-administered group are shown in Table 7 and FIG. 42, and results of the number of survived days are shown in Table 8.

TABLE 6

| Days after administration | Non-administered group | KM871 | hIL-2 | KM871-hIL-2 |
|---|---|---|---|---|
| 0 | 0 | 0 | 0 | 0 |
| 5 | 75 | 60 | 36 | 49 |
| 7 | 131 | 82 | 67 | 34 |
| 9 | 306 | 146 | 115 | 87 |
| 11 | 756 | 494 | 359 | 231 |
| 12 | 1325 | 939 | 489 | 332 |
| 14 | 2333 | 1701 | 1147 | 733 |
| 16 | 3656 | 3331 | 2268 | 1432 |
| 20 | 7799 | 8345 | 5765 | 3381 |

Unit is mm$^3$

TABLE 7

| Days after administration | Non-administered group | KM871 | hIL-2 | KM871-hIL-2 |
|---|---|---|---|---|
| 0 | 1.000 | 1.000 | 1.000 | 1.000 |
| 5 | 1.000 | 0.796 | 0.484 | 0.656 |
| 7 | 1.000 | 0.624 | 0.510 | 0.261 |
| 9 | 1.000 | 0.477 | 0.376 | 0.285 |
| 11 | 1.000 | 0.654 | 0.475 | 0.305 |
| 12 | 1.000 | 0.709 | 0.369 | 0.251 |
| 14 | 1.000 | 0.729 | 0.492 | 0.314 |
| 16 | 1.000 | 0.911 | 0.620 | 0.392 |
| 20 | 1.000 | 1.070 | 0.739 | 0.434 |

TABLE 8

| Group | Survived days after commencement of administration (day) | Average value (day) |
|---|---|---|
| Non-administered group | 24/27/27/30/30 | 27.6 |
| hIL-2 | 26/28/32/32/33 | 30.2 |
| KM871 | 27/30/30/32/35 | 30.8 |
| KM871-hIL-2 | 32/32/43/51/57 | 43.0 |

As shown in Tables 6, 7 and 8 and FIG. 42, KM871-hIL-2 showed more potent growth inhibition effect and life-prolonging effect than those of the hIL-2 alone or antibody alone.

e. Evaluation by Solid Tumor Advanced Stage Model of B16·29-10 Cell

The GD3-expressing B16 cell B16·29-10 was suspended in PBS to a density of $1\times10^8$ cells/ml, and 50 μl of the suspension was transplanted subcutaneously in C57 BL/6 mice (male, 7 week-old, available from Charles River Japan). By setting the following administration groups, tumor volumes on the 6th day after the tumor transplantation were calculated by the measuring method described in "d" of the item 3(2) of Example 3 to select individuals within the range of from 10 to 80 mm$^3$, and then each of the following agents was administered intravenously once a day continuously for 8 days.

| Non-administered group | |
|---|---|
| hIL-2: | 10 µg/day (0.667 nmol) |
| KM871: | 50 µg/day (0.333 nmol) |
| KM871: | 200 µg/day (1.33 nmol) |
| KM871-hIL-2: | 24 µg/day (0.133 nmol) |
| KM871-hIL-2: | 60 µg/day (0.333 nmol) |

The test was carried out using 3 animals only in the KM871-hIL-2 60 µg/day administration group, and 5 animals for each of the other groups. Each agent was prepared to a concentration of 200 µl/animal by diluting with citrate buffer. Starting on the day of transplantation, the tumor diameter was measured periodically using slide calipers, and the antitumor effect was judged based on the ratio of the average value of tumor volumes on the measured day and tumor volumes on the day of commencement of the administration in each mouse in each treated groups (hereinafter referred to as "V/V0") to the V/V0 in non-administered group and on the number of survived days after commencement of the administration.

Figure 43:
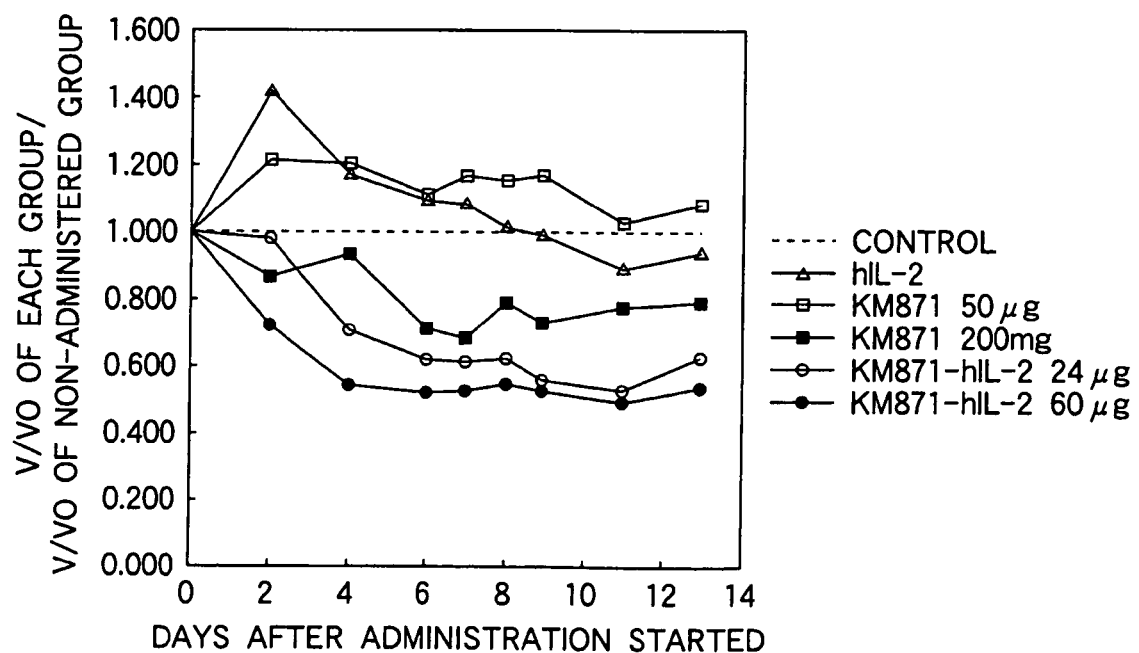
FIG. 43 is a drawing showing results of the measurement of growth inhibition effects of KM871-hIL-2 on a solid tumor advanced stage model of BL/6 mice into which a GD3-positive B16 cell line B16·29-10 is subcutaneously transplanted. The ordinate of the graph shows the ratio of average value of V/V0 values in each group to average value of V/V0 values in the control group. V/V0 indicates the ratio of the tumor volume of each mouse on each measured day to the tumor volume on the day of commencement of the administration. The abscissa shows days after commencement of the agent administration. Dotted line, "Δ", "□", "■", "○" and "●" indicate control, the hIL-2-administered group, the KM871-administered group at 50 μg/day, the KM871-administered group at 200 μg/day, the KM871-hIL-2-administered croup at 24 μg/day and KM871-hIL-2-administered group at 60 μg/day.

Results of V/V0 in each group are shown in Table 9, results of the ratio of the V/V0 in each group to the V/V0 in non-administered group are shown in Table 10 and FIG. 43, and results of the number of survived days are shown in Table 11.

TABLE 9

| Days | Non-administered group | hIL-2 10 µg | KM871 50 µg | KM871 200 µg | KM871-hIL-2 24 µg | KM871-hIL-2 60 µg |
|---|---|---|---|---|---|---|
| 0 | 1.00 | 1.00 | 1.00 | 1.00 | 1.00 | 1.00 |
| 2 | 2.15 | 3.03 | 2.57 | 1.86 | 2.09 | 1.54 |
| 4 | 5.36 | 6.15 | 6.37 | 4.98 | 3.79 | 2.88 |
| 6 | 13.18 | 14.31 | 14.43 | 9.35 | 8.12 | 6.85 |
| 7 | 16.45 | 17.68 | 18.99 | 11.22 | 10.05 | 8.58 |
| 8 | 21.09 | 21.31 | 24.05 | 16.56 | 13.04 | 11.50 |
| 9 | 28.95 | 28.42 | 33.43 | 21.08 | 16.10 | 15.19 |
| 11 | 54.97 | 48.52 | 56.07 | 42.65 | 29.13 | 27.01 |
| 13 | 93.70 | 86.85 | 100.34 | 74.16 | 58.17 | 49.80 |

TABLE 10

| Days | Non-administered group | hIL-2 10 µg | KM871 50 µg | KM871 200 µg | KM871-hIL-2 24 µg | KM871-hIL-2 60 µg |
|---|---|---|---|---|---|---|
| 0 | 1.000 | 1.000 | 1.000 | 1.000 | 1.000 | 1.000 |
| 2 | 1.000 | 1.406 | 1.196 | 0.862 | 0.973 | 0.718 |
| 4 | 1.000 | 1.147 | 1.187 | 0.928 | 0.706 | 0.537 |
| 6 | 1.000 | 1.086 | 1.096 | 0.710 | 0.616 | 0.520 |
| 7 | 1.000 | 1.075 | 1.155 | 0.682 | 0.611 | 0.522 |
| 8 | 1.000 | 1.011 | 1.141 | 0.785 | 0.619 | 0.545 |
| 9 | 1.000 | 0.982 | 1.155 | 0.728 | 0.556 | 0.525 |
| 11 | 1.000 | 0.883 | 1.020 | 0.776 | 0.530 | 0.491 |
| 13 | 1.000 | 0.927 | 1.071 | 0.791 | 0.621 | 0.531 |

TABLE 11

| Group | | Survived days after commencement of administration (day) | Average value (day) |
|---|---|---|---|
| Non-administered group | | 15/23/23/24/34 | 23.8 |
| hIL-2 | | 15/15/18/27/29 | 20.8 |
| KM871 | 50 µg | 19/20/23/30/34 | 25.2 |

TABLE 11-continued

| Group | | Survived days after commencement of administration (day) | Average value (day) |
|---|---|---|---|
| KM871 | 200 µg | 18/19/23/27/34 | 24.2 |
| KM871-hIL-2 | 24 µg | 29/38/39/41/49 | 39.2 |
| KM871-hIL-2 | 60 µg | 29/32/37 | 32.7 |

As shown in Tables 9, 10 and 11 and FIG. 43, KM871-hIL-2 showed more potent growth inhibition effect and life-prolonging effect than those of the hIL-2 alone or antibody alone.

f. Effect of Combination use of KM871 and KM871-hIL-2 in Solid Tumor Advanced Stage Model of B16·29-10 Cell The GD3-expressing B16 cell B16·29-10 obtained in "b" of the item 3(1) of Example 3 was suspended in PBS to give a density of $1 \times 10^8$ cells/ml, and 50 µl of the suspension was transplanted subcutaneously in C57 BL/6 mice (male, 7 week-old, available from Charles River Japan). By setting the following administration groups, tumor volumes on the 6th day after the tumor transplantation (0th day) were calculated by the measuring method described in d. of the item 3(2) of Example 3 to select individuals within the range of from 10 to 100 $mm^3$, and then each of the following agents was administered intravenously.

| Non-administered group | |
|---|---|
| hIL-2: | 10 µg/day × 5 days continuous administration (0th to 4th days) |
| KM871: | 800 µg/day × single administration (0th day) |
| KM871 + KM871-hIL-2: | 800 µg/day × single administration (0th day) + 15 µg/day × 5 days continuous administration (0th to 4th days) |
| KM871 + KM871-hIL-2: | 800 µg/day × single administration (0th day) + 60 µg/day × 5 days continuous administration (0th to 4th days) |

The test was carried out using 5 animals for each group. Each agent was prepared to give a concentration of 200 µl/animal by diluting with a citrate buffer. Starting on the day of transplantation, the tumor diameter was measured periodically using slide calipers, and the antitumor effect was judged based on the ratio of the V/V0 in each treated group to the V/V0 in non-administered group and on the number of survived days after commencement of the administration. Results of V/V0 in each group are shown in Table 12, results of the ratio of the V/V0 in each group to the V/V0 in non-administered group are shown in Table 13 and FIG. 44, and results of the number of survived days are shown in Table 14.

TABLE 12

| Days | Non-administered group | hIL-2 10 µg × 5 | KM871 800 µg × 1 | KM871 + KM871-hIL-2 800 µg × 1 + 15 µg × 5 | KM871 + KM871-hIL-2 800 µg × 1 + 60 µg × 5 |
|---|---|---|---|---|---|
| 0 | 1.00 | 1.00 | 1.00 | 1.00 | 1.00 |
| 2 | 3.09 | 2.76 | 1.81 | 1.68 | 1.49 |
| 4 | 8.54 | 4.10 | 4.10 | 2.56 | 2.68 |
| 6 | 17.48 | 9.96 | 14.17 | 6.42 | 6.03 |

TABLE 12-continued

| Days | Non-administered group | hIL-2 10 µg × 5 | KM871 800 µg × 1 | KM871 + KM871-hIL-2 800 µg × 1 + 15 µg × 5 | KM871 + KM871-hIL-2 800 µg × 1 + 60 µg × 5 |
|---|---|---|---|---|---|
| 8 | 46.84 | 20.63 | 25.08 | 11.62 | 10.58 |
| 10 | 63.99 | 33.09 | 49.33 | 22.98 | 17.65 |
| 12 | 104.89 | 57.06 | 75.47 | 38.46 | 27.76 |

TABLE 13

| Days | Non-administered group | hIL-2 10 µg × 5 | KM871 800 µg × 1 | KM871 + KM871-hIL-2 800 µg × 1 + 15 µg × 5 | KM871 + KM871-hIL-2 800 µg × 1 + 60 µg × 5 |
|---|---|---|---|---|---|
| 0 | 1.00 | 1.00 | 1.00 | 1.00 | 1.00 |
| 2 | 1.00 | 0.89 | 0.59 | 0.54 | 0.48 |
| 4 | 1.00 | 0.48 | 0.48 | 0.30 | 0.31 |
| 6 | 1.00 | 0.57 | 0.81 | 0.37 | 0.34 |
| 8 | 1.00 | 0.44 | 0.54 | 0.25 | 0.23 |
| 10 | 1.00 | 0.52 | 0.77 | 0.36 | 0.28 |
| 12 | 1.00 | 0.54 | 0.72 | 0.37 | 0.26 |

TABLE 14

| Group | | Survived days after commencement of administration (day) | Average value (day) |
|---|---|---|---|
| Non-administered group | | 9/12/16/16/29 | 16.4 |
| hIL-2 | | 17/17/24/32/36 | 25.2 |
| KM871 | | 8/16/17/26/31 | 19.6 |
| KM871 + KM871-hIL-2 | 15 µg | 17/24/29/32/43 | 29.7 |
| KM871 + KM871-hIL-2 | 60 µg | 29/29/36/36/43 | 34.6 |

Figure 44:
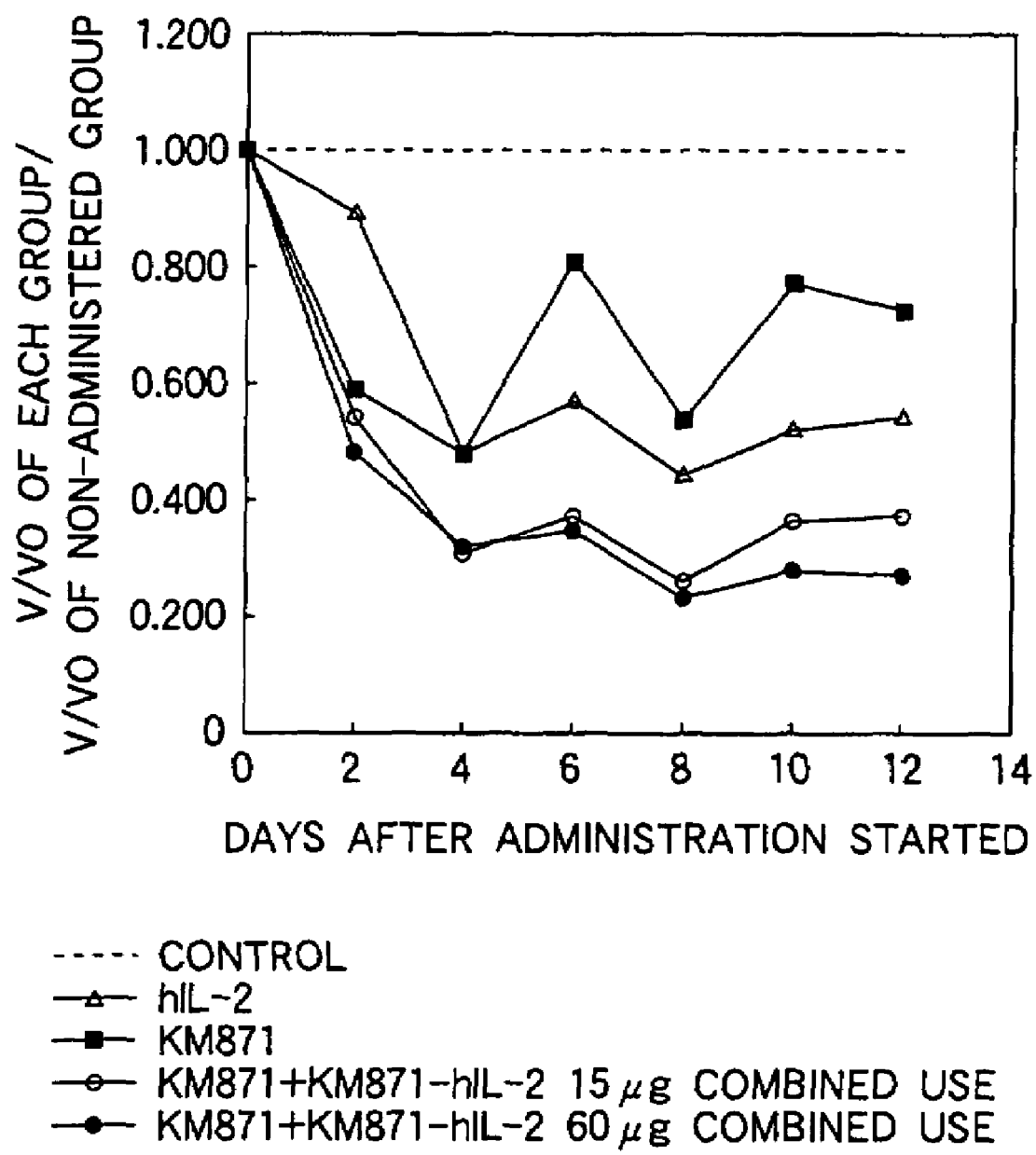
FIG. 44 is a drawing showing results of the measurement of growth inhibition effects by combined administration of anti-GD3 chimeric antibody KM871 and KM871-hIL-2 on a solid tumor advanced stage model of BL/6 mice into which a GD3-positive B16 cell line B16·29-10 is subcutaneously transplanted. The ordinate of the graph shows the ratio of the average value of V/V0 values in each group to the average value of V/V0 values in the control group. V/V0 indicates the ratio of tumor volume of each mouse on each measured day to tumor volume on the day of commencement of the administration. The abscissa shows days after commencement of the agent administration. Dotted line, "Δ", "■", "○" and "●" indicate control, the hIL-2-administered group, the KM871-administered group, the combined administration group of KM871 and KM871-hIL-2 at 15 μg/day and the combined administration group of KM871 and KM871-hIL-2 at 60 μg/day.

As shown in Table 12, Table 13, FIG. 44 and Table 14, combined administration of KM871 and KM871-hIL-2 showed more potent growth inhibition effect and life-prolonging effect than those of the hIL-2 alone or antibody alone. The results show a possibility that combined administration of KM871-hIL-2 and KM871 will become an excellent therapeutic method for GD3-positive cancers.

4. Analysis of In Vivo Antitumor Mechanism of KM871-hIL-2

(1) Activation of Mouse Effector Cell and Enhancement of Cytotoxic Activity by KM871-hIL-2

In order to evaluate activation of mouse effector cell by the hIL-2 moiety of KM871-hIL-2 and accompanying enhancement of cytotoxic activity, the cytotoxic activity was measured in accordance with the method shown below.

a. Preparation of Mouse Effector Cell Suspension

The following administration groups were set using C57 BL/6 mice (female, 8 week-old, Japan SLC), and each agent was administered intravenously.

| Non-administered group | |
|---|---|
| hIL-2: | 10 µg (0.667 nmol)/day × 5 days of continuous administartion (0th to 4th days) |
| KM871-hIL-2: | 60 µg (0.333 nmol)/day × single administration (2nd day) |
| KM871-hIL-2: | 60 µg (0.333 nmol)/day × two administrations' (0th day and 2nd day) |

After completion of all administrations on the 4th day, the spleen was excised, mashed using a slide glass in 6 ml of RPMI1640-FBS(10) medium and then passed through a 70 µm diameter nylon mesh (manufactured by Falcon) to prepare a suspension of splenocytes. A density separation medium for mouse lymphocytes (5 ml), Lympholite-M, was put into a 15 ml tube, overlaid gently with 5 ml of the thus obtained splenocyte suspension and then centrifuged at room temperature for 20 minutes at 1,000×g. The lymphocyte layer of the interface was recovered using a dropping pipette, 10 ml of RPMI1640-FBS(10) medium was added thereto, and the mixture was centrifuged (800×g, 4° C., 10 minutes) and then the supernatant was discarded for washing. After repeating the washing procedure again, an effector cell suspension was prepared to give a final density of $2×10^7$ cells/ml by adding RPMI1640-FBS(10) medium.

b. Preparation of Target Cell Suspension

In accordance with the method described in "a" of the item 7(4) of Example 1, the GD3-expressing B16 cell B16·29-10 obtained in "b" of the item 3(1) of Example 3 was labeled with $^{51}Cr$ to give $2×10^5$ cells/ml of a target cell suspension.

c. Measurement of Cytotoxic Activity

Figure 45:
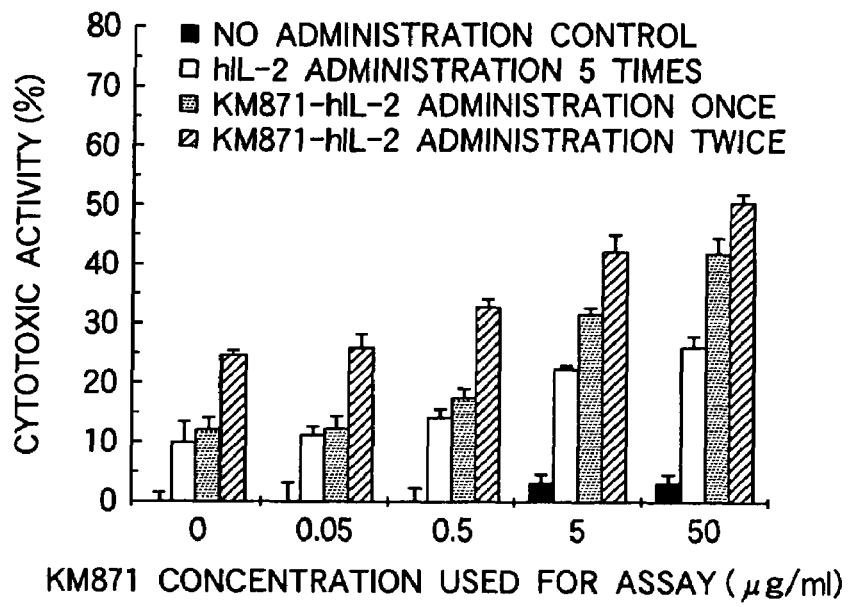
FIG. 45 is a drawing showing results of measurement of the activation and accompanying enhance in cytotoxic activity of BL/6 mouse spleen cells by hIL-2 or KM871-hIL-2. The ordinate and the abscissa are the cytotoxic activity and the concentration of KM871 used in the cytotoxic activity measurement, respectively. Black bar, white bar, gray bar and shaded bar indicate the activity when spleen cells of non-administered control mice are used, the activity when spleen cells of mice to which hIL-2 is administered five times are used, the activity when spleen cells of mice to which KM871-hIL-2 is administered once are used and the activity when spleen cells of mice to which KM871-hIL-2 is administered five times are used, respectively.

Each of 100 µl of the effector cell suspension prepared in "a", 50 µl of the target cell suspension prepared in "b" ($1×10^4$ cells/well) and KM871 serially diluted with RPMI1640-FBS(10) medium to give a final concentration of 0, 0.05, 0.5, 5 or 50 µg/ml was added to each well of a 96 well U bottom plate. In this case, the ratio of the effector cells to the target cells, becomes 200:1. After the reaction at 37° C. for 10 hours, the plate was centrifuged and the amount of $^{51}Cr$ in the supernatant was measured by a γ-counter. The amount of the spontaneously dissociated $^{51}Cr$ was calculated by carrying out the same procedure using the medium alone instead of the effector cell suspension and antibody solution and measuring the amount of $^{51}Cr$ in the supernatant. The amount of the total dissociated $^{51}Cr$ was calculated by carrying out the same procedure by adding the medium alone instead of the antibody solution, and 1 N hydrochloric acid instead of the effector cell suspension, and measuring the amount of $^{51}Cr$ in the supernatant. The cytotoxic activity was calculated by the method described in "b" of the item 7(4) of Example 1. Results are shown in FIG. 45. As shown in FIG. 45, it was found that KM871-hIL-2 induces the cytotoxic activity higher than the 5 times administration of hIL-2, by both of its single and two times administrations.

(2) Analysis of Effector Cells Activated by KM871-hIL-2 (Immunofluorescent Method)

In order to measure influences of the administration of KM871-hIL-2 on effector cells relating to the antitumor effect in the mouse model, a flow cytometer analysis was carried out by the following procedure. The GD3-expressing B16 cell B16·29-10 obtained in b. of the item 3(1) of Example 3 was suspended in PBS to a density of $1×10^7$ cells/ml, and 50 µl of the suspension was transplanted under the ventral skin of a C57 BL/6 mouse (male, 7 week-old, available from Charles River Japan). By setting the following administration groups, each agent was administered intravenously once a day continuously for 5 days, starting on the day of tumor transplantation.

| Non-administered group | |
|---|---|
| hIL-2: | 10 µg/day (0.667 nmol) |
| KM871-hIL-2: | 60 µg/day (0.333 nmol) |

Regarding KM871-hIL-2 (60 µg/day), a group in which the frequency of administration was reduced to two times (on the day of transplantation and the 3rd day after transplantation) was also set. The test was carried out using two animals for each group. After completion of all administrations on the 4th day after transplantation, the spleen was excised, mashed using a slide glass in 6 ml of RPMI1640-FBS(10) medium and then passed through a 70 µm diameter nylon mesh (manufactured by Falcon) to prepare a suspension of splenocytes. A density separation medium for mouse lymphocytes (5 ml), Lympholite-M, was put into a 15 ml tube, overlaid gently with 5 ml of the thus obtained splenocyte suspension and then centrifuged at room temperature for 20 minutes at 1,000×g. The lymphocyte layer of the interface was recovered using a dropping pipette, 10 ml of RPMI1640-FBS(10) medium was added thereto, and the mixture was centrifuged (800×g, 4° C., 10 minutes) and then the supernatant was discarded for washing. After repeating the washing procedure again, a spleen lymphocyte suspension was prepared to give a final density of $3 \times 10^7$ cells/ml by adding 1% BSA-PBS containing 5% mouse serum (manufactured by Chemicon). The lymphocyte suspension was dispensed in 50 µl into a 96 well u bottom plate and each of the following fluorescence-labeled antibodies was further added thereto to carry out the reaction at 4° C. for 1 hour.

| | |
|---|---|
| Phycoerythrin (hereinafter referred to as "PE") - labeled rat anti-mouse CD4 antibody (manufactured by CEDERLANE): | 3 µl |
| FITC-labeled rat anti-mouse CD8 antibody (manufactured by Serotec): | 5 µl |
| FITC-labeled rat anti-mouse NK cell antibody (manufactured by Serotec): | 15 µl |
| FITC-labeled rat anti-mouse macrophage antibody (manufactured by Serotec): | 10 µl |
| PE-labeled rat anti-mouse neutrophil antibody (manufactured by Caltac): | 5 µl |

Figure 46:
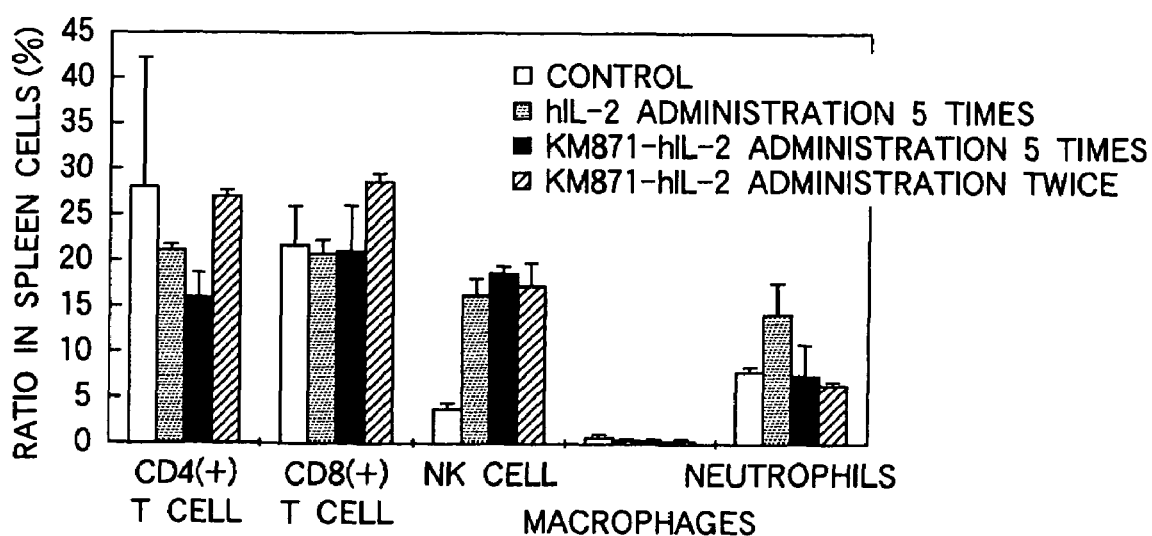
FIG. 46 is a drawing showing the ratio of the number of cells of each cell group in spleen cells of BL/6 mouse to which hIL-2 or KM871-hIL-2 is administered, measured by an immunofluorescent method. The ordinate and the abscissa are the ratio in spleen cells of each cell group and each cell group, respectively. White bar, gray bar, black bar and shaded bar indicate the ratio in spleen cells of non-administered control mice, the ratio in spleen cells of mice to which hIL-2 is administered five times, the ratio in spleen cells of mice to which KM871-hIL-2 is administered five times and the ratio in spleen cells of mice to which KM871-hIL-2 is administered twice, respectively.

By analyzing using a flow cytometer EPICS ELITE (manufactured by Coulter), the ratio of a group stained with each antibody to the total intact cells was calculated, and results are shown in Table 15 and FIG. 46. Each numeral in the table shows the average value of two animals in each group (unit: %).

TABLE 15

| | CD4 + T cell | CD8 + T cell | NK cell | Macrophage | Neutrophil |
|---|---|---|---|---|---|
| No treatment | 28.5 | 21.7 | 3.71 | 0.643 | 7.63 |
| hIL-2 5 × administration | 21.3 | 20.7 | 16.2 | 0.448 | 13.9 |
| KM871-hIL-2 5 × administration | 16.1 | 20.9 | 18.6 | 0.392 | 7.26 |
| KM871-hIL-2 2 × administration | 27.2 | 28.8 | 17.0 | 0.498 | 6.06 |

As shown in Table 15 and FIG. 46, increase in the ratio of NK cells in spleen lymphocytes was observed by the administration of both hIL-2 and KM871-hIL-2. The results show a possibility that the antitumor effect of KM871-hIL-2 is enhanced via the proliferation of NK cells.

(3) Effector Cell Analysis of Antitumor Effect Using In Vivo Depletion Method (In Vitro Cytotoxic Activity)

Figure 47:
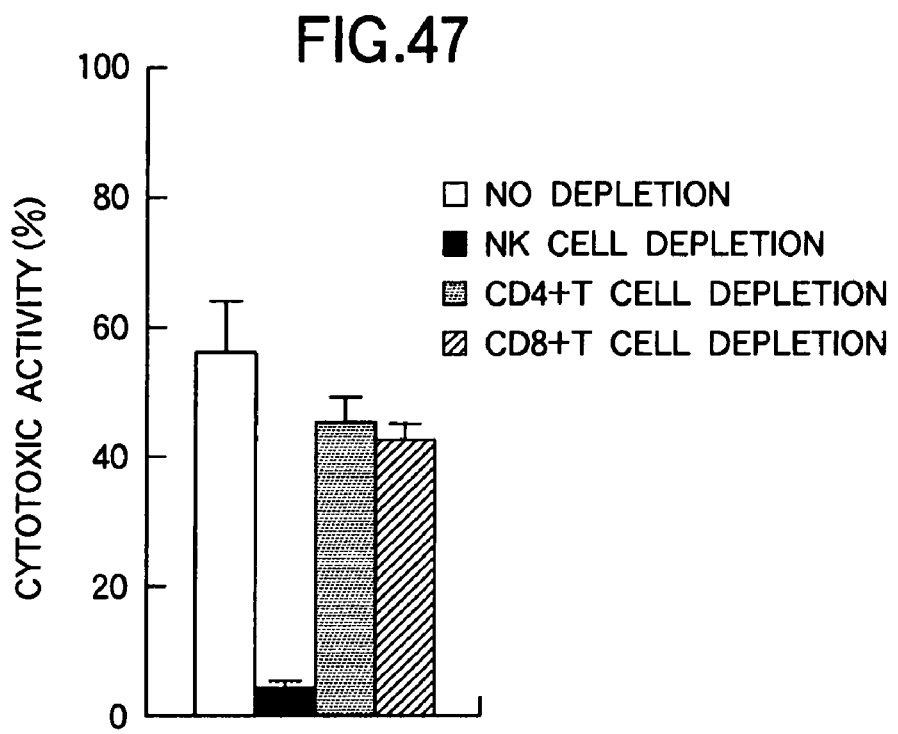
FIG. 47 is a drawing showing a result of measurement of cytotoxic activity by spleen cells when KM871-hIL-2 is administered to BL/6 mice from which each of NK cell, CD4-positive T cell and CD8-positive T cells are depleted. The ordinate shows cytotoxic activity. White bar, black bar, gray bar and shaded bar indicate the cytotoxic activity of mouse spleen cells which is not subjected to the removing treatment, the cytotoxic activity of NK cell-depleted mouse spleen cells, the cytotoxic activity of CD4-positive T cell-depleted mouse spleen cells and the cytotoxic activity of CD8-positive T cell-depleted mouse spleen cells, respectively.

Mechanism analysis of the antitumor effect of KM871-hIL-2 was carried out by the method shown below, using mice prepared by administering antibodies against NK cell, CD4-positive T cell (helper T cell) and CD8-positive T cell (cytotoxic T cell), as IL-2 responsive effector cells in antitumor immunity, into mice to thereby deplete respective cell group from the animal body. The GD3-expressing B16 cell B16·29-10 obtained in "b" of the item 3(1) of Example 3 was suspended in PBS to a density of $5 \times 10^6$ cells/ml, and 100 µl of the suspension was injected intravenously in each of C57 BL/6 mice (male, 7 week-old, available from Charles River Japan). Also, KM871-hIL-2 was administered intravenously at a dose of 24 µg/day once a day for continuous 5 days (0th day to 4th day) starting on the day of tumor transplantation (0th day). At the same time, no administration group was also set as a control group. In addition, KM871-hIL-2 administration groups and no administration groups were also set in the same manner on mice into which each of anti-mouse NK1.1 antibody, anti-mouse CD4 antibody and anti-mouse CD8 antibody was administered by intraperitoneal injection at a dose of 0.5 mg/day three times (−3rd day, 1st day and 3rd day). Five days after the tumor transplantation, the spleen was excised and the cytotoxic activity was measured by the method described in the item 4(1) of Example 3. In this case, the concentration of KM871 at the time of assay was fixed to 10 µg/ml, and the assay time was set to 4 hours. Results are shown in FIG. 47. As shown in FIG. 47, it was found that the main effector cell of the antitumor effect of KM871-hIL-2 in the mice model is NK cell.

(4) Effector Cell Analysis of Antitumor Effect Using In Vivo Depletion Method (In Vivo Antitumor Activity)

Mechanism analysis of the antitumor effect of KM871-hIL-2 was carried out by the method shown below, using mice prepared by administering antibodies against NK cell, CD4-positive T cell (helper T cell) and CD8-positive T cell (cytotoxic T cell), as IL-2 responsive effector cells in antitumor immunity, into mice to thereby deplete respective cell group from the animal body. The GD3-expressing B16 cell B16·29-10 obtained in "b" of the item 3(1) of Example 3 was suspended in PBS to give a density of $5 \times 10^6$ cells/ml, and 100 µl of the suspension was injected intravenously in each of C57 BL/6 mice (male, 7 week-old, manufactured by Charles River Japan). Also, KM871-hIL-2 was administered intravenously at a dose of 24 µg/day once a day for continuous 5 days (0th day to 4th day) starting on the day of tumor transplantation (0th day). At the same time, no administration group was also set as a control group. In addition, KM871-hIL-2 administration groups and no administration groups were also set in the same manner on mice into which each of anti-mouse NK1.1 antibody, anti-mouse CD4 antibody and anti-mouse CD8 antibody were administered by intraperitoneal injection at a dose of 0.5 mg/day four times (−3rd day, 1st day, 3rd day and 7th). On the 15th day after tumor transplantation, the lungs were excised and the visible black metastatic foci on the surface were counted, and results are shown in Table 16 and FIG. 48.

TABLE 11

| Group | | Survived days after commencement of administration (day) | Average value (day) |
|---|---|---|---|
| Non-administered group | | 15/23/23/24/34 | 23.8 |
| hIL-2 | | 15/15/18/27/29 | 20.8 |
| KM871 | 50 μg | 19/20/23/30/34 | 25.2 |
| KM871 | 200 μg | 18/19/23/27/34 | 24.2 |
| KM871-hIL-2 | 24 μg | 29/38/39/41/49 | 39.2 |
| KM871-hIL-2 | 60 μg | 29/32/37 | 32.7 |

Figure 48:
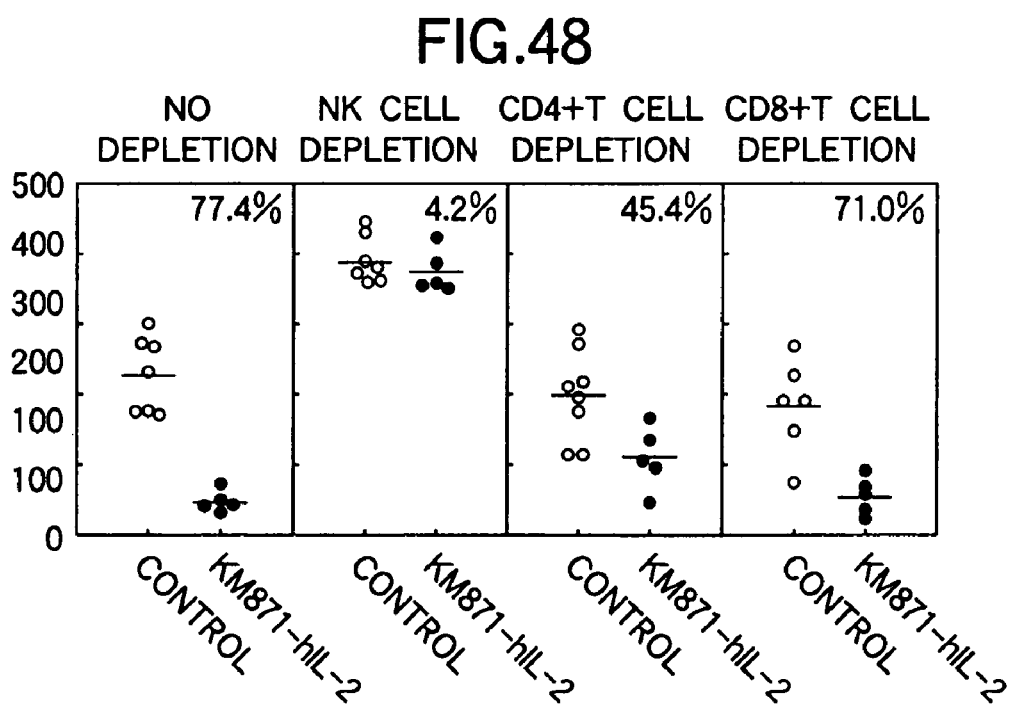
FIG. 48 is a drawing showing results of the measurement of anti-metastatic effects of KM871-hIL-2 on BL/6 mice in which a GD3-positive B16 cell line B16·29-10 is transplanted into mice from which each of NK cell, CD4-positive T cell and CD8-positive T cell are depleted. The ordinate shows the number of metastatic foci. "○","●", horizontal bar and the value in the graph indicate the number of metastatic foci of mouse lung, the number of metastatic foci of KM871-hIL-2-administered mouse lung, the average value of each group and the metastasis inhibition ratio by KM871-hIL-2 administration.

As shown in Table 16 and FIG. 48, it was found that the main effector cell of the antitumor effect of KM871-hIL-2 in the model animals is NK cell. Also, since partial inhibition of the antitumor effect was found by the elimination of CD4-positive T cell, a possibility was suggested that CD4-positive T cell is indirectly concerned in the antitumor effect of KM871-hIL-2 by activating NK cell.

INDUSTRIAL APPLICABILITY

According to the present invention, a human CDR-grafted antibody which specifically reacts with GD3 or the antibody fragment thereof and derivatives of an antibody against ganglioside GD3 or the antibody fragment thereof are provided.

Free Text of Sequence Listings

SEQ ID NO:9—Explanation of artificial sequence: Amino acid sequence obtained by synthetic DNA SEQ ID NO:10—Explanation of artificial sequence: Amino acid sequence obtained by synthetic DNA SEQ ID NO:11—Explanation of artificial sequence: Synthetic DNA SEQ ID NO:12—Explanation of artificial sequence: Synthetic DNA SEQ ID NO:13—Explanation of artificial sequence: Synthetic DNA SEQ ID NO:14—Explanation of artificial sequence: Synthetic DNA SEQ ID NO:15—Explanation of artificial sequence: Synthetic DNA SEQ ID NO:16—Explanation of artificial sequence: Synthetic DNA SEQ ID NO:17—Explanation of artificial sequence: Synthetic DNA SEQ ID NO:18—Explanation of artificial sequence: Synthetic DNA SEQ ID NO:19—Explanation of artificial sequence: Synthetic DNA SEQ ID NO:20—Explanation of artificial sequence: Synthetic DNA SEQ ID NO:21—Explanation of artificial sequence: Synthetic DNA SEQ ID NO:22—Explanation of artificial sequence: Synthetic DNA SEQ ID NO:23—Explanation of artificial sequence: Synthetic DNA SEQ ID NO:24—Explanation of artificial sequence: Synthetic DNA SEQ ID NO:25—Explanation of artificial sequence: Synthetic DNA SEQ ID NO:26—Explanation of artificial sequence: Synthetic DNA SEQ ID NO:27—Explanation of artificial sequence: Synthetic DNA SEQ ID NO:28—Explanation of artificial sequence: Synthetic DNA SEQ ID NO:29—Explanation of artificial sequence: Synthetic DNA SEQ ID NO:30—Explanation of artificial sequence: Synthetic DNA SEQ ID NO:31—Explanation of artificial sequence: Synthetic DNA SEQ ID NO:32—Explanation of artificial sequence: Synthetic DNA SEQ ID NO:33—Explanation of artificial sequence: Synthetic DNA SEQ ID NO:34—Explanation of artificial sequence: Synthetic DNA SEQ ID NO:35—Explanation of artificial sequence: Synthetic DNA SEQ ID NO:36—Explanation of artificial sequence: Synthetic DNA SEQ ID NO:37—Explanation of artificial sequence: Synthetic DNA SEQ ID NO:38—Explanation of artificial sequence: Synthetic DNA SEQ ID NO:39—Explanation of artificial sequence: synthetic DNA SEQ ID NO:40—Explanation of artificial sequence: Synthetic DNA SEQ ID NO:41—Explanation of artificial sequence: Synthetic DNA SEQ ID NO:42—Explanation of artificial sequence: Synthetic DNA SEQ ID NO:43—Explanation of artificial sequence: Synthetic DNA SEQ ID NO:44—Explanation of artificial sequence: Synthetic DNA SEQ ID NO:45—Explanation of artificial sequence: Synthetic DNA SEQ ID NO:46—Explanation of artificial sequence: Synthetic DNA SEQ ID NO:47—Explanation of artificial sequence: Synthetic DNA SEQ ID NO:48—Explanation of artificial sequence: Synthetic DNA SEQ ID NO:49—Explanation of artificial sequence: Synthetic DNA SEQ ID NO:50—Explanation of artificial sequence: Synthetic DNA SEQ ID NO:51—Explanation of artificial sequence: Synthetic DNA SEQ ID NO:52—Explanation of artificial sequence: Synthetic DNA SEQ ID NO:53—Explanation of artificial sequence: Amino acid sequence obtained by synthetic DNA SEQ ID NO:54—Explanation of artificial sequence: Amino acid sequence obtained by synthetic DNA SEQ ID NO:57—Explanation of artificial sequence: Amino acid sequence obtained by synthetic DNA

The invention claimed is:

1. An antibody conjugate, comprising a humanized antibody or an antibody fragment thereof which is conjugated with a therapeutic agent, wherein the humanized antibody or the antibody fragment thereof specifically binds to ganglioside GD3 and comprises:
   the H chain V region having the amino acid sequence of SEQ ID NO:9; and
   the L chain V region having the amino acid sequence of SEQ ID NO:54.

2. An antibody conjugate, comprising a humanized antibody produced by the transformant KM8871 (FERM BP-6790) or an antibody fragment thereof which is conjugated with a therapeutic agent, wherein the humanized antibody or the antibody fragment thereof specifically binds to ganglioside GD3.

3. The antibody conjugate according to claim 1, wherein the antibody fragment comprises:
   the H chain V region having the amino acid sequence of SEQ ID NO:9; and
   the L chain V region having the amino acid sequence of SEQ ID NO:54.

4. The antibody conjugate according to claim 1, wherein the therapeutic agent is a cytokine.

5. The antibody conjugate according to claim 4, wherein the cytokine is human interleukin-2 (hIL-2).

6. An antibody conjugate, comprising a humanized antibody or an antibody fragment thereof which is conjugated with a therapeutic agent, wherein the humanized antibody or the antibody fragment thereof specifically binds to ganglioside GD3, the humanized antibody is produced by transformant KM8871 (FERM BP-6790) and the therapeutic agent is hIL-2.

7. An antibody conjugate, comprising a humanized-antibody or an antibody fragment thereof which is conjugated with hIL-2,
   wherein the humanized antibody or the antibody fragment thereof specifically binds to ganglioside GD3 and comprises:
   the H chain V region having the amino acid sequence of SEQ ID NO:9; and
   the L chain V region having the amino acid sequence of SEQ ID NO:54,
   wherein the H chain V region conjugated with hIL-2 has the amino acid sequence of SEQ ID NO:53.

8. A humanized antibody or an antibody fragment thereof which specifically binds to ganglioside GD3 and comprises:
   the H chain V region having the amino acid sequence of SEQ ID NO:9; and the L chain V region having the amino acid sequence of SEQ ID NO:10 in which at least one or more amino acid residue selected from $41^{st}$ position Gly, $44^{th}$ position Pro, $83^{rd}$ position Phe and $87^{th}$ position Tyr is replaced with Asp, Val, Ile and Phe, respectively.

9. The humanized antibody or the antibody fragment thereof according to claim 8, wherein the antibody fragment comprises:
the H chain V region having the amino acid sequence of SEQ ID NO:9; and
the L chain V region having the amino acid sequence of SEQ ID NO:54.

10. The humanized antibody KM8871 or the antibody fragment thereof according to claim 8 or 9, wherein the humanized antibody is produced by the transformant KM8871 (FERM BP-6790).

11. A transformant KM8871 (FERM BP-6790) which produces the humanized antibody according to claim 8 or 9.

12. The antibody conjugate of claim 6, wherein the antibody conjugate is produced by the transformant KM8871hIL2 (FERM BP-6791).

* * * * *